(12) United States Patent
Wolf et al.

(10) Patent No.: US 7,759,541 B2
(45) Date of Patent: Jul. 20, 2010

(54) TRANSGENIC ANIMALS FOR ASSESSING DRUG METABOLISM AND TOXICITY

(75) Inventors: Charles Roland Wolf, Perthshire (GB); Nico Scheer, Cologne (DE); Nicole Faust, Rösrath (DE)

(73) Assignee: ITI Life Sciences (GB)

( * ) Notice: Subject to any disclaimer, the term of this patent is extended or adjusted under 35 U.S.C. 154(b) by 0 days.

(21) Appl. No.: 11/757,972

(22) Filed: Jun. 4, 2007

(65) Prior Publication Data
US 2008/0148416 A1 Jun. 19, 2008

Related U.S. Application Data

(63) Continuation-in-part of application No. PCT/GB2005/004772, filed on Dec. 13, 2005.

(60) Provisional application No. 60/707,077, filed on Aug. 10, 2005.

(30) Foreign Application Priority Data

Dec. 13, 2004 (GB) ................................. 0427172.2
Aug. 5, 2005 (GB) ................................. 0516187.2

(51) Int. Cl.
*A01K 67/027* (2006.01)

(52) U.S. Cl. ............................................. 800/18; 800/8
(58) Field of Classification Search ............... 800/8, 800/18; 435/325
See application file for complete search history.

(56) References Cited

U.S. PATENT DOCUMENTS

2004/0128703 A1 * 7/2004 Shizuya

FOREIGN PATENT DOCUMENTS

| WO | WO 02/083897 | 10/2002 |
| WO | WO 2004/007708 | 1/2004 |

OTHER PUBLICATIONS

Xie, Nature, Jul. 27, 2000, vol. 406, p. 435-439.*
Robertson, Mol. Pharmacol., 2003, vol. 64, p. 42-50.*
Xie (Drug discovery today, 2002, vol. 7, No. 9, p. 509-515).*
Zhang (Biochem. Pharmacol., 2003, vol. 65, p. 1889-1896).*
Ma (Drug Metab. Dispos. 2007, Vo. 35, No. 2, p. 194-200).*
Auerbach et al., *Nucleic Acids Res.*, 2003, 31(12), 3194-3207.
Call, LM et al., "A cre-lox recombination system for the targeted integration of cirucular yeast artificial chromosomes into embryonic stem cells," *Hum. Mol. Genet.*, 2000, 9(12), 1745-1751.
Chen, CJ et al., "Genomic organization of the human multidrug resistance (MDR1) gene and origin of P-glycoproteins," *J. Biol. Chem.*, 1990, 265(1), 506-514.
Henderson, CJ et al., *J. Biol. Chem.*, 2003, 278, 13480-13486.
Huang et al., *Molecular Endocrinology*, 2004, 18(10), 2402-2408.
Li, ZW et al., "Generation of mice with 200-kb amyloid precursor protein gene deletion by Cre recombinase-mediated site-specific recombination in embryonic stem cells," *PNAS USA*, 1996, 93(12), 6158-6162.
Erratum: Li, ZW et al., *PNAS USA*, 1996, 93(21), 12052.
Ma et al., *Drug Metab. Dispos.*, 2007, 35(2), 194-200.
Maglich et al., *J. Biol. Chem.*, 2003, 278(19), 17277-17283.
Raguz, S. et al., "Activation of the MDR1 upstream promoter in breast carcinoma as a surrogate for metastatic invasion," *Clin Cancer Res.*, 2004, 10(8), 2776-2783.
Robertson, G.R. et al., "Transgenic Mouse Models of Human CYP3A4 Gene Regulation," *Molecular Pharamacology*, Baltimore, MD, 2003, 64(1), 42-50.
Su, H. et al., "Nested chromosomal deletions induced with retroviral vectors in mice," *Nat. Genet.*, 2000, 24(1), 92-95.
Ueda, K. et al., "Isolation and sequence of the promoter region of the human multidrug-resistance (P-glycoprotein) gene," *J. Biol. Chem.*, 1987, 262(36), 17432-17436.
Xie et al., "Humanized xenobiotic response in mice expressing nuclear receptor SXR," *Nature*, 2000, 406(6794), 435-439.
Xie et al., *Drug Discov Today*, 2002, 7(9), DDT7, 509-515.
Zhang, J. et al., "Modulation of Acetaminophen-Induced Hepatotoxicity by the Xenobiotic Receptor CAR," *Science*, 2002, 298, 422-424.
Zhang, W. et al., "In vivo activation of the human CYP3A4 promoter in mouse liver and regulation by prename X receptors," *Biochemical Pharmacology*, 2003, 65(11), 1889-1896.
Goodwin, B., et al., "Transcriptional Regulation of the Human CYP3A4 Gene by the Constitutive Androstane Receptor", Molecular Pharmacology, 2002, vol. 62, No. 2, 359-365.
Lehmann, J.M., et al., "The Human Orphan Nuclear Receptor PXR Is activated by Compounds That Regulate CYP34A Gene Expression and Cause Drug Interactions", J. Clinical Investigation, 1998, vol. 102, No. 5, 1016-1023.

\* cited by examiner

*Primary Examiner*—Michael C. Wilson
(74) *Attorney, Agent, or Firm*—Woodcock Washburn LLP

(57) ABSTRACT

The present invention relates to transgenic non-human animals, tissues or cells derived therefrom and methods of producing them. The transgenic non-human animals or tissues or cells derived therefrom provide a system capable of expressing human proteins responsible for drug metabolism in place of the homologous endogenous non-human animal proteins and for the controlled expression of human genes introduced into the animal so that the expression of the human genes is regulated in a manner more closely analogous to that seen in vivo in humans.

1 Claim, 84 Drawing Sheets

Humanization and Knock out of PXR and CAR

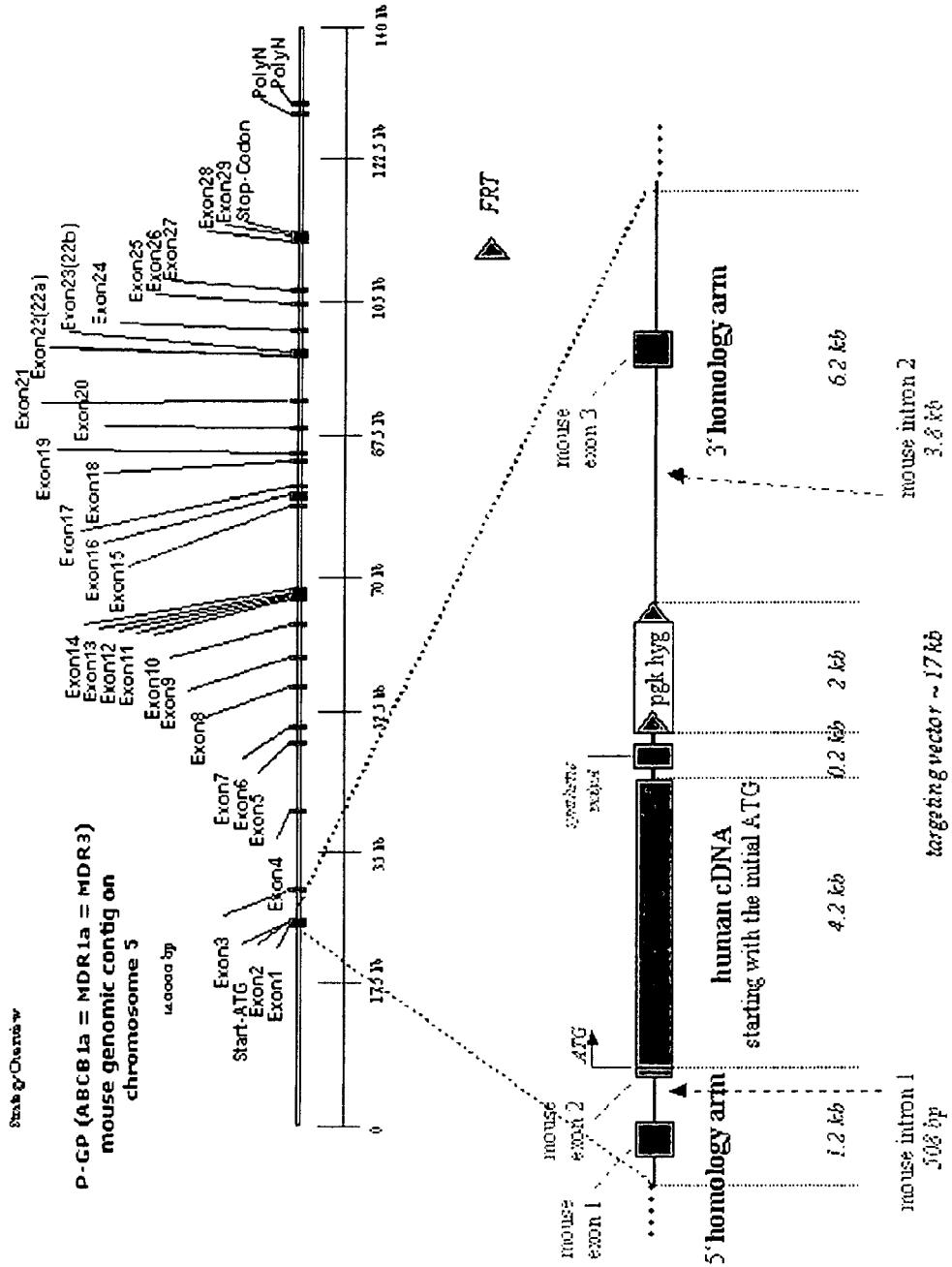

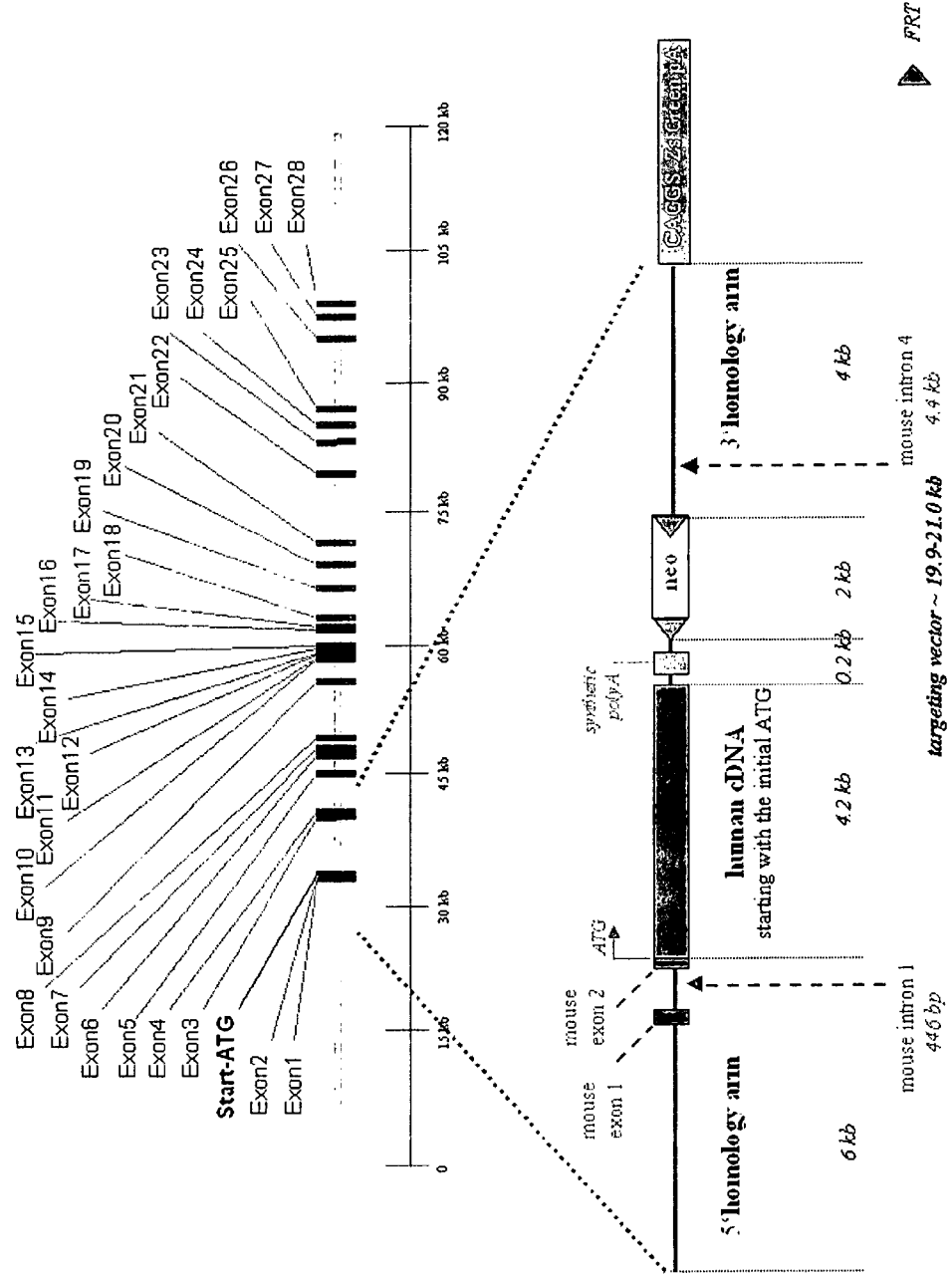
FIG. 5 (Mdr1b)

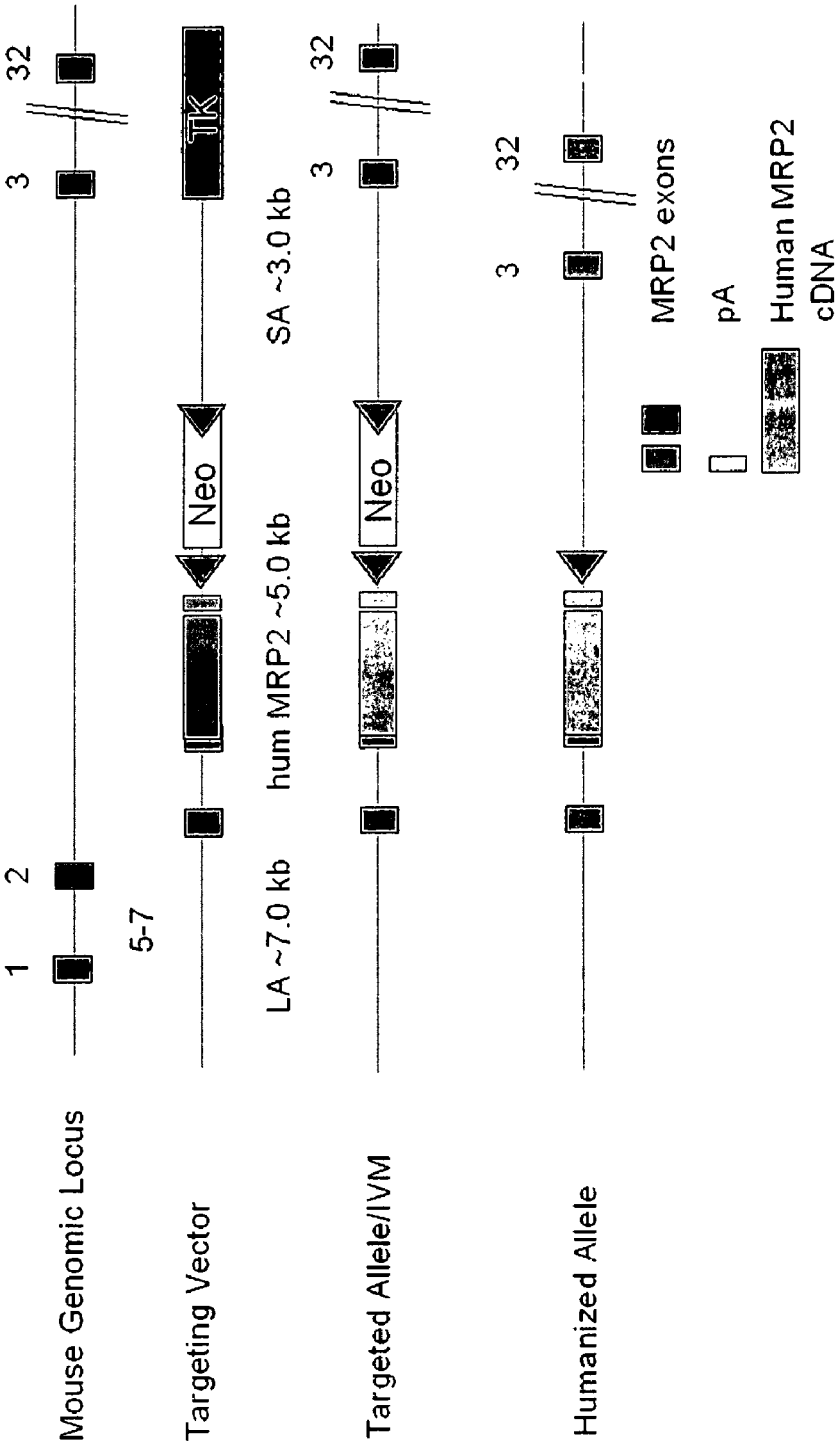
FIG. 6 (MRP2)

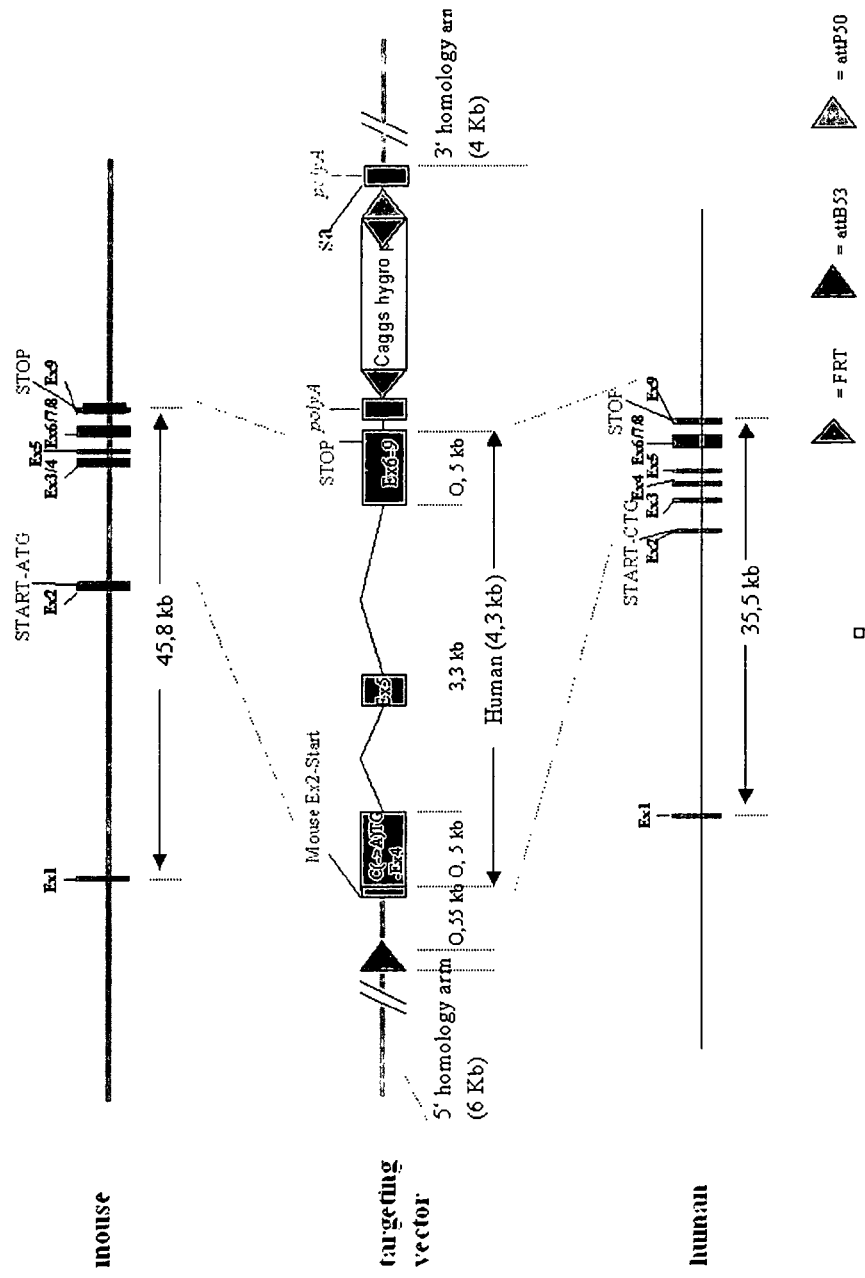
FIG. 7 (PXR)
PXR-humanization: targeting strategy

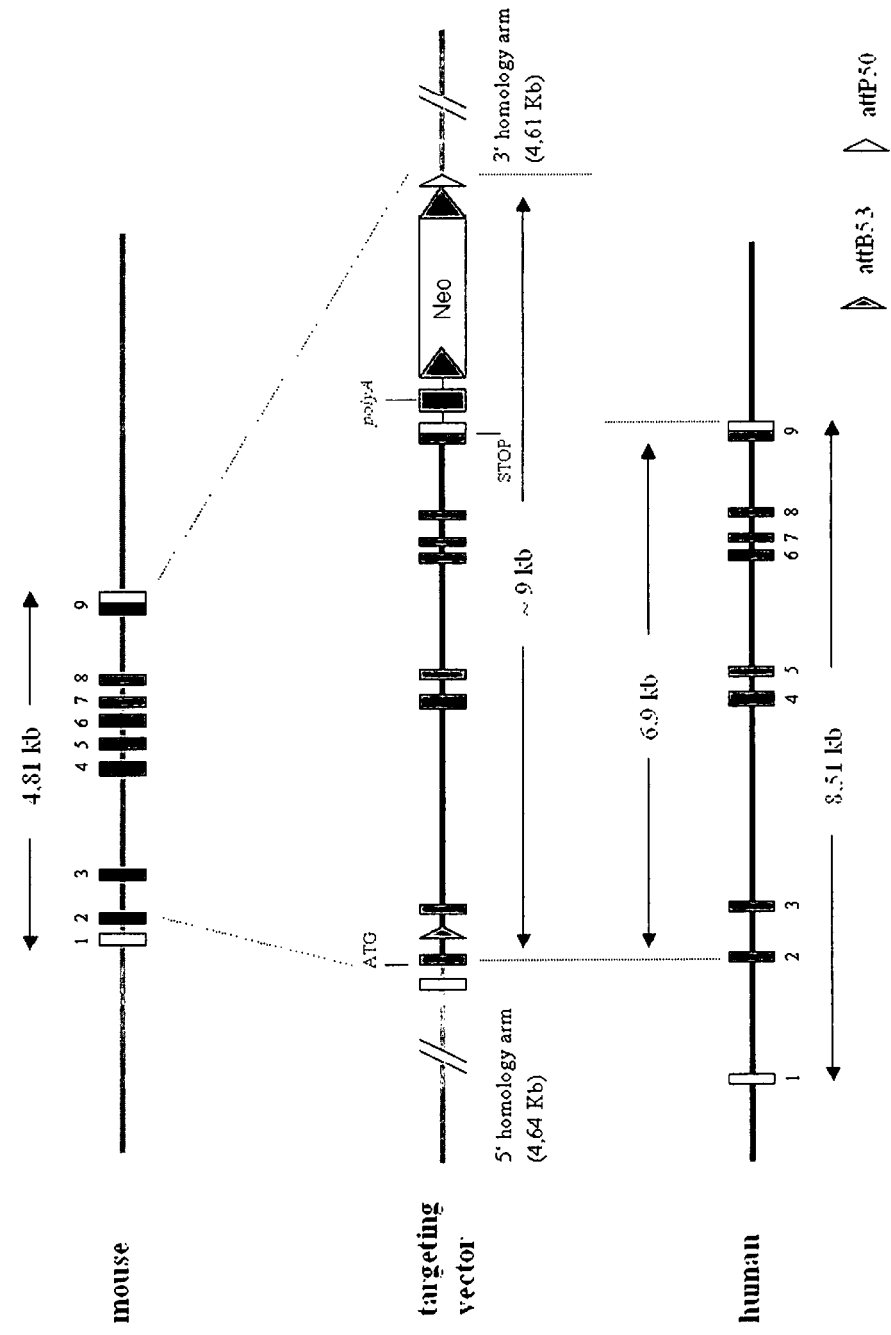
FIG. 8 (CAR)
CAR humanization: targeting strategy

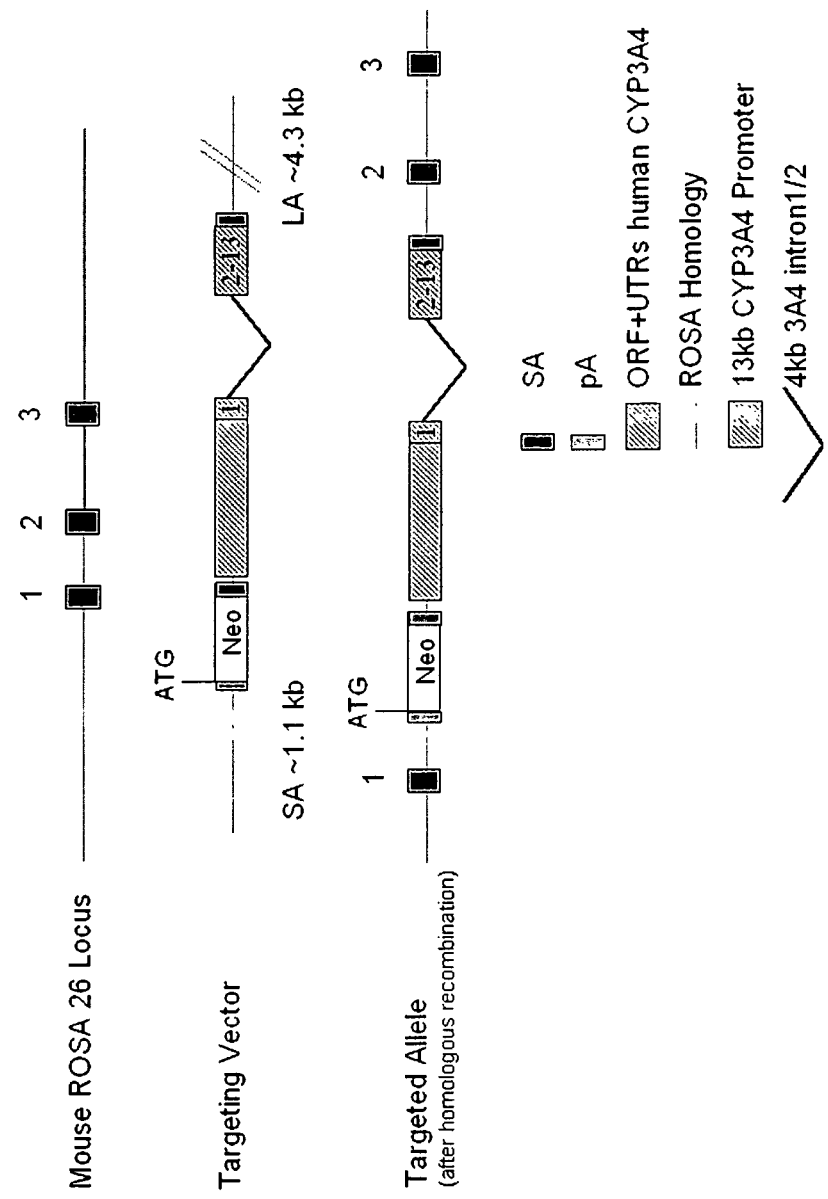
FIG. 9 (CYP3A4)

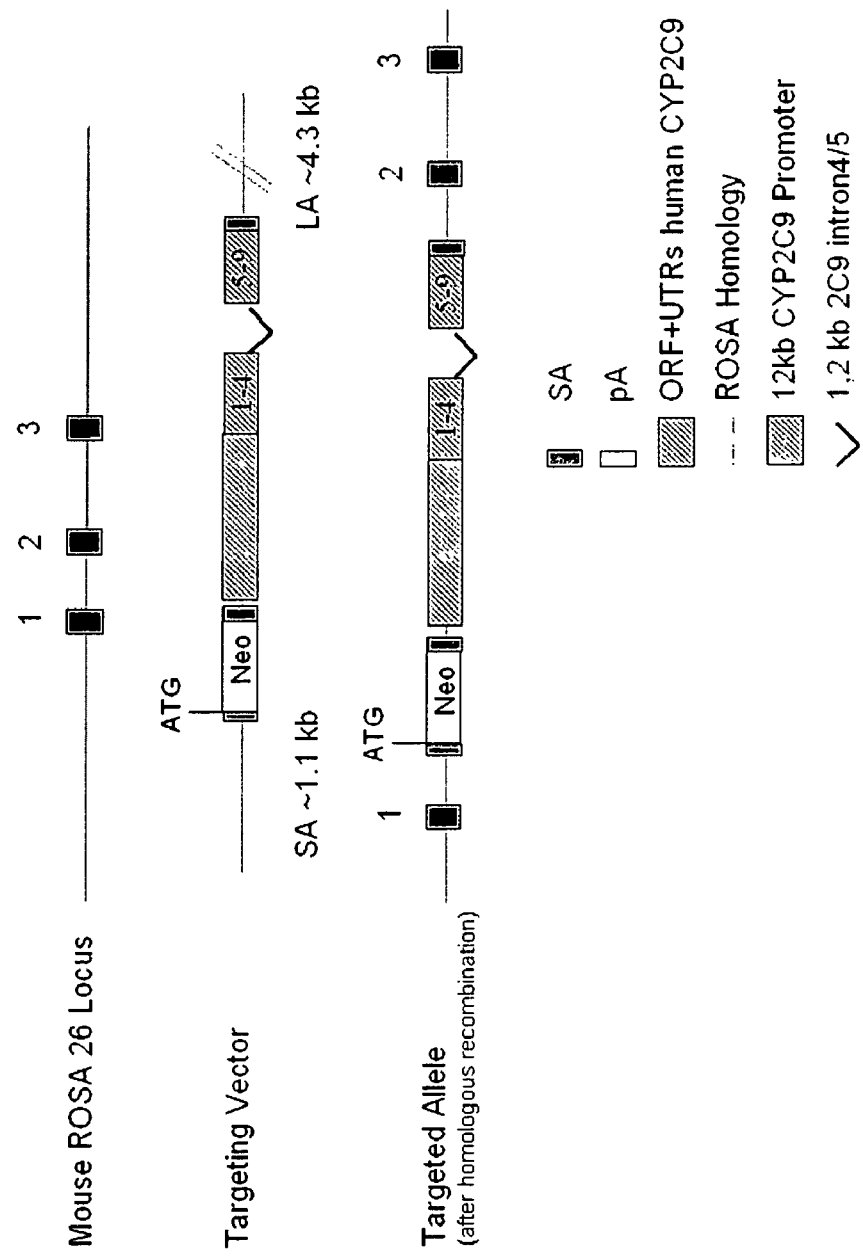
FIG. 10 (CYP2C9)

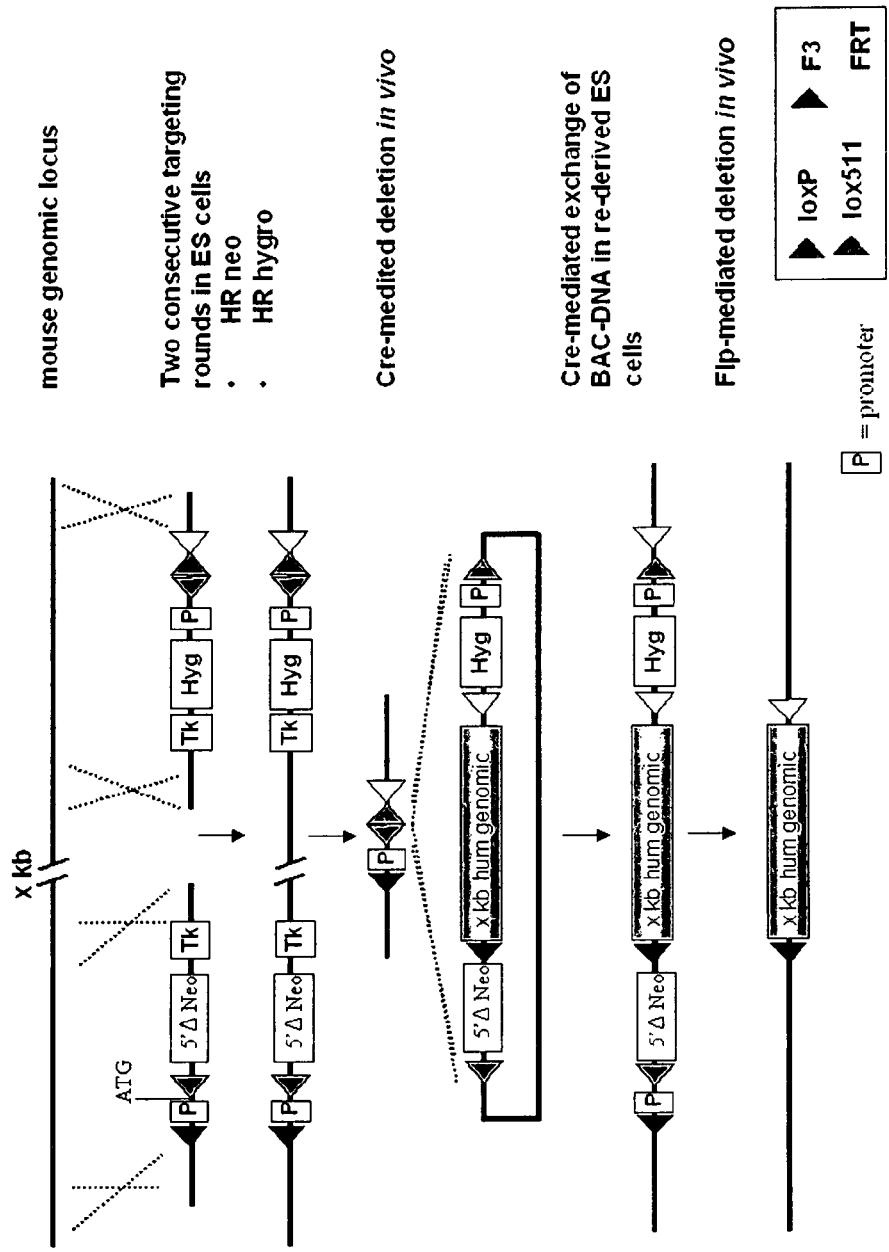
FIG. 11 (overall strategy for cluster exchange)

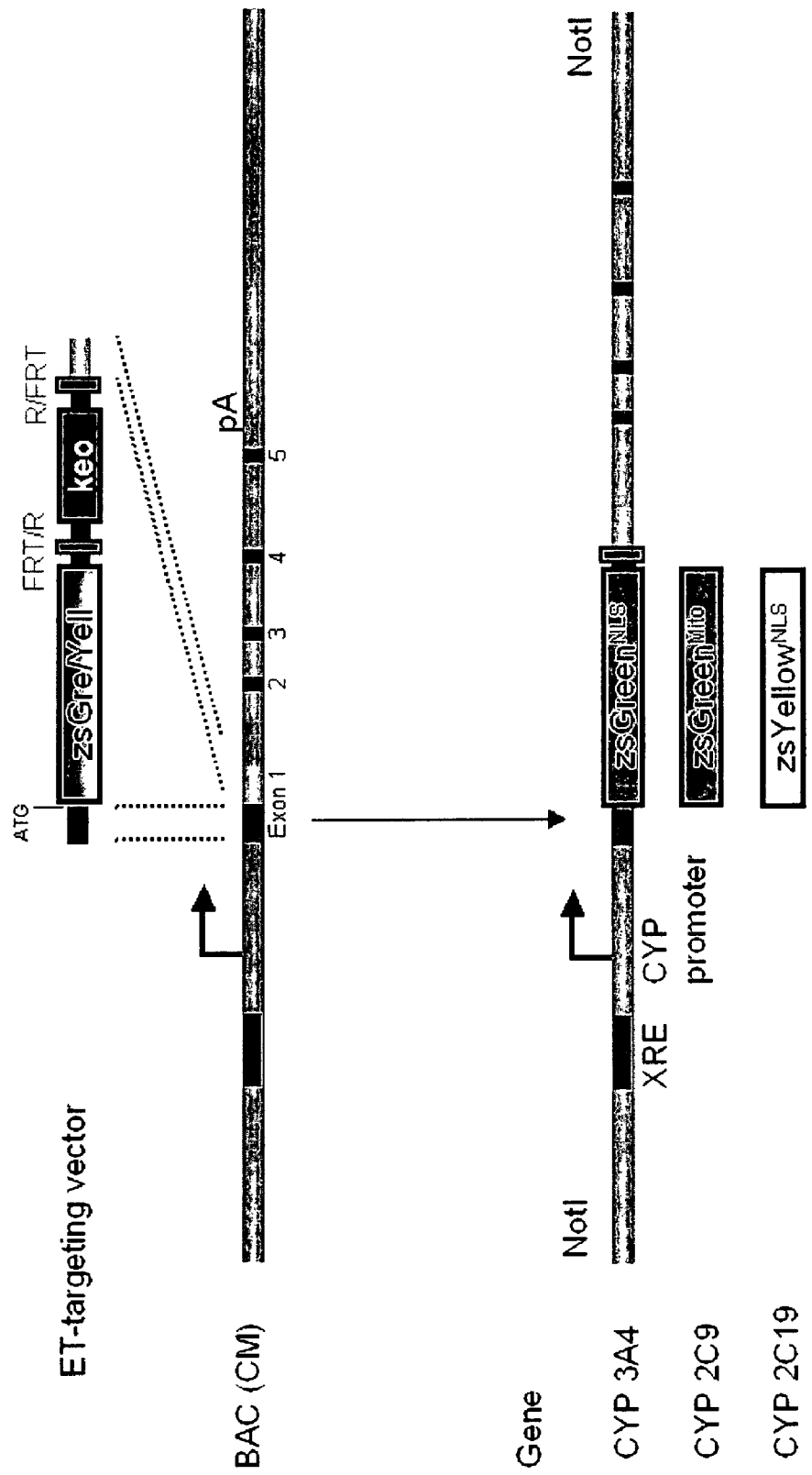
FIG. 12 (Reporter project strategy)

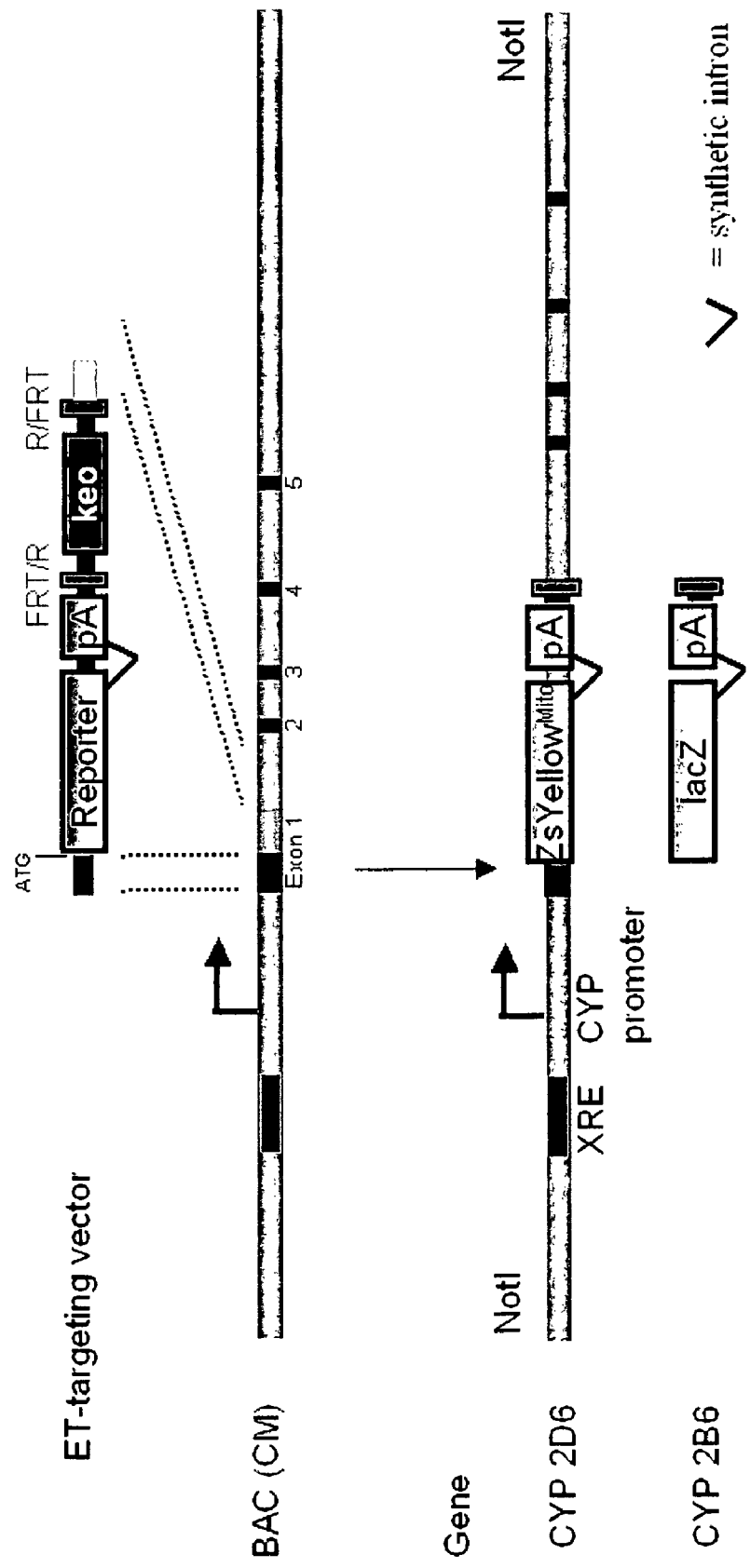
FIG. 13 (Reporter project strategy for CYP2D6 and CYP2B6)

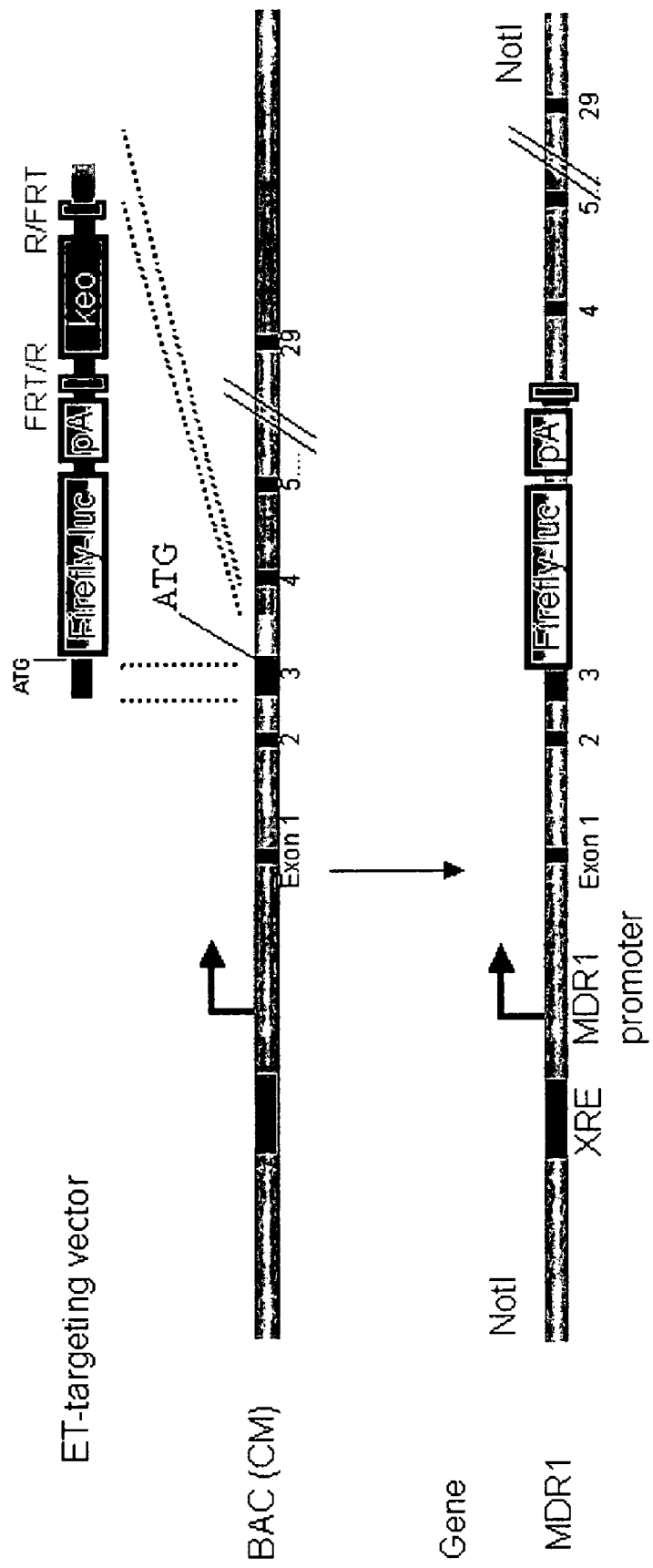
FIG. 14 (reporter project strategy for MDR1)

FIG. 15 (Example of a PXR typing PCR)
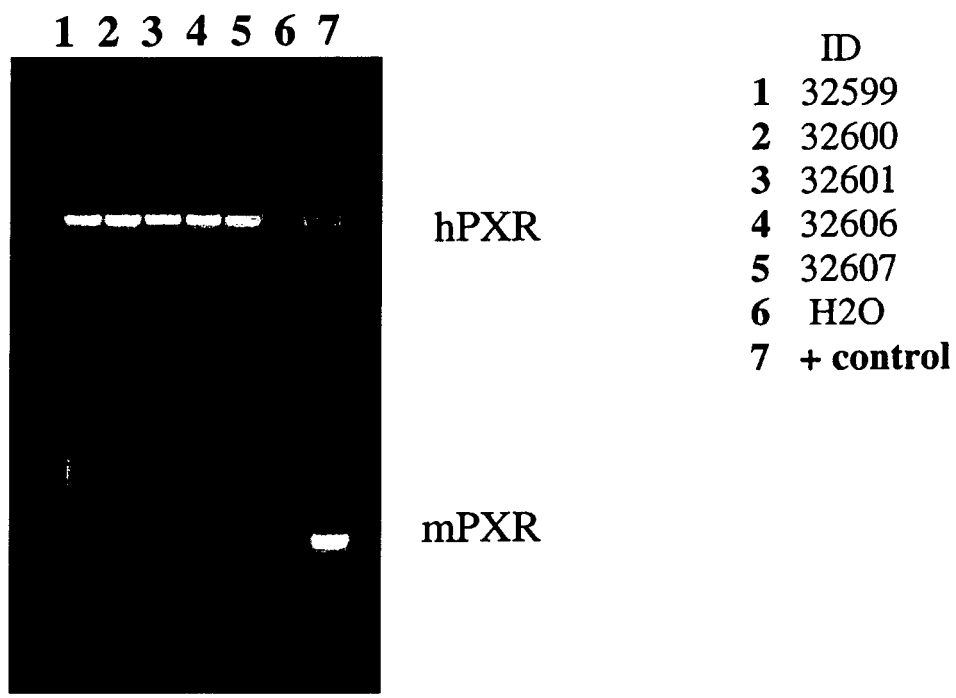
|   | ID |
|---|---|
| 1 | 32599 |
| 2 | 32600 |
| 3 | 32601 |
| 4 | 32606 |
| 5 | 32607 |
| 6 | H2O |
| 7 | + control |
| Primer combination | Detected Genotype | Size of expected fragment |
|---|---|---|
| PxTf1/PxTHr1 | Humanized PXR | 386 bp |
| PxTf1/PxTMr1 | Mouse PXR | 700 bp |

| Gene | TaqMan® Genomic Assay catalogue # | TaqMan® Genomic Assay batch # |
|---|---|---|
| Human PXR | hPXR_Hs00243666_m1 | 295782 |
| Mouse PXR | mPXR_Mm00803092_m1 | 295782 |
| Mouse β-actin | β-actin_Mm607939_s1 | 312686 |

TaqMan® Genomic Assays used.

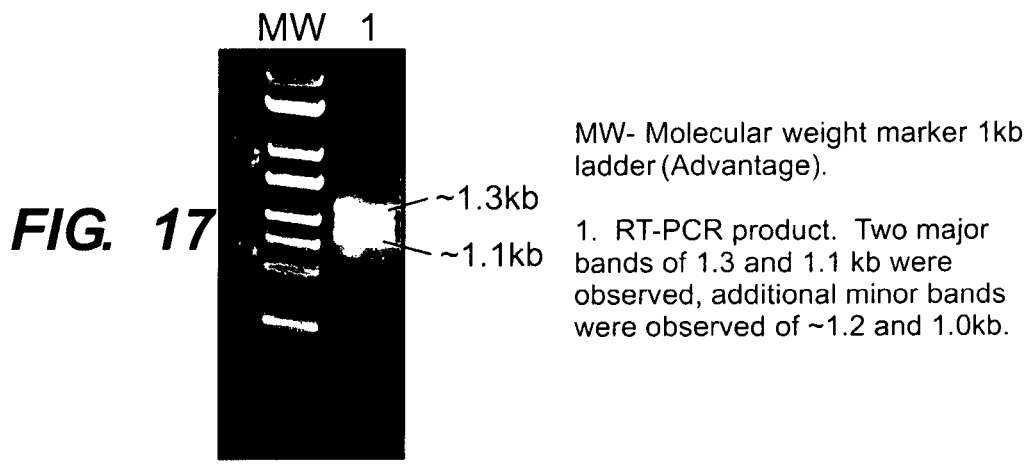
FIG. 17
MW- Molecular weight marker 1kb ladder (Advantage).
1. RT-PCR product. Two major bands of 1.3 and 1.1 kb were observed, additional minor bands were observed of ~1.2 and 1.0kb.
FIG. 18
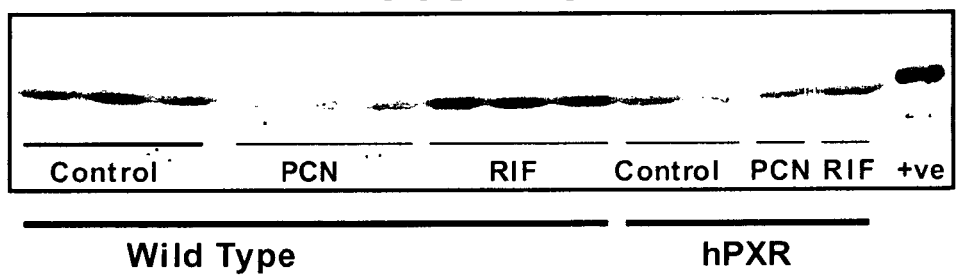
FIG. 19
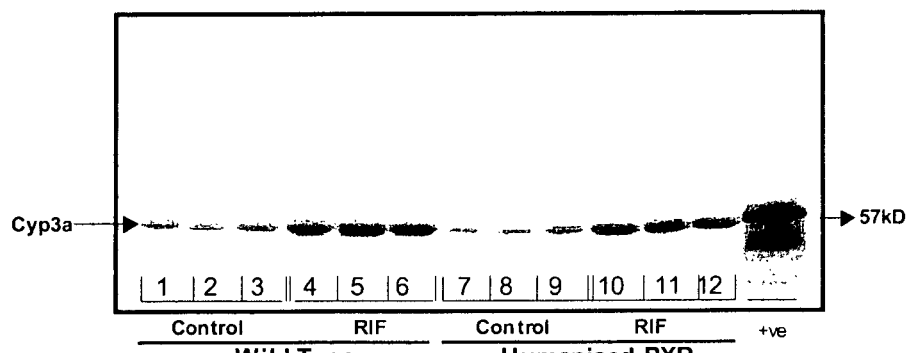
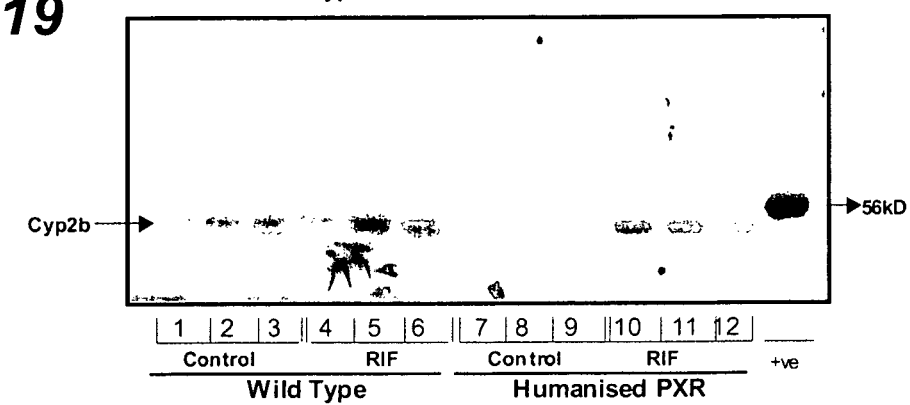

Testosterone 7-alpha hydroxylation -TCPOBOP

Testosterone 6-beta hydroxylation -TCPOBOP

Testosterone 16-alpha hydroxylation - TCPOBOP

Testosterone 16-beta hydroxylation - TCPOBOP

PCR Results

M 1 2 3 4 5 6 7 8 9 10 11 12 13 14 15 16 M

M = Marker

| No. | DNA | PCR name | Detected allele | PCR SOP |
|---|---|---|---|---|
| 1 | Control(H$_2$O) | m PXR | Mouse PXR | 1057 |
| 2 | W t | | | |
| 3 | D42749 | | | |
| 4 | D42752 | | | |
| 5 | Control(H$_2$O) | PXR hum targ | Humanised PXR | 1058 |
| 6 | W t | | | |
| 7 | D42749 | | | |
| 8 | D42752 | | | |
| 9 | Control(H$_2$O) | mCAR | MouseCAR | 1062 |
| 10 | W t | | | |
| 11 | D42749 | | | |
| 12 | D42752 | | | |
| 13 | Control(H$_2$O) | CAR hum | Humanised CAR | 1063 |
| 14 | W t | | | |
| 15 | D42749 | | | |
| 16 | D42752 | | | |

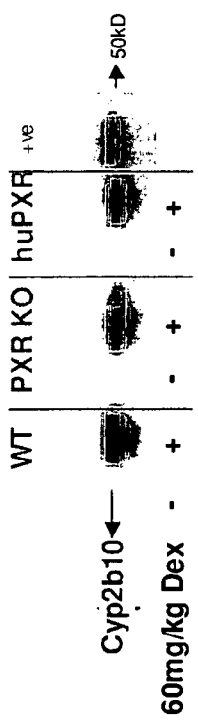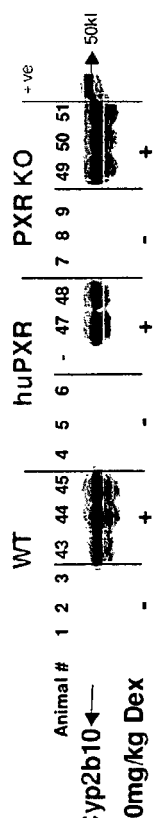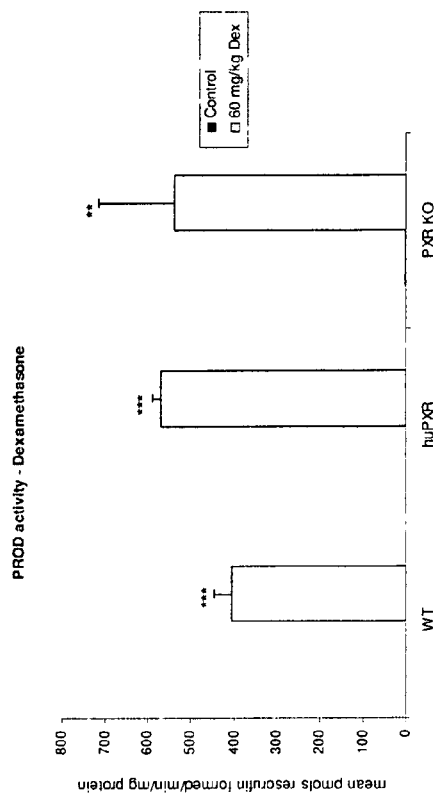
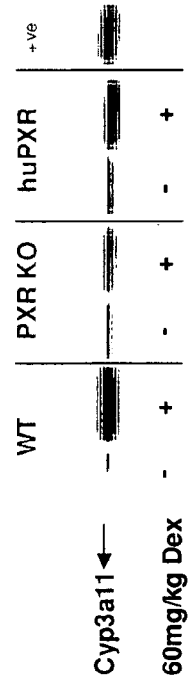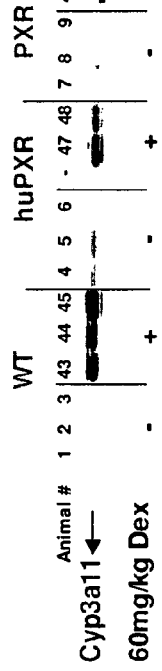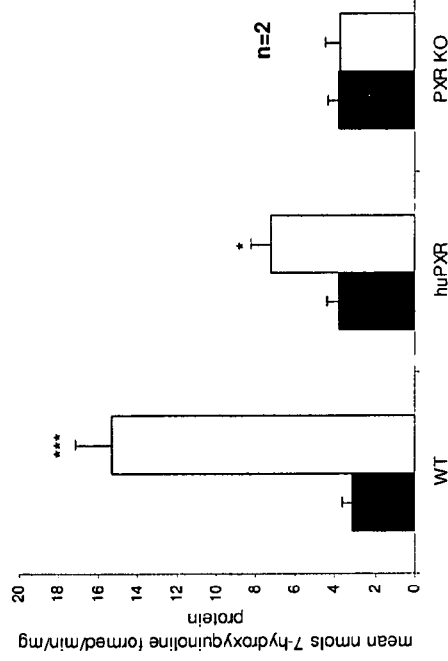
Fig. 34

Fig. 38

|  | 3a11 | | 2b10 | |
|---|---|---|---|---|
|  | RIF | DEX | RIF | DEX |
| WT | +++ | +++ | NC | +++ |
| huPXR | +++ | ++ | NC | +++ |
| PXR KO | NC | NC | NC | +++ |

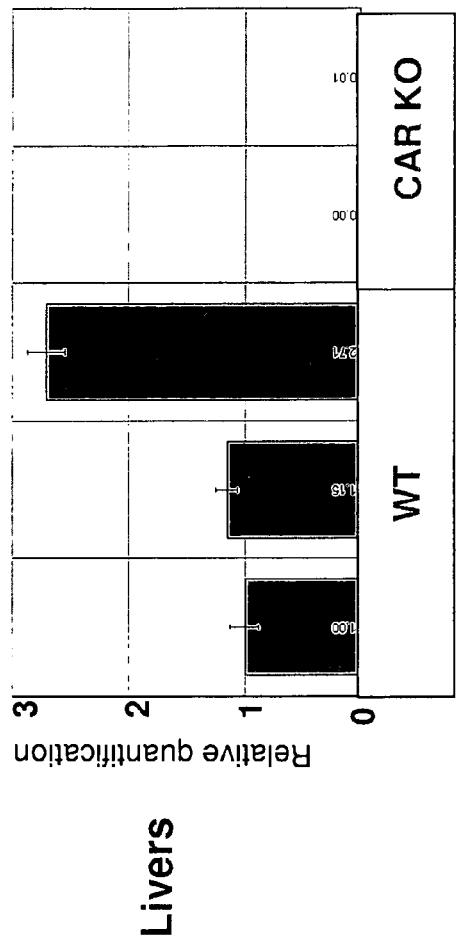
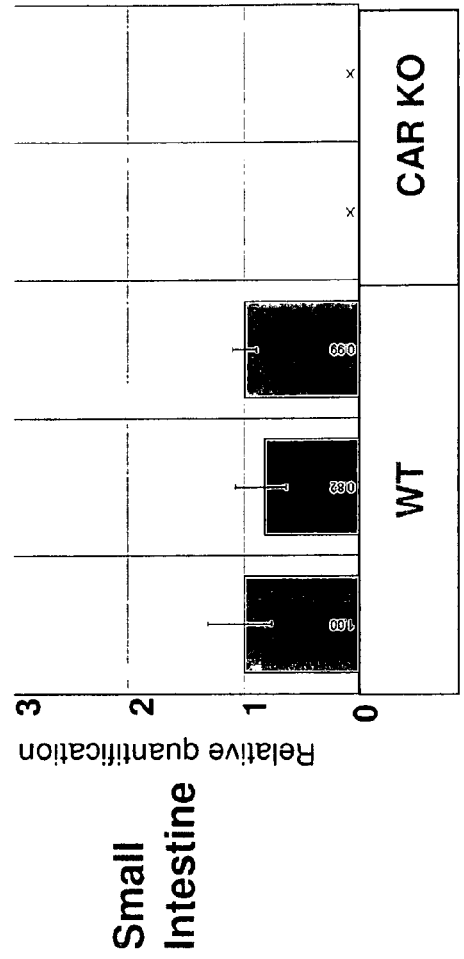
Fig. 39

Fig. 40
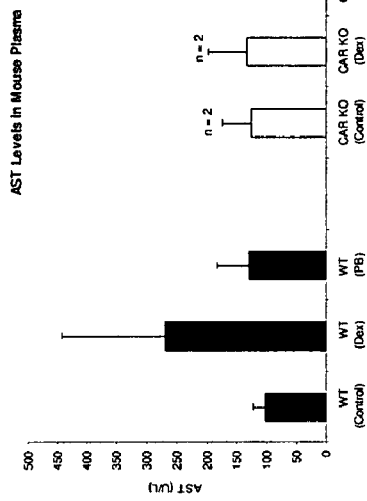
Liver/body weight ratios
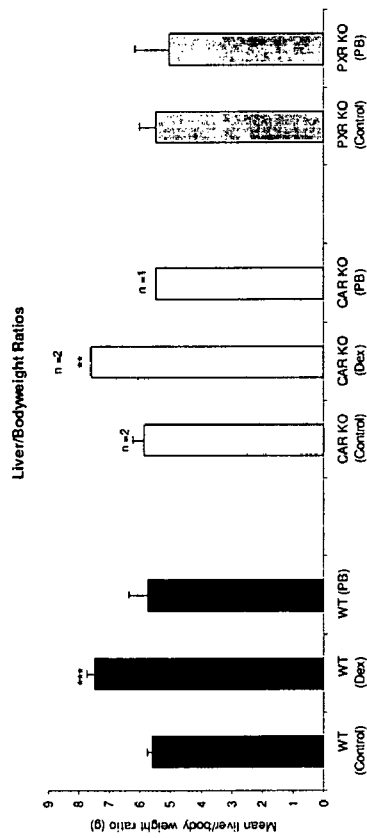
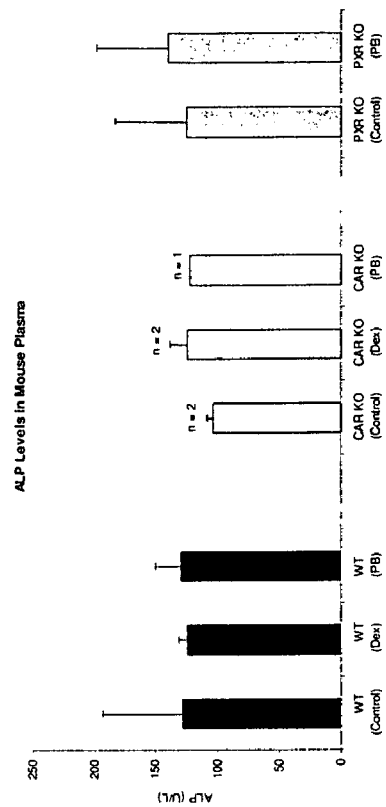
AST
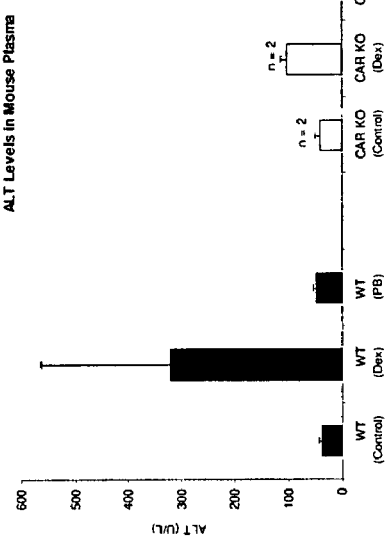
ALP

Fig. 44
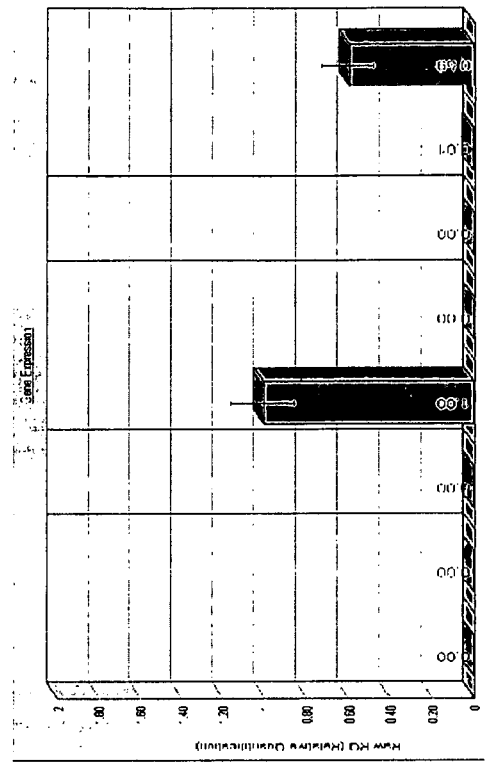
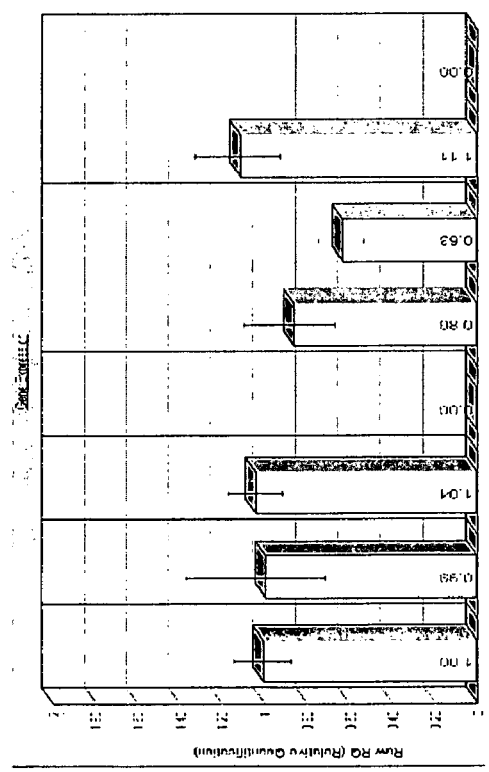
Liver

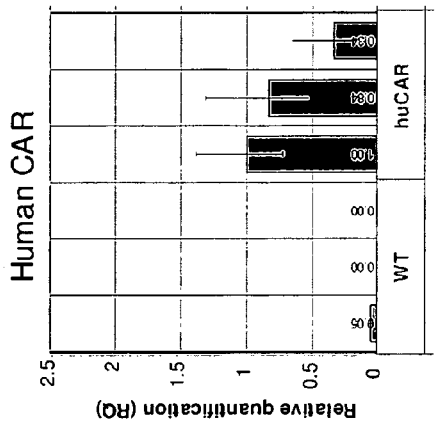
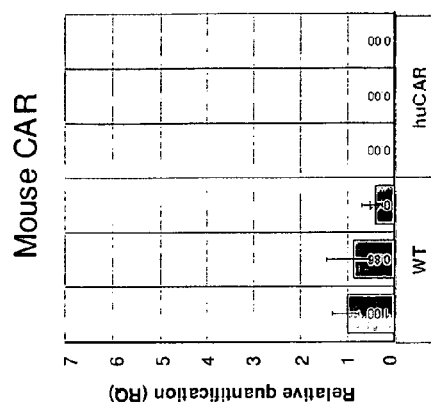
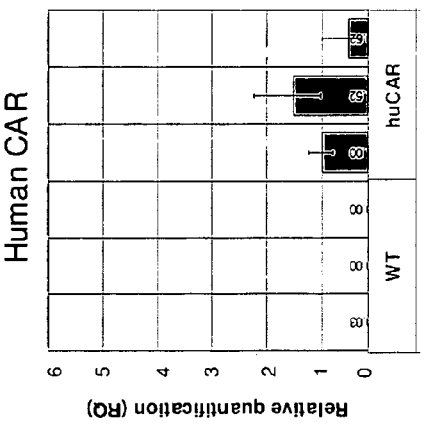
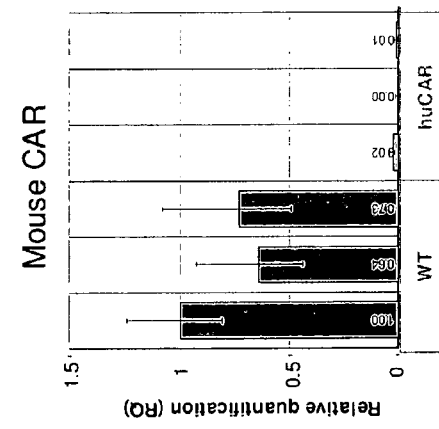
Fig. 45

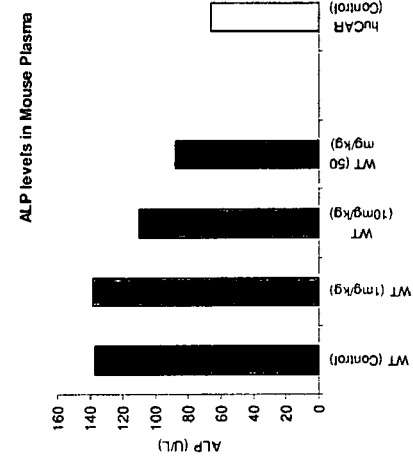
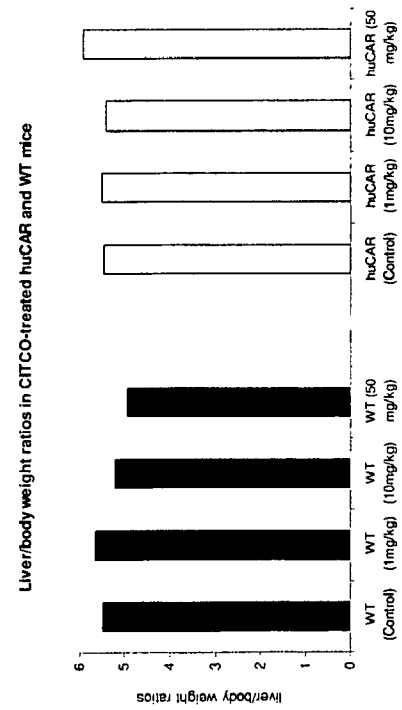
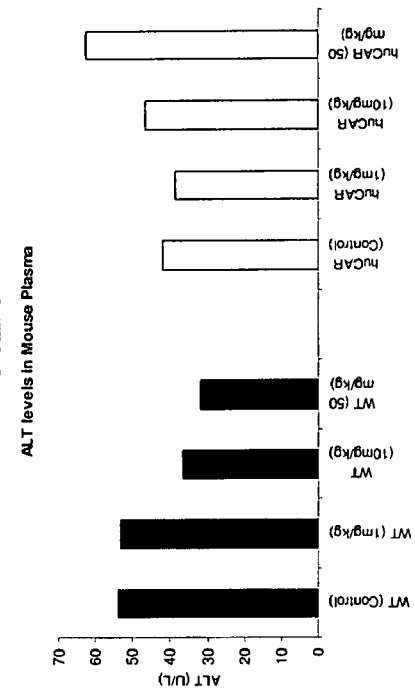
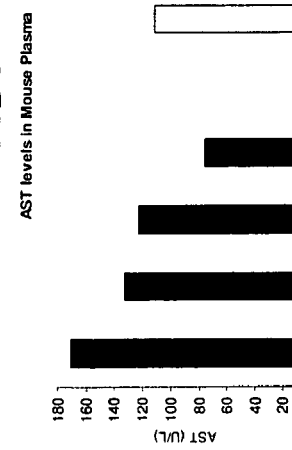
Fig. 46

Fig. 50
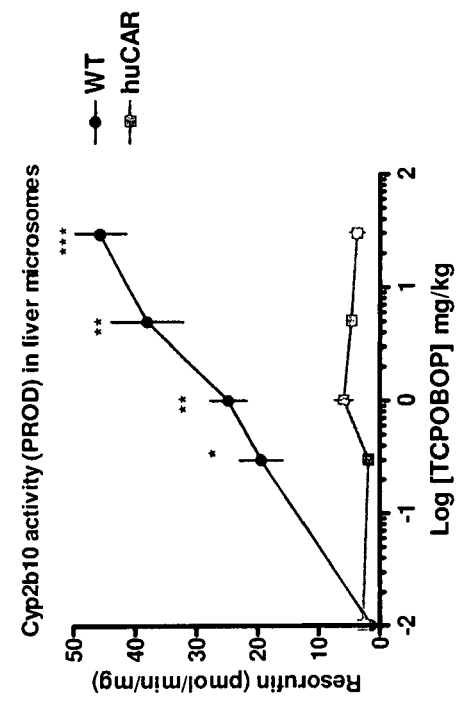
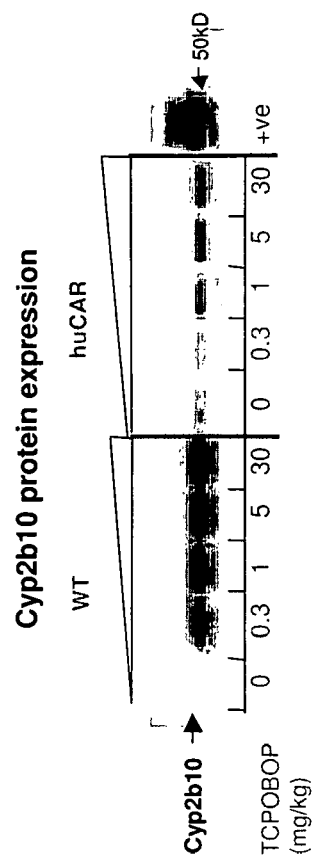
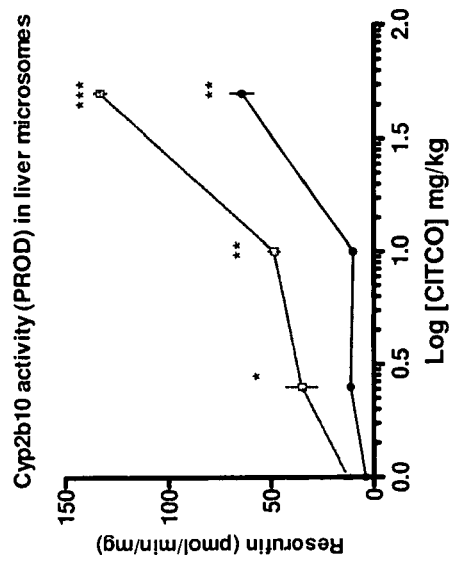
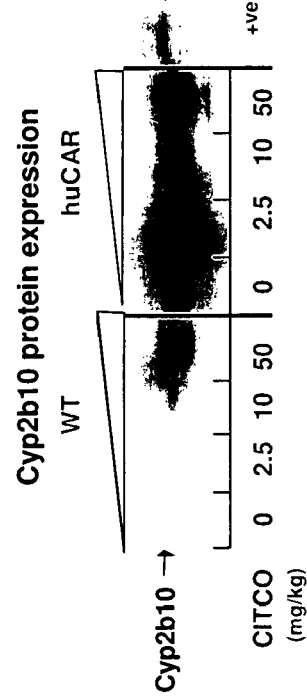

Fig. 55

| | MOUSE | | HUMAN | |
|---|---|---|---|---|
| | 3a11 | 2b10 | 3a11 | 2b10 |
| Phenobarbital | CAR | CAR | CAR | CAR |
| TCPOBOP | CAR | CAR | -ve | CAR |
| CITCO | -ve | -ve | CAR | CAR |
| Rifampicin | PXR | -ve | PXR | - |
| Dexamethasone | PXR | other | PXR | other |
| PCN | PXR | PXR | PXR | |
| Clotrimazole | other | CAR | | |

CYP2D6 reporter
wt control
Fig. 60

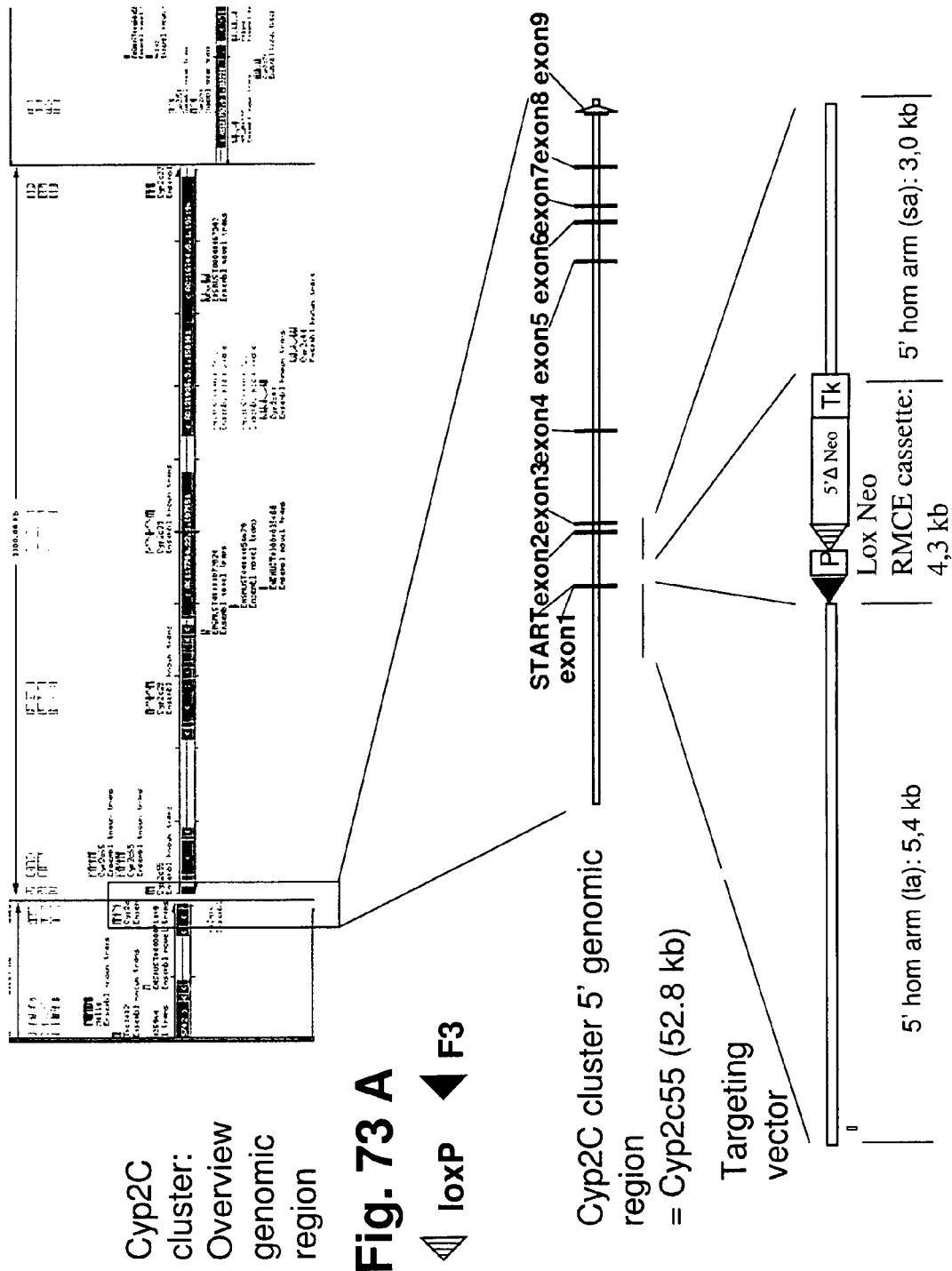

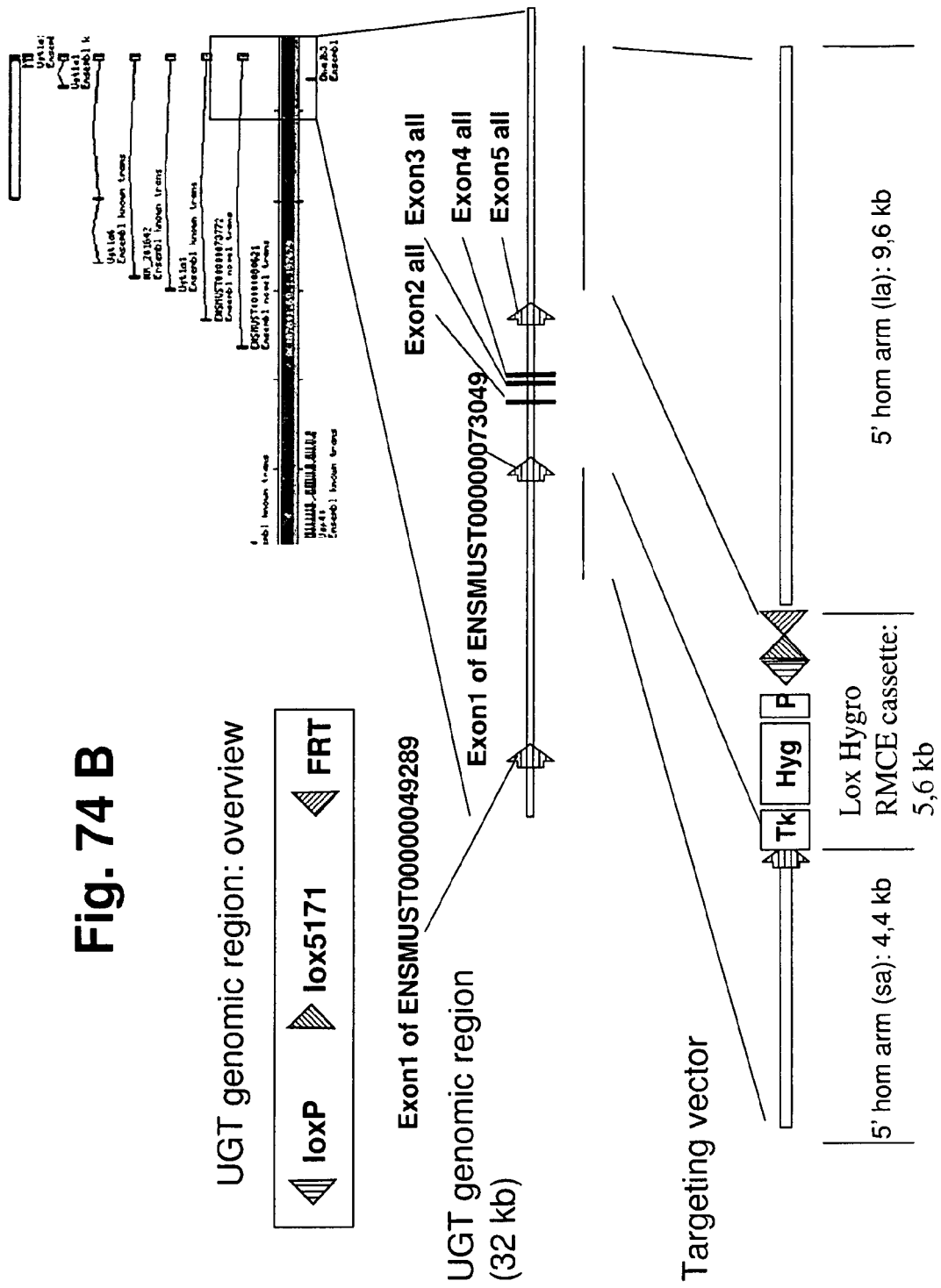

Fig. 79 ET-targeting vector

Fig. 83

| | Mouse Lines | | | | | | | | | |
|---|---|---|---|---|---|---|---|---|---|---|
| | 3a11 | | | | | 2b10 | | | | |
| | WT | huPXR | PXR KO | huCAR | CAR KO | WT | huPXR | PXR KO | huCAR | CAR KO |
| Rifampicin | + | +++ | NC | | | NC | NC | NC | | |
| PCN | ++ | NC* | | | | ++ | NC* | | | |
| Dex | ++ | NC/+ | NC | ++ | | +++ | +++ | +++ | +++ | |
| Clotrimazole | + | + | | | | ++ | ++ | | | |
| TCPOBOP | ++ | ++ | | NC | | +++ | +++ | | NC | |
| PB | ++ | ++ | | ++ | | +++ | +++ | | +++ | |

Table: Effect of inducing agents on PXR and CAR target genes in mouse liver.
+, slight increase in expression compared to vehicle-treated mice of the same strain,
++, medium increase in expression compared to vehicle-treated mice of the same strain
+++, strong increase in expression compared to vehicle-treated mice of the same strain
NC, no change in expression compared to vehicle-treated mice of the same strain
*, only tested 1 and 3 mg/kg PCN PXR mediated
CAR mediated
Both/other NRs

TRANSGENIC ANIMALS FOR ASSESSING DRUG METABOLISM AND TOXICITY

CROSS REFERENCE TO RELATED APPLICATIONS

This application is a continuation-in-part of International Application number PCT/GB2005/004772 filed Dec. 13, 2005, which claims priority to GB 0427172 filed Dec. 13, 2004, and claims priority to GB 0516187.2 filed Aug. 5, 2005, and U.S. Provisional Application No. 60/707,077 filed Aug. 10, 2005, the contents of which are all incorporated herein by reference in their entirety.

FIELD OF THE INVENTION

The present invention relates to transgenic non-human animals, tissues or cells derived therefrom and methods of producing them. The transgenic non-human animals or tissues or cells derived therefrom provide a system capable of expressing human proteins responsible for drug metabolism in place of the homologous endogenous non-human animal proteins and for the controlled expression of human genes introduced into the animal so that the expression of the human genes is regulated in a manner more closely analogous to that seen in vivo in humans. The transgenic non-human animals or tissues or cells derived therefrom are for use, especially but not exclusively, in assessing xenobiotic or drug metabolism, toxicity or other properties or functions of the introduced human proteins such as metabolism and/or biosynthesis of endogenous compounds.

BACKGROUND TO THE INVENTION

A significant proportion of therapeutic drug candidates fail to become marketable drugs because of adverse metabolism or toxicity discovered during clinical trials. These failures represent a very significant waste of development expenditure and consequently there is a need for new technologies that can more reliably, quickly and economically predict at the pre-clinical development stage the metabolic and toxicological characteristics of drug candidates in man. At present, most pre-clinical metabolic and toxicity testing of drug candidates relies on laboratory animals, human and/or mammalian cell lines and/or tissues in culture. However, none of these methods is completely reliable in predicting metabolism or toxicity in a human subject. Metabolic and toxicological data from animals can differ significantly from that obtained from a human subject due to species differences in the biochemical mechanisms involved. In addition, interpretation of data derived from in vitro human cell cultures or isolated human tissue studies can be problematic since such systems are not available for all organs and tissues or they fail to retain the same metabolic characteristics as they possess in vivo.

It is known in the prior art that the metabolism, distribution and toxicity of most drugs depends on their interactions with four distinct main classes of proteins:

a) Phase-1 drug-metabolising enzymes, such as the cytochromes P450 which generally add or expose polar groups on the xenobiotic molecule;

b) Phase-2 drug-metabolising enzymes, such as transferases, in particular the glucuronyl transferases, glutathione transferases, sulphonyl transferases and acetyl transferases which conjugate the polarised xenobiotic molecule to a hydrophilic group thereby facilitating its subsequent excretion;

c) Drug transporter proteins, such as the ATP-binding cassette proteins which include the multi-drug resistance proteins (MDRs) and multi-drug resistance-associated proteins (MRPs) and the organic anion transporting polypeptides (OATPs) which facilitate the transport of drugs and other xenobiotic molecules across plasma membranes;

d) Transcription factors, such as the pregnane X receptor (PXR) and the constitutive androstane receptor (CAR) which regulate the transcription of genes encoding proteins of the preceding classes, in particular the cytochromes P450.

Variation between species is known in each of these protein classes both with respect to the multiplicity of proteins within each class, the function of the proteins themselves and with respect to genetic regulation of their expression.

It is known from WO2004/007708 how to produce non-human transgenic animals expressing functioning human P450s in which the functions of endogenous cytochromes P450 have been annulled by deletion of individual P450 genes or by deletion of the cytochrome P450 reductase gene encoding the enzyme on which the function of all cytochromes P450 depends. However, the described animal model has limitations in that not only are the introduced P450s restricted to particular organs or tissues of the non-human animal but also there is no provision to regulate expression of the human P450s in a manner that is analogous to that seen in the human. One of the prior art models is also limited in that additional modifications are needed to provide cytochrome P450 reductase activity to the introduced human P450s without reactivating endogenous non-human P450s. A yet further disadvantage resides in the lack of provision to reproduce human phase-2 metabolism, thus the system is unable to provide an entire metabolic profile.

It is also known from the prior art to humanise the induction characteristics of cytochromes P450 in the mouse by expressing human PXR (Xie et al, Nature Vol 406, 435-9, 2000) or human CAR (Zhang et al, Science Vol 298, 422-4, 2002) in a mouse wherein the mouse PXR gene and/or mouse CAR gene respectively have been deleted. While such animals demonstrate induction patterns of endogenous P450s that reproduce those seen in the human they have undesirable characteristics because the cytochromes P450 whose expression is regulated analogously to the human are still non-human cytochromes P450. A further disadvantage is that because the PXR or CAR genes themselves are not regulated as they are in the human by virtue of the transgene being driven by a heterologous tissue-specific promoter (albumin promoter), over-expression of the heterologous gene can occur which can have the result that a normal metabolic pathway is bypassed. Moreover, the PXR and CAR transgenes are derived from a cDNA rather than a genomic clone, thus the transgenic non-human animals consequently lack the sequences necessary correctly to reproduce all the transcriptional and post-transcriptional regulation of PXR or CAR expression hence their expression is restricted to the liver and may not be of a physiological level. In addition these models do not encode for splice variants of the human gene. Another drawback of the PXR/CAR models is that they are unsuitable to combine with modifications of other genes within one animal since the humanisation of each gene is achieved by two independent genomic alterations: (i) knock-out of the endogenous gene (ii) transgenesis with the human orthologue under control of the albumin promoter at a different genomic location.

Ma et al. (Drug Metab Dispos. 2007 February; 35(2):194-200) introduced the complete human PXR gene, including 5' and 3' flanking sequences, into PXR knock-out mice by bacterial artificial chromosome (BAC) transgenesis. They observed selective expression of human PXR in the liver and intestine. Treatment of PXR-humanised mice with PXR ligands mimicked the human response, as both hepatic and intestinal Cyp3a11 mRNA and protein were strongly induced by rifampicin, a human-specific PXR ligand, but not by pregnenolone 16α-carbonitrile (PCN), a rodent-specific PXR ligand. In wild-type mice, Cyp3a11 mRNA was strongly induced by PCN, but not by rifampicin.

There is therefore a need for improvements in animal models of human metabolism that can control expression of the human genes introduced into the animal so that their expression is regulated in a manner more closely analogous to that seen in humans. There is also a need for more aspects of the human metabolic pathway to be reproduced. Effective animal models of human metabolism require not only expression of the relevant human proteins but also annulment of the functions of the homologous endogenous proteins.

One reason why the present invention embodies a surprising advance over the prior art is that many prior art researchers appear to be of the view that the problem posed by the need for models of drug metabolism is already solved. For example, Xie and Evans (2002, DDT7, p509) state that humanising PXR is "one of the rare examples where replacing a single transcriptional regulator allows conversion of species-specific gene regulation". Furthermore, it is evident that workers have turned their attention to techniques that differ markedly to those that utilise transgenic animal systems. For example, attempts are being made to humanise the mouse liver as an organ by using human hepatocytes, the aim being to obtain a mouse model for drug metabolism in humans. This work is labour-intensive though, and in the inventors' opinion is of dubious relevance to the situation in reality.

The present invention is the first methodology that takes into account all of the problems that prior art systems suffer from and that seeks to resolve these problems in a practical manner. The inventors have recognised that in order to provide transgenic non-human animal models with humanised drug metabolism pathways that overcome the undesirable features of the animal models described in the prior art a number of criteria should ideally be satisfied:

a) Regulation of the expression of introduced human proteins such that patterns of expression in the human are reproduced;
b) Expression of multiple human proteins so that multiple aspects of human metabolism are reproduced;
c) Annulled expression or function of multiple endogenous genes so that interference from non-human metabolic pathways on the functions of introduced human proteins is significantly reduced.

In the present invention, we provide methods of producing non-human animal cell and non-human transgenic animals that incorporate at least some if not all of these desired qualities. Such non-human animal cell and non-human transgenic animals possess desirable characteristics not available in the prior art in that they can model entire human pathways of xenobiotic metabolism rather than just individual elements of pathways and that such models are provided for all tissues and organs. This is achieved through the application of technical approaches hitherto not available in the prior art with respect to obtaining regulation of transgene expression analogous to that seen in human cells through the use of extensive regulatory DNA sequences and with respect to annulment of endogenous metabolic pathways through deletion or gene exchange. A number of relevant human proteins are expressed in a single animal.

STATEMENT OF THE INVENTION

According to a first aspect of the invention there is provided a non-human animal, tissue or cells derived therefrom incorporating at least one human DNA sequence encoding at least one transcription factor under control of a transcription factor promoter and whose endogenous equivalent genes have optionally been annulled, the non-human animal, tissue or cells derived therefrom further incorporating at least one or more of the following further human DNA sequences selected from the group comprising:

(i) a DNA sequence encoding a phase-1 drug-metabolising enzyme;
(ii) a DNA sequence encoding a phase-2 drug-metabolising enzyme; and/or
(iii) a DNA sequence encoding a drug transporter protein;

and whose endogenous equivalent gene or genes have optionally been annulled.

Throughout the specification and the claims which follow, unless the context requires otherwise, the word "comprise", or variations such as "comprises" or "comprising" will be understood to imply the inclusion of a stated integer or group of integers but not the exclusion of any other integer or group of integers.

Reference herein to "endogenous equivalent gene" of the non-human animal is intended to include a gene or genes whose expression product retains the same, similar or identical function as the human counterpart gene. For example, the human transcription factor gene known as PXR (NR1I2 nuclear receptor subfamily 1, group I, member 2), Entrez GeneID: 8856, has a murine counterpart of the same name whose Entrez GeneID is 18171. The proteins encoded by these genes have an equivalent function in the organisms from which they are derived.

Generally, the introduced transcription factor gene, the phase-1 drug-metabolising enzyme gene, the phase-2 drug-metabolising enzyme gene and/or the drug transporter protein gene will share a degree of homology with the endogenous gene with which it is equivalent. Preferably, the degree of homology will be greater than 30%, greater than 40%, greater than 50%, greater than 60%, greater than 70%, greater than 80%, greater than 90%, or even greater than 95%.

In the case of drug-metabolising enzyme genes, equivalence between genes can be assessed by a combination of substrate specificity, mode of regulation (for example, by transcription factors or exogenous drugs), sequence homology and tissue distribution. Certain genes have exact equivalents; examples of such genes are CYP2E1, CYP1A1, CYP1A2. CYP2B6 and CYP2D are examples where there is only one gene in the human, but numerous equivalent genes in the mouse. There are four CYP2C genes in the human, and numerous equivalent genes in the mouse. In such circumstances, preferably at least one, more preferably two, three, four, five or more or even all of the equivalent murine genes are annulled. CYP3A4 is an example where there is no obvious orthologue in the mouse, but Cyp3a11 could be considered at least one equivalent mouse gene because of its hepatic expression, mode of regulation and sequence homology.

Reference herein to "annulled" is intended to include silencing or deletion or rendering inactive so that the non-human animal's endogenous equivalent gene is unable to express the gene product(s), at least not to any level that is significant to the drug metabolism process. For instance, the expression level of an annulled gene may be less than 20%, preferably less than 10%, more preferably less than 5%, more preferably less than 2%, even more preferably 1% or less of the wild type expression level. The expression of an annulled gene may preferably be decreased to the point at which it cannot be detected. Although annulling the non-human animal's endogenous equivalent gene(s) is preferred, in some embodiments the non-human animal's endogenous equivalent gene(s) are not annulled. For example, human DNA sequences encoding proteins involved in drug metabolism may be inserted into the mouse Rosa26 locus, which does not itself result in silencing, deletion or rendering inactive of a mouse gene involved in drug metabolism.

Partial Genomic Sequences

In the prior art techniques disclosed to date, researchers have generated transgenic models that incorporate human genes into non-human systems, notably the mouse. However, in devising these systems, little attention has been paid to retaining the context of the human gene as it exists in its natural state.

Generally, cDNA sequences have been used in the prior art rather than respecting the intron/exon structure of the human gene, e.g. by incorporating at least one intron of the human gene. This means that any splice variants that might naturally be generated, cannot form. Splice variants are important for a number of reasons. First, they may have a function. Second, they may have a dominant negative effect, for example, by binding to their usual protein partners and altering biological effects of the protein. Third, they may sequester ligand. A system that accurately reflects the in vivo situation therefore preferably mirrors the balance of splice variants that exist in any biological system.

Using cDNA also means that mRNA levels are artificially generated and may not reflect the reality of the natural physiological situation.

In contrast, the present invention attempts to mirror the in vivo situation by providing the human gene in its entirety where this is possible. This means that the intron-exon junctions are retained as in the natural system so that splicing events can happen exactly as in the natural situation. Where, perhaps because of the length of a gene, it is not simple to transpose the entire human gene into a transgenic system, the invention seeks to use a combination of cDNA and genomic DNA in its constructs so that important intron-exon boundaries, where the majority of splicing events occur, are retained.

Thus, the human DNA sequence encoding a transcription factor, drug-metabolizing enzyme or drug transporter protein can be a partial human genomic gene sequence or a complete human genomic gene sequence.

According to the invention, therefore, where it is known that the majority of splice variants occur as a result of splicing variation within a particular intron, this intron is preferably incorporated as genomic DNA in the construct, while less influential intronic sequences are not retained. This has the result that levels of functional mRNA and functional protein mirror the levels that are found in vivo in response to exposure to a particular drug or drug cocktail. This is what is ideally required for a physiologically-relevant model.

Accordingly, whilst cDNA sequences may be used, in preference to these sequences, the invention may use a combination of cDNA and genomic sequences from the gene that is to be humanised. When a combination of cDNA and genomic sequences is used, the human DNA sequence contains some but not all of the introns and exons of the human gene. A number of non-human animal models involving constructs comprising a combination of human cDNA and genomic sequences have been generated by the inventors.

For example, in the case of a transgenic animal expressing the human PXR gene, due to the large size of more than 35 kb of the human PXR gene, the intron-exon structure between exons 4 and 6 is preferably maintained, since most splice variants are observed in this genomic region, since it is located within the ligand-binding domain (e.g. see FIG. 2). This advantageously retains the sequence where most splice variants are observed and is conveniently located within the ligand-binding domain. In other preferred embodiments, the intron-exon structure between exons 4 and 8 of the human PXR gene is maintained (e.g. see FIG. 61). In other preferred embodiments, the intron-exon structure between exons 2 and 9 of the human PXR gene is maintained (e.g. see FIG. 63).

Another example is provided by the case of the humanization cassette preferably used for CYP3A4: this may contain the 13 kb human CYP3A4 promoter, exon 1 and intron 1 as in the normal genomic constitution and a human cDNA consisting of exons 2-13 (e.g. see FIG. 9).

Another example is provided by the case of the humanization cassette preferably used for CYP2C9: this may contain the 12 kb human CYP2C9 promoter, a human cDNA of exons 1-4, intron 4 and a cDNA of exons 5-9 (e.g. see FIG. 10).

Another example is provided by the case of the humanization cassette preferably used for PPARα: this may maintain the intron-exon structure between exons 3 and 8 of the human PPARα gene, e.g. by including at least part of intron 5 and/or intron 6 (see FIG. 67).

Complete Genomic Sequences

Complete genomic DNA sequences may be used. For instance, in the case of a transgenic animal expressing the human CAR gene, the relatively small size of the human CAR, which comprises roughly 7 kb from exon 2-9, makes it simple to retain the complete genomic structure in the targeting vector. The construct should preferably retain the intron-exon structure between exons 2 and 9. This advantageously retains the complete genomic structure within the targeting vector and permits coverage of all splice variants of human CAR. Preferably, the genomic human CAR sequence is fused to the translational start site of the mouse CAR gene. The human CAR sequence then contains all genomic sequences of exons 1-9. The 5' and 3'UTRs may be human or may be retained from the mouse genome. All other parts of the coding sequences of the mouse CAR gene can be deleted.

Use of complete genomic gene sequences may conveniently be achieved by use of a cluster of human DNA sequences, as described in more detail elsewhere herein (e.g. see FIGS. 71, 73 and 74).

When a complete genomic DNA sequence is used, the human DNA sequence will contain all of the introns and exons of the human gene, and may optionally further comprise some or all of the regulatory sequences normally associated with the human gene (as described in more detail elsewhere herein).

Transcription Factors

Preferably, the human DNA encoding a transcription factor is selected from the group comprising the pregnane X receptor (PXR, also known as the steroid and xenobiotic receptor SXR) and the constitutive androstane receptor (CAR) or multiples thereof or a combination thereof. Animals and cells according to this aspect of the invention are advantageous for the reasons described in detail above. For example, recent evidence further supports the contention that the ligand binding domains of the murine and human CAR proteins are divergent relative to other nuclear hormone receptors, resulting in species-specific differences in xenobiotic responses (Huang et al., 2004, Molecular endocrinology 18(10):2402-

2408). Results reported in this paper demonstrate that a single compound can induce opposite xenobiotic responses via orthologous receptors in rodents and humans.

Transgenic mice for human CAR have been created and are described in the examples included herein. Detailed investigations of the induction of drug metabolism pathways in CAR humanised and knock-out mice have been performed. Various different experimental approaches have confirmed that non-human transgenic animals that are humanised with respect to CAR, or which do not express any CAR (knock-out), can readily be obtained using the methods and strategies described herein.

Transgenic mice for human PXR have been created and are described in the examples included herein. Human PXR is found to be expressed in both the liver and GI tract of mice in the predicted manner at levels equivalent to those of the endogenous mouse gene. In this way, typical problems faced by conventional techniques of this type, such as over- or under-expression are avoided. Furthermore, currently available humanised PXR models use the albumin promoter to drive human PXR which has been crossed into a PXR-null background. Therefore, PXR is expressed at very high levels in this model and there is no PXR in any tissue other than the liver. This severely compromises the use of this model to understand the role of hPXR in controlling gene expression in the GI tract or at the blood brain barrier or, indeed, in any other tissue.

In this model, the PXR protein has also been shown to be functional as the mice are responsive to compounds such as rifampicin and TCPOBOP that are known to induce gene expression via this pathway. Strain differences between wild type and the humanised mice have been demonstrated. For example, the humanised mice are shown to be more responsive to compounds such as rifampicin, that are known to be more active to hPXR. Humanised PXR animals thus demonstrated an altered sensitivity to rifampicin relative to the wild type.

Furthermore, there was clearly greater background P450 enzyme activity as measured by 16-beta-hydroxylation of testosterone and 7-benzyloxyquinoline demethylation between wild type and humanised PXR mice.

In experiments using the inducing agent TCPOBOP, the hepatic microsomal metabolism of testosterone was measured. Again clear differences between the wild type and the humanised PXR animals were observed. In particular, the 7-alpha-hydroxylation of testosterone was constitutively higher in the huPXR animals relative to the wild types.

Consistent with the strain differences in wild type and human PXR, there were marked differences in the sensitivity of the mouse lines to induction by TCPOBOP. In the case of testosterone 16-alpha-hydroxylation, this activity was significantly induced in wild type animals but not in humanised PXR animals. Of particular interest was the observation that the induction of testosterone 16-beta-hydroxylation was much more marked in wild type than in huPXR animals. Indeed, at a dose of 1 mg/kg, induction of testosterone 16-beta-hydroxylation was approximately 6-fold in wild type animals but only 1.7-fold in the huPXR animals. This again demonstrates a reduced sensitivity of the humanised mice relative to controls.

Detailed investigations of the induction of drug metabolism pathways in PXR humanised and knock-out mice have been performed. Various different experimental approaches have confirmed that non-human transgenic animals that are humanised with respect to PXR, or which do not express any PXR (knock-out), can readily be obtained using the methods and strategies described herein.

Transgenic animals (such as mice) and cells according to the invention preferably demonstrate the functional properties described above and in the examples herein. For example, such cells and animals preferably do not display induction of Cyp2b10 activity in response to rifampicin. However, such cells and animals do display an induction effect for Cyp3a11, not only with rifampicin but also for TCPOBOP.

It will be appreciated that other human DNA(s) encoding a transcription factor may also be used in the present invention providing that they are capable of regulating a phase-1 drug-metabolising enzyme, a phase-2 drug-metabolising enzyme and/or a drug transporter protein. Examples include PPARs (α, δ and γ), NRF2, the Ah receptor, HNF1 and HNF4. Targeting strategies suitable for knock-in (humanisation) and knock-out of PPARα and the Ah receptor are described in more detail elsewhere herein (see FIGS. 67 and 68).

Preferably, the human DNA encoding a transcription factor comprises both the pregnane X receptor (PXR) and the constitutive androstane receptor (CAR). In this embodiment of the invention the transgenic animal or tissue or cells derived therefrom may be considered as "double-humanised" for these transcription factor genes. Such double-humanised models are advantageous over models that only incorporate a single gene (either PXR or CAR) because many drug metabolising enzymes or drug transporters possess elements that are responsive to the binding of both CAR and PXR. Furthermore, the numbers of PXR-responsive elements often differ from the numbers of CAR-responsive elements and so regulation by both transcription factors is generally important. Consequently, models that take account of the effects of both factors are preferable and more closely mirror the physiological situation in vivo.

Mice transgenic for both human PXR and human CAR have been created and are described in the examples included herein. Preliminary studies have been performed on the activity of these transcription factors in combination, determined by measuring barbiturate-induced sleeping time. Sleeping time has been known for many years to be directly proportional to the hepatic cytochrome P450 activity and this activity can be at least in part ascribed to the P450 levels in the liver determined by CAR and PXR function. Whereas wild type mice given a narcotic dose of pentobarbitone slept for 21 minutes, the double humanised mice for CAR and PXR slept for 34 minutes. These mice therefore demonstrate a significant difference to their wild type controls indicating that the double humanised mouse has a marked difference in its response to drugs relative to the wild type animals.

Detailed investigations of the induction of drug metabolism pathways in PXR and CAR double-humanised and double-knock-out mice have been performed. Various different experimental approaches have confirmed that non-human transgenic animals that are humanised with respect to both PXR and CAR, or which do not express any PXR or CAR (double-knock-out), can readily be obtained using the methods and strategies described herein.

Transgenic animals (such as mice) and cells according to this aspect of the invention preferably demonstrate the functional properties described above. For example, cells and animals transgenic for human PXR preferably do not display induction of Cyp2b10 activity in response to rifampicin, but do display an induction effect for Cyp3a11, not only with rifampicin but also for TCPOBOP.

The inventors have also noted that the capacity of promoters to induce enzyme expression is different in different tissues. Accordingly, it is of utmost importance for human transcription factors to be used rather than endogenous transcription factors from another animal. Furthermore, the regulatory sequences of the transcription factors and the genes that they regulate should mirror the natural physiological situation as closely as possible. Thus, regulatory sequences are preferably of human origin or non-human animal origin. In more preferred embodiments, the regulatory sequences are of human origin or originate from the target non-human animal (e.g. mouse). This enables the wild-type expression pattern to be retained, as explained elsewhere herein. The use of as many human transcription factors, human drug metabolising enzymes and human drug transporters as possible is important to ensure that this happens.

The ratio of protein levels that are generated by a particular drug are also of significant importance. For example, the action of mouse PXR stimulates expression of different proteins than the action of human PXR and at different levels. The levels of a particular drug and its metabolites depends crucially on which drug metabolising enzymes and transporters are expressed and so, again, it is of utmost importance for human transcription factors to be used rather than endogenous transcription factors from another animal.

The use of human transcription factors is also important from a toxicological standpoint. For example, PXR is naturally regulated by bile acids and other physiological compounds and toxic conditions such as biliary necrosis and biliary cholestasis can result from exposure to a particular drug. It may therefore be that as a result of differences between drug metabolism between human and a test animal, a toxic effect will be noted in that animal that would not be evident in the human.

The regulatory sequences governing expression of the transcription factor(s) may preferably be either of human origin, or may originate from the target animal species e.g. the mouse (as described in more detail elsewhere herein).

The genes that are inserted into the transgenic model are preferably inserted at the point in the genome where the endogenous equivalent gene or gene cluster naturally occurs. This has the advantage that the context of the gene locus is retained, which means that the fidelity of transcription from this site is as close as possible to the level of transcription that occurs in the wild type system.

The inventors have validated aspects of drug metabolism pathways in transgenic animals (e.g. huPXR, huCAR and huPXR/huCAR mice) using appropriate assays as described elsewhere herein. The functional properties displayed by the inventors' transgenic mice in these assays reveal that the transgenic animals, tissues and cells of the invention have significant utility in analysis of drug metabolism and toxicity.

In some experiments, the inventors validated aspects of drug metabolism pathways in transgenic animals using inducers of the components of those pathways that are known to act more potently in humans or in mice, as summarised below:

| Inducer | More potent in: |
| --- | --- |
| Rifampicin (Rif) | human |
| CITCO | human |
| Phenobarbital (PB) | mouse/human |
| Dexamethasone (Dex) | mouse |
| 5-Pregnen-3β-ol-20-one-16α-carbonitrile (PCN) | mouse |
| Clotrimazole | mouse |
| TCPOBOP | mouse |

Species-specific inducers of drug metabolism, such as those listed above, may act primarily via CAR or PXR, or via both PXR and CAR (e.g. see FIG. 55). The species-specific induction of CAR and PXR can be discriminated using assays that allow a distinction to be made between induction via PXR and incuction via CAR, such as by measuring Cyp3a11 or Cyp2b10 levels or activity (e.g. see FIG. 48). An overview of the effects of the inducers listed above on induction of Cyp3a11 and Cyp2b10 in mice and humans is provided in FIGS. 55 and 83.

Accordingly, the invention provides a transgenic mouse, tissue or cells derived therefrom incorporating a human DNA sequence encoding PXR under the control of an endogenous promoter, and optionally having its equivalent endogenous murine PXR genes annulled, which mouse, tissue or cells:

(i) is more sensitive to rifampicin-mediated induction of the expression and/or activity of a cytochrome P450 than the corresponding wild-type mouse, tissue or cells derived therefrom; and/or (ii) is less sensitive to dexamethasone-mediated or pregnenolone-16a carbonitrile-mediated or clotrimazole-mediated induction of the expression and/or activity of a cytochrome P450 than the corresponding wild-type mouse, tissue or cells derived therefrom.

Preferably, the cytochrome P450 is a Cyp3a enzyme, such as Cyp3a11.

The invention also provides a transgenic mouse, tissue or cells derived therefrom incorporating a human DNA sequence encoding CAR under the control of an endogenous promoter, and optionally having its equivalent endogenous murine CAR genes annulled, which mouse, tissue or cells:

(i) is more sensitive to CITCO-mediated induction of the expression and/or activity of a cytochrome P450 than the corresponding wild-type mouse, tissue or cells derived therefrom; and/or (ii) is less sensitive to TCPOBOP-mediated induction of the expression and/or activity of a cytochrome P450 than the corresponding wild-type mouse, tissue or cells derived therefrom.

Preferably, the cytochrome P450 is a Cyp2b enzyme, such as Cyp2b10.

Cytochrome P450 expression and activity levels can be determined by appropriate assays, as described elsewhere herein (see FIG. 48). For example, cytochrome P450 (e.g. Cyp3a11 or Cyp2b10) expression levels can be determined by western blotting. Cytochrome P450 activity can be determined by a 7-benzyloxyquinoline (BQ) activity assay (for Cyp3a) or a pentoxyresorufin-O-deethylation (PROD) activity assay (for Cyp2b).

The invention also provides a transgenic mouse, tissue or cells derived therefrom that possesses a combination of the functional properties mentioned herein. Thus, the invention provides a transgenic mouse, tissue or cells derived therefrom incorporating human DNA sequences encoding PXR and CAR under the control of endogenous promoters, and optionally having its equivalent endogenous PXR and CAR genes annulled, which mouse, tissue or cell:

(i) is more sensitive to rifampicin-mediated induction of the expression and/or activity of a cytochrome P450 than the corresponding wild-type mouse, tissue or cells derived therefrom; or (ii) is less sensitive to dexamethasone-mediated or pregnenolone-16α carbonitrile-mediated or clotrimazole-mediated induction of the expression and/or activity of a cytochrome P450 than the corresponding wild-type mouse, tissue or cells derived therefrom; and (iii) is more sensitive to CITCO-mediated induction of the expression and/or activity of a cytochrome P450 than the corresponding wild-type mouse, tissue or cells derived therefrom; or (iv) is less sensitive to TCPOBOP-mediated induction of the expression and/or activity of a cytochrome P450 than the corresponding wild-type mouse, tissue or cells derived therefrom.

The invention also provides a transgenic mouse, tissue or cells derived therefrom incorporating a human DNA sequence encoding PXR under the control of an endogenous promoter, and optionally having its equivalent endogenous PXR gene annulled, which displays increased dexamethasone-mediated hepatotoxicity relative to the corresponding wild-type mouse. Dexamethasone-mediated hepatotoxicity can be determined by measuring ALT levels using an appropriate assay and an appropriate dose of dexamethasone (e.g. at least 20 mg/kg, at least 30 mg/kg, at least 40 mg/kg, at least 50 mg/kg, or at least 60 mg/kg. Suitable assays are described elsewhere herein.

Preferred transgenic (knock-in and knock-out) mice containing altered transcription factor genes are described in more detail elsewhere herein.

Ma et al. (Drug Metab Dispos. 2007 February; 35(2):194-200) introduced the complete human PXR gene, including 5' and 3' flanking sequences, into PXR knock-out mice by bacterial artificial chromosome (BAC) transgenesis. They observed selective expression of human PXR in the liver and intestine. Treatment of PXR-humanised mice with PXR ligands mimicked the human response, as both hepatic and intestinal Cyp3a11 mRNA and protein were strongly induced by rifampicin, a human-specific PXR ligand, but not by pregnenolone 16α-carbonitrile (PCN), a rodent-specific PXR ligand. In wild-type mice, Cyp3a11 mRNA was strongly induced by PCN, but not by rifampicin. However, Ma et al. relates exclusively to PXR humanisation, and furthermore does not disclose or suggest many aspects of the present invention, such as the use of mixed cDNA/genomic constructs, comparison of different transgenic non-human animals, use of reporter constructs (see below) or expression of human sequences under the control of non-human animal regulatory sequences. Another drawback of the model described by Ma et al. is that it is unsuitable to combine with modifications of other genes within one animal, because PXR humanisation is achieved by two independent genomic alterations: (i) knock-out of the endogenous PXR gene, and (ii) transgenesis with the human PXR gene at a different genomic location.

Phase-1 Drug-Metabolising Enzymes

Preferably, the human DNA encoding a phase-1 drug-metabolising enzyme is selected from the group comprising the cytochromes P450, including but not limited to CYP1A1, CYP1A2, CYP3A4, CYP2B6, CYP2C9, CYP2C19, CYP2D6, and CYP2B6. It will be appreciated that other DNAs encoding a phase-1 drug-metabolising enzyme may also be included in the present invention, providing that they are capable of modifying a xenobiotic by adding or exposing a polar group on the xenobiotic molecule.

The choice of human P450 isoforms for introduction into P450-humanised non-human animals is predominantly driven by the known relative importance of various P450 isoforms in metabolism in the relevant tissue. Thus, for example, to date the single most significant P450 isoform recognised in the human liver is CYP3A4, and so CYP3A4 is therefore probably the first human P450 isoform of choice for P450 humanisation of liver. The choice of human P450s for the multi-P450-humanised mouse of the present invention is dictated by the need of the user. In this respect it is expected that any one or more of the following human isoforms will be preferred: 3A4, 2D6, 2B6, 2C9, 2C19, 1A1, 1A2, 2C8. However, it will be appreciated that the isoform(s) incorporated into the animal cell is/are dependent on the user's requirement. In this way, the humanised transgenic animal may be "designed" to investigate the role of specific isoforms in the metabolic process.

According to the teaching of the invention, single genes, gene clusters or combinations of single genes or gene clusters may be replaced. Whole gene clusters should preferably be replaced where possible, rather than simply replacing individual genes. This generates a situation in which the ratios of the expression levels of genes in any gene cluster are the same as the ratios in which these genes are expressed in vivo. This is a phenomenon that has not received attention in the prior art. The CYP3A, CYP2C and CYP2D clusters are preferred clusters of phase-1 drug-metabolising enzymes for replacement according to the present invention. Either one, both or even all of these gene clusters may be replaced according to the present invention.

According to the invention, therefore, partial, or preferably complete cascades of genes that are implicated in a particular pathway may preferably be replaced. This ensures that the partial redundancy of gene function is retained and so, again, the real physiological situation is mirrored. An example can be provided by the CYP3A P450 cluster. In humans, there are four functional genes in this cluster, that have overlapping substrate specificity. The CYP3A5 protein will, for example, metabolise CYP3A4 substrates. Therefore, if one is attempting to generate a model of drug metabolism, incorporating the CYP3A5 gene in any state other than as part of its entire gene cluster is distancing the generated model from reality.

In contrast, following prior art teachings, were a researcher to decide that it might be a good idea to generate an animal transgenic for the CYP3A5 gene, he would only know to incorporate this gene, and would not think to incorporate the entire gene cluster of which it forms a part. Furthermore, using prior art techniques, it would insert at an arbitrary site and not in its natural contextual position in the genome. Worse still, its expression would be under the direction of a strong promoter specific for the liver. This strategy would very likely generate a large amount of CYP3A5 protein in the liver, and because of the large amounts of protein provided, this protein would metabolise substrates at a greater rate than those on which it would act in vivo. For all these reasons, the method of the invention is advantageous over systems that have been described previously.

Preferably, the clusters of phase 1 drug metabolising enzymes that are used for humanisation are the CYP3A cluster and the CYP2C cluster.

In view of the redundancy in protein function between the human and commonly used target transgenic animals such as the mouse, humanisation for phase 1 drug metabolising enzymes is preferably performed against a deleted background in which only some (for example 1, 2, 3, 4 or 5), and preferably none of the target animal phase 1 drug metabolising enzymes are expressed at significant levels.

Preferred transgenic (knock-in and knock-out) mice containing altered phase-1 drug-metabolising enzyme genes are described in more detail elsewhere herein.

Phase-2 Drug-Metabolising Enzymes

Preferably, the human DNA encoding a phase-2 drug-metabolising enzyme is selected from the group comprising the glucuronyl transferases, for instance, the UGT1A gene or gene cluster, the glutathione transferases, for instance GST (glutathione S-transferases), the sulphonyl transferases and the acetyl transferases. It will be appreciated that other DNAs encoding a phase-2 drug-metabolising enzyme may also be included in the present invention providing that they are capable of conjugating a product of phase-1 metabolism.

Preferably, a cluster of phase 2 drug metabolising enzymes that is used for humanisation is the UGT1A gene cluster.

Preferred transgenic (knock-in and knock-out) mice containing altered phase-2 drug-metabolising enzyme genes are described in more detail elsewhere herein.

Drug Transporters

Preferably, the human DNA encoding a drug transporter protein is selected from the group comprising the ATP-binding cassette proteins which include but are not limited to the multi-drug resistance proteins, for instance MDR-1 and multi-drug resistance-associated proteins (MRPs), for example, MRP1 and/or MRP2, or from the organic anion transporting polypeptides (OATPs). It will be appreciated that other DNAs encoding a drug transporter protein may also be included in the present invention providing that they are capable of facilitating the transport of drugs and other xenobiotic molecules across plasma membranes.

Preferably, the multidrug resistance protein is MDR1.

Preferably, the multi-drug resistance-associated protein is MRP2.

Preferred transgenic (knock-in and knock-out) mice containing altered drug transporter protein genes are described in more detail elsewhere herein.

Regulatory Sequences

The present invention resides in part in the humanisation of transgenic non-human animal cell, tissue or animals especially for transcriptional factor(s), wherein the transcriptional factor transgenes are driven by transcriptional factor promoters, that is to say they are "knocked-in" rather than utilising heterologous albumin/tissue specific promoters. Thus the animals of the present invention are able to express the human proteins at not only the appropriate physiological levels but in all tissues, rather than just the liver as is known from the prior art.

It will be appreciated that any human DNA sequences include coding sequences for proteins selected from the group of classes of: human phase-1 metabolism enzymes; human phase-2 metabolism enzymes; human drug transporters; human transcription factors, may ideally be operatively linked to human regulatory DNA sequences. However, the use of human regulatory sequences is not essential, and other endogenous regulatory sequences can be used, e.g. mouse sequences.

Preferably, these human DNA sequences of the above-described transcription factors and other proteins are whole genes or are DNA constructs comprising regulatory sequences that may either be derived from humans or animals. In cases where the regulatory sequences are not of human origin, the regulatory sequences may be derived from the target animal, for example, the mouse. By regulatory sequences is meant to include any promoter or enhancer sequences, 5' or 3' UTRs, poly-A termination sequences or other DNA sequences, that are necessary for transcription of the gene of interest or which modulate expression of the gene of interest. Transcripts used for insertion of human sequences are preferably terminated by a poly A motif.

Heterologous promoters have generally been used in the prior art, and those used (such as the albumin promoter) are generally strong promoters, are ligand independent in their action and are constitutively switched on. In normal development, albumin is only expressed neo-natally. This divorces the expression of the protein encoded by the gene from the natural situation in reality, in that the regulatory signals that direct transcription of the gene and the subsequent translation of the mRNA product are not retained in the transgenic system. Researchers in the prior art turned to the use of such promoters for a variety of reasons. Partly, it was felt necessary to do so because the transcription signals provided by the endogenous promoters were not deemed to be strong enough. Furthermore, it was thought necessary to use promoters that had been shown to be effective in the mouse.

In contrast, the invention preferably incorporates the endogenous promoter with the human gene so that the fidelity of wild type human expression is retained, developmentally, temporally and in a tissue-specific manner.

By "endogenous promoter" is meant a promoter that naturally directs expression of the gene of interest. An endogenous promoter may thus be a human promoter, or may alternatively be the promoter that is endogenous to that introduced gene in the transgenic animal subject. For example, in the case of transgenic mice, the expression of the human gene may be directed by the endogenous mouse promoter for that gene. Thus, it is not essential to insert a human regulatory sequence, e.g. a human promoter. By incorporation of all of the 5' upstream sequence that is necessary for promoter activity, preferably including any enhancers, it has been found that it is not in fact necessary to use strong, constitutive promoters; as in the natural situation, the endogenous promoter, in its entirety, is perfectly capable of directing expression of the relevant protein in a physiologically relevant manner. An example is provided by the CYP3A4 gene, which possesses strong enhancer elements up to 13 kb upstream of the transcription initiation point. Whilst incorporation of all this sequence allows the appropriate mechanism of transcription to occur, omission of these upstream sequences leads to a system in which incomplete or insufficient regulatory sequences are present to allow the fidelity of gene expression to be retained.

In some embodiments of the invention, use of the non-human animal's endogenous regulatory sequences may be preferred. Such embodiments allow expression of human DNA sequences under the control of the non-human animal's endogenous regulatory sequences, such that the components of the non-human animal's gene expression pathway (e.g. regulatory sequences, transcription factors) can interact. Such embodiments may more closely mirror the in vivo situation in humans in some cases, e.g. where the relevant human regulatory sequence is not capable of interacting with the non-human animal's transcription factors, or said interaction does not provide a relevant level of expression of the human DNA sequence. There are disclosed herein embodiments in which a human DNA sequence is expressed under the control of mouse promoter. Thus, the invention also provides a transgenic non-human animal (e.g. mouse), tissue or cells derived therefrom incorporating a human DNA sequence encoding a protein involved in drug metabolism, wherein said human DNA sequence is operatively linked to an endogenous regulatory sequence of the non-human animal, and the endogenous equivalent gene in the non-human animal is optionally annulled.

One result of using promoters such as the albumin promoter that were exclusively used in the prior art is that the effects of expression of a gene can only be monitored in a particular tissue—in the case of the albumin promoter, this is the liver. Prior art workers were not discouraged by this limitation, because the liver was generally viewed as being the only important tissue for studying drug metabolism, and therefore only expression in the liver was desired. Expression elsewhere in tissues other than the liver was seen as artefactual and therefore a hindrance to an effective model rather than being in any way advantageous. Another drawback of the prior art systems based on the use of the albumen promoter is that for that system to work, a murine PXR null background is required. This means that PXR is not expressed anywhere other than from the transgene in the liver, which has very wide-ranging effects on drug metabolism; such a mouse no longer reflects the natural tissue distribution of a natural mouse.

The inventors are of the view that the liver is not the only important tissue for drug metabolism. Accordingly, what the prior art workers perceived as an advantage, i.e. that exclusive liver-specific expression enabled an accurate assessment of the real physiological situation, the inventors see as a distinct disadvantage because other potentially important tissues are ignored. The invention allows a global, holistic snapshot to be obtained of the drug metabolism process.

Use of the endogenous promoter also carries other advantages with it. In particular, the fidelity of developmental expression is retained. Whereas prior art systems have used liver-specific promoters that sponsor liver expression exclusively, the use of the natural endogenous promoter ensures that the protein is expressed in the tissues in which it naturally occurs, and not only in the adult animal, but also at each developmental stage. This also carries with it the advantage that the transgenic animals are more likely to be viable and thus useful as drug screens and in the development of downstream crosses. It also allows the animals to be used to screen for teratogenic effects of a test compound, as placental expression of transcription factors and drug metabolising enzymes is retained.

Furthermore, the inventors have also noted the existence of a potential "repression" effect whereby a particular drug compound reduces the level of a particular drug transporter or metabolising enzyme and so alters the rate or pathway of disposition. For example, were the levels of human CYP3A4 to decrease, for example as a result of repression of mouse PXR rather than the conventional human transcription factor partner, then an alternative pathway of disposition may be exaggerated. This would give a misleading impression of the enzyme levels that are induced by a particular drug in an organism. It would also give a misleading impression of the rate and type of metabolism that would operate in the human on exposure to that particular drug.

The inventors have also noted that the duration of induced expression by a particular drug is of great importance. For example, some drugs that are candidates for use in humans may not be metabolised efficiently in the mouse. This means that such a drug remains present at a systemically high concentration for a significant period. This means that transcription factors such as PXR will remain activated for this period, being constantly activated for this period. Associated levels of drug metabolising enzymes, drug transporters and other such enzymes will as a result also be highly expressed during the entire period that the drug remains in the animal. This clearly is misleading and in contrast to the equivalent situation in the human where the metabolism of the drug may be significantly more efficient.

Using the human promoter rather than the mouse promoter may be preferable to drive the expression of transcription factors, phase 1 drug metabolising enzymes, phase 2 drug metabolising enzymes, and/or drug transporters, as it allows the idiosyncrasies of the human expression system to be retained. Again using the example of the mouse CYP3A genes, these have a different number of PXR and CAR response elements to the number that is present in the human CYP3A4 gene. Were the equivalent mouse promoter to be used, then the response to transcriptional activation of PXR by exposure of the animal to drug would be correspondingly different to the response that is evident in a human system. It is also true that in many cases, the benefit of using the human promoter is that a true mouse orthologue does not exist. This would then lead to greater or lesser production of the drug metabolising protein in response to a particular drug, so potentially exaggerating or diminishing the role of that protein in the metabolism of that drug. For example, in a particular mouse system known in the prior art, it may be that because of inappropriately high levels of expression of CYP3A4, driven by an inappropriate promoter, the tested drug is metabolised too quickly for any potentially beneficial effect to be evident. This is of course misleading.

In contrast, using the natural human promoter means that, following this example, the appropriate amount of CYP3A4 would be produced in response to drug activation, and furthermore, would be produced in the correct tissue. The natural physiological response to a particular drug will then be mimicked, in terms of the amount of CYP3A4 that is produced, not only in the liver, but also, say, in the gastro-intestinal tract. If the drug is in fact a substrate for CYP3A4, then it will be metabolised at a rate and in a manner that mirrors the situation in the human. In contrast, a prior art method that uses an albumin promoter to direct expression of inappropriately large amounts of CYP3A4 will distort the role of this protein and give misleading results. For instance, the drug might in fact only be a weak substrate for CYP3A4, but will nevertheless be metabolised aggressively if high amounts of the protein are present.

Thus, regulatory sequences are preferably of human origin or non-human animal origin. In more preferred embodiments, the regulatory sequences are of human origin or originate from the target non-human animal (e.g. mouse). This enables the wild-type expression pattern to be retained (developmentally, temporally and spatially).

As a result, the human protein is produced in the correct place at the correct time. This imparts a realism to the model that is simply not possessed in the prior art systems.

Preferred Constructs

In some circumstances, the target gene and the human incorporated gene may share a leader sequence. This may be achieved by retaining at least one intron from the target non-human animal gene in the construct, which usually results in a better expression. This strategy also ensures that the gene product will be guided to the right intracellular location. The human leader sequence might be able to fulfil that function as well, but it is often safer to use the mouse leader instead. For instance, in the case of MRP2, the "leader sequence" of the mouse protein, which is encoded by exon 1, may be retained. The human cDNA without sequences from exon 1 is then introduced into exon 2 of the mouse genomic sequence. The original splice sites for mouse intron 1 will be retained, so that this construct encodes a fusion protein of amino acids from mouse exon 1 and human exons 2-32. This construct ensures a high level of expression and also that the MRP2 is guided to its correct location, the plasma membrane.

In other cases, the incorporated human gene may be brought under control of the promoter of the appropriate target animal gene. For example, in the case of MDR1, the cDNA of human MDR1 may be fused to the translational start site of the corresponding mouse genes (Mdr1a or Mdr1b). In the example of PXR, a hybrid of human PXR cDNA and genomic sequences may be fused to the translational start site of the mouse PXR gene, whereby the mouse Start-ATG is retained. In the case of CAR, the human sequence may be fused to the translational start site of the mouse CAR gene.

As explained above, the use of a partial or complete human genomic DNA sequence provides significant advantages, e.g. by permitting production of splice variants.

Thus, in a further aspect the invention provides a transgenic non-human animal, tissue or cells derived therefrom incorporating a human DNA sequence encoding a protein involved in drug metabolism under the control of an endogenous regulatory sequence, wherein the human DNA sequence comprises at least one intron, such that at least one splice variant is produced when the human DNA sequence is transcribed in the transgenic non-human animal, tissue or cells derived therefrom. In this aspect of the invention, the endogenous equivalent gene encoding the protein in the non-human animal is optionally annulled.

In some embodiments of this aspect of the invention, the protein involved in drug metabolism is a transcription factor, a phase-1 drug-metabolising enzyme, a phase-2 drug-metabolising enzyme and/or a drug transporter protein as described elsewhere herein. In other embodiments of this aspect of the invention, the protein involved in drug metabolism is a phase-1 or phase-2 drug-metabolizing enzyme, as described elsewhere herein. In other embodiments of this aspect of the invention, the protein involved in drug metabolism is a drug transporter protein as described elsewhere herein.

As explained above, whole gene clusters should preferably be replaced where possible, rather than simply replacing individual genes, because the resulting drug metabolism pathways more closely resemble the in vivo situation in humans.

Thus, in a further aspect the invention provides a transgenic non-human animal, tissue or cells derived therefrom incorporating a human DNA sequence encoding a cluster of proteins involved in drug metabolism under the control of endogenous regulatory sequences. In this aspect of the invention, a corresponding cluster of endogenous equivalent genes is optionally annulled. In preferred embodiments of this aspect of the invention, the intron-exon structure of the human DNA sequence is maintained (i.e. genomic sequences rather than cDNA sequences are used, as described elsewhere herein).

The invention provides non-human animals, tissue or cells derived therefrom into which a human DNA sequence encoding a protein involved in drug metabolism has been inserted, and in which an endogenous gene encoding a protein involved in drug metabolism is optionally annulled. However, non-human animals, tissues or cells derived therefrom in which an endogenous gene for a protein involved in drug metabolism has been annulled, and which do not further comprise a human DNA sequence encoding a protein involved in drug metabolism are also useful in the invention. Such "knock-out" non-human animals, tissues or cells are particularly useful in parallel with the "knock-in" (humanised) non-human animals, tissues or cells of the invention, because comparison of experimental data generated using knock-in and knock-out mice can reveal further useful information regarding pathways of drug metabolism.

Thus, in a further aspect the invention provides a method for investigating xenobiotic metabolism or toxicity, comprising the use of:
(i) a non-human animal, tissue or cells derived therefrom incorporating a human DNA sequence encoding a protein involved in drug metabolism under the control of an endogenous regulatory sequence and optionally having its endogenous equivalent gene annulled;
(ii) a corresponding non-human animal, tissue or cells derived therefrom whose endogenous equivalent gene has been annulled but which does not incorporate a human DNA sequence encoding the protein involved in drug metabolism; and
(iii) optionally a corresponding wild-type non-human animal, tissue or cells derived therefrom.

Preferred non-human animals of type (i) include those specified elsewhere herein (e.g. those having the genotype huPXR, huCAR, huPPARα, huAhR, huCYP3A4, huCYP3A cluster, huCYP2C9, huCYP2C cluster, huCYP2D6, huCYP1A1/1A2, huUGT, huMDR1/mdr1a$^{-/-}$, huMDR1/mdr1b$^{-/-}$, huMDR1/mdr1a$^{-/-}$/mdr1b$^{-/-}$, or huMRP2).

Preferred non-human animals of type (ii) include those specified elsewhere herein (e.g. those having the genotype koPXR, koCAR, koPPARα, koAhR, koCyp3a11, koCyp3a cluster, koCyp2c cluster, koCyp1a1/Cyp1a2, koCyp2d cluster, or koUGT).

Thus, such methods may involve e.g., comparing drug metabolism in (i) a non-human animal with the genotype huPXR, and (ii) a non-human animal with the genotype koPXR (and optionally (iii) a wild-type non-human animal).

Preferably, such methods comprise the use of:
(i) two or more, three or more, four or more, or five or more non-human animals, tissues or cells derived therefrom incorporating respectively two or more, three or more, four or more, or five or more human DNA sequences encoding different proteins involved in drug metabolism under the control of endogenous regulatory sequences, each non-human animal, tissue or cells optionally having its endogenous equivalent gene annulled;
(ii) two or more, three or more, four or more, or five or more corresponding non-human animals, tissues or cells derived therefrom whose endogenous equivalent genes have been annulled but which do not incorporate human DNA sequences encoding the relevant drug metabolism proteins; and
(iii) optionally a corresponding wild-type non-human animal, tissue or cells derived therefrom.

Such methods may involve e.g., comparing drug metabolism in (i) non-human animals with the genotypes huPXR, huCAR, huCYP2C cluster, huUGT, and (ii) non-human animals with the genotypes koPXR, koCAR, koCyp2c cluster, koUGT (and optionally (iii) a wild-type non-human animal).

In other methods of the invention wherein different transgenic non-human animals are compared, the effect(s) of different regulatory sequences are investigated.

Thus, in a further aspect the invention provides a method for investigating xenobiotic metabolism or toxicity, comprising the use of:
(i) a first non-human animal, tissue or cells derived therefrom incorporating a human DNA sequence encoding a protein involved in drug metabolism under the control of an endogenous human regulatory sequence, the non-human animal, tissue or cells optionally having its endogenous equivalent gene annulled;
(ii) a second non-human animal, tissue or cells derived incorporating a human DNA sequence encoding a protein involved in drug metabolism under the control of an endogenous non-human animal regulatory sequence, the non-human animal, tissue or cells optionally having its endogenous equivalent gene annulled;
(iii) optionally a corresponding non-human animal, tissue or cells derived therefrom whose endogenous equivalent gene has been annulled but which does not incorporate a human DNA sequence encoding the protein involved in drug metabolism; and
(iv) optionally a corresponding wild-type non-human animal, tissue or cells derived therefrom.

For example, drug metabolism can be compared between (i) a first non-human animal with the genotype huPXR, wherein the human DNA sequence encoding PXR is under the control of an endogenous human regulatory sequence, and (ii) a second non-human animal with the genotype huPXR, wherein the human DNA sequence encoding PXR is under the control of an endogenous non-human animal regulatory sequence (and optionally (iii) knock-out and/or (iv) wild-type non-human animals). Such methods enable subtle differences in gene regulation and expression levels between humans and model organisms (e.g. mice) to be elucidated.

Other comparative methods are possible. The skilled person will readily be able to select an appropriate 'panel' of non-human animals, tissues or cells derived therefrom as disclosed herein. The type and number of non-human animals, tissues or cells required for comparison will depend on the type of analysis required (e.g. depending on the drug metabolism pathway of interest and/or the drug of interest). The invention provides transgenic non-human animals, tissues or cells derived therefrom of various genotypes (see elsewhere herein). The invention provides a tool kit from which the skilled person can select the tools required for the desired analysis. Thus, the invention provides a method for investigating xenobiotic metabolism or toxicity, comprising the use of at least two, at least three, at least four, at least five, at least six, at least seven, at least eight, at least nine, or at least ten types of non-human animal, tissue or cells derived therefrom, wherein each type of non-human animal, tissue or cells comprises a different genetic modification (e.g. knock-in, knock-out, altered regulatory sequence) affecting the amino acid sequence or expression of a protein involved in drug metabolism. The 'holistic' methods disclosed herein, in which multiple different types of transgenic non-human animal, tissue or cells are compared, enable a more rigorous analysis of drug metabolism and toxicity than the prior art methods that involve use of fewer types of transgenic non-human animal, tissue or cell.

The methods of the invention wherein different transgenic non-human animals are compared may involve administering the same drug at the same dose to the different types of non-human animal (e.g. "knock-in", "knock-out" and wild-type, human or non-human regulatory sequences) and comparing the metabolism or toxicity of that drug between the different animals.

Transgenic Animals

In preferred embodiments of the present invention as described above and below, the transgenic non-human animal and tissues or cells derived therefrom is preferably a mouse but may be another mammalian species, for example another rodent, for instance a rat, hamster or a guinea pig, or another species such as a monkey, pig, rabbit, or a canine or feline, or an ungulate species such as ovine, caprine, equine, bovine, or a non-mammalian animal species. More preferably, the transgenic non-human animal or mammal and tissues or cells are derived from a rodent, more preferably, a mouse.

Although the use of transgenic animals poses questions of an ethical nature, the benefit to man from studies of the types described herein is considered vastly to outweigh any suffering that might be imposed in the creation and testing of transgenic animals. As will be evident to those of skill in the art, drug therapies require animal testing before clinical trials can commence in humans and under current regulations and with currently available model systems, animal testing cannot be dispensed with. Any new drug must be tested on at least two different species of live mammal, one of which must be a large non-rodent. Experts consider that new classes of drugs now in development that act in very specific ways in the body may lead to more animals being used in future years, and to the use of more primates. For example, as science seeks to tackle the neurological diseases afflicting a 'greying population', it is considered that we will need a steady supply of monkeys on which to test the safety and effectiveness of the next-generation pills. Accordingly, the benefit to man from transgenic models such as those described herein is not in any limited to mice, or to rodents generally, but encompasses other mammals including primates. The specific way in which these novel drugs will work means that primates may be the only animals suitable for experimentation because their brain architecture is very similar to our own.

The invention aims to reduce the extent of attrition in drug discovery. Whenever a drug fails at a late stage in testing, all of the animal experiments will in a sense have been wasted. Stopping drugs failing therefore saves test animals' lives. Therefore, although the present invention relates to transgenic animals, the use of such animals should reduce the number of animals that must be used in drug testing programmes.

An advantage of the present invention is that it avoids problems of species divergence between the human and other mammals that have conventionally been used as test models. One example is provided by the family of peroxisome proliferator activated receptors (PPARs), to which various drugs were in the past developed as hypolipidaemia agents. The development of these drugs was stopped, as they were identified in mouse models to be epigenetic carcinogens. It eventually turned out that that the difference in toxicity between species could be attributed to differences in levels of PPARα in the liver. The phenomenon apparent in the mouse does not occur in humans, because of lower levels of PPARα protein that are present in the liver. There are very clear advantages to models that exhibit bona fide levels of protein expression that reflect those present in the human body.

Preferably, the human DNA sequences are each independently linked to human or non-human animal regulatory DNA sequences (e.g. the endogenous human or non-human promoter). This linkage is distinct from the prior art and provides the advantage of improvement over prior art models as this further advances the mirroring of an in vivo human situation.

A particular advantage of the humanised transgenic animals, cells and tissues, of the present invention is that they combine the benefits of normal experimental animal models with those of human cell or tissue culture in a single system. This system or humanised transgenic animal will provide the pharmaceutical industry with an improved alternative for use in all pre-clinical metabolism, toxicity and drug disposition studies.

Cells

Another aspect of the invention relates to cells, modified so as to possess properties according to any one of the above-described aspects of the invention. Hepatocytes and neuronal cells are preferred cell types according to the present invention. The cells may be animal cells, including mammalian cells, such as non-human cells or rodent cells, more specifically, mouse cells.

Cells according to this aspect of the invention may be created from transgenic animals according to the invention using standard techniques, as will be clear to the skilled reader, imbued with knowledge of the present invention. Suitable methods are described in many standard laboratory manuals, such as Davis et al., Basic Methods in Molecular Biology (1986); Sambrook Molecular Cloning; A Laboratory Manual, Third Edition (2000); Ausubel et al., 1991 [supra]; Spector, Goldman & Leinwald, 1998).

In one aspect, such cells may be non-human animal cells, such as mouse cells, generated according to any one of the above-described aspects of the invention. One preferred method of generating such cells is to cross a humanised mouse, as described above, with SV40 immortalised mouse (for example, the immorta-mouse (Taconix). Cells may subsequently be isolated from such animals according to well known techniques in the art. In contrast to prior art transgenic systems, which used the albumin promoter that is only active in the liver and thus only able to generate hepatocytes, cells from transgenic animals generated according to the present invention may be of a diverse selection of different cell types, including cells of significant importance to pharmacokinetics analyses, such as hepatocytes and neuronal cells.

Stem cells isolated from transgenic animals according to the invention, with properties as described above are also useful aspects of the present invention. Such cells may be pluripotent, or partially differentiated. Stem cells may be adult stem cells or embryonic stem cells. More generally, stem cells employed may be from a post-embryonic developmental stage e.g. foetal, neonatal, juvenile, or adult. Stem cells isolated in this manner may be used to generate specific types of cells such as hepatocytes and neuronal cells. Such cells also form an aspect of the present invention.

Preferred Selections of Replaced Genes

According to a further aspect of the invention, there is provided a non-human animal, tissue or cells derived therefrom incorporating:
  (i) at least one human DNA sequence encoding a transcription factor; and
  (ii) at least one human DNA sequence encoding a drug transporter protein;

and whose endogenous equivalent genes have optionally been annulled.

The inventors are of the view that in the case of models of drug metabolism, it is important to generate animals that are not just transgenic for particular drug metabolising enzymes, but also to incorporate in these models, proteins that are transporters of drugs i.e. drug transporter proteins. For example, many compounds that activate PXR, the nuclear transcription factor, are also substrates for MDR1 and are thus transported out of cells by this protein. Therefore, in order to create a faithful model of the in vivo situation, animals must preferably be transgenic for drug transporter proteins, otherwise a misleading impression will be obtained of the intracellular effects of any particular concentration of drug. Of the drug transporter proteins, MDR1 is preferred. In the case of prior art transgenic mice models, of course, the redundancy of drug transporters that is generated by the presence of both mdr1a and mdr1b can generate misleading results and so preferably, both these mouse genes should be knocked out and replaced with the human mdr1 gene.

The expression of genes encoding drug transporter proteins such as MDR1 is also activated by the PXR-based signalling system. Accordingly, because the expression of the phase I, phase II and drug transporter genes is linked by PXR, in addition to the fact that the products of these genes have varied effects on the levels and metabolism of drugs and their metabolites, the integrity of co-ordinated regulation that is maintained according to the present invention is extremely advantageous, particularly when compared to prior art systems.

In addition, MDR is expressed at a significant degree in the gastro-intestinal (GI) tract and in the environment of the blood-brain barrier. Since both the GI tract and the blood brain barrier are significant sources of drug transport into the blood stream, the presence of physiologically-relevant MDR expression levels imparts an important aspect of the drug metabolism process to the drug model and in demonstrating pharmacological activity. The presence of MDR in the GI tract, for example, can render orally-delivered drug not bio-available. MDR is very important for drug transport both in an out of the brain. MDR also transports drugs from somatic cells in the liver into the bile.

Other preferred combinations of drug metabolism genes are listed as follows.

According to a further aspect of the invention, there is provided a non-human animal, tissue or cells derived therefrom incorporating:
  (i) at least one human DNA sequence encoding a transcription factor; and
  (ii) at least one human DNA sequence encoding a phase-1 drug-metabolising enzyme; and/or
  (iii) at least one human DNA sequence encoding a drug transporter protein;

and whose endogenous equivalent genes have optionally been annulled.

According to a further aspect of the invention, there is provided a non-human animal, tissue or cells derived therefrom incorporating:
  (i) at least one human DNA sequence encoding a transcription factor; and
  (ii) at least one human DNA sequence encoding a phase-2 drug-metabolising enzyme; and/or
  (iii) at least one human DNA sequence encoding a drug transporter protein; and whose endogenous equivalent genes have optionally been annulled.

According to a further aspect of the invention, there is provided a non-human animal, tissue or cells derived therefrom incorporating:
  (i) at least one human DNA sequence encoding a transcription factor;
  (ii) at least one human DNA sequence encoding a phase-1 drug-metabolising enzyme;
  (iii) at least one human DNA sequence encoding a phase-2 drug-metabolising enzyme; and
  (iv) at least one human DNA sequence encoding a drug transporter protein; and whose endogenous equivalent genes have optionally been annulled.

Preferably, these aspects include any one or more of the features hereinbefore described. In preferred embodiments of these aspects, one or more of the human DNA sequences is a partial or complete genomic sequence as described elsewhere herein.

According to a yet further aspect of the invention there is provided a non-human animal, tissue or cells derived therefrom incorporating human DNA sequences encoding a PXR and a CAR transcription factor and at least one human DNA sequence encoding a phase-1 drug-metabolising enzyme and at least one human DNA sequence encoding a phase-2 drug-metabolising enzyme and at least one human DNA sequence encoding a drug transporter protein, wherein the endogenous equivalent genes in the non-human animal, tissue or cells have optionally been annulled. According to a yet further aspect of the invention there is provided a non-human animal, tissue or cells derived therefrom incorporating:
  (i) a human DNA sequence encoding a PXR and/or a CAR transcription factor;
  (ii) a human DNA sequence encoding the CYP3A4 enzyme; and
  (iii) a human DNA sequence encoding the MDR1 protein. This aspect of the invention is of particular utility in that the CYP3A4 enzyme is of particular importance in the GI tract and therefore an animal humanised for this isoform will be of importance in investigating the role of drug metabolism in drug bioavailability in the gut. In addition, as set out above, the MDR1 protein is known to be expressed at the blood-brain barrier and when incorporated into the above described humanised mouse will provide a truly representative scenario of the uptake of drugs/xenobiotics into and out of the brain in man.

According a yet further aspect of the invention there is provided a non-human animal, tissue or cells derived therefrom incorporating:
(i) a human DNA sequence encoding a PXR and/or a CAR transcription factor;
(ii) a human DNA sequence encoding the CYP3A4 enzyme;
(iii) a human DNA sequence encoding the UGT1A enzyme; and
(iv) a human DNA sequence encoding the MDR1 protein.

Other preferred combinations include combinations of a PXR and/or a CAR transcription factor, a human DNA sequence encoding the MDR1 protein and one or more of: CYP2A9, the CYP3A-cluster, the CYP2C-cluster and UGT or the UGT0-cluster.

Particularly preferred transgenic non-human animals, tissues and cells of the invention have a genotype as specified in the following list. The prefix "hu" refers to humanisation of the relevant endogenous non-human animal gene, and the prefix "ko" refers to a knock-out of the relevant endogenous non-human animal gene.

Unless otherwise required by the context, references to genes and genotypes herein that are in capitals (e.g. CYP3A4) refer to a human gene or gene cluster (and possibly also to a gene or gene cluster in a non-human animal), whereas references to genes and genotypes not in capitals (e.g. Cyp3a11) refer to a gene or gene cluster in a non-human animal (e.g. mouse).

Transcription Factors
huPXR;
koPXR;
huCAR;
koCAR;
huPPARα;
koPPARα;
huAhR; and
koAhR.

Drug-Metabolizing Enzymes
huCYP3A4;
koCyp3a11;
huCYP3A cluster;
koCyp3a cluster;
huCYP2C9;
huCYP2C cluster;
koCyp2c cluster;
huCYP2D6;
koCyp2d cluster;
huCYP1A1/1A2 (meaning both CYP1A1 and CYP1A2 are humanised);
koCyp1a1/Cyp1a2 (meaning both Cyp1a1 and Cyp1a2 are knocked out);
huUGT; and
koUGT.

Drug Transporter Proteins
huMDR1/mdr1a$^{-/-}$;
koMDR1a;
huMDR1/mdr1b$^{-/-}$;
koMDR1b;
huMDR1/mdr1a$^{-/-}$/mdr1b$^{-/-}$;
koMDR1a/koMDR1b;
huMRP2; and
koMRP2.

Particularly preferred transgenic non-human animals, tissues and cells of the invention incorporate a combination of two or more of the genotypes described herein, some examples of which are specified in the following list, wherein the symbol "/" indicates a combination of relevant genotypes.

Complex Genotypes
huPXR/huCAR;
koPXR/huCAR;
huPXR/koCAR;
koPXR/koCAR;
huCYP2C9/huPXR;
koCyp2c cluster/huPXR;
huCYP2D6/huPXR;
huCYP3A4/huPXR;
koCyp3a11/huPXR;
huCYP3A4/koCyp3a11/huPXR;
koCyp3a cluster/huPXR;
huMDR1/mdr1a$^{-/-}$/huPXR;
huMDR1/mdr1b$^{-/-}$/huPXR;
huMDR1/mdr1a$^{-/-}$/mdr1b–/–/huPXR;
huMRP2/huPXR;
huCYP3A cluster/huPXR/huCAR;
huCYP3A4/huPXR/huCAR;
huCYP3A4/koCyp3a11/huPXR/huCAR;
huCYP3A cluster/huMDR1/mdr1a/mdr1b$^{-/-}$/huPXR/huCAR;
huCYP3A cluster/huMDR1/mdr1a/mdr1b$^{-/-}$/huUGT/huMRP2/huPXR/huCAR;
huCYP3A cluster/huCYP2C cluster/huMDR1/mdr1a$^{-/-}$/mdr1b$^{-/-}$/huPXR/huCAR;
huCYP3A cluster/huCYP2C cluster/huMDR1/mdr1a$^{-/-}$/mdr1b$^{-/-}$/huUGT/huMRP2/huPXR/huCAR;
huCYP2C cluster/huPXR/huCAR;
huCYP2C9/huPXR/huCAR;
huUGT/huPXR/huCAR;
huUGT/huMRP2/huPXR/huCAR;
huMDR1/mdr1a$^{-/-}$/mdr1b$^{-/-}$/huPXR/huCAR; and
huMRP2/huPXR/huCAR.

Transgenic non-human animals, tissues and cells having a combination of two or more genetic manipulations as described herein are particularly preferred, because the drug metabolism pathways in those non-human animals, tissues and cells more closely resemble the in vivo situation in humans. Such non-human animals, tissues and cells may incorporate 2 or more, 3 or more, 4, or more 5 or more, 6 or more, 7 or more, 8 or more, 9 or more, or 10 or more of the genetic manipulations as described herein.

Suitable methods and targeting vectors for generating the transgenic non-human animals, tissues or cells of the invention are described elsewhere herein, and specific targeting strategies are described in the Examples herein and schematically illustrated in the Figures. Each of the specific targeting strategies and targeting vectors described and illustrated herein forms a further aspect of the invention. Thus, the invention provides a method of introducing into a non-human animal cell at least one human DNA sequence encoding a protein involved in drug metabolism using a targeting strategy or targeting vector(s) substantially as described herein or substantially as depicted in the Figures herein.

In particular, the invention provides a transgenic mouse, tissue or cells derived therefrom comprising one or more of the following features:

| A. Transcription Factors | |
|---|---|
| huPXR and koPXR | Knock-in of a DNA sequence encoding human PXR into the mouse PXR locus, enabling expression of human PXR under the control of the mouse PXR promoter.<br>The DNA sequence encoding human PXR preferably comprises at least part of intron 4 and/or intron 5 of the human PXR gene (e.g. FIGS. 2 and 64).<br>The DNA sequence encoding human PXR may further comprise at least part of intron 6 and/or intron 7 of the human PXR gene (e.g. FIG. 61).<br>The DNA sequence encoding human PXR may further comprise at least part of intron 2, intron 3 and/or intron 8 of the human PXR gene (e.g. FIG. 63).<br>The targeting vector(s) preferably include sequence elements that enable PXR knock-out (e.g. Phi-C31-mediated knock-out) to produce koPXR. |
| huCAR and koCAR | Knock-in of a DNA sequence encoding human CAR into the mouse CAR locus, enabling expression of human CAR under the control of the mouse CAR promoter.<br>The DNA sequence encoding human CAR preferably comprises at least part of intron 2, intron 3, intron 4, intron 5, intron 6, intron 7 and/or intron 8 of the human CAR gene (e.g. FIG. 3).<br>The targeting vector(s) preferably include sequence elements that enable CAR knock-out (e.g. Phi-C31-mediated knock-out) to produce koCAR. |
| huPPARα and koPPARα | Knock-in of a DNA sequence encoding human PPARα into the mouse PPARα locus, enabling expression of human PPARα under the control of the mouse PPARα promoter.<br>The DNA sequence encoding human PPARα preferably comprises at least part of intron 5 and/or intron 6 of the human PPARα gene (e.g. FIG. 67).<br>The targeting vector(s) preferably include sequence elements that enable PPARα knock-out (e.g. Cre-mediated knock-out) to produce koPPARα. |
| huAhR and koAhR | Knock-in of a DNA sequence encoding human AhR into the mouse AhR locus, enabling expression of human AhR under the control of the mouse AhR promoter.<br>The DNA sequence encoding human AhR preferably comprises exons 3-11 of the human AhR gene (e.g. FIG. 68).<br>The targeting vector(s) preferably include sequence elements that enable AhR knock-out (e.g. Cre-mediated knock-out) to produce koAhR. |

| B. Drug-Metabolizing Enzymes | |
|---|---|
| huCYP3A4 | Knock-in of a DNA sequence encoding human CYP3A4 into the mouse Rosa26 locus, enabling expression of human CYP3A4 under the control of a human CYP3A4 promoter.<br>The DNA sequence encoding human CYP3A4 preferably comprises at least part of intron 1 of the human CYP3A4 gene (e.g. FIG. 69). |
| koCyp3a11 | Knock-in of ZsGreen reporter gene into the mouse Cyp3a11 locus, enabling expression of ZsGreen under the control of the mouse Cyp3a11 promoter (e.g. FIG. 70). |
| huCYP3A cluster and koCyp3a cluster | Insertion of a DNA sequence encoding the human CYP3A cluster into the mouse Cyp3a cluster, enabling expression of the human CYP3A cluster under the control of human CYP3A promoters.<br>The targeting vector(s) preferably include sequence elements that enable Cre-mediated deletion of the mouse Cyp3a cluster, to produce koCyp3a (e.g. FIG. 71).<br>The targeting vector(s) preferably include sequence elements that enable Cre-mediated insertion of the human CYP3A cluster subsequent to Cre-mediated deletion of the mouse Cyp3a cluster, to produce huCYP3A.<br>The targeting vector(s) preferably include sequence elements that enable deletion of selection cassettes subsequent to insertion of the human CYP3A cluster into the mouse Cyp3a cluster. |
| huCYP3A4 and koCyp3a cluster | Knock-in of a DNA sequence encoding human CYP3A4 into the mouse Cyp3a cluster, enabling expression of human CYP3A4 under the control of a human CYP3A4 promoter.<br>Mice in which the Cyp3a cluster is deleted may also be generated. |
| huCYP2C9 | Knock-in of a DNA sequence encoding human CYP2C9 into the mouse Rosa26 locus, enabling expression of human CYP2C9 under the control of a human CYP2C9 promoter. |

-continued

| | B. Drug-Metabolizing Enzymes |
|---|---|
| | The DNA sequence encoding human CYP2C9 preferably comprises at least part of intron 4 of the human CYP2C9 gene (e.g. FIG. 72). |
| huCYP2C cluster and koCyp2c cluster | Insertion of a DNA sequence encoding the human CYP2C cluster into the mouse Cyp2c cluster, enabling expression of the human CYP2C cluster under the control of human CYP2C promoters. The targeting vector(s) preferably include sequence elements that enable Cre-mediated deletion of the mouse Cyp2c cluster, to produce koCyp2c (e.g. FIG. 73). The targeting vector(s) preferably include sequence elements that enable Cre-mediated insertion of the human CYP2C cluster subsequent to Cre-mediated deletion of the mouse Cyp2c cluster, to produce huCYP2C. The targeting vector(s) preferably include sequence elements that enable deletion of selection cassettes subsequent to insertion of the human CYP2C cluster into the mouse Cyp2c cluster. |
| huCYP2C9 and koCyp2c cluster) | Knock-in of a DNA sequence encoding human CYP2C9 into the mouse Cyp2c cluster, enabling expression of human CYP2C9 under the control of a human CYP2C9 promoter. Mice in which the Cyp2c cluster is deleted may also be generated. |
| huCYP2D6 and koCyp2d cluster | Knock-in of a DNA sequence encoding human CYP2D6 into the mouse Cyp2d cluster, enabling expression of human CYP2D6 under the control of a human CYP2D6 promoter. Mice in which the Cyp2d cluster is deleted may also be generated. |
| huCYP3A4 and koCyp3a11 | Knock-in of a DNA sequence encoding human CYP3A4 into the mouse Cyp3a cluster, enabling expression of human CYP3A4 under the control of the mouse Cyp3a11 promoter. Mice in which the Cyp3a cluster is deleted may also be generated. |
| huCYP1A1/ CYP1A2 and koCYP1A1/ CYP1A2 | Knock-in of DNA sequences encoding human CYP1A1 and human CYP1A2 into the mouse Cyp1a cluster, enabling expression of human CYP1A1 and CYP1A2 under the control of human CYP1A1 and CYP1A2 promoters. Mice in which the Cyp1a cluster is deleted may also be generated. |
| huUGT cluster and koUGT cluster | Insertion of a DNA sequence encoding the human UGT1 cluster into the mouse Ugt1 cluster, enabling expression of the human UGT1 cluster under the control of human UGT1 promoters. The targeting vector(s) preferably include sequence elements that enable Cre-mediated deletion of the mouse Ugt1 cluster, to produce koUGT (e.g. FIG. 74). The targeting vector(s) preferably include sequence elements that enable Cre-mediated insertion of the human UGT1 cluster subsequent to Cre-mediated deletion of the mouse Ugt1 cluster, to produce huUGT. The targeting vector(s) preferably include sequence elements that enable deletion of selection cassettes subsequent to insertion of the human UGT1 cluster into the mouse Ugt1 cluster. |

| | C. Drug Transporter Proteins |
|---|---|
| huMDR1/mdr1a$^{-/-}$ | Knock-in of a DNA sequence encoding human MDR1 into the mouse Mdr1a locus, enabling expression of human MDR1 under the control of the mouse Mdr1a promoter. The DNA sequence encoding human MDR1 is preferably a human MDR1 cDNA sequence (e.g. FIG. 75). |
| huMDR1/mdr1b$^{-/-}$ | Knock-in of a DNA sequence encoding human MDR1 into the mouse Mdr1b locus, enabling expression of human MDR1 under the control of the mouse Mdr1b promoter. The DNA sequence encoding human MDR1 is preferably a human MDR1 cDNA sequence (e.g. FIG. 76). |
| huMDR1/ mdr1a$^{-/-}$/ mdr1b$^{-/-}$ | Knock-in of DNA sequences encoding human MDR1 into the mouse Mdr1a and Mdr1b loci, enabling expression of human MDR1 under the control of the mouse Mdr1a and Mdr1b promoters. The DNA sequences encoding human MDR1 are preferably human MDR1 cDNA sequences (e.g. FIGS. 75 and 76). |
| huMRP2 | Knock-in of a DNA sequence encoding human MPR2 into the mouse Mrp2 locus, enabling expression of human MPR2 under the control of the mouse Mrp2 promoter. The DNA sequence encoding human MPR2 is preferably a human MPR2 cDNA sequence (e.g. FIG. 77). |

By intron 'n' herein is meant the intron between exons 'n' and 'n+1'. Thus, intron 4 is that between exons 4 and 5, and intron 5 is that between exons 5 and 6, etc.

As noted elsewhere herein, the skilled person will readily be able to select an appropriate 'panel' of non-human animals, tissues or cells derived therefrom as disclosed herein. The invention provides a tool kit from which the skilled person can select the tools required for the desired analysis. Thus, the invention provides a method for investigating xenobiotic metabolism or toxicity, comprising the use of at least two, at least three, at least four, at least five, at least six, at least seven, at least eight, at least nine, or at least ten types of non-human animal, tissue or cells derived therefrom, wherein each type of non-human animal, tissue or cells comprises a different genetic modification introduced using a targeting strategy or targeting vectors substantially as described herein or substantially as depicted in the Figures herein.

Further details of the preferred targeting strategies and constructs are provided in the Examples and Figures herein. In particular, preferred targeting strategies are illustrated schematically in FIGS. 1-14 and 61-82.

Ma et al. (Drug Metab Dispos. 2007 February; 35(2):194-200) introduced the complete human PXR gene, including 5' and 3' flanking sequences, into PXR knock-out mice by bacterial artificial chromosome (BAC) transgenesis. They observed selective expression of human PXR in the liver and intestine. Treatment of PXR-humanised mice with PXR ligands mimicked the human response, as both hepatic and intestinal Cyp3a11 mRNA and protein were strongly induced by rifampicin, a human-specific PXR ligand, but not by pregnenolone 16α-carbonitrile (PCN), a rodent-specific PXR ligand. In wild-type mice, Cyp3a11 mRNA was strongly induced by PCN, but not by rifampicin. However, Ma et al. relates exclusively to PXR humanisation, and furthermore does not disclose or suggest many aspects of the present invention, such as the use of mixed cDNA/genomic constructs, comparison of different transgenic non-human animals, use of reporter constructs (see below) or expression of human sequences under the control of non-human animal regulatory sequences. Another drawback of the model described by Ma et al. is that it is unsuitable to combine with modifications of other genes within one animal, because PXR humanisation is achieved by two independent genomic alterations: (i) knock-out of the endogenous PXR gene, and (ii) transgenesis with the human PXR gene at a different genomic location.

Preferred Sequences

Preferred targeting strategies and constructs are described herein. Preferred nucleic acid sequences for insertion into non-human animals, tissues or cells derived therefrom are recited in SEQ ID NOs:1-4.

SEQ ID NO:1 is a human PXR nucleotide sequence obtainable using a targeting vector of the invention. The first three nucleotides of SEQ ID NO:1 (atg) are the translational start site from the mouse PXR gene; the start site of the human PXR gene (ctg) is not present. SEQ ID NO:1 comprises sequences from introns 4 and 5 of the human PXR gene, and is obtainable using a targeting strategy as illustrated schematically in FIGS. 2, 7 and 64.

SEQ ID NO:2 is a human PXR nucleotide sequence obtainable using another targeting vector of the invention. The first three nucleotides of SEQ ID NO:2 (atg) are the translational start site from the mouse PXR gene; the start site of the human PXR gene (ctg) is not present. SEQ ID NO:2 comprises sequences from introns 6, 7 and 8 of the human PXR gene, and is obtainable using a targeting strategy as illustrated schematically in FIG. 61.

SEQ ID NO:3 is a human PXR nucleotide sequence obtainable using a targeting vector of the invention. The first three nucleotides of SEQ ID NO:3 (atg) are the translational start site from the mouse PXR gene; the start site of the human PXR gene (ctg) is not present. SEQ ID NO:3 comprises sequences from introns 2, 3, 4, 5, 6, 7 and 8 of the human PXR gene, and is obtainable using a targeting strategy as illustrated schematically in FIG. 63.

SEQ ID NO:4 is a human CAR nucleotide sequence obtainable using a targeting vector of the invention. SEQ ID NO:4 contains a 53 bp Phi-C31 recognition site (attB53), which was inserted into intron 2 of the human CAR gene. SEQ ID NO:4 comprises sequences from introns 2, 3, 4, 5, 6, 7 and 8 of the human CAR gene, and is obtainable using a strategy as illustrated schematically in FIGS. 3, 8 and 65.

Accordingly, in one aspect the invention provides a transgenic non-human animal, tissue or cells derived therefrom, that comprises a DNA sequence as recited in SEQ ID NO:1, SEQ ID NO:2, SEQ ID NO:3 or SEQ ID NO:4. Preferably, the DNA sequence is stably integrated at the locus of the endogenous equivalent gene (i.e. within the murine PXR or CAR locus). The invention also provides a nucleic acid targeting vector that comprises a DNA sequence as recited in SEQ ID NO:1, SEQ ID NO:2, SEQ ID NO:3 or SEQ ID NO:4, and which further comprises 5' and 3' flanking nucleic acid sequences that are homologous to 5' and 3' regions in the locus of the endogenous equivalent gene, and which optionally further comprises nucleic acid sequence elements that permit conditional deletion of the human DNA sequence after its integration in the locus of the endogenous equivalent gene. The invention also provides a non-human animal, tissue or cells derived therefrom containing such a nucleic acid targeting vector.

Preferred non-human animals, tissues or cells and targeting vectors comprise a nucleic acid molecule that is at least 70%, at least 75%, at least 80%, at least 85%, at least 90%, at least 95%, at least 98% or at least 99% identical over its entire length to a nucleic acid molecule as recited in SEQ ID NO:1, SEQ ID NO:2, SEQ ID NO:3 or SEQ ID NO:4, or a DNA sequence that is complementary to such a nucleic acid molecule.

Methods for Introducing Replacement Genes

According to a further aspect of the invention there is provided a method of introducing at least one functional human transcription factor, at least one phase-1 drug metabolising enzyme, at least one phase-2 drug-metabolising enzyme and at least one drug transporter protein into non-human cell(s) whose own endogenous equivalent genes expressing the aforesaid proteins have optionally been rendered inactive, the method comprising introducing DNAs encoding said human transcription factor, phase-1 and 2 drug metabolising enzyme and drug transporter protein such that said human expression products remain functional, even where the cell's own endogenous genes are rendered inactive. Constructs of any one of the above-described aspects of the invention may be used.

Preferably, endogenous non-human genes whose protein products are analogous to the protein products of the introduced human DNA sequences are deleted. This can be done preferably either by direct targeting with their human counterparts or by flanking these genes or gene clusters with recognition sites and subsequent recombinase-mediated deletion (e.g. Cre-mediated or Phi-C31-mediated deletion).

According to the present invention, genes that are inserted into the transgenic model are preferably inserted at the point in the genome where the endogenous equivalent gene or gene cluster naturally occurs. This has the advantage that the context of the gene locus is retained which means that the fidelity of transcription from this site is as close as possible to the level of transcription that occurs in the wild type system.

Furthermore, according to the invention, the endogenous equivalent gene or genes to those that are inserted into the transgenic system optionally have been annulled. "Annulled" is meant to include silencing or deletion or rendering inactive so that the non-human animal's endogenous equivalent gene is unable to express the gene product(s). A preferable way in which to annul the expression of the endogenous equivalent gene or genes and simultaneously to insert the replacement gene at the point at which it naturally occurs is by the process of homologous recombination, described above. According to this methodology, homology arms of sequence complementary to sites in the target genome flank the insertion sequence and these are used to direct insertion of the desired human gene or genes.

For example, in the case of MDR1, the drug transporter protein, different animal species have different MDR1 isotypes and expression profiles. The mouse has two genes encoding active drug transporters (MDR1a and MDR1b), whose tissue expression is mutually exclusive. In contrast, MDR1 is the only functioning drug transporter of the two MDR genes present in the human (MDR1 and MDR3). When creating a mouse transgenic for MDR, therefore, MDR1 should preferably replace both the endogenous MDR genes, MDR1a and MDR1b.

Another example can be provided by the case of CYP2D6, where there are nine genes in the mouse, corresponding to only one functional gene in humans. Replacement of the mouse gene cluster with the human gene is relatively simple though, since the latter spans less than around 40 kb of genomic sequence.

DNA sequences may be deleted by, for example, Cre/lox-mediated deletions. This type of deletion is suitable for deleting of large fragments of DNA (200 kb to several megabases). The method has been described in the following papers (Li Z W, Stark G, Gotz J, Rulicke T, Gschwind M, Huber G, Muller U, Weissmann C. Generation of mice with a 200-kb amyloid precursor protein gene deletion by Cre recombinase-mediated site-specific recombination in embryonic stem cells Proc Natl Acad Sci USA. 1996 Jun. 11; 93(12):6158-62. Erratum in: Proc Natl Acad Sci USA 1996 Oct. 15; 93(21):12052 and in Su H, Wang X, Bradley A. Nested chromosomal deletions induced with retroviral vectors in mice. Nat. Genet. 2000 January; 24(1):92-5).

Cre/lox-mediated insertions of large fragments may also be used to insert the human DNA sequences by a method described in Call L M, Moore C S, Stetten G, Gearhart J D. A cre-lox recombination system for the targeted integration of circular yeast artificial chromosomes into embryonic stem cells. Hum Mol. Genet. 2000 Jul. 22; 9(12):1745-51.

Preferably, the non-human transgenic animal is humanised for a drug transporter protein by the hitherto undisclosed "knock-in" approach, as shown in the schematic representation of accompanying FIGS. 1, 2 and 3.

Preferably, the non-human transgenic animal of the present invention is humanised for both PXR and CAR alone or in combination, more preferably in combination.

Preferably, the human genes are at least partially conserved within a construct.

Preferably, in the case of a transgenic animal expressing the human PXR gene, the PXR construct retains the intron-exon structure between exons 4 and 6. This advantageously retains the sequence where most splice variants are observed and is conveniently located within the ligand-binding domain. The preferred human PXR sequence therefore contains the cDNA of exons 1-4, the genomic sequences of intron 4, exon 5 and intron 5 and the cDNA for exons 6-9.

It will be appreciated that alternative splice products between these exons, which might account for proteins with distinct ligand-binding capacity, will be covered by the constructs of the present invention.

Preferably, the CAR construct retains the intron-exon structure between exons 2 and 9. This advantageously retains complete genomic structure within the targeting vector and permits coverage of all splice variants of human CAR.

Other preferred constructs are described above.

In one embodiment of the invention the transgenic animals are produced de novo so as to include all the aforementioned features by methods wherein, for example, cre/lox mediated deletion of large fragments of DNA (200 kb to several megabase) are achieved (Li Z W, et al. Generation of mice with a 200-kb amyloid precursor protein gene deletion by Cre recombinase-mediated site-specific recombination in embryonic stem cells Proc Natl Acad Sci USA. 1996 Jun. 11; 93(12):6158-62. Erratum in: Proc Natl Acad Sci USA 1996 Oct. 15; 93(21):12052 and in Su H et al Nested chromosomal deletions induced with retroviral vectors in mice. Nat. Genet. 2000 January; 24(1):92-5), and where cre/lox-mediated insertions of large fragments are achieved as described in Call et al. A cre-lox recombination system for the targeted integration of circular yeast artificial chromosomes into embryonic stem cells. Hum Mol. Genet. 2000 Jul. 22; 9(12):1745-51.

In another embodiment of the invention the transgenic non-human animal of the present invention is produced by crossing. For example, the animal of WO2004/007708 might be crossed with those transgenic animals that have been humanised with PXR and/or CAR and include further modifications with respect to phase-2 drug metabolising enzymes and drug transporter protein in either transgenic strain of the non-human animal.

In a further embodiment of the invention the transgenic non-human animal is produced de novo so as to include all of the aforementioned features, by the methods as hereinafter disclosed.

It will be appreciated that ideally all of the introduced human DNAs are substantially under the control of human promoters.

Model Systems

Advantageously, the present invention provides a non-human transgenic animal that mimics the human mechanisms of metabolism, disposition or toxicity of drugs or other xenobiotic compounds on a non-human animal cell by introducing into a non-human animal cell one or more human DNA sequences comprising coding and regulatory sequences necessary to reproduce the regulation and function of one or more proteins responsible for human metabolism, disposition or toxicity of drugs or other xenobiotic compounds where the said non-human animal cell has undergone deletion of endogenous genes encoding proteins whose functions are analogous to those encoded by the introduced human DNA sequences so that the non-human animal cell can be used as a model system for determining the metabolism, disposition or toxicity of drugs or other xenobiotic compounds in a homologous human cell.

It is possible, according to the invention, to "personalise" a particular transgenic system to suit a phenomenon that is worthy of investigation. For example, CYP3A4 gene expression levels may vary as much as 60 times between individuals, and in any individual may also vary over time. This is partly because of inherent genetic differences, but more importantly due to variability in exposure to drugs, toxins, food products and other environmental variables. The system is an adaptive response system which will only keep high enzyme levels for as long as they are needed. Any other implementation would be wasteful. This means that it is not generally appropriate, in any test system, merely to test the effect of a particular drug concentration at one level of CYP3A4. The effects of the drug must ideally be assessed at high CYP3A4 levels and also at low CYP3A4 levels so that response is tested in both a high and a low P450 environment. Of course, systems according to the prior art, using the albumin promoter, simply cannot reflect the real situation found in vivo.

Another example is provided by the CYP2D6 protein, which plays a major role in the metabolism of neuroleptic drugs (e.g. anti-depressants and drugs used for treatment of schizophrenia), and is thus of significant importance. Pharmaceutical companies are reluctant to back a drug that is metabolised by CYP2D6 and therefore need to know as soon as possible during development of any drug, whether or not it has a CYP2D6 liability. This gene shows variation between individuals, and in fact expression is absent in around 6% of Caucasian individuals. It would be of immense benefit to be able to study the metabolism of drugs, particularly of anti-depressants, in environments of both high and low CYP2D6 levels.

These advantages also allow carcinogenicity testing to be performed as well as the acute pharmacological tests described above. For example, according to the invention, P450 levels, either as single genes or a multiple genes and preferably as clusters of genes, may be raised to artificially high levels in order to test for potentially carcinogenic effects of metabolites. At physiologically normal levels, the effects of such metabolites might not be evident. The marked species difference in carcinogenicity of compounds between rodents and man result in the main from the different rates of generation of toxic or mutagenic metabolites, along with other differences in pharmacokinetics and distribution. The ability to increase gene levels in entire clusters is important as it retains the substrate crosstalk between the different proteins expressed by the genes in the cluster.

Bespoke systems of this type may also be exploited to investigate disease. An example is provided by Gilbert syndrome, a phenomenon caused by a polymorphism in the UGT1A1 gene implicated in drug metabolism. According to the invention, a transgenic model animal may incorporate the polymorphism-containing gene in order to allow this syndrome to be evaluated.

According to a yet further aspect of the invention there is provided a host cell transfected with a nucleic acid construct(s) according to any one of the previous aspects of the invention. The cell type is preferably of human or non-human mammalian origin but may also be of other animal, plant, yeast or bacterial origin.

According to a yet further aspect of the invention, there is provided a transgenic non-human animal in which the cells of the non-human animal express the protein(s) encoded by the nucleic acid construct(s) according to any one of the previous aspects of the invention. The transgenic animal is preferably a mouse, because of currently available technology, but may be another mammalian species, for example another rodent, for instance a rat or a guinea pig, or another species such as rabbit, pig, or a canine or feline, or an ungulate species such as ovine, equine, bovine, or a non-mammalian animal species.

In embodiments of the invention relating to the preparation of a transgenic host cell or a transgenic non-human animal comprising the use of a nucleic acid construct as previously described, the cell or non-human animal may be subjected to further transgenesis, in which the transgenesis is the introduction of an additional gene or genes or protein-encoding nucleic acid sequence or sequences. The transgenesis may be transient or stable transfection of a cell or a cell line, an episomal expression system in a cell or a cell line, or preparation of a transgenic non-human animal by pronuclear microinjection, through recombination events in non-embryonic stem (ES) cells, random transgenesis in non-human embryonic stems (ES) cells or by transfection of a cell whose nucleus is to be used as a donor nucleus in a nuclear transfer cloning procedure.

Methods of preparing a transgenic cell or cell line, or a transgenic non-human animal, in which the method comprises transient or stable transfection of a cell or a cell line, expression of an episomal expression system in a cell or cell line, or pronuclear microinjection, recombination events in ES cells, or other cell line or by transfection of a cell line which may be differentiated down different developmental pathways and whose nucleus is to be used as the donor for nuclear transfer; wherein expression of an additional nucleic acid sequence or construct is used to screen for transfection or transgenesis in accordance with the previous aspects of the invention. Examples include use of selectable markers conferring resistance to antibiotics added to the growth medium of cells, for instance neomycin resistance marker conferring resistance to G418. Further examples involve detection using nucleic acid sequences that are of complementary sequence and which will hybridise with, or a component of, the nucleic acid sequence in accordance with the previous aspects of the invention. Examples would include Southern blot analysis, northern blot analysis and PCR.

Non-human animal cell or transgenic non-human animals produced by the method of the invention can be used as model systems for determining the metabolism of drugs or other xenobiotic compounds in a human.

According to a yet further aspect of the invention there is provided use of a transgenic animal, tissues and/or cells derived therefrom as hereinbefore described that have been modified to contain and express DNA encoding at least one functional human transcription factor, at least one phase-1 drug metabolising enzyme, at least one phase-2 drug-metabolising enzyme and at least one drug transporter protein so as to investigate xenobiotic metabolism or toxicity in said a transgenic animal, tissues and/or cells derived therefrom or other properties or functions of the introduced human proteins such as metabolism and/or biosynthesis of endogenous compounds.

The system of the present invention allows function and regulation of human mechanisms of xenobiotic metabolism, disposition and toxicity to be studied in any tissue or cell type, for instance gastrointestinal tract, blood-brain barrier, liver, kidney in a single animal, tissue or cell derived therefrom.

The system of the present invention may be applied to study effects of human metabolism, disposition or toxicity on anti-tumour effects of a drug in an animal xenograft experiment by expressing humanised metabolic pathways in a non-human grafted tumour cell line and/or in the host animal.

Reporters

The present invention also, advantageously provides non-human animal cells and transgenic non-human animals incorporating introduced reporter genes so that such cells or animals can be used to determine indications of pathways of metabolism of drugs or other xenobiotic compounds in a human cell by convenient assay of the products of reporter gene expression.

Where reporter genes have been incorporated in non-human animal cell or transgenic non-human animals produced by the method of the invention (see below), the cells or animals can be used to determine regulation of genes and also give indications of the likely mechanism and metabolism of drugs or other xenobiotic compounds in an homologous human cell by assaying expression of the reporter gene DNA sequence. The cells or animals can also be used to give indications of the extent of metabolism of drugs or other xenobiotic compounds. For example, analysis of the distribution of reporter gene expression within any particular tissue allows the extent of induction of gene expression to be monitored in response to a particular drug compound.

According to a further aspect of the invention there is provided a non-human animal, tissue or cells derived therefrom incorporating a promoter linked transcriptionally to a human DNA sequence encoding:
(i) a transcription factor; and
(ii) a DNA sequence encoding a phase-1 drug-metabolising enzyme; and/or
(iii) a DNA sequence encoding a phase-2 drug-metabolising enzyme; and/or
(iv) a DNA sequence encoding a drug transporter protein.

The promoter of the transcription factor and/or phase 1 and/or phase 2 drug-metabolising enzyme and/or drug transporter protein may thus be linked to a reporter which allows monitoring for the relative regulation of at least one enzyme involved in drug/xenobiotic disposition. Such an embodiment advantageously allows not only for relative regulation of the enzymes but regulation in both a tissue-specific manner in the transgenic animal or in the whole animal itself in a non-invasive manner as well as the extent and potency of gene induction. Reporters may be linked to the promoters of two or more of (i), (ii), (iii) or (iv) listed above.

Reporter genes are nucleic acid sequences encoding directly or indirectly assayable proteins. They are used to replace other coding regions whose protein products are unsuitable or not amenable to the assay envisaged. Suitable reporter genes that are known in the art and may be used in the present invention are selected from those genes encoding proteins including but not limited to: chloramphenicol-acetyltransferase, β-galactosidase, β-glucuronidase, luciferase, beta-galactosidase, green fluorescent protein, secreted alkaline phosphatase (SEAP), major urinary protein (MUP) or human chorionic gonadotrophin (hCG). It will be understood that the above list of suitable reporter genes is not exhaustive or exclusive and is not intended to limit the scope of the application. The skilled artisan may select another reporter system which will equally be applicable to the present invention.

According to the invention, the promoters that are preferred targets for linkage to reporter genes are PXR, CAR, CYP3A4, Cyp3a11, CYP2C9, CYP2C19, CYP2B6, CYP2D6, UGT1A, MRP2 and MDR1.

The reporter embodiments of the invention can be used in comparative methods. The skilled person will readily be able to select an appropriate 'panel' of reporter non-human animals, tissues or cells derived therefrom as disclosed herein. The type and number of non-human animals, tissues or cells required for comparison will depend on the type of analysis required (e.g. depending on the drug metabolism pathway of interest and/or the drug of interest). The invention provides transgenic non-human animals, tissues or cells derived therefrom of various reporter genotypes (see elsewhere herein). The invention provides a tool kit from which the skilled person can select the tools required for the desired analysis.

Thus, the invention provides a method for investigating xenobiotic metabolism or toxicity, comprising the use of:
(i) a first non-human animal, tissue or cells derived therefrom comprising a first endogenous regulatory sequence (e.g. a mouse or human promoter) operatively linked to a DNA sequence whose expression can conveniently be measured by assay of transcription and/or translation products; and
(ii) a second non-human animal, tissue or cells derived therefrom comprising a second endogenous regulatory sequence (e.g. a mouse or human promoter) different to said first endogenous regulatory sequence operatively linked to a DNA sequence whose expression can conveniently be measured by assay of transcription and/or translation products wherein the first and second endogenous regulatory sequences are regulatory sequences normally associated with genes encoding proteins involved in drug metabolism.

The invention also provides a method for investigating xenobiotic metabolism or toxicity, comprising the use of at least two, at least three, at least four, at least five, at least six, at least seven, at least eight, at least nine, or at least ten types of non-human animal, tissue or cells derived therefrom, wherein each type of non-human animal, tissue or cells comprises a different endogenous regulatory sequence (e.g. a mouse or human promoter) operatively linked to a DNA sequence whose expression can conveniently be measured by assay of transcription and/or translation products (i.e. a reporter sequence), and wherein each endogenous regulatory sequence is a regulatory sequence normally associated with a gene encoding a protein involved in drug metabolism.

In some embodiments, the DNA sequence whose expression can conveniently be measured by assay of transcription and/or translation products will be the same in the different non-human animals, tissues or cells, but in other embodiments different reporter sequences are used.

These methods of the invention wherein different transgenic non-human animals are compared may involve administering the same drug at the same dose to the different types of non-human animal (i.e. to different types of reporter) and comparing the metabolism or toxicity of that drug between the different animals.

Particularly preferred transgenic non-human animals, tissues and cells of the invention have a genotype as specified in the following list. The prefix "hu" refers to humanisation of the relevant endogenous non-human animal gene. The prefix "r" denotes that an endogenous regulatory sequence (e.g. a mouse or human promoter) for the relevant gene is operatively linked to a DNA sequence whose expression can conveniently be measured by assay of transcription or translation products (i.e. a reporter sequence).

Reporter Constructs
rCYP3A4;
rCYP2D6;
rCYP2B6;
rCyp3a11;
rMDR1;

Particularly preferred transgenic non-human animals, tissues and cells of the invention incorporate a combination of two or more of the genotypes described herein above, some examples of which are specified in the following list, wherein the symbol "/" indicates a combination of genetic modifications.

In the following complex genotypes, only a single reporter is present. However, use of multiple reporters within a single non-human animal, tissue or cells derived therefrom is also envisaged.

Complex Reporter Constructs rCYP2B6/huCAR;
rCyp3a11/huPXR;
rCyp3a11/huPXR;
rCYP3A4/huPXR;

rCYP2C9/huPXR;
rCYP2D6/huPXR;
rCYP2C19/huPXR;
rMDR1/huPXR;
rCYP3A4/huPXR/huCAR;
rCYP2C9/huPXR/huCAR;
rCYP2D6/huPXR/huCAR;
rCYP2C19/huPXR/huCAR;
rCYP2B6/huPXR/huCAR;
rCYP3A4/huCYP2B6/huPXR/huCAR;
rMDR1/huPXR/huCAR;
rCYP3A4/huCYP2C9/huPXR/huCAR;
rCYP2D6/huCYP2C19/huPXR/huCAR;
rCYP2B6/huMDR1/mdr1a$^{-/-}$/mdr1b$^{-/-}$/huPXR/huCAR;
rCYP3A4/huCYP2C9/huCYP2D6/huCYP2C19/huPXR/huCAR;
rCYP3A4/huCYP2D6/huPXR/huCAR;
rCYP3A4/huCYP2C9/huCYP2B6/huMDR1/mdr1a$^{-/-}$/mdr1b$^{-/-}$/huPXR/huCAR;
rCYP3A4/huCYP2B6/MDR1/huPXR/huCAR;
rCYP3A4/huCYP2C9/huCYP2D6/huCYP2C19/huCYP2B6/MDR1/huPXR/huCAR; and
rCYP3A4/huCYP2D6/huCYP2B6/huMDR1/mdr1a/mdr1b$^{-/-}$/huPXR/huCAR.

Transgenic non-human animals, tissues and cells having a complex genotype as listed above are particularly preferred, because the drug metabolism pathways in those non-human animals, tissues and cells more closely resemble the in vivo situation in humans.

Suitable methods and constructs for generating the transgenic non-human animals, tissues or cells of the invention are described elsewhere herein, and specific targeting strategies are described in the Examples herein and schematically illustrated in the Figures. Each of the specific targeting strategies and constructs described and illustrated herein forms a further aspect of the invention. Thus, the invention provides a method of generating a non-human animal cell comprising a reporter construct as described herein using a targeting strategy or vector substantially as described herein or substantially as depicted in the Figures herein.

In particular, the invention provides a transgenic mouse, tissue or cells derived therefrom comprising one or more of the following genetic manipulations:

| | |
|---|---|
| rCYP2B6 | Expression of a reporter gene under the control of a human CYP2B6 promoter sequence. Preferably, a reporter gene and a human promoter sequence are inserted into the mouse Cyp2b6 locus. Preferably, the reporter gene is a LacZ reporter gene (e.g. FIG. 78). |
| rCYP2D6 | Expression of a reporter gene under the control of a human CYP2D6 promoter sequence. Preferably, a reporter gene and a human promoter sequence are inserted into the mouse Cyp2d6 locus. Preferably, the reporter gene is a ZsYellow reporter gene (e.g. FIG. 79). |
| rCYP3A4 | Expression of a reporter gene under the control of a human CYP3A4 promoter sequence. Preferably, a reporter gene and a human promoter sequence are inserted into the mouse Cyp3a4 locus. Preferably, the reporter gene is a hCG-ZsGreen reporter gene (e.g. FIG. 80). |
| rCyp3a11 | Expression of a reporter gene under the control of a mouse Cyp3a11 promoter sequence. Preferably, a reporter gene is inserted into the mouse Cyp3a11 locus. Preferably, the reporter gene is a Firefly luciferase (e.g. FIG. 81) or a ZsGreen (e.g. FIG. 70) reporter gene. |
| rMDR1 | Expression of a reporter gene under the control of a human MDR1 promoter sequence. Preferably, the human MDR1 promoter sequence comprises both upstream and downstream promoter sequences. Preferably, a reporter gene and a human promoter sequence are inserted into the mouse Rosa26 locus. Preferably, the reporter gene is a Firefly luciferase reporter gene (e.g. FIG. 82). |

Further details of the preferred reporter strategies and constructs are provided in the Examples and Figures herein.

Animals, tissues and cells according to these aspects of the invention allow very useful elements of the process of gene regulation in drug metabolism to be elucidated. For example, although PXR is known to be of great significance in the transcriptional control of the CYP3A4 gene, there are likely to be other important active mechanisms. Exposing a CYP3A4 reporter animal or cell to a drug compound in either a humanised PXR or a PXR null background would be useful in exploring other ways of regulating CYP3A4 than by way of PXR. Another case of interest would be to expose an mdr1 reporter animal or cell to a drug compound in both a humanised PXR and PXR null background to detect aspects of mdr1 expression that are independent of PXR regulation.

Accordingly, animals, tissues and cells according to this aspect of the invention may comprise a promoter linked transcriptionally to a human DNA sequence encoding a phase-1 drug-metabolising enzyme; a DNA sequence encoding a phase-2 drug-metabolising enzyme; and/or a DNA sequence encoding a drug transporter protein in a null background for PXR, CAR or any other transcription factor. By "null background" is meant that the gene or genes have been annulled, according to the definition provided above. Such animals, cells, or tissues might be compared under similar conditions (for example, in the presence and absence of a drug or drugs) to in a humanised PXR or CAR background. Accordingly, animals, tissues and cells according to this aspect of the invention may comprise a promoter linked transcriptionally to a human DNA sequence encoding a phase-1 drug-metabolising enzyme; a DNA sequence encoding a phase-2 drug-metabolising enzyme; and/or a DNA sequence encoding a drug transporter protein in a humanised background for a transcription factor. Such a transcription factor may be PXR alone, CAR alone, PXR and CAR or any other single transcription factor or combination of transcription factors described herein.

By "linked transcriptionally" is meant that the activity of the promoter dictates the expression level of the reporter protein. Preferably, a reporter gene is fused to the translational start site of the corresponding human gene whose promoter is to be investigated. In the case of the CYP3A4, CYP2C9 and CYP2C19 promoters, the transcript of the reporter gene may not be terminated by a polyA motif, but the constructs are designed such that the endogenous polyA motif is potentially used. These constructs are therefore dependent on a correct splicing of the exons 3' to the reporter (see FIG. 12). In the cases of CYP2D6 and CYP2B6, the transcript of the reporter gene is preferably terminated by a polyA motif linked to the reporter gene with a synthetic intron (see FIG. 13). In case of MDR1, the transcript of the reporter gene is preferably terminated by a polyA motif without an additional intron (see FIG. 14).

According to a further aspect of the invention there is provided a non-human animal, tissue or cells derived therefrom incorporating at least one human DNA sequence encoding at least one transcription factor under control of a transcription factor promoter and whose endogenous equivalent genes have optionally been annulled, the non-human animal, tissue or cells further incorporating a promoter linked transcriptionally to a human DNA sequence encoding:

(i) a DNA sequence encoding a phase-1 drug-metabolising enzyme; and/or
(ii) a DNA sequence encoding a phase-2 drug-metabolising enzyme; and/or
(iii) a DNA sequence encoding a drug transporter protein.

The non-human animal, and tissues or cells of this aspect of the invention may incorporate a promoter linked transcriptionally to a DNA sequence encoding a phase-1 drug-metabolising enzyme and a DNA sequence encoding a phase-2 drug-metabolising enzyme. The non-human animal, and tissues or cells may incorporate a promoter linked transcriptionally to a DNA sequence encoding a phase-1 drug-metabolising enzyme and a DNA sequence encoding a drug transporter protein. The non-human animal, and tissues or cells may incorporate a promoter linked transcriptionally to a DNA sequence encoding a phase-2 drug-metabolising enzyme and a DNA sequence encoding a drug transporter protein. Examples of suitable phase-1 drug-metabolising enzymes, phase-2 drug-metabolising enzymes and drug transporter proteins are described herein.

In another aspect, for example, the promoter activity of the mdr1 gene may be investigated. In this scenario, animals, tissues and cells may comprise a promoter linked transcriptionally to a human DNA sequence encoding a transcription factor, a promoter linked transcriptionally to a human DNA sequence encoding a phase-1 drug-metabolising enzyme; and/or a promoter linked transcriptionally to a DNA sequence encoding a phase-2 drug-metabolising enzyme in a humanised or null background for mdr1.

According to this aspect of the invention there is provided a non-human animal, tissue or cells derived therefrom incorporating at least one human DNA sequence encoding at least one drug transporter protein under control of a drug transporter promoter and whose endogenous equivalent genes have optionally been annulled, the non-human animal, tissue or cells further incorporating a promoter linked transcriptionally to a human DNA sequence encoding:

(i) a DNA sequence encoding a transcription factor; and/or
(ii) a DNA sequence encoding a phase-1 drug-metabolising enzyme; and/or
(iii) a DNA sequence encoding a phase-2 drug-metabolising enzyme.

The non-human animal, and tissues or cells of this aspect of the invention may incorporate a promoter linked transcriptionally to a DNA sequence encoding a phase-1 drug-metabolising enzyme and a DNA sequence encoding a phase-2 drug-metabolising enzyme. The non-human animal, and tissues or cells may incorporate a promoter linked transcriptionally to a DNA sequence encoding a phase-1 drug-metabolising enzyme and a DNA sequence encoding a transcription factor. The non-human animal, and tissues or cells may incorporate a promoter linked transcriptionally to a DNA sequence encoding a phase-2 drug-metabolising enzyme and a DNA sequence encoding a transcription factor. Examples of suitable phase-1 drug-metabolising enzymes, phase-2 drug-metabolising enzymes and transcription factor proteins are described herein.

According to a yet further aspect of the invention, there is provided a nucleic acid construct comprising a targeting vector substantially as depicted in any of FIGS. 1-14 and 61-82.

Preferably, the construct further includes for the humanisation and corresponding knock-out of at least one phase-1 drug metabolising enzyme, at least one phase-2 drug-metabolising enzyme and at least one drug transporter protein in either the same construct or further independent constructs.

Cells

In another aspect of the invention, an animal cell is produced by any one of the above-described aspects of the invention. In preferred aspects, at least one human regulatory DNA sequence associated with the gene encoding a protein responsible for determining the human metabolism, disposition, distribution or toxicity of drugs or other xenobiotic compounds is operatively linked to a DNA sequence whose expression can conveniently be measured by assay of transcription or translation products to produce a reporter gene DNA sequence which is introduced into the non-human animal cell. This embodiment provides linkage with one or more reporter sequences such as human chorionic gonadotrophin (hCG).

Assays

The animals, tissues and cells of the present invention may be used to determine how a drug compound is metabolised by a human. In particular, it is possible to examine whether a drug compound modulates the activity or expression levels of a transcription factor, a drug metabolising enzyme or a drug transporter protein. It is possible to examine the ratio of the levels of activation or expression of a transcription factor, a drug metabolising enzyme or a drug transporter protein induced by a drug compound. It is possible to examine whether a drug compound influences the disposition or distribution of a transcription factor, a drug metabolising enzyme or a drug transporter protein within the tissues of the body. It is possible to examine whether a drug compound influences the duration of expression of a transcription factor, a drug metabolising enzyme or a drug transporter protein.

It is possible to measure a phenotypic change in the animal, such as a physiological effect. Such a physiological effect may be, for example, a disease condition (such as biliary necrosis) or a toxic side-effect.

It is possible to examine the rate of metabolism of a drug compound. The rate of metabolism may be determined by measuring the toxicity or activity mediated by the administration of the compound, measuring the half-life of the compound, or measuring the level of a drug metabolising enzyme. For example, the rate of metabolism of the compound may be measured as the rate of formation of the oxidized product or the formation of a subsequent product generated from the oxidized intermediate. Alternatively, the rate of metabolism may be represented as the half-life or rate of disappearance of the initial compound or as the change in toxicity or activity of the initial compound or a metabolite generated from the initial compound. The half-life may be measured by determining the amount of the drug compound present in samples taken at various time points. The amount of the drug compound may be quantified using standard methods such as high-performance liquid chromatography, mass spectrometry, western blot analysis using compound specific antibodies, or any other appropriate method.

It is also possible to examine whether a drug compound is metabolised to a toxic or carcinogenic metabolite, for example, by measuring its covalent binding to tissues, proteins or DNA or by measuring glutathione depletion.

Preferably, measurements of the type described above are performed at more than 1, 3, 5, 10 or more time points after administration of the drug compound.

Accordingly, further aspects of the invention relate to screening methods that are provided to determine the effect of a drug compound on the activity or expression level of a transcription factor, a drug metabolising enzyme or a drug transporter protein.

Such methods involve administering a drug compound to a transgenic animal according to any one of the aspects of the invention described above, or a tissue or cell derived therefrom.

The screening step may involve measuring the induction of a gene coding for a transcription factor, a drug metabolising enzyme or a drug transporter protein. The screening step may involve measuring the level of expression of a transcription factor, a drug metabolising enzyme or a drug transporter protein or the duration of such expression. The screening step may involve measuring the distribution of expression of a transcription factor, a drug metabolising enzyme or a drug transporter protein.

The assay can be performed in the presence and absence of the drug compound to ascertain differences in distribution, metabolism and toxicity. The effects of the drug compound in the presence and absence of a particular gene or genes can be ascertained by evaluating the effects of the drug compound on different transgenic animals, cells or tissues. For example, the effects of the drug compound could be evaluated between an animal with a null background and an animal humanised for the gene or genes of interest (e.g. PXR, CAR, MDR1, a phase I metabolising enzyme or a phase 2 metabolising enzyme).

Thus, in a further aspect the invention provides methods for investigating xenobiotic metabolism or toxicity as described herein, comprising administering a drug compound to 2 or more, 3 or more, 4 or more, 5 or more, 6 or more, 7 or more, 8 or more, 9 or more, or 10 or more of the non-human animals, tissues or cells described herein. Preferably, such methods further include a step of comparing the experimental results obtained for different non-human animals, tissues or cells.

More than one drug compound may be administered. For example, a drug compound is determined to activate the CAR transcription factor if the compound mediates induction of the CAR gene. A CAR receptor inverse agonist such as clotrimazole can also administered to an animal expressing the human CAR receptor as a control.

Assays according to further aspects of the invention may provide a screening method for determining whether the metabolism of a first drug compound is modulated by a second drug compound. This method involves administering the first compound in the presence and absence of the second compound to a transgenic animal according to any one of the above-described aspects of the invention, or a tissue or cell derived therefrom, and monitoring for a phenotypic effect. Alternatively, as above, the screening step may involve measuring the induction of a gene, the level, duration or distribution of expression, of a transcription factor, a drug metabolising enzyme or a drug transporter protein. The second compound is determined to modulate the metabolism of the first compound if the second compound effects a change in any one of these tested factors. For example, a physiological effect may be assayed by measuring the toxicity or activity mediated by the administration of the first compound or measuring the half-life of the first drug compound.

In this manner, assays may be used to facilitate the identification of analogs of a drug compound that have reduced or undetectable ability to activate or induce expression of a particular protein, and thus are expected to have fewer side-effects or a longer half-life in vivo.

BRIEF DESCRIPTION OF THE DRAWINGS

The invention will now be described by way of example only with reference to the following figures wherein:

FIG. 4 shows a possible mouse mdr1a targeting vector;

FIG. 5 shows a possible mouse mdr1b targeting vector;

FIG. 6 shows a possible construct for MRP2 humanisation;

FIG. 7 shows a possible targeting strategy for PXR humanisation;

FIG. 8 shows a possible targeting strategy for CAR humanisation;

FIG. 9 shows a possible strategy for CYP3A4 humanisation;

FIG. 10 shows a possible strategy for CYP2C9 humanisation;

FIG. 11 shows a possible overall strategy for cluster exchange;

FIG. 12 shows a possible overall strategy for reporter constructs;

FIG. 13 shows a possible reporter project strategy for CYP2D6 and CYP2B6;

FIG. 14 shows a possible reporter project strategy for MDR1;

FIG. 15 shows an example of a PXR typing PCR;

FIG. 17 shows RT-PCR of huPXR transcripts in transgenic mice;

FIG. 18 shows Western blotting of PXR protein from wild type and hPXR mice. Proteins from the livers of treated wild-type and huPXR mice were probed with an antibody specific for the PXR protein. The standard (+ve) was a his-tagged murine PXR;

FIG. 19 shows Western blotting of Cyp3a and Cyp2b induction by rifampicin. Microsomal proteins from the livers of rifampicin treated wild-type and huPXR mice were probed with antibodies for the Cyp 3a11 protein (top panel) and Cyp 2b10 (bottom panel);

FIG. 20 shows enzyme activity assays of Cyp3a and Cyp2b10 induction by rifampicin (100 mg/kg). Shown are the results from enzyme activity assays on liver microsomes using activity of pentoxyresorufin-O-deethylation (PROD) which is attributed to expression level of Cyp 2b10 and the activity of 7-benzyloxyquinoline (BQ) which is attributed to expression level of Cyp 3a;

FIG. 34 shows effects of dexamethasone administration on the expression and activity of Cyp3a11 and Cyp2b10 in wild-type, huPXR and koPXR mice.

FIG. 38 shows an overview of the effects of rifampicin and dexamethasone on Cyp3a11 and Cyp2b10 expression in wild-type, huPXR and koPXR mice. A medium increase compared to vehicle-treated mice is denoted by '++', a strong increase compared to vehicle-treated mice is denoted by '+++', and no change compared to vehicle-treated mice is denoted by 'NC'.

FIG. 39 shows the results of TaqMan® analysis of CAR mRNA in the livers and intestines of untreated wild-type and koCAR mice, demonstrating that basal expression of CAR mRNA was completely lost in the koCAR mouse.

FIG. 40 shows hepatotoxicity data for wild-type, koCAR and koPXR mice, after treatment with dexamethasone or phenobarbital.

FIG. 44 shows that human CAR mRNA, but not mouse CAR mRNA, is expressed in the livers of huCAR mice (TaqMan® analysis).

FIG. 45 shows further results of CAR mRNA analysis in wild-type and huCAR mice by TaqMan® analysis, for liver and small intestine.

FIG. 46 shows CITCO hepatotoxicity data for wild-type and huCAR mice.

FIG. 50 shows a comparison of the effects of CITCO and TCPOBOP in wild-type and huCAR mice.

FIG. 55 provides an overview of the effects of selected drug-metabolism inducers on the expression of Cyp3a11 and Cyp2b10 in mouse and human.

FIG. 60 shows tissue samples from wild-type and rCyp2D6/huPXR reporter mice, illustrating the spatial expression pattern for Cyp2D6 in liver microsomes.

FIG. 71A shows a strategy for 5' targeting of the mouse Cyp3a cluster. FIG. 71B shows a strategy for 3' targeting of the mouse Cyp3a cluster (at the Cyp3a25 locus).

FIG. 73A shows a strategy for 5' targeting of the mouse Cyp2c cluster. FIG. 73B shows a strategy for 3' targeting of the mouse Cyp2c cluster. FIG. 73C shows an overview of a cluster exchange strategy.

FIG. 74A shows a strategy for 5' targeting of the mouse UGT cluster. FIG. 74B shows a strategy for 3' targeting of the mouse UGT cluster. FIG. 74C shows an overview of a cluster exchange strategy.

FIG. 83 shows an overview of the effects of various inducing agents on PXR and CAR target genes in the livers of wild-type, huPXR, koPXR and huCAR mice. A slight increase in expression compared to vehicle-treated mice of the same strain is denoted by a '+', a medium increase in expression compared to vehicle-treated mice of the same strain is denoted by a '++', a strong increase in expression compared to vehicle-treated mice of the same strain is denoted by a '+++', and no change compared to vehicle-treated mice of the same strain is denoted by 'NC'.

DETAILED DESCRIPTION OF ILLUSTRATIVE EMBODIMENTS

EXAMPLES

Example 1

The Humanised PXR/CAR Mouse

Figure 1:
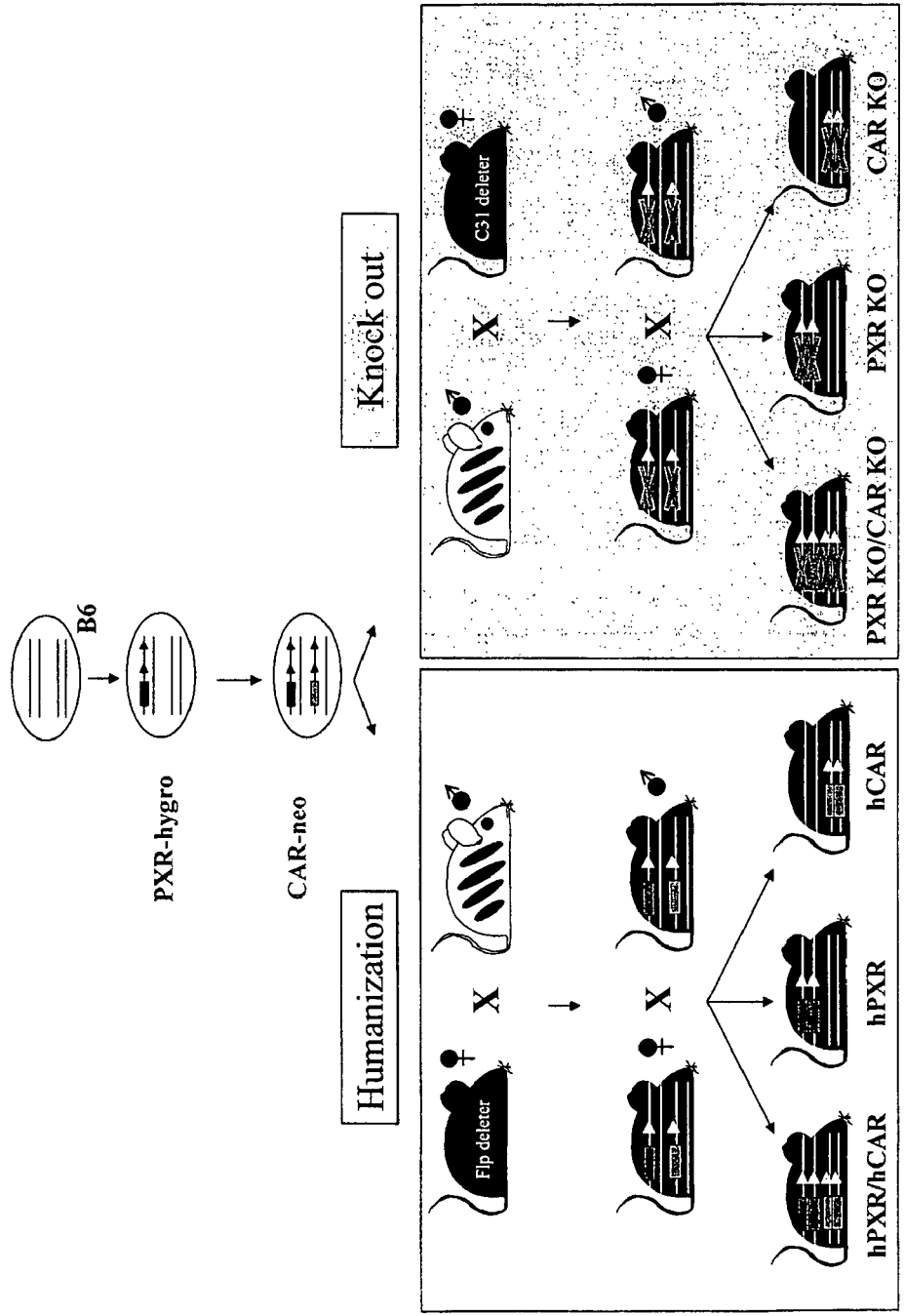
FIG. 1 shows a schematic representation of humanisation and knock out of PXR/CAR.

The method provides for the humanisation of mice for PXR and CAR alone or as a double humanised form for each of the genes (see FIG. 1). We have combined these different humanisations by a step-wise transformation of embryo stem cells (ES cells) rather than by conventional breeding and thus are able to generate PXR/CAR double humanised ES cells, which are usable for subsequent modifications with human DNA sequence encoding a phase-1 or 2 drug-metabolising enzyme human DNA sequences encoding a drug transporter protein.

The application of PhiC31 recombination sites enabled us to knock out both genes by crossing the humanised animal to a Phi31 deleter strain.

Figure 2:
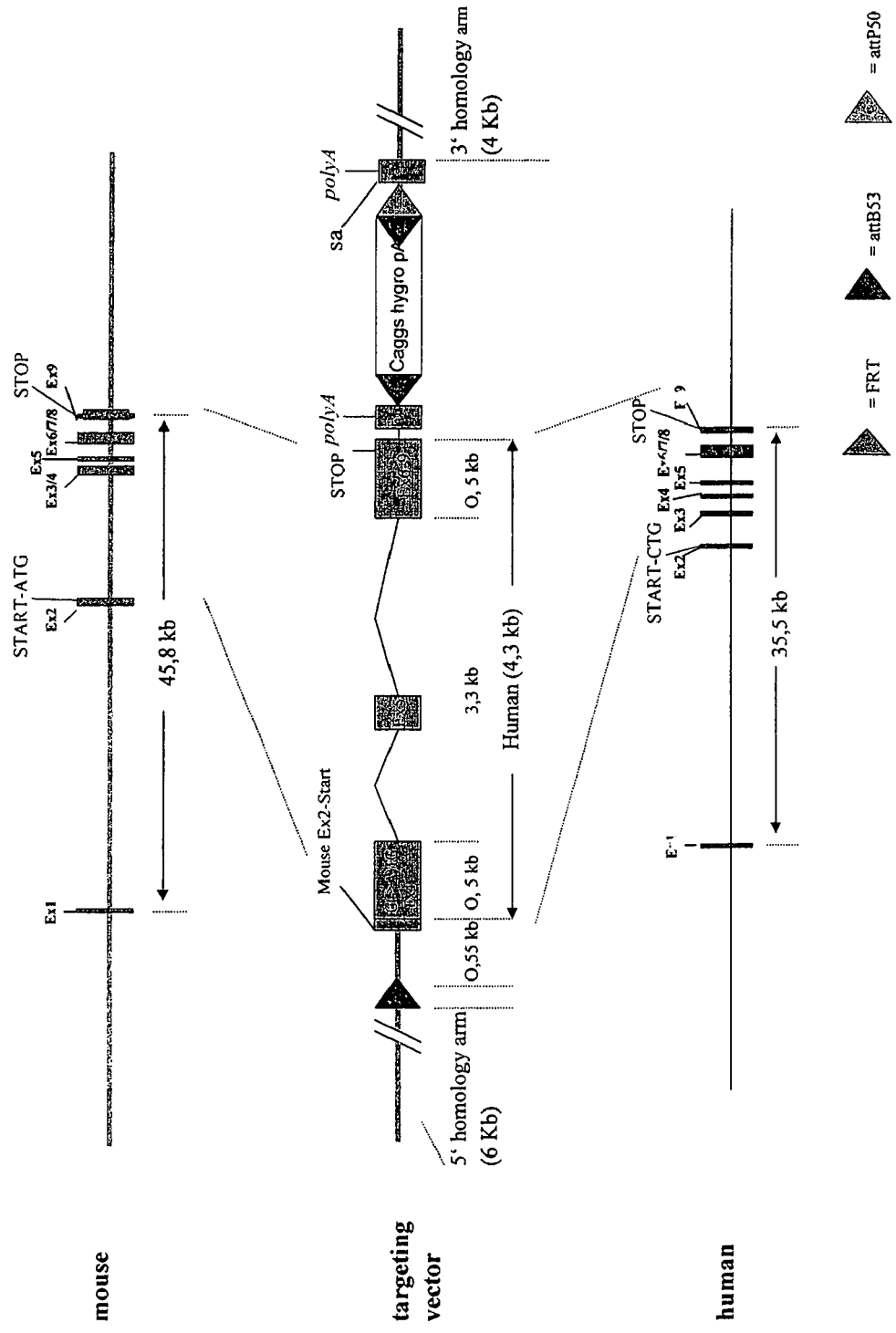
FIG. 2 shows a schematic representation of a composite cDNA with genomic sequences for the PXR humanisation strategy.
Figure 3:
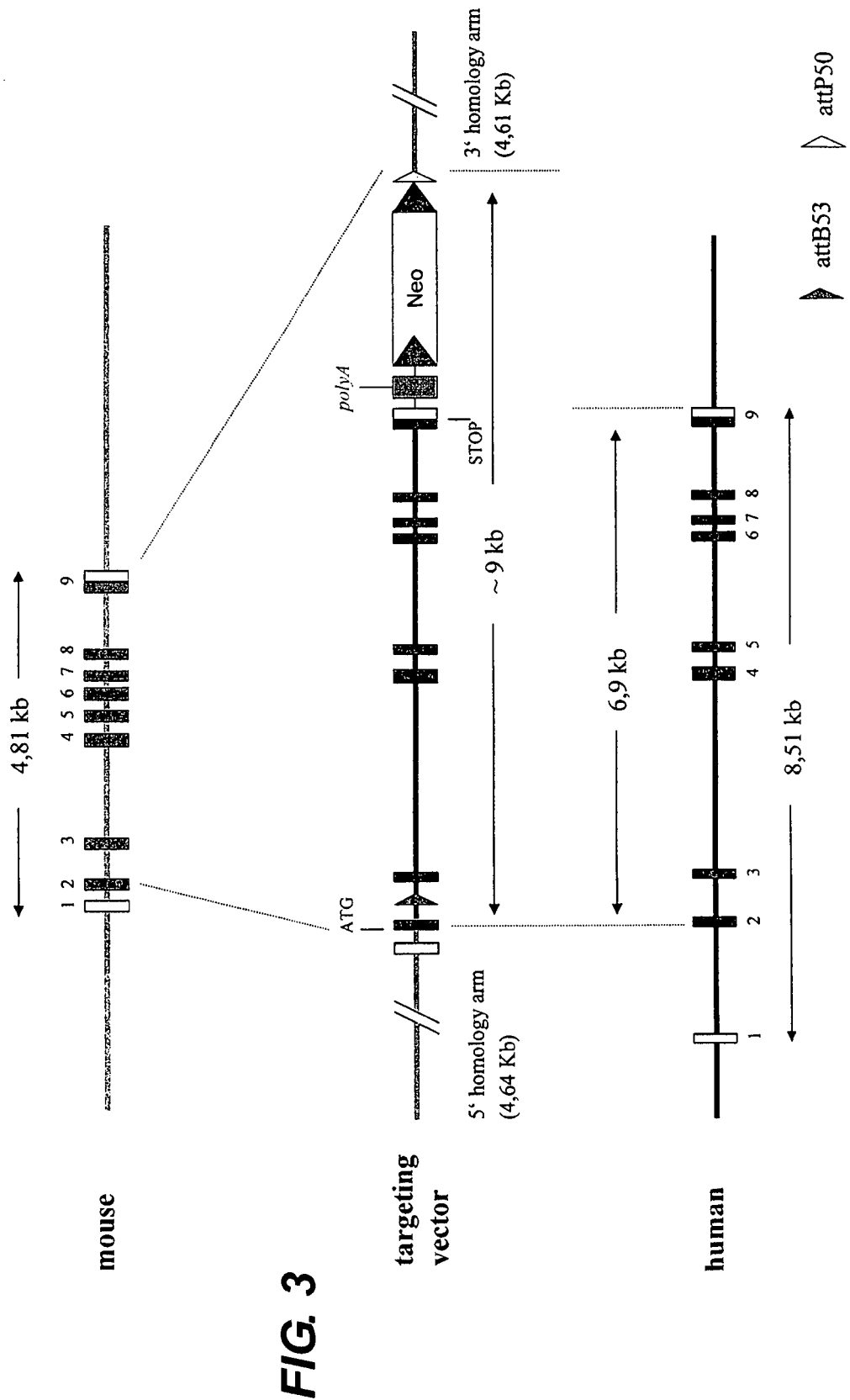
FIG. 3 shows a schematic representation of a composite cDNA with genomic sequences for the CAR humanisation strategy.
Figure 16A:
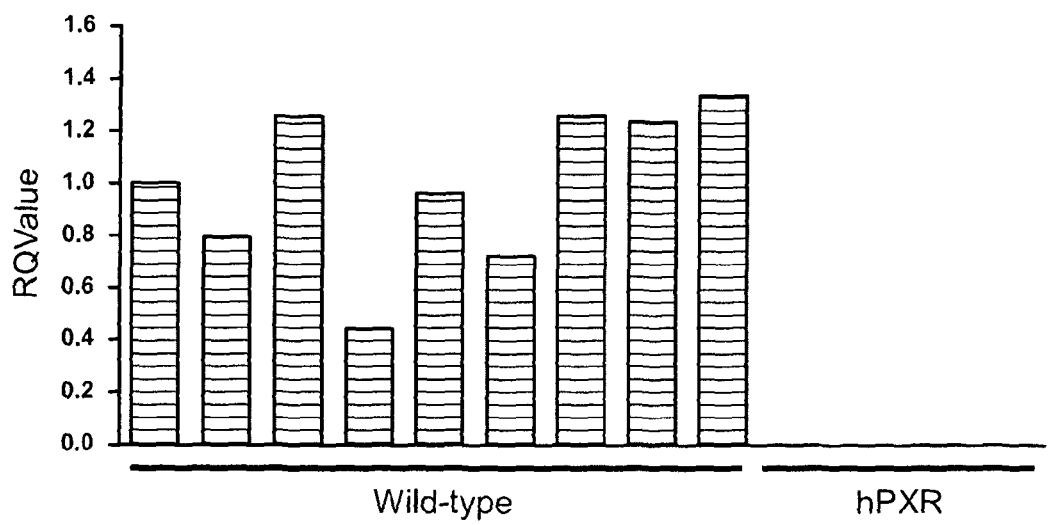
FIG. 16 shows Taqman typing of wild type and transgenic mice. All probes and primers used were pre-optimised TaqMan® Genomic Assay kits, which were purchased from Applied Biosystems. All assays used were inventoried by Applied Biosystems. Shown are the results from TaqMan analysis of liver (A, B) and small intestine (C, D) of nine wild-type and four hPXR mice, using assays specific for the mouse PXR mRNA transcript (A, C) or the human PXR mRNA transcript (B, D)
Figure 16B:
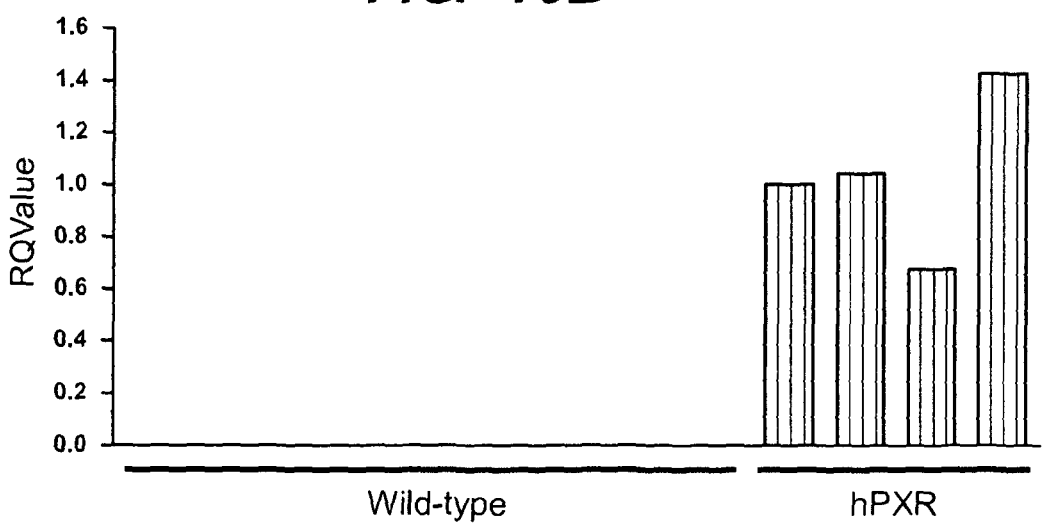
Figure 16C:
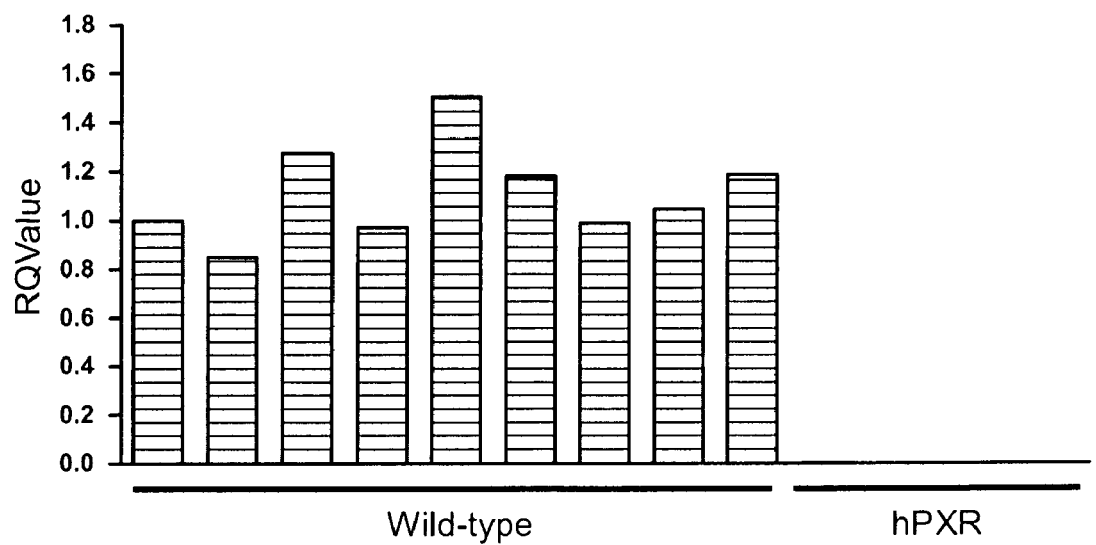
Figure 16D:
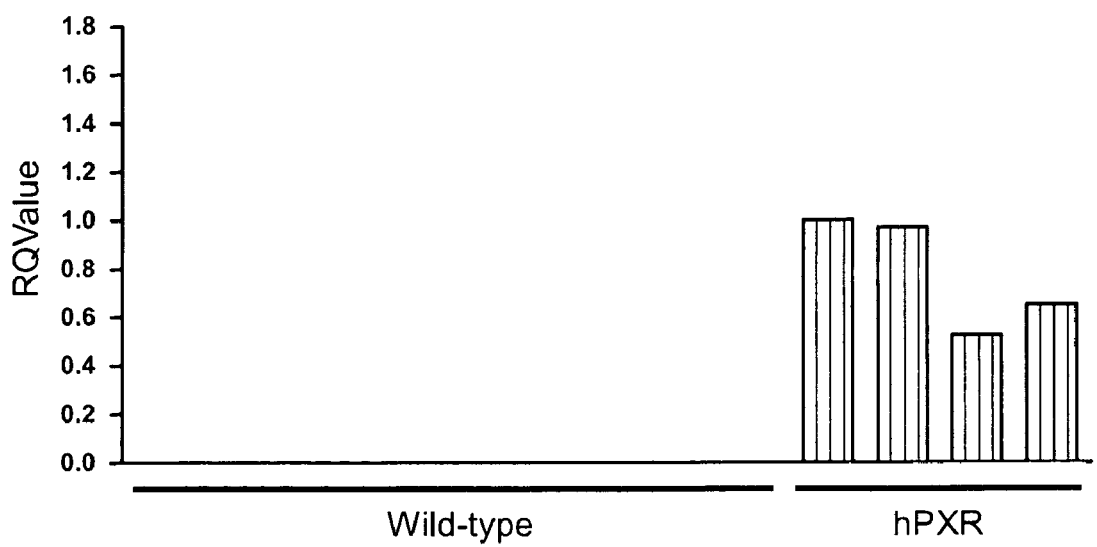

In contrast to existing models, we utilise a "knock-in" approach to replace the endogenous genes by their human orthologues (FIGS. 2 and 3). Therefore the PXR and CAR genes will be kept under their normal genomic context and expression levels and transcript distribution is advantageously physiologically regulated or controlled. As a result of this, the model of the present invention will resemble the human situation more closely than prior art attempts.

Additionally, genomic structures of human genes are at least partially conserved within the construct of the present invention. In the example of PXR, we have used a composite construct of cDNA and genomic sequences (see FIG. 2). Due to the large size of more than 35 kb of the human PXR gene, we kept the intron-exon structure solely between 4 and 6, since most splice variants are observed in this genomic region since it is located within the ligand-binding domain. The relatively small size of the human CAR, which comprises roughly 7 kb from exon 2-9, enabled us to retain the complete genomic structure in our targeting vector (FIG. 3).

The ES cells comprising humanised PXR and/or CAR can be further modified with human genes that regulate drug metabolising enzymes (phase1 and 2) and/or drug transporter proteins. It will be possible to cross the animals cells with humanised PXR/CAR with the HRN mouse below or to create a de novo non-human transgenic animal with all of the aforementioned criteria.

Example 2

The HRN™ Mouse

All P450s require reducing electrons supplied by the enzyme cytochrome P450 reductase (CPR). Deletion of CPR therefore simultaneously inactivates all P450s. While CPR deletion is lethal in the embryo, HRN™ mice use a developmentally regulated conditional CPR deletion targeted to postnatal liver cells. HRN™ mice therefore survive to adulthood and can breed while nevertheless completely lacking hepatic P450-mediated metabolism (Henderson C J et al. J Biol. Chem. 278:13480-6, 2003). They therefore provide a suitable background on which to express human P450 activities in order to achieve P450 humanisation.

Transgenic Mouse Production

An adenoviral vector may be used to introduce the human P450/CPR combination to HRN™ cells. Alternatively, germ line transgenic animals incorporating the same transgenes can be produced. This is achieved by first generating transgenic mice incorporating the selected CYP3A4/CPR humanisation transgenes and then crossbreeding these with HRN™ mice to produce CYP3A4-humanised animals. Production of CYP3A4/CPR transgenic mice is achieved by using targeted transfection of embryonic stem cells and subsequent blastocyst injection. Crossbreeding of CYP3A4/CPR transgenics with HRN™ to produce P450-humanised animals may be used for the production of multi-P450-humanised mice. Alternatively, embryonic stem cells may be produced where the CPR gene is flanked by loxP sites and where expression sequences for targeted human P450(s) and CPR or for human P450-CPR fusion protein(s) have been introduced. Animals derived from such embryonic stem cells may then be crossbred with various animal strains in which cre recombinase is expressed under the control of different promoters to produce offspring P450-humanised in different tissues or under different induction conditions, depending on the tissue specificity or inducibility of the promoter controlling cre recombinase expression.

Humanisation Strategies

In order to establish the optimal method of expressing functional human P450 activities in HRN™ cells, experimental transgenes encoding cytosolic fusion proteins, targeted fusion proteins, targeted CPR with separate cytosolic P450s are compared and evaluated. In each case, the ability of the P450 to interact with the CPR component is determined by expressing these alternatives in appropriate cell culture systems and then testing them in vivo by adenovirus transfection of HRN™ mice.

Example 3

Humanization Projects

Type 1: Expression of Human cDNA from the Corresponding Mouse Promoter

Projects: MDR1-Humanization

Methods: The targeting vectors are constructed with standard molecular cloning procedures. These vectors are designed in such a way, that the cDNA of human MDR1 is fused to the translational start site of the corresponding mouse genes (Mdr1a and Mdr1b). The Mdr1a targeting vector carries an FRT-flanked hygromycin resistance cassette, the Mdr1b targeting vector an F3-flanked neomycin resistance cassette. In both cases the transcripts are terminated by a polyA motif. In case of Mdr1a the targeting event removes the 3'part of exon2, in case of Mdr1b the 3'part of exon2 to exon4 are deleted. See FIGS. 4 and 5.

In two consecutive rounds of standard electroporation in C57BL/6N mouse ES cells both mouse genes are modified due to homologous recombination. Clones from each round of transfection are selected with G418 and hygromycin, respectively, and positive clones are identified by Southern blot analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

Type 2: Expression of a Fusion of Mouse Gene and Human cDNA from the Corresponding Mouse Promoter Projects: MRP2-Humanization Methods: The targeting vector is constructed with standard molecular cloning procedures. The vector is designed in such a way, that the "Leader sequence" of the mouse protein, which is encoded by exon1, will be retained. The human cDNA without sequences from exon1 is introduced into exon2. The original splice sites for mouse intron1 will be retained, so that this construct potentially encodes a fusion protein of amino acids from mouse exon1 and human exon2-32. The transcript is terminated by a polyA motif. The targeting vector carries an FRT-flanked neomycin resistance cassette (see FIG. 6).

The targeting vector is transfected by standard electroporation into C57BL/6N mouse ES cells. Clones are selected with G418 and positive clones are identified by Southern blot analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

Type 3: Expression of a Hybrid of Human cDNA and Genomic Sequences from the Corresponding Mouse Promoter Projects: PXR Humanization Methods: The targeting vector is constructed with standard molecular cloning procedures. The vector is designed in such a way, that a hybrid of human PXR cDNA and genomic sequences is fused to the translational start site of the mouse PXR gene, whereby the mouse Start-ATG is retained. The human PXR sequence contains the cDNA of exon1-4, genomic sequences of intron4, exon5 and intron5 and cDNA of exon6-9. This human PXR sequence is provided herein as SEQ ID NO:1. The transcript is terminated by a polyA motif. The targeting vector carries an FRT-flanked hygromycin resistance cassette and a splice acceptor polyA motif 3' to the selection cassette. Furthermore, att sites have been inserted into mouse intron1 and 3' to the splice acceptor polyA motif, which allow the generation of a PXR knock out by removal of the intermediate sequences with the site-specific Phi-C31 recombinase (see FIG. 7).

The targeting vector is transfected by standard electroporation into C57BL/6N mouse ES cells. Clones are selected with hygromycin and positive clones are identified by Southern blot analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

Confirmation that the Murine PXR Gene has Been Exchanged for the Human Counterpart Humanised mice for PXR have been generated using the above strategy and are phenotypically normal following visual inspection. They have been typed using PCR (see FIG. 15). The mice live to at least 3 months age. Examples include male "30643": DOB Dec. 12, 2004. Remained alive at Apr. 19, 2005. Female "30792": DOB Dec. 19, 2004. Remained alive at Apr. 19, 2005. These mice can be successfully bred:

30643×30792 set up at Feb. 1, 2004
Litter born Feb. 22, 2005—6 pups—weaned Mar. 30, 2005
Litter born at Apr. 6, 2005—7 pups—to be weaned Further typing has been performed using Taqman® analysis (see FIG. 16). This analysis clearly demonstrated the presence of a murine PXR transcript only in the wild type animals and the presence of the human transcript only in the transgenic mouse lines demonstrated that gene exchange had taken place and that the gene construct was being actively transcribed in the correct tissues.

RT-PCR was then performed to confirm the presence of a full-length human PXR transcript in the humanised mice (see FIG. 17). This analysis demonstrated the presence of two transcripts of size 1.3 and 1.1 kilo-bases, indicating that the entire humanised PXR gene had been transcribed. The size of the fragments obtained indicated that the correct, as well as alternative spliced variants were present.

Sequence analysis of the full length transcript confirmed that an open reading frame for the entire PXR mRNA had been produced. The presence of PXR was subsequently confirmed by Western blot analysis using an antibody raised against the murine PXR.

Demonstration that the Human PXR was Functional

In order to demonstrate that the human PXR protein was functional, mice were challenged with PXR-activating compounds including pregnenolone-16a carbonitrile (PCN), dexamethasone, TCPOBOP and rifampicin (Rif). While rifampicin is reported to be a more potent PXR inducer in humans, dexamethasone and PCN are reported to be more potent inducers in mice. Thus, these inducers enable the PXR phenotype of the non-human animals, tissues and cells of the invention to be discriminated.

Dosing solutions were prepared on the day of administration by adding corn oil to the requisite quantity of test substance and stirring to obtain a solution or fine suspension. The concentration of PCN was 10 mg/ml and Rif 2.5 mg/ml of supplied chemical, without any correction for purity. Records of preparation were retained.

Control animals were administered vehicle (corn oil) daily by intraperitoneal injection. The volume of vehicle and solutions of inducing agents administered was 10 ml/kg bodyweight. This route of administration was chosen for consistency with previously published work. Animals received 4 daily doses and were killed approximately 24 hours after the last dose.

Quantification of Cyp3a11, Cyp2b10 and PXR protein in liver microsomes of all mice samples was carried out by SDS-PAGE and Western blotting. To detect murine and human PXR protein, an antibody (RF8) was employed. For the identification of Cyp3a and Cyp2b, anti-cyp2b antibodies were used, (CH32 and CH4, respectively). Results are shown in FIG. 18.

These data demonstrated a protein of the correct molecular weight identified in both the wild type mice and the humanised PXR mice. The molecular weights of the two proteins were shown to be the same, which is consistent with the calculated molecular weight from the predicted amino acid sequence. In addition, it was interesting to note that the level of expression of PXR between the murine and humanised animals was very similar, consistent with the fact that expression is driven off the same promoter.

Analysis for the PXR inducible proteins in the cytochrome P450 Cyp3a gene family demonstrated a marked induction in the humanised PXR mouse (see FIG. 19). Interestingly, the cytochrome P450 Cyp2b10 was not markedly induced by this treatment, demonstrating that the induction was via the PXR protein and not by the alternative transcription factor, constitutive androstane receptor (CAR). In this experiment, Cyp3a11 was also induced by rifampicin in wild type animals. Although rifampicin is reported to exhibit species differences in its ability to interact with PXR, the fact that no differences were observed here could be accounted for by the high dose of compound used.

Enzyme Activity Assays

Figure 20:
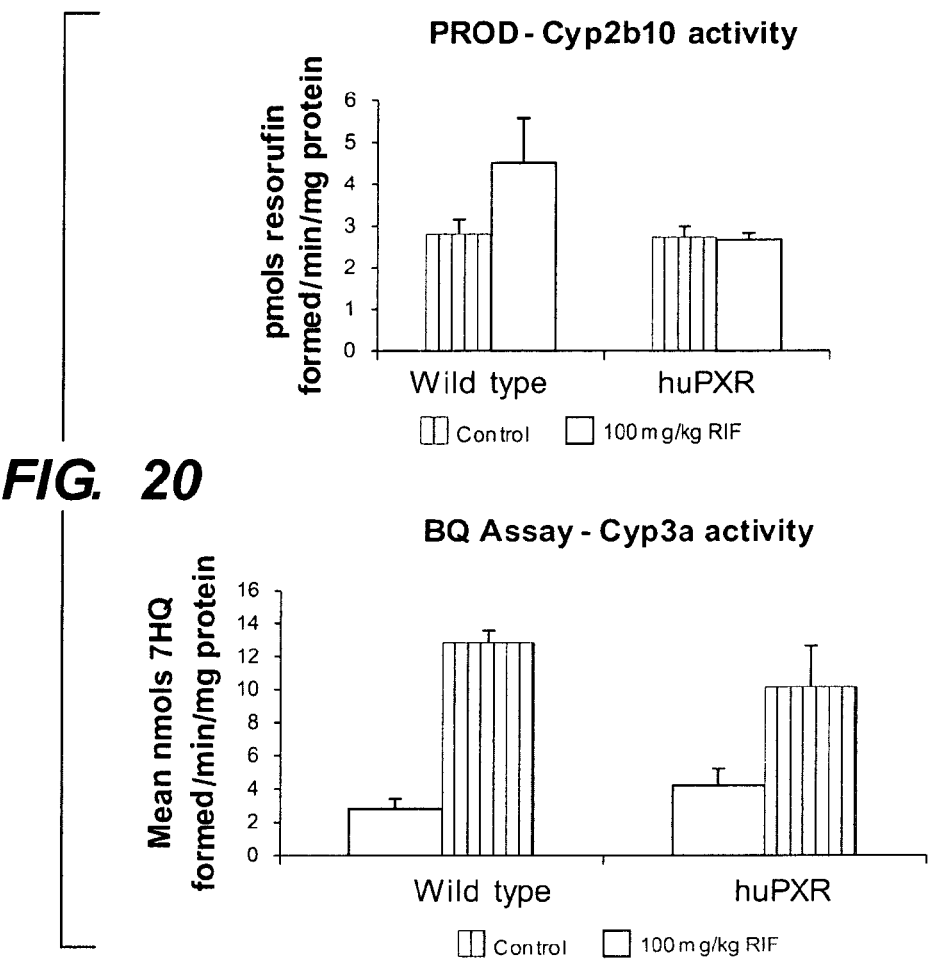

Using enzyme activity assays on liver microsomes, we were able to confirm the Western blot results. The activity in pentoxyresorufin-O-deethylation (PROD) is attributed to expression level of Cyp 2b10 and the activity of 7-benzyloxyquinoline (BQ) is attributed to expression level of Cyp 3a. Enzyme activity data for Cyp3a and Cyp2b induction by rifampicin are shown in FIG. 20.

Induction Study in huPXR Mice Using Low Doses of Rifampicin and TCPOBOP

In order to demonstrate strain differences between wild type and the huPXR mouse, mice were challenged with low doses of rifampicin or TCPOBOP. These compounds were chosen because rifampicin has been reported to be a more efficient inducer of human PXR than murine transcription factor, and TCPOBOP is reported to be a more efficient inducer of cytochrome P450 gene expression in the mouse than in human systems.

The study consisted of 3 animals per group. Control groups consisted of mice treated with either corn oil daily for 4 days or mice administered a single injection of corn oil. The treated mice were dosed with inducing agents as detailed in Table 3.1.

TABLE 3.1

Experimental design for the induction study in huPXR mice using low doses of rifampicin and TCPOBOP

| Mouse Strain | Inducing agent | Dose (mg/kg) | Vehicle | Regimen |
|---|---|---|---|---|
| C57BL/6J | Control I | — | Corn oil | 4 × ip daily |
| huPXR | Control I | — | Corn oil | 4 × ip daily |
| C57BL/6J | RIF | 3 | Corn oil | 4 × ip daily |
| C57BL/6J | RIF | 10 | Corn oil | 4 × ip daily |
| huPXR | RIF | 3 | Corn oil | 4 × ip daily |
| huPXR | RIF | 10 | Corn oil | 4 × ip daily |
| C57BL/6J | Control II | — | Corn oil | Single ip |
| huPXR | Control II | — | Corn oil | Single ip |
| C57BL/6J | TCPOBOP | 0.3 | Corn oil | Single ip |
| C57BL/6J | TCPOBOP | 1 | Corn oil | Single ip |
| huPXR | TCPOBOP | 0.3 | Corn oil | Single ip |
| huPXR | TCPOBOP | 1 | Corn oil | Single ip |

PXR activity was determined by measuring the metabolism of a number of cytochrome P450 substrates which are metabolised to different extents by different cytochrome P450 enzymes. The following assays were performed:
- 7-benzyloxyquinoline (BQ) activity was determined in liver microsomes.
- Testosterone hydroxylase activity was determined in liver microsomes (LMS HPLC-006).
- The specific activities of these reactions was expressed per mg protein as determined using the Lowry assay (LMS Spec-0001).

Figure 21:
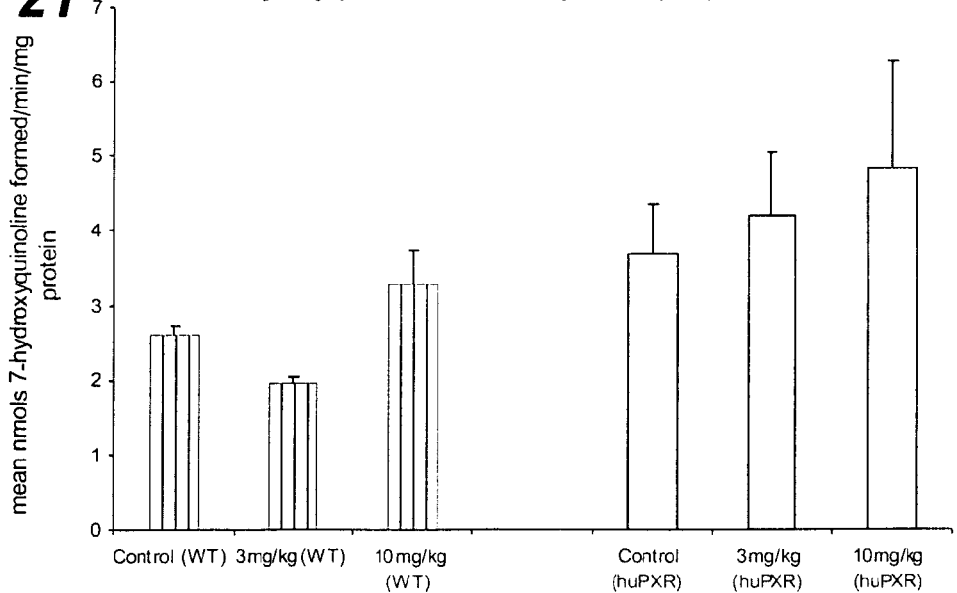
FIG. 21 shows enzyme activity assays in liver microsomes following induction by rifampicin (3 mg/kg and 10 mg/kg)—7-benzyloxyquinoline. Shown are the results from enzyme activity assays on liver microsomes using the activity 7-benzyloxyquinoline.

In the first experiment, 7-benzyloxyquinoline was taken as substrate. In the rifampicin treated animals, in the first instance, there was clearly a difference between the background CYP3A enzyme activity between wild type and humanised PXR mice (FIG. 21). In addition, although this enzyme activity was not inducible by rifampicin, there was a marked difference in enzyme activity between the wild type and humanised PXR animals at a dose of 3 mg/kg.

Figure 22:
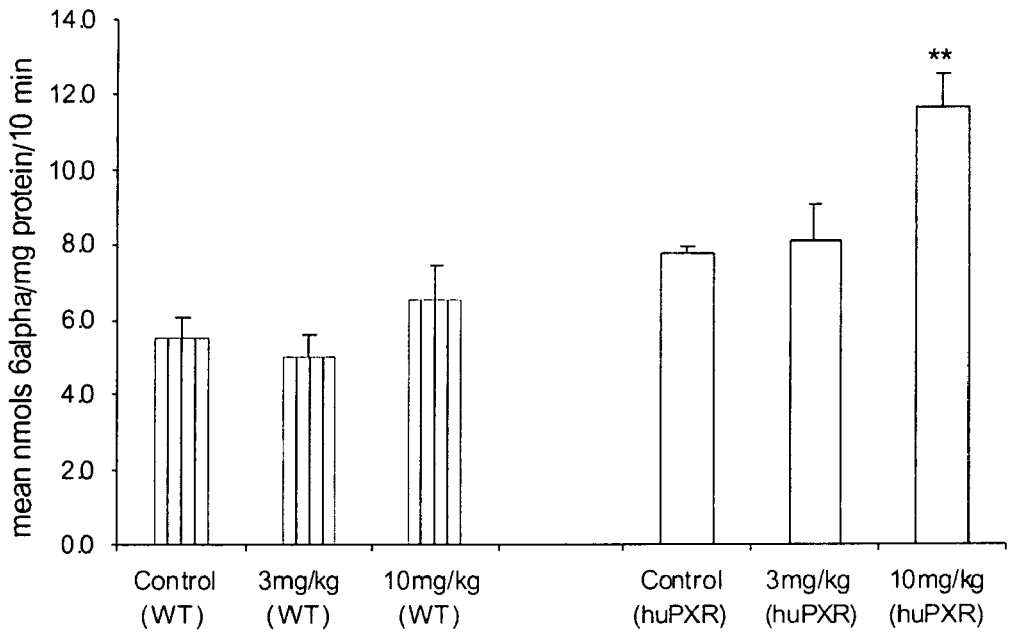
FIG. 22 shows enzyme activity assays in liver microsomes following induction by rifampicin (3 mg/kg and 10 mg/kg)—6-beta-hydroxylation of testosterone ($p<0.01$)

In subsequent experiments, testosterone hydroxylation was measured in liver microsome fractions from wild type and huPXR mice. It was interesting to note that at a dose of 10 mg/kg there was no induction of 6-beta-hydroxylation of testosterone in wild type animals whereas there was a significant induction in the human PXR animals, demonstrating an altered sensitivity of these mice to rifampicin relative to the wild type (FIG. 22).

Figure 23:
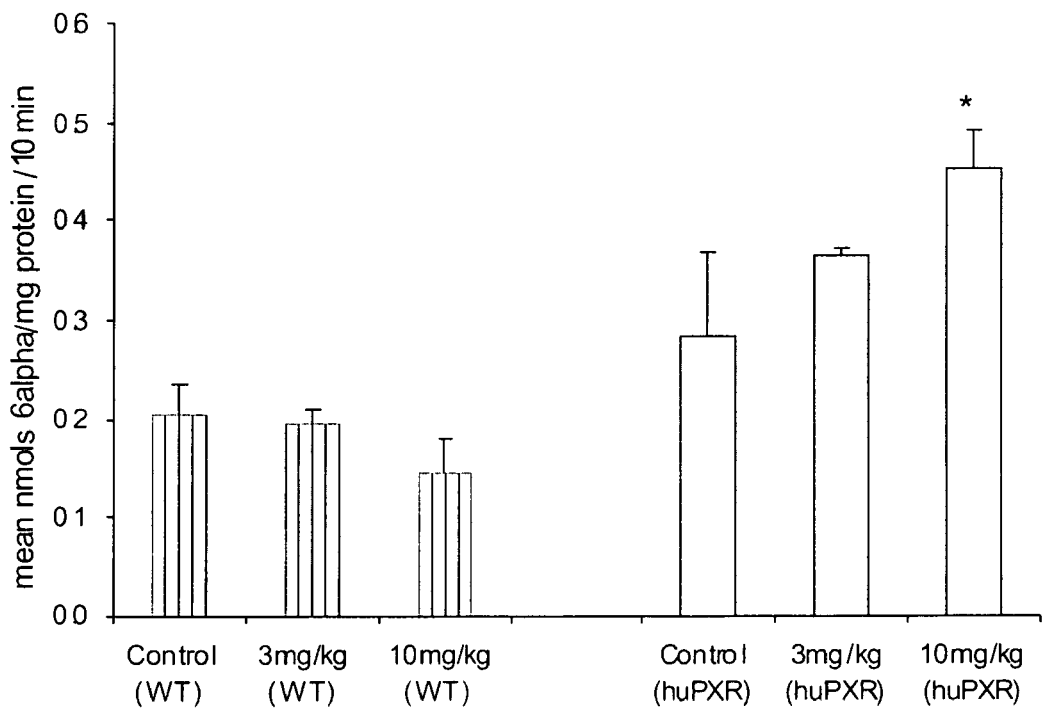
FIG. 23 shows enzyme activity assays in liver microsomes following induction by rifampicin (3 mg/kg and 10 mg/kg)—16-beta-hydroxylation of testosterone ($p<0.05$)

There was a similar finding for the measurement of the 16-beta-hydroxylation of testosterone which, similar to the 7-benzyloxyquinoline demethylation, exhibited higher activity in controls (FIG. 23). Again, this activity was induced in the huPXR animals but not in the wild type. Indeed, the activity was approximately 3-fold in the huPXR mice.

There was a similar finding in the 2-alpha-hydroxylation of testosterone. In addition, the induction of Cyp3a11 by rifampicin demonstrates that the huPXR is functionally active in the huPXR mice.

Figure 24:
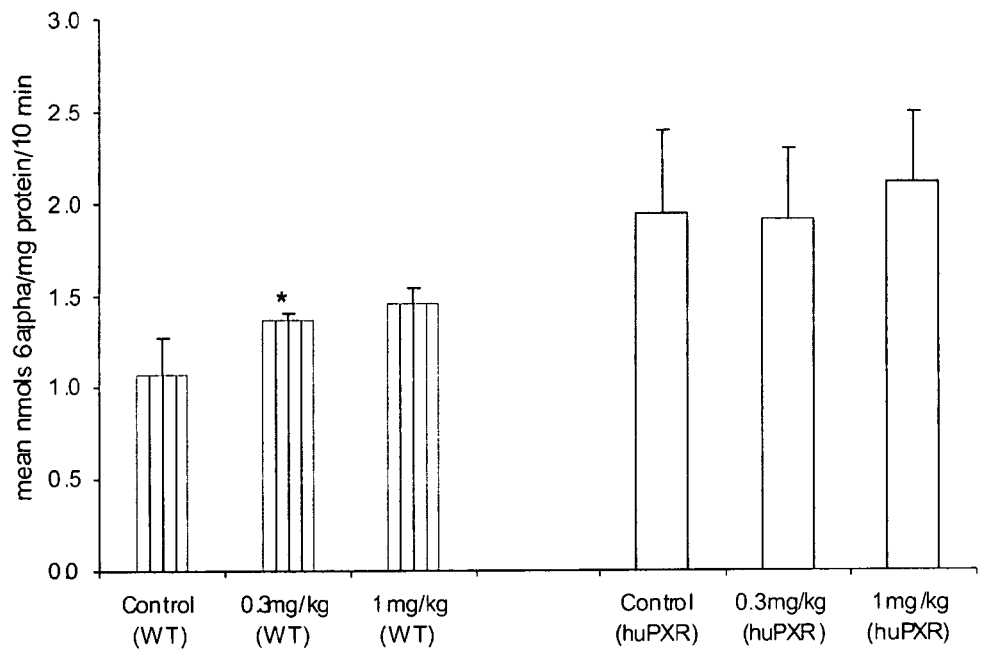
FIG. 24 shows enzyme activity assays in liver microsomes following induction by TCPOBOB (0.3 mg/kg and 1.0 mg/kg)—7-alpha-hydroxylation of testosterone which was constitutively higher in the huPXR animals relative to the wild types.

In experiments using the inducing agent TCPOBOP the hepatic microsomal metabolism of testosterone was also measured. Again clear differences between the wild type and the huPXR animals were observed. In particular, the 7-alpha-hydroxylation of testosterone was constitutively higher in the huPXR animals relative to the wild types (FIG. 24).

Figure 25:
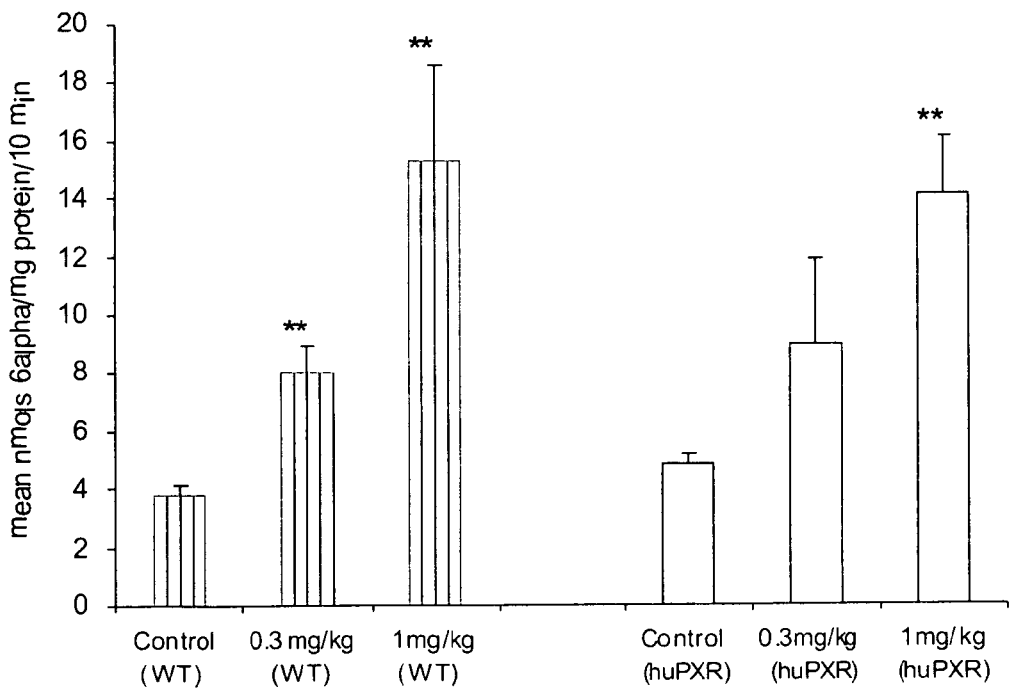
FIG. 25 shows enzyme activity assays in liver microsomes following induction by TCPOBOB (0.3 mg/kg and 1.0 mg/kg)—6-beta-hydroxylation of testosterone.

The 6-beta-hydroxylation of testosterone was inducible in both strains of mouse. Although there were no significant differences between the wild type and huPXR mice, this does demonstrate again that the human PXR is active (FIG. 25).

Figure 26:
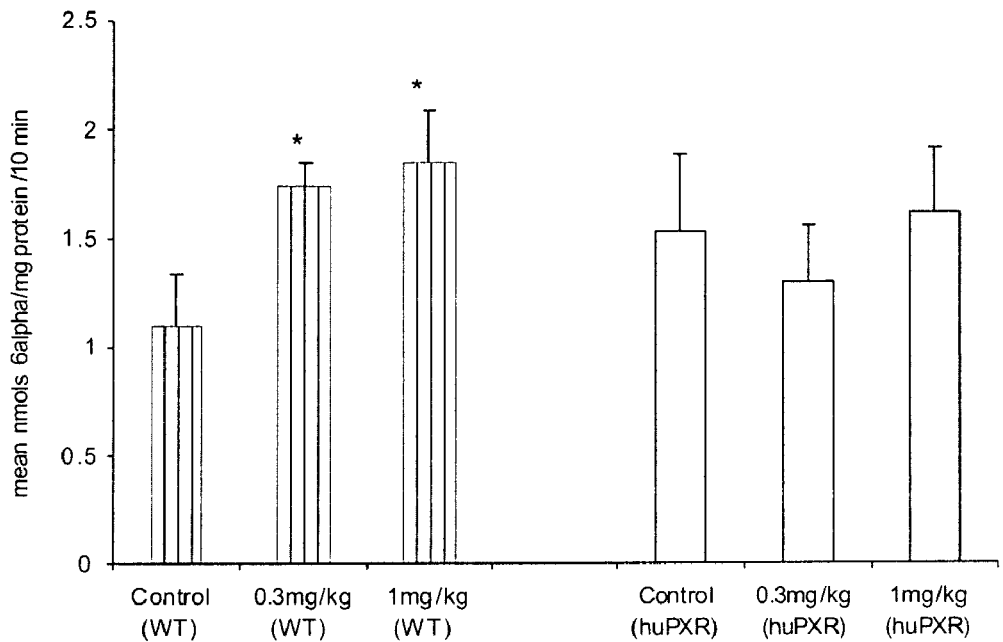
FIG. 26 shows enzyme activity assays in liver microsomes following induction by TCPOBOB (0.3 mg/kg and 1.0 mg/kg)—16-alpha-hydroxylation of testosterone. These demonstrate that this activity was significantly induced in wild type animals ($p<0.05$) but not in huPXR animals.
Figure 27:
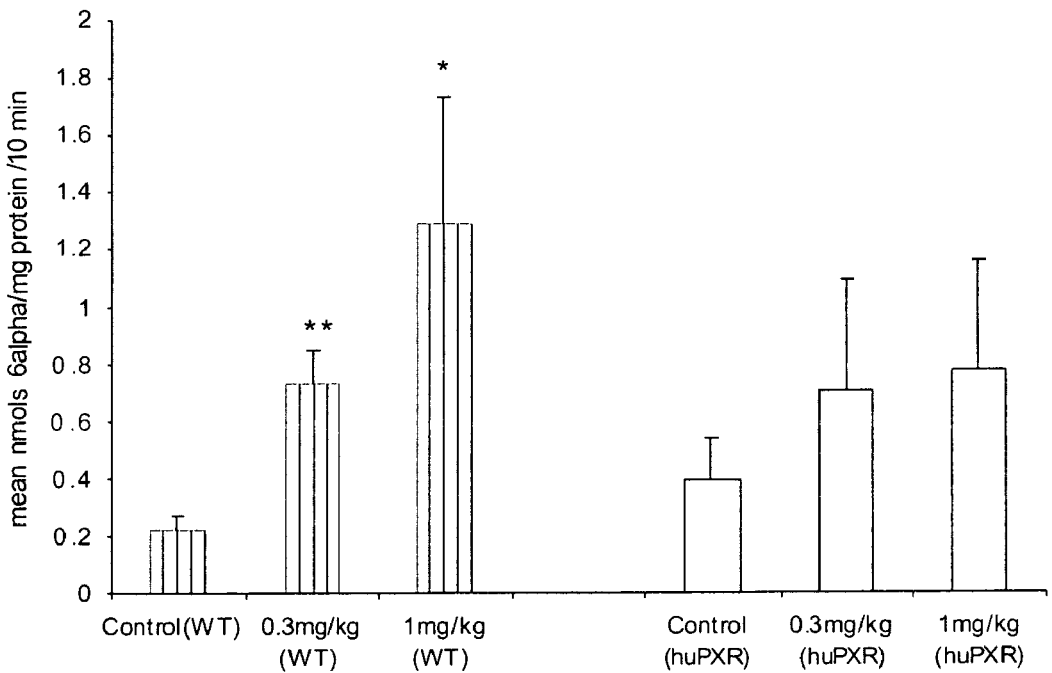
FIG. 27 shows enzyme activity assays in liver microsomes following induction by TCPOBOB (0.3 mg/kg and 1.0 mg/kg)—16-beta-hydroxylation of testosterone. These demonstrate that this activity was much more marked in wild type than in huPXR animals.

Consistent with the strain differences in wild type and human PXR, there were marked differences in the sensitivity of the mouse lines to induction by TCPOBOP. In the case of testosterone 16-alpha-hydroxylation, this activity was significantly induced in wild type animals but not in huPXR animals, and of particular interest was the observation that the induction of testosterone 16-beta-hydroxylation was much more marked in wild type than in huPXR animals (see FIGS. 26 and 27 respectively). Indeed, at a dose of 1 mg/kg, induction of testosterone 16-beta-hydroxylation was approximately 6-fold in wild type animals but only 1.7-fold in the huPXR animals. This again demonstrates a reduced sensitivity of the humanised mice relative to controls.

Further Investigation of Rifampicin Induction Profiles in huPXR Mice

Figure 29:
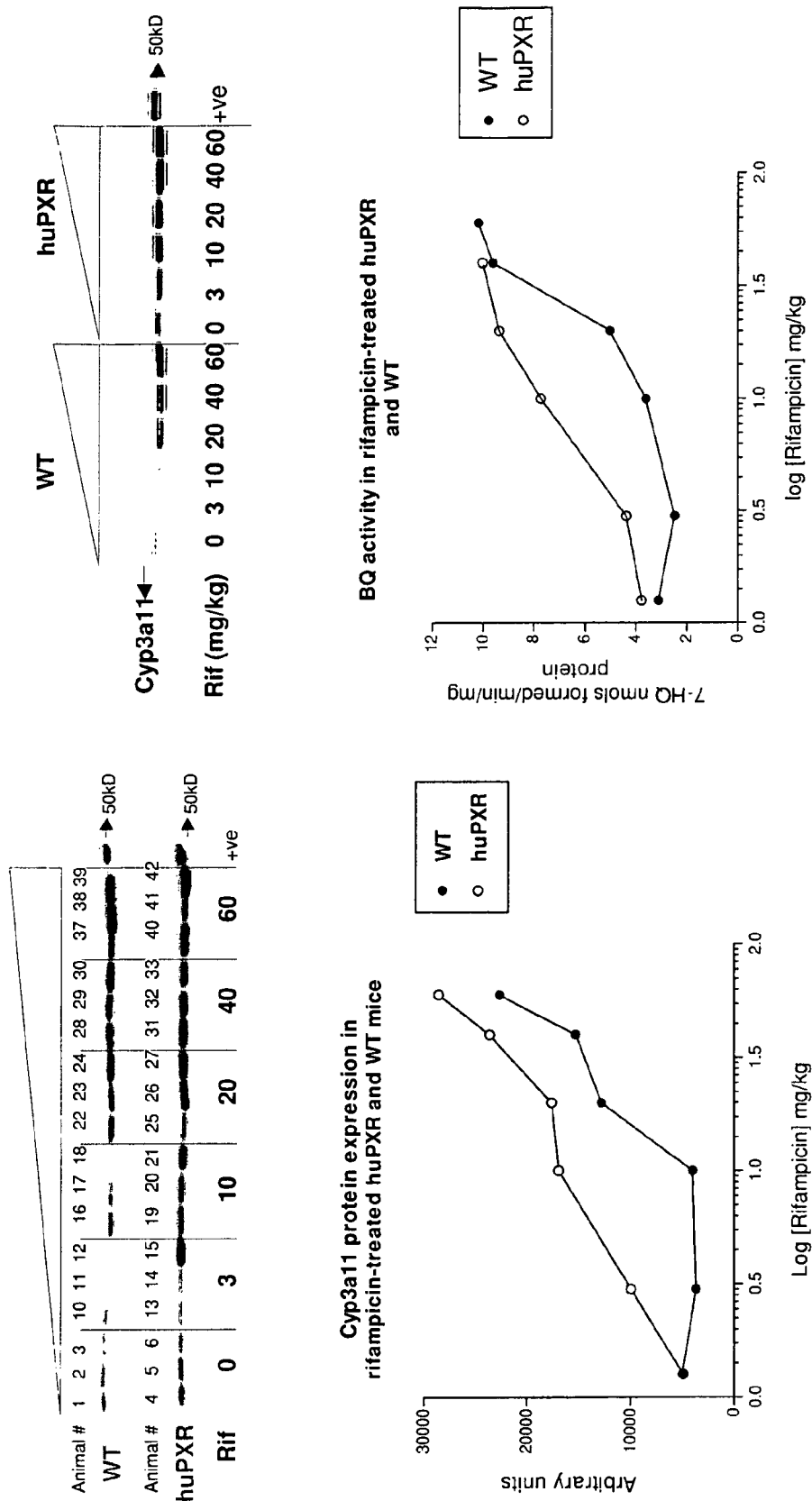
FIG. 29 shows a Cyp3a11 induction profile in response to rifampicin treatment in wild-type and huPXR mice.

The response of huPXR mice to administration of rifampicin (Rif) was further compared to wild type mice in an induction study. Increasing amounts of rifampicin (0, 3, 10, 20, 40, 60 mg/kg mouse body weight) were administered to wild-type and huPXR mice (FIG. 29). For each dosage, observations were made in triplicate, i.e., each different dose was administered to three animals.

Expression of Cyp3a11 was quantified by SDS-PAGE followed by Western blotting and densitometric quantification (FIG. 29). A clear difference was observed between huPXR and wild-type mice. Induction of the expression of the Cyp3a11 protein clearly began to increase at lower rifampicin doses in huPXR mice than in the wild-type mice.

This result was consistent with measurements of BQ activity (an assay for Cyp3a11) in the rifampicin-treated huPXR and wild-type mice: in the BQ assay the amount of 7-HQ product formed in huPXR mice increased more rapidly with the increasing rifampicin dose than in wild-type mice (FIG. 29).

These observations with rifampicin are consistent with successful humanisation of Cyp3a11 induction in the huPXR mice.

Investigation of Dexamethasone Induction Profiles in huPXR Mice

The response of huPXR mice to administration of dexamethasone was evaluated in comparison to wild-type mice in an induction study. Increasing amounts of dexamethasone (0, 1, 3, 10 mg/kg mouse body weight) were administered to wild-type and huPXR mice (FIG. 30).

Figure 30:
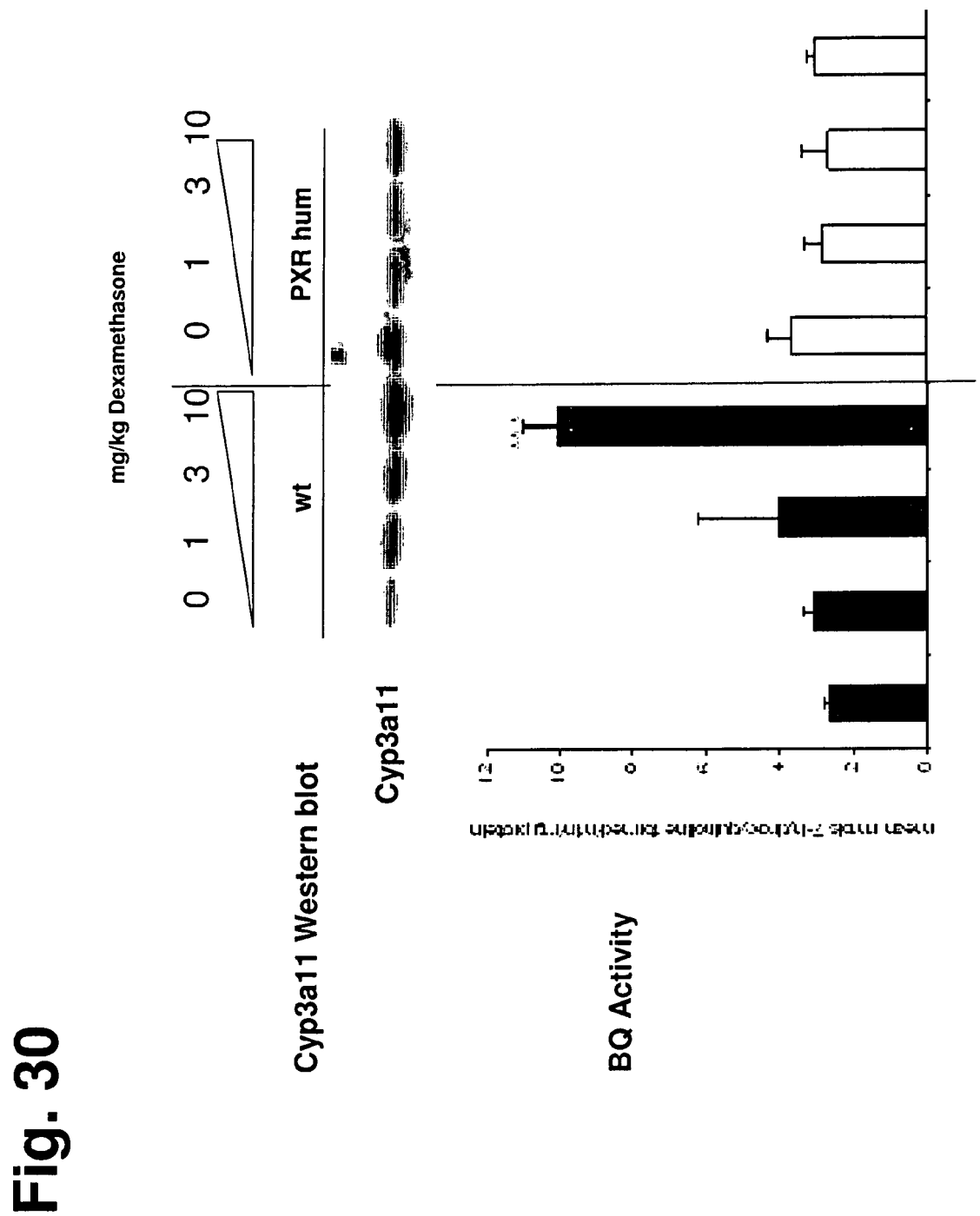
FIG. 30 shows a Cyp3a11 induction profile in response to dexamethasone treatment in wild-type and huPXR mice.

Expression of Cyp3a11 was measured by SDS-PAGE followed by Western blotting (FIG. 30). A clear difference was observed between huPXR and wild-type mice. Cyp3a11 expression was induced by increasing amounts of dexamethasone only in the wild-type mouse (i.e. not in the huPXR mouse).

This result is consistent with measurements of BQ activity (an assay for Cyp3a11) in the dexamethasone-treated huPXR and wild-type mice. In the BQ assay the amount of 7-HQ product formed in huPXR mice increased with the dexamethasone dose only in wild-type mice, not in huPXR mice (FIG. 30).

Together with the induction profiles obtained with rifampicin (see above), these results further confirm that PXR humanisation was achieved in the huPXR mice.

This is the first report of a mouse model where the human PXR gene has been exchanged for the endogenous murine protein. The advantages of such a model relative to other PXR humanised mice lie in the fact that:—

- The construct used allows the studies to be undertaken to understand the role of alternative splicing of PXR in controlling its level of expression.
- Use of the endogenous mouse promoter PXR is expressed in all tissues in a similar fashion to those of the endogenous gene.
- The level of PXR expression seems to be very similar to the endogenous gene, therefore problems with potential over/under expression are reduced.
- The currently available humanised PXR models use the albumin promoter to drive human PXR which has been crossed into a PXR null background. Therefore, PXR is expressed at very high levels in this model and there is no PXR in any tissue other than the liver. This severely compromises the use of this model to understand the role of hPXR in controlling gene expression in the GI tract or at the blood brain barrier or, indeed, in any other tissue.

Humanised PXR mice have a number of utilities. For example, such mice can be used to understand the role of human PXR in the control of gene expression in any tissue in the mouse. They can also be used to evaluate whether drugs in development or environmental chemicals have the capacity to modulate human PXR functions in a manner which may be beneficial or deleterious. The model also allows studies into understanding the role of human PXR in mediating the potential toxic effects of drugs or chemicals which may result from perturbations in, for example, bile acid homeostasis and therefore their relevance to man. The model can also be used to evaluate chemicals that may be either antagonistic or agonistic to this signalling pathway.

The koPXR Mouse

Figure 31:
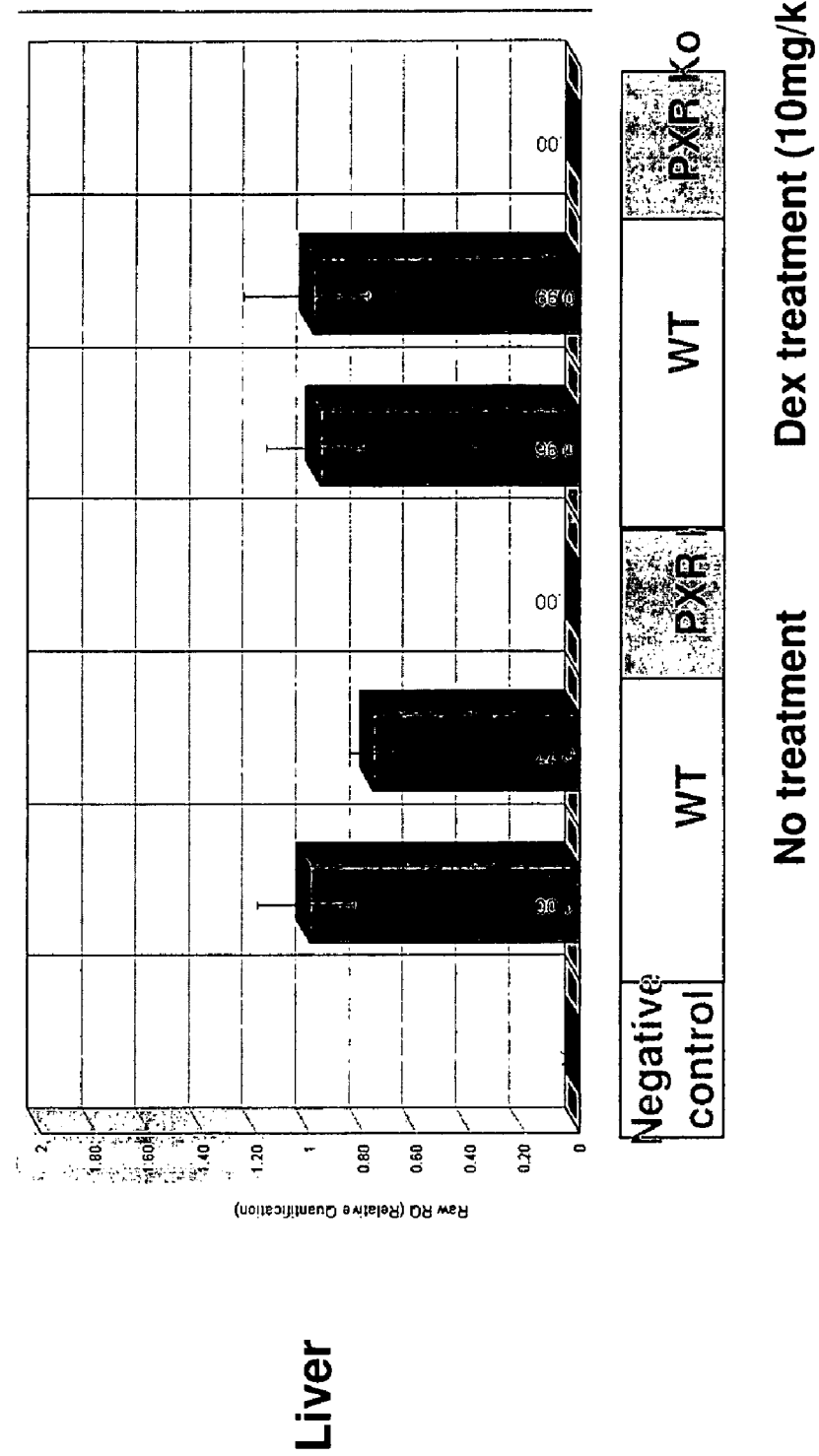
FIG. 31 shows the results of TaqMan® analysis of PXR mRNA in the livers of wild-type and koPXR mice.

TaqMan® analysis of PXR mRNA in wild-type and koPXR mice, both in the absence of any PXR-inducing drug and following administration of 10 mg/kg dexamethasone, confirmed that expression of PXR mRNA was completely lost in the koPXR mouse (FIG. 31).

Further Validation of the huPXR and koPXR Lines

The inventors have performed numerous further experiments to confirm the functional validation of the huPXR and koPXR mice.

Effects of Rifampicin in huPXR, koPXR and Wild-Type Lines

Upon administration of 60 mg rifampicin per kg body weight to wild-type, huPXR or koPXR mice, expression of Cyp3a11 was increased in both wild-type and huPXR, but not in koPXR mice. Experiments were conducted in triplicate. Cyp3a11 expression levels were measured by SDS-PAGE followed by Western blotting. Both pooled and individualized results of the Western blotting experiments are shown in FIG. 32.

Figure 32:
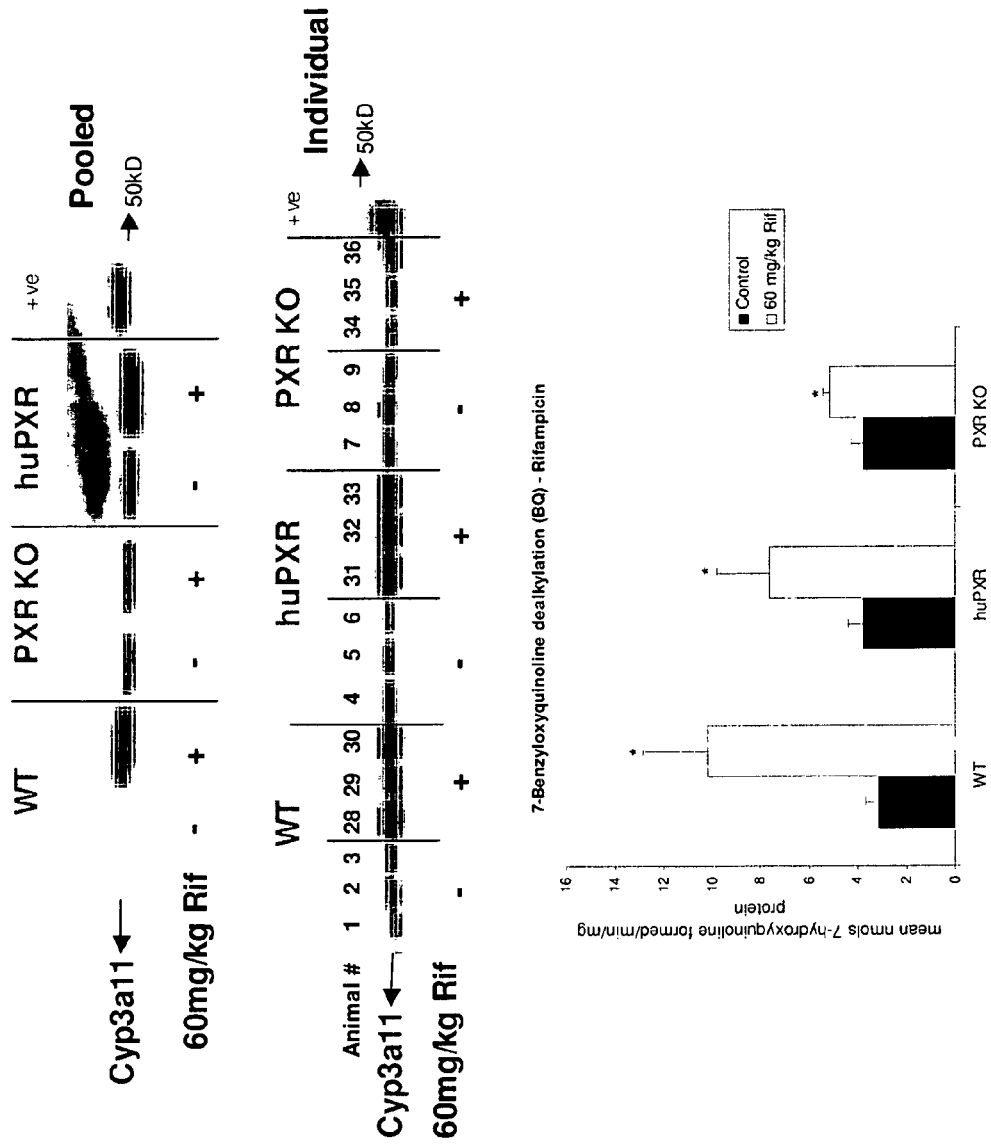
FIG. 32 shows effects of rifampicin administration on Cyp3a11 expression and activity in wild-type, huPXR or koPXR mice.

These observations were consistent with the results of the BQ dealkylation assay, which was carried out following rifampicin treatment in parallel to the Western blotting experiments and showed corresponding marked differences between the wild-type, huPXR and koPXR mice (FIG. 32). In the BQ assay, rifampicin administration led to only minimal 7-hydroxyquinoline formation in the koPXR (PXR KO) strain, and intermediate 7-hydroxyquinoline formation in the huPXR. BQ dealkylation was induced more strongly in the wild-type than in huPXR or koPXR. These results illustrate how differences in Cyp3a11 induction profiles between wild-type, huPXR and koPXR mice are more readily identifiable at lower rifampicin doses (see FIG. 30).

Figure 33:
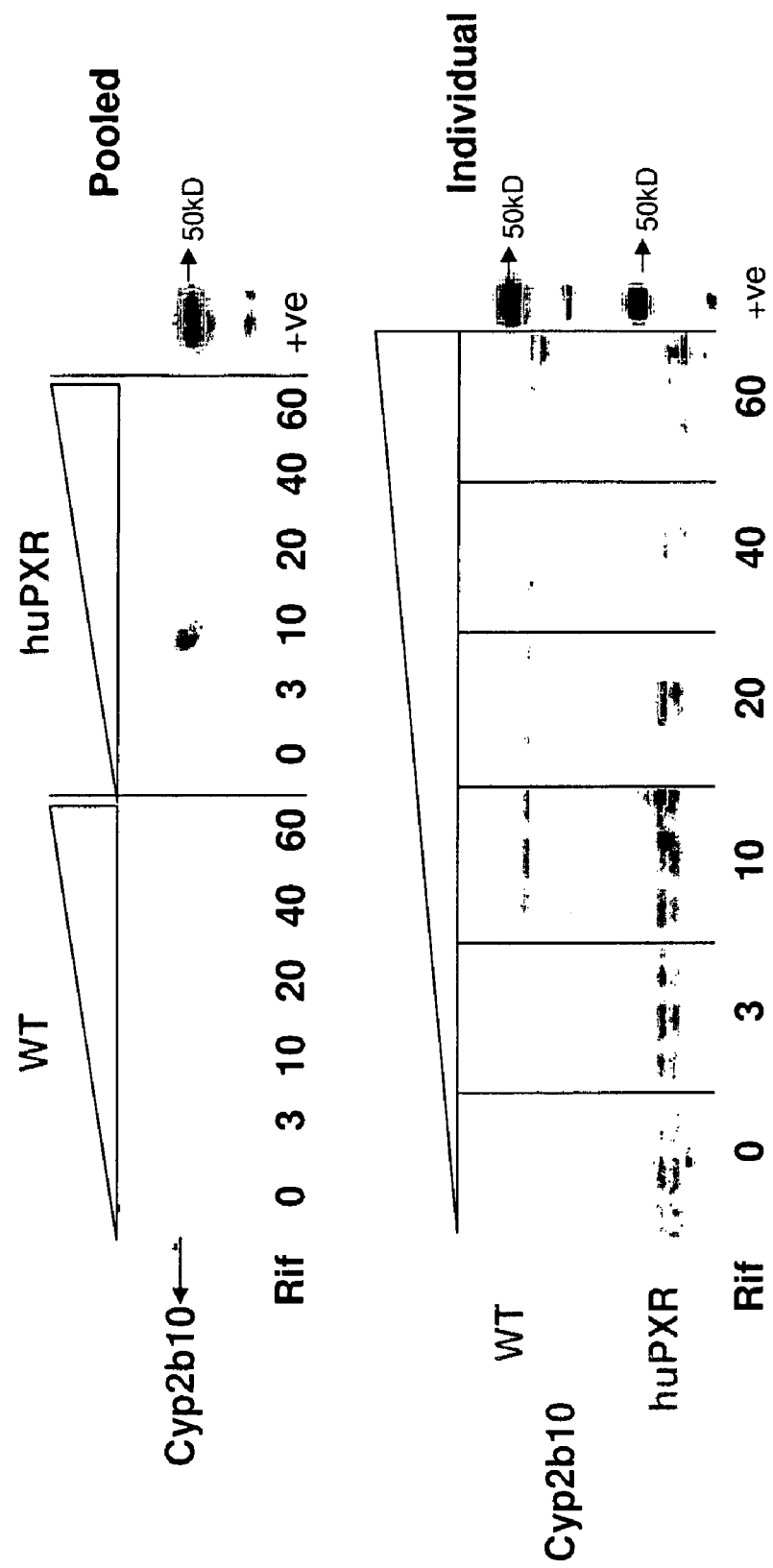
FIG. 33 shows that rifampicin does not induce Cyp2b10 expression in wild-type and huPXR mice.

In contrast to the above observations relating to Cyp3a11, treatment with rifampicin did not induce expression or activity of Cyp2b10 in either wild-type or huPXR mice (FIG. 33).

Effects of Dexamethasone in huPXR, koPXR and Wild-Type Lines

Upon administration of 60 mg dexamethasone (Dex) per kg body weight to wild-type, huPXR or koPXR mice, expression of Cyp3a11 was substantially increased in wild-type mice, somewhat less increased in huPXR mice, and only marginally increased in koPXR mice. Experiments were conducted in triplicate. Cyp3a11 expression levels were measured by SDS-PAGE followed by Western blotting. Both pooled and individualized results of the Western blotting experiments are shown in FIG. 34.

Figure 35:
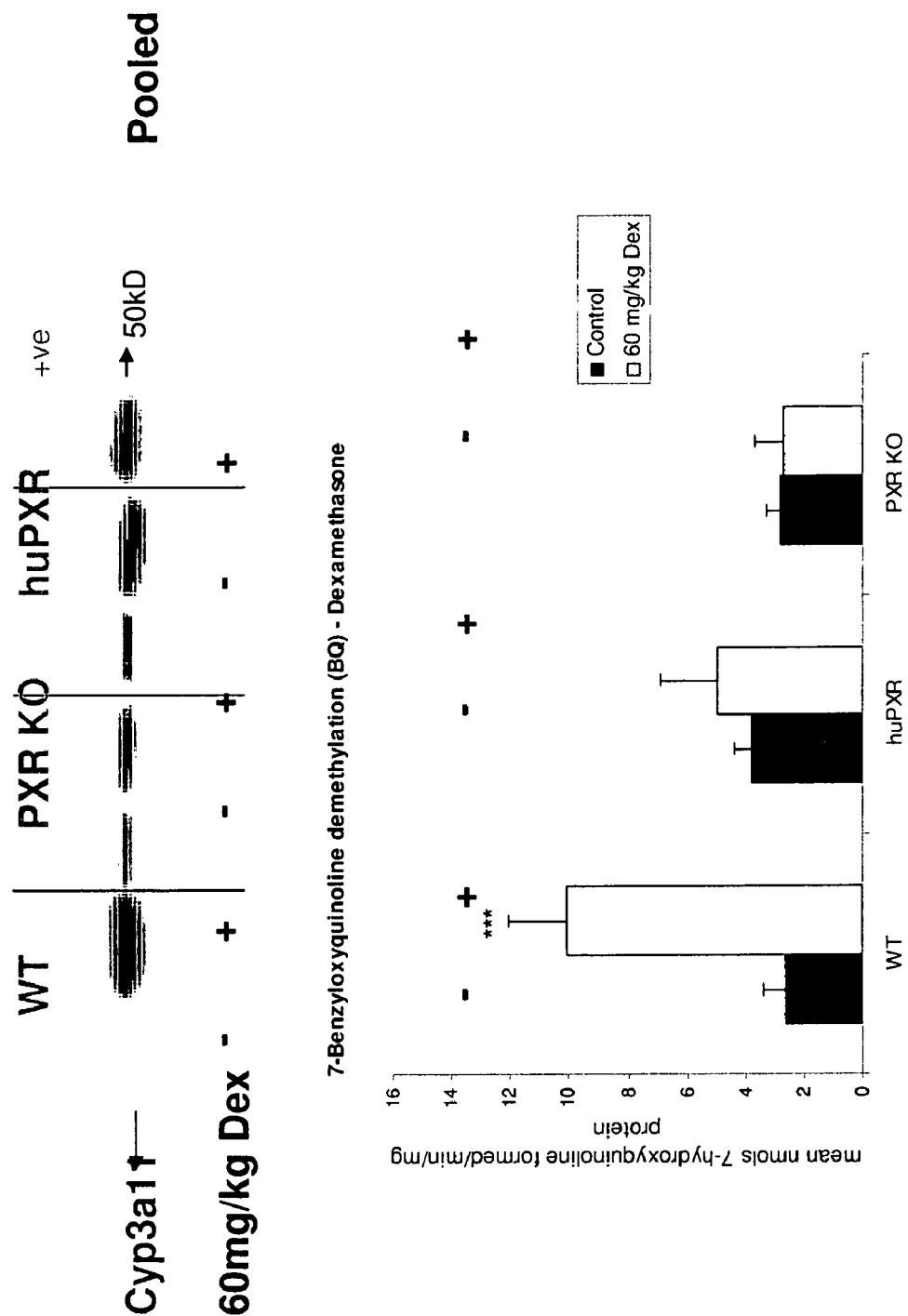
FIG. 35 shows effects of dexamethasone administration on Cyp3a11 expression and activity in wild-type, koPXR and huPXR mice.

These observations were consistent with the results of the BQ dealkylation assay, which was carried out following dexamethasone treatment in parallel to the Western blotting experiments and showed corresponding marked differences between the wild-type, huPXR and PXR mice (FIG. 34). In the BQ assay, upon dexamethasone administration, no 7-hydroxyquinoline formation was observed in the koPXR (PXR KO) strain, and intermediate 7-hydroxyquinoline formation was observed in the huPXR strain. Dexamethasone most strongly induced BQ dealkylation in the wild-type. These results were confirmed in an independent repeat experiment (FIG. 35).

Western blotting revealed that Cyp2b10 is induced following dexamethasone administration (60 mg/kg) in wild-type, huPXR and koPXR mice (FIG. 34, showing both pooled and individualised results), and corresponding results were obtained in the PROD activity assay (FIG. 34).

Hepatotoxicity Assessment in huPXR, koPXR and Wild-Type Mice

Figure 36:
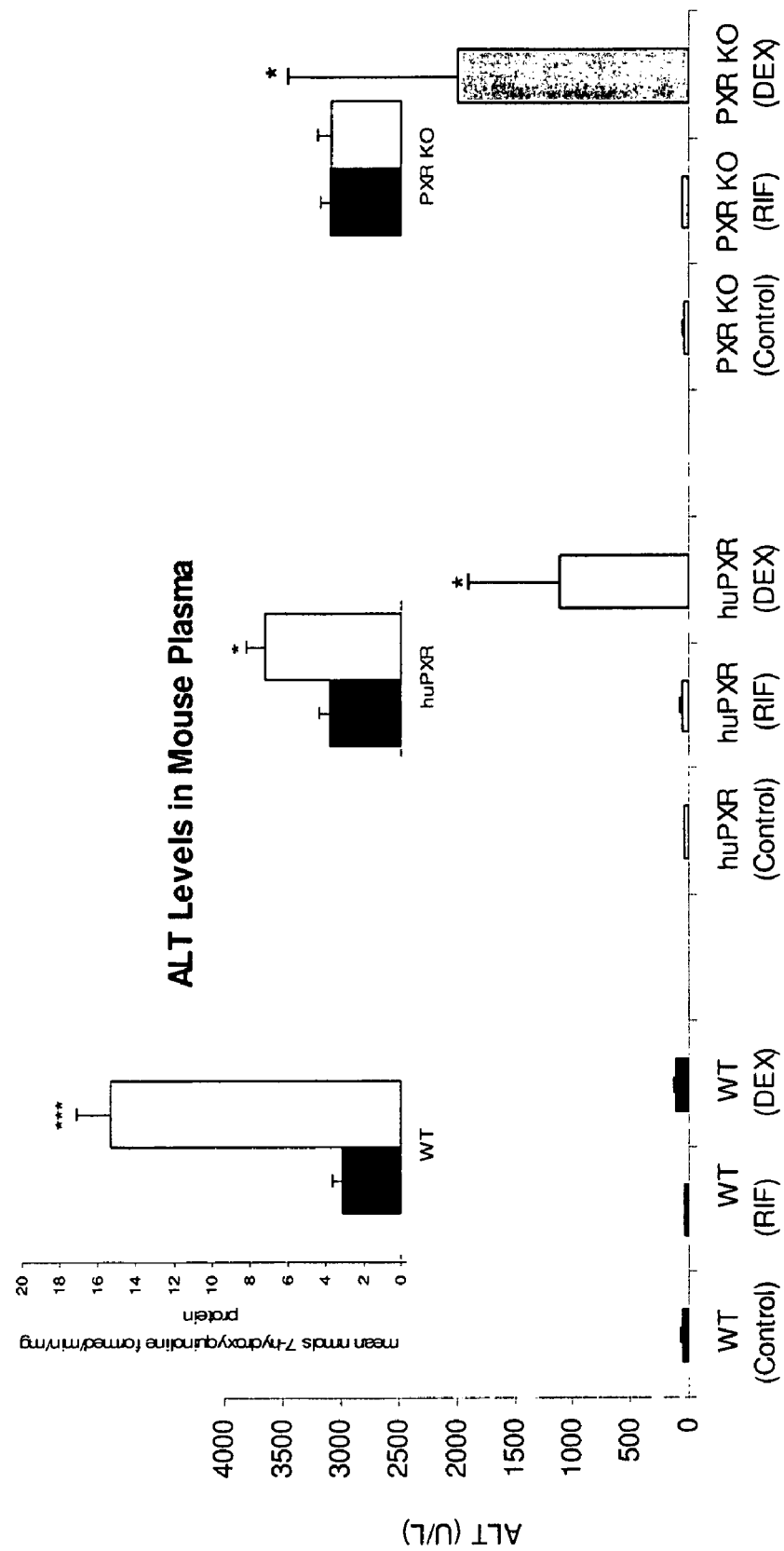
FIG. 36 shows species-specific differences in dexamethasone mediated hepatotoxicity in huPXR and koPXR mice.

Following administration of either rifampicin or dexamethasone, evaluation of indicators of hepatotoxicity revealed species-specific differences. Following administration of dexamethasone, alanine aminotransferase (ALT) levels in mouse plasma were increased about 22-fold in huPXR mice and about 40-fold in koPXR mice, whereas no increase was observed in wild-type mice (FIG. 36). It is possible that these results arise from hepatotoxic effects caused by the absence of murine PXR-mediated metabolism of dexamethasone in koPXR and huPXR. One dexamethasone-treated huPXR mouse died prior to termination of the experiment. In contrast, rifampicin treatment led to no increase in ALT levels (FIG. 36).

In FIG. 36, the results of the BQ demethylation activity assay obtained at the same dosage of dexamethasone are shown for comparison (black bars: untreated control; white bars: 60 mg/kg dexamethasone).

Figure 37:
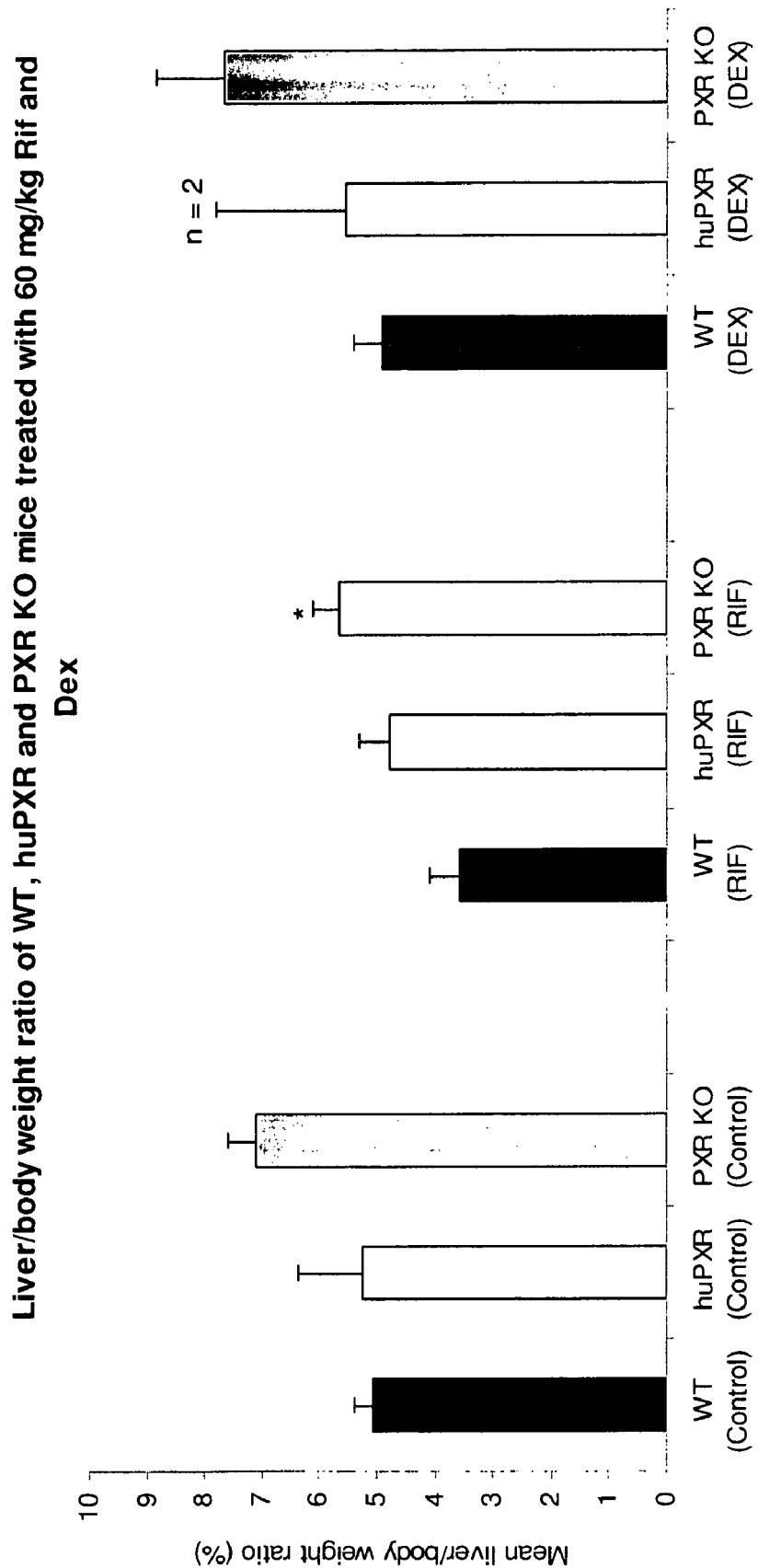
FIG. 37 shows the liver/body weight ratios of wild-type, huPXR and koPXR mice following administration of either 60 mg/kg rifampicin or dexamethasone.

Liver/body weight ratios of wild-type, huPXR and koPXR mice were measured following administration of either rifampicin or dexamethasone. In each case, the ratio was greatest for the koPXR strain (FIG. 37).

FIG. 38 provides a summary of the effects of rifampicin and dexamethasone (each at 60 mg/kg) on Cyp3a11 and Cyp2b10 expression, in wild-type, huPXR and koPXR mice.

Type 4: Expression of a Human Genomic Sequence from the Corresponding Mouse Promoter Projects: CAR Humanization Methods: The targeting vector is constructed with standard molecular cloning procedures. The vector is designed in such a way, that the genomic human CAR sequence is fused to the translational start site of the mouse CAR gene. The human CAR sequence contains all genomic sequences of exons 1-9, except the 5' and 3'UTRs, which are retained from the mouse genome. This human CAR sequence is provided herein as SEQ ID NO:2. All other parts of the coding sequences of the mouse CAR gene will be deleted. The transcript is terminated by a polyA motif. The targeting vector carries an FRT-flanked neomycin resistance cassette. Furthermore, att sites have been inserted into human intron2 and 3' to the selection marker, which allow the generation of a CAR knock out by removal of the intermediate sequences with the site-specific Phi-C31 recombinase (see FIG. 8).

The targeting vector is transfected by standard electroporation into PXR humanized C57BL/6N mouse ES cells. Clones are selected with hygromycin and positive clones are identified by Southern blot analysis. Selected clones are expanded, injected into BALBc-blastocysts and transferred into foster mothers according to standard operating procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

The targeting vector is transfected by standard electroporation into C57BL/6N mouse ES cells. Clones are selected with hygromycin and positive clones are identified by Southern blot analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

The koCAR Mouse

As mentioned above, the insertion of att sites into mouse intron1 (attB53) and 3' to the splice acceptor polyA motif (attP50), allows the generation of a CAR knock-out mouse, referred to herein interchangeably as koCAR or CAR KO, etc. To generate this knock-out, sequences between the att sites were removed using the site-specific Phi-C31 recombinase (see FIG. 65).

TaqMan® analysis of CAR mRNA in the livers and intestines of untreated wild-type and koCAR mice confirmed that basal expression of CAR mRNA was completely lost in the koCAR mouse (FIG. 39).

Functional Validation of koPXR and koCAR Mice

Liver/body weight ratios of wild type, koCAR and koPXR mice are shown in FIG. 40, for untreated animals, and animals treated with dexamethasone or phenobarbital. For the same animals, plasma levels of alanine aminotransferase (ALT), alkaline phosphatase (ALP) and aspartate aminotransferase (AST) were also measured (see FIG. 40). No hepatotoxicity was detected in the wild-type, koPXR or koCAR mice at the doses of dexamethasone and phenobarbital tested. Both compounds were administered at 40 mg/kg.

Figure 41:
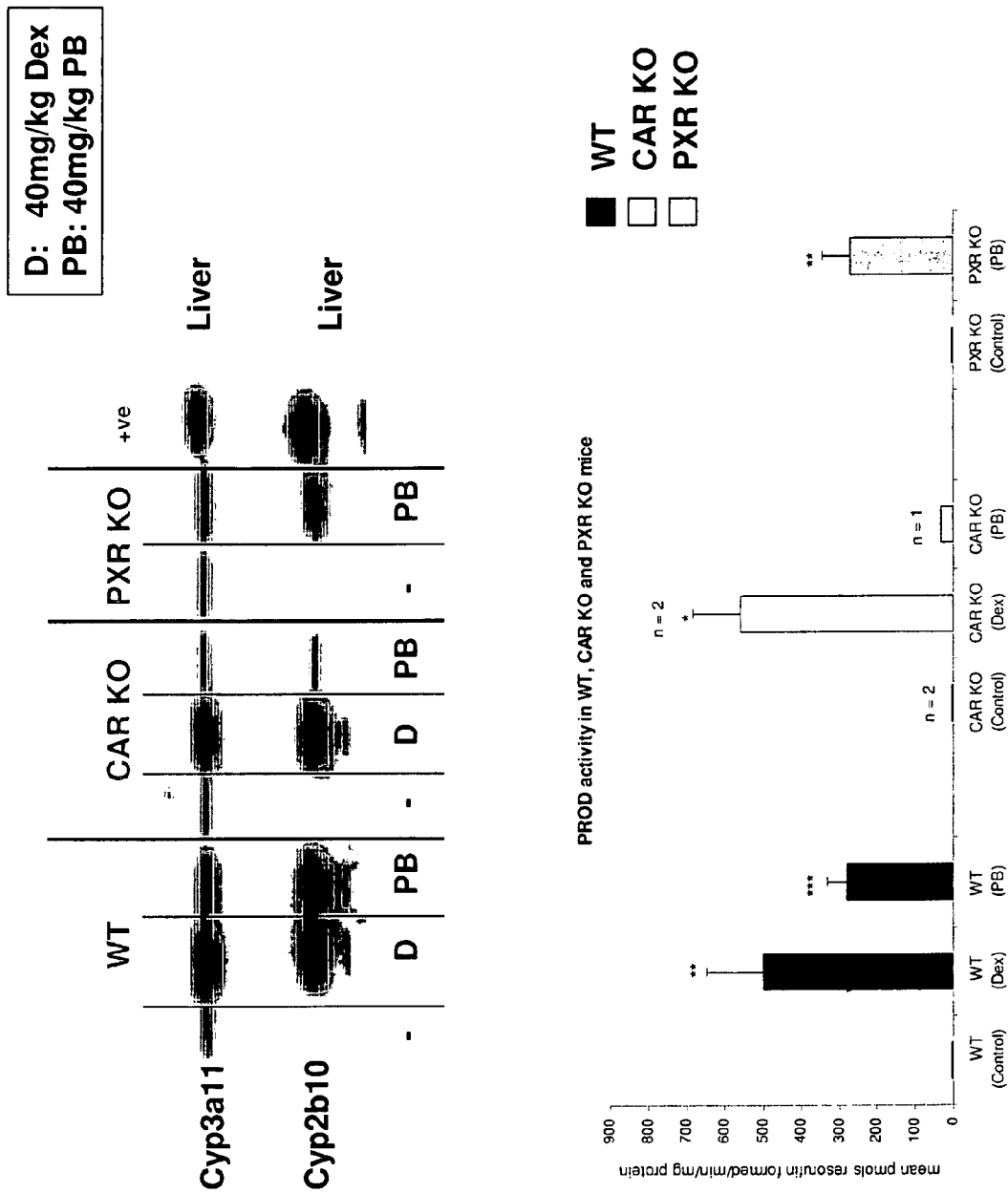
FIG. 41 shows effects of dexamethasone and phenobarbital administration on the livers of koCAR and koPXR mice.

Cyp3a11 and Cyp2b10 expression in the liver of wild-type, koCAR and koPXR mice was analysed by Western blotting for untreated animals and animals treated with dexamethasone (40 mg/kg) or phenobarbital (40 mg/kg). Pentoxyresurfin-O-deethylation (PROD) activity, which is reflective of Cyp2b10 expression and CAR activity, was analysed in the same animals. The results of these analyses are shown in FIG. 41. In koCAR mice, phenobarbital-induced expression of both Cyp3a11 and Cyp2b10 was significantly reduced. However, expression of both Cyp3a11 and Cyp2b10 was still induced by dexamethasone treatment in koCAR mice, as was PROD activity.

Figure 42:
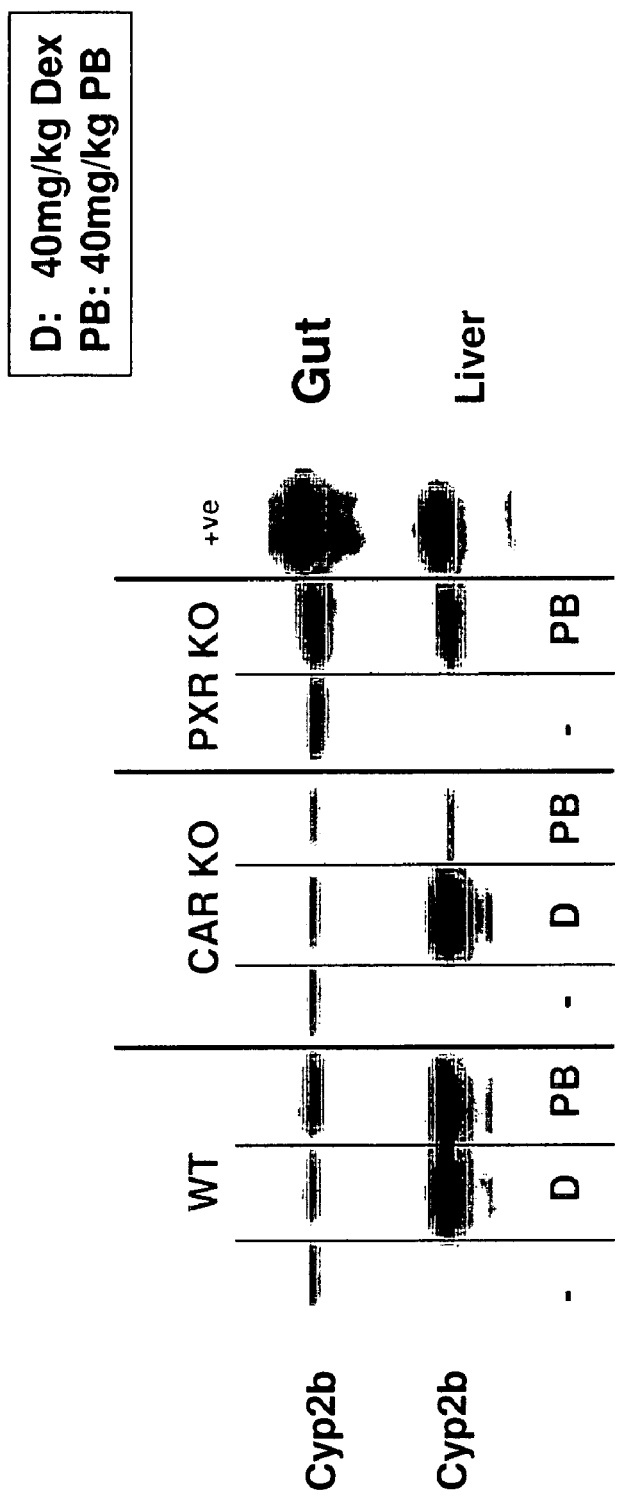
FIG. 42 shows effects of dexamethasone and phenobarbital administration on the guts and livers of koCAR and koPXR mice.

Cyp2b10 expression in the gut of wild-type, koCAR and koPXR mice was also analysed by Western blotting for untreated animals and animals treated with dexamethasone (40 mg/kg) or PB (40 mg/kg). These results are compared with the results of the equivalent study in liver in FIG. 42. The induction of Cyp2l0 expression by dexamethasone observed in liver of koCAR mice was not observed in gut tissue.

Figure 43:
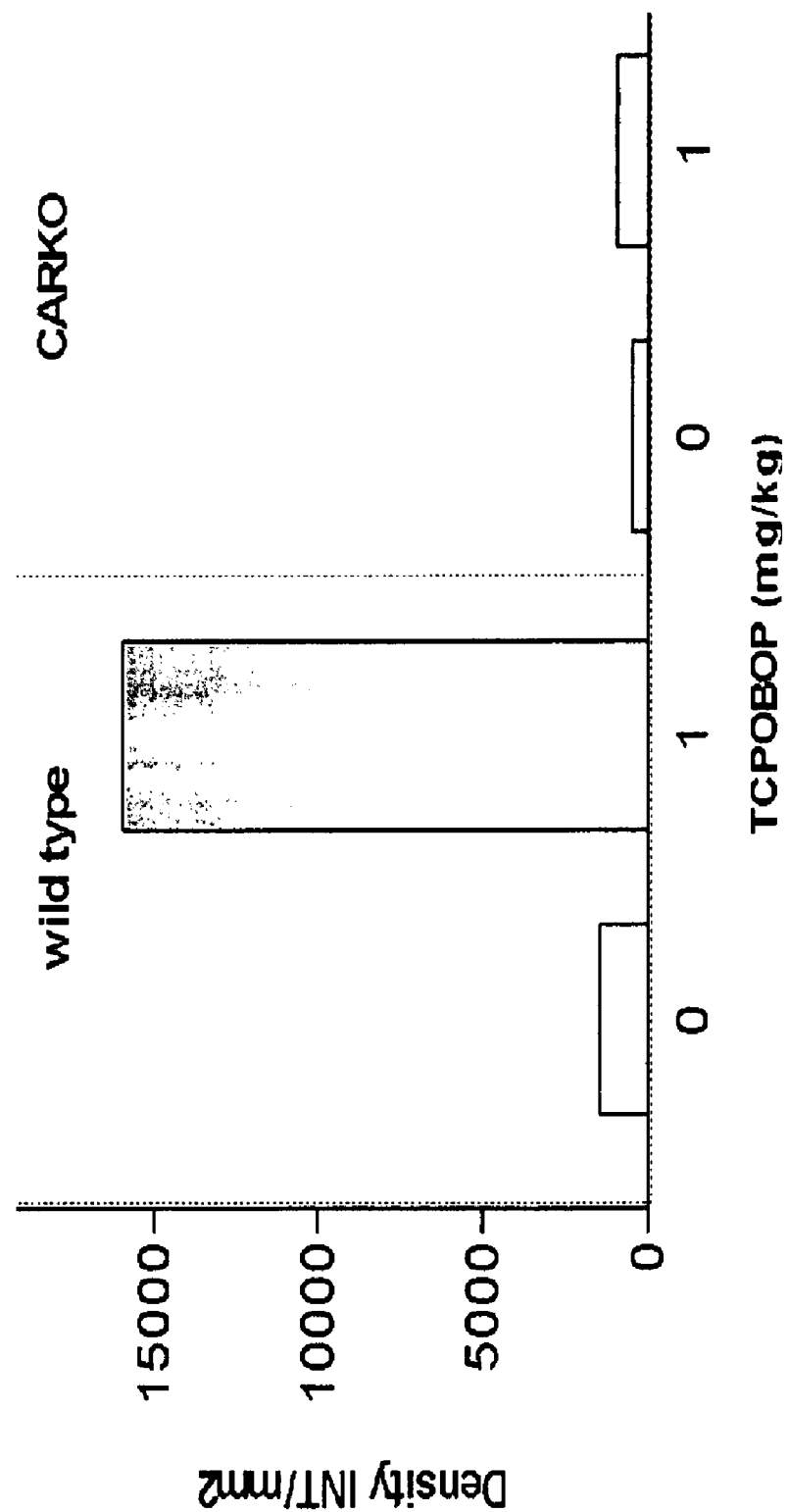
FIG. 43 shows densitometric quantification of Western blot bands obtained from TCPOBOP-treated livers of wild-type and koCAR mice.

Cyp2b10 expression in liver was also compared in koCAR and wild type mice after treatment with TCPOBOP (1 mg/kg). The results of densitometric quantification of Western blot bands obtained from liver samples are shown in FIG. 43. In contrast to the wild type, no Cyp2b10 was induced at 1 mg/kg TCPOBOP in koCAR mice.

Further Validation of the huCAR and koCAR Lines

A TaqMan® analysis using mouse and human-specific probes demonstrated that only human CAR mRNA (not mouse CAR mRNA) is expressed in the livers of huCAR mice generated according to the invention (FIG. 44).

PCR analysis of CAR transcripts confirmed that the full-length human mRNA and all human splice variants as reported by Auerbach et al. (Nucleic Acids Res. 2003 Jun. 15; 31(12):3194-207) are expressed in the huCAR mice. In addition to the reference splicing isoform of exons 6, 7 and 8, the three further isoforms described in Auerbach et al. were observed, i.e. (a) a variant comprising a 12-base-pair insertion leading to a 5' extension of exon 7, (b) a variant comprising a 15-base-pair insertion leading to a 5' extension of exon 8, and (c) a variant wherein exon 7 is deleted (leading to an in-frame deletion of 39 amino acids).

Further TaqMan® analyses of CAR mRNA in wild-type and huCAR mice, for both liver and small intestine, are shown in FIG. 45. Only human CAR mRNA (not also mouse CAR transcripts) were observed in huCAR mice.

Liver/body weight ratios of wild type and huCAR mice are shown in FIG. 46 for untreated animals, and animals treated with 1, 10 or 50 mg/kg of the human CAR activator CITCO (6-(4-chlorophenyl)imidazo[2,1-b][1,3]thiazole-5-carbaldehyde O-(3,4-dichlorobenzyl)oxime; Maglich et al., J Biol. Chem. 2003 May 9; 278(19):17277-83). Plasma levels of alanine aminotransferase (ALT), alkaline phosphatase (ALP) and aspartate aminotransferase (AST) were also measured (see FIG. 46). No hepatotoxicity was detected in either the wild-type or huCAR mice at the CITCO doses tested (1 mg/kg, 10 mg/kg and 50 mg/kg).Cyp3a11 and Cyp2b10 expression in the liver of wild-type and huCAR mice was analysed by Western blotting for untreated animals and animals treated with increasing amounts of the human CAR activator CITCO. Varying doses of CITCO were administered in a single injection (0, 1, 10, 50 mg CITCO per kg mouse body weight) and animals were sacrificed after 48 hours.

Figure 47:
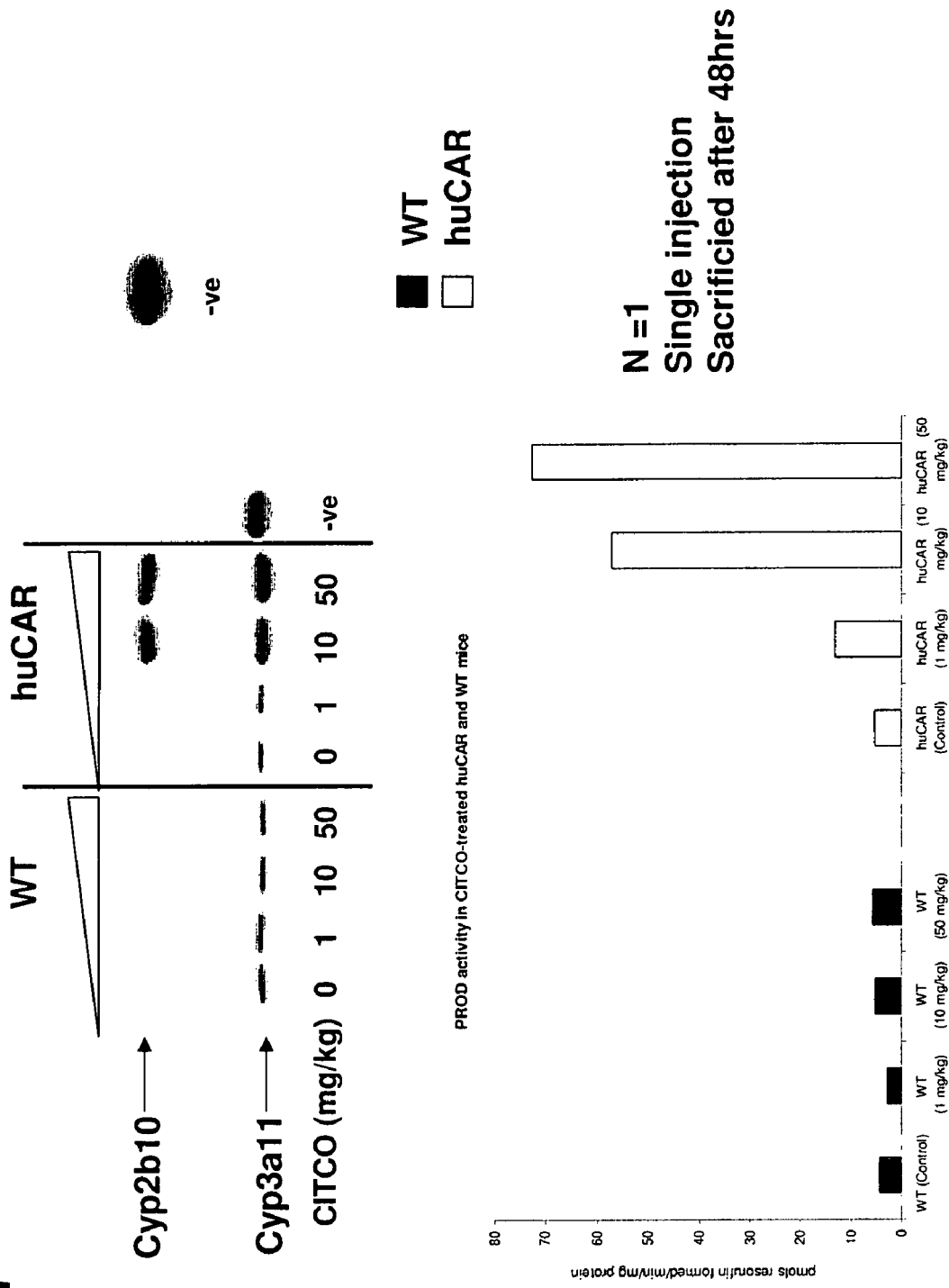
FIG. 47 shows effects of CITCO in wild-type and huCAR mice.

The results of this CITCO study are shown in FIG. 47. The response of huCAR mice to treatment with CITCO clearly differed from that of wild-type mice. While CITCO did not induce expression of either Cyp2b10 or Cyp3a11 in wild type mice, expression of both proteins was clearly induced by CITCO in huCAR mice (see the bands at 10 and 50 mg CITCO per kg mouse body weight in FIG. 47).

Figure 48:
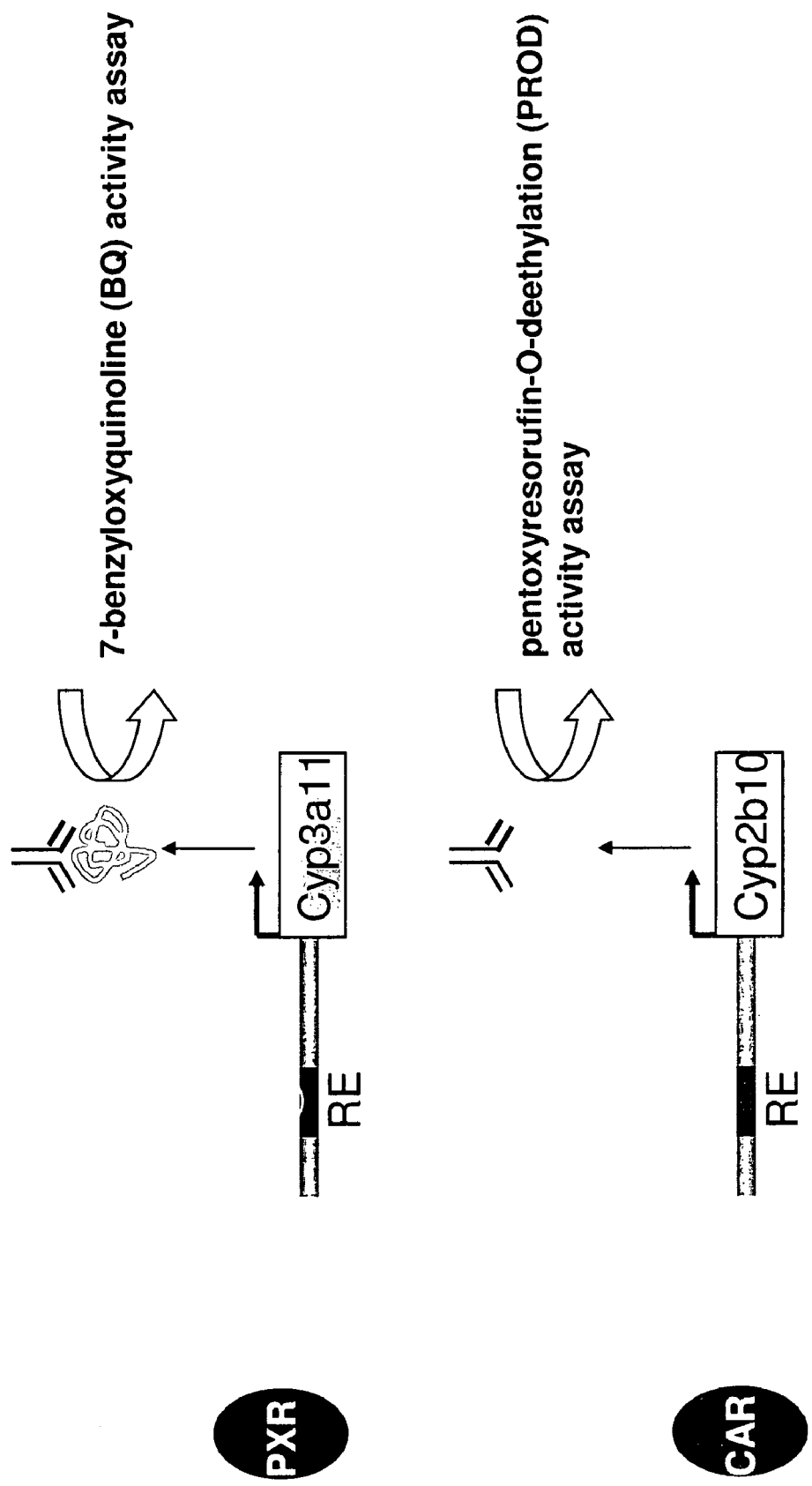
FIG. 48 is a schematic illustration of the rationale for screening assays for PXR and CAR activity.

As in the validation of the huPXR and koPXR mice described above, induction analyses by Western blotting were supplemented with enzyme activity assays. While PXR induces expression of Cyp3a11, CAR induces the expression of both Cyp3a11 and Cyp2b10. Cyp3a11 and Cyp2b10 expression may each be specifically assessed by means of the 7-benzylquinoline (BQ) assay and the pentoxyresorufin-O-deethylation (PROD) assay, respectively. BQ (Cyp3a11)

activity in the absence of PROD (Cyp2b10) activity therefore indicates PXR activity, whereas any PROD (Cyp2b10) activity indicates CAR activity (see FIG. 48).

The above visualisation by Western blotting of the Cyp2b10 induction profile under the influence of CITCO is consistent with the results obtained in the PROD activity assay, which is reflective of Cyp2b10 expression and thus CAR activity. In the huCAR mouse, but not in the wild-type, the administration of increasing amounts of the human-specific inducing agent CITCO led to a marked, dose-dependent induction of PROD activity (FIG. 47).

Figure 49:
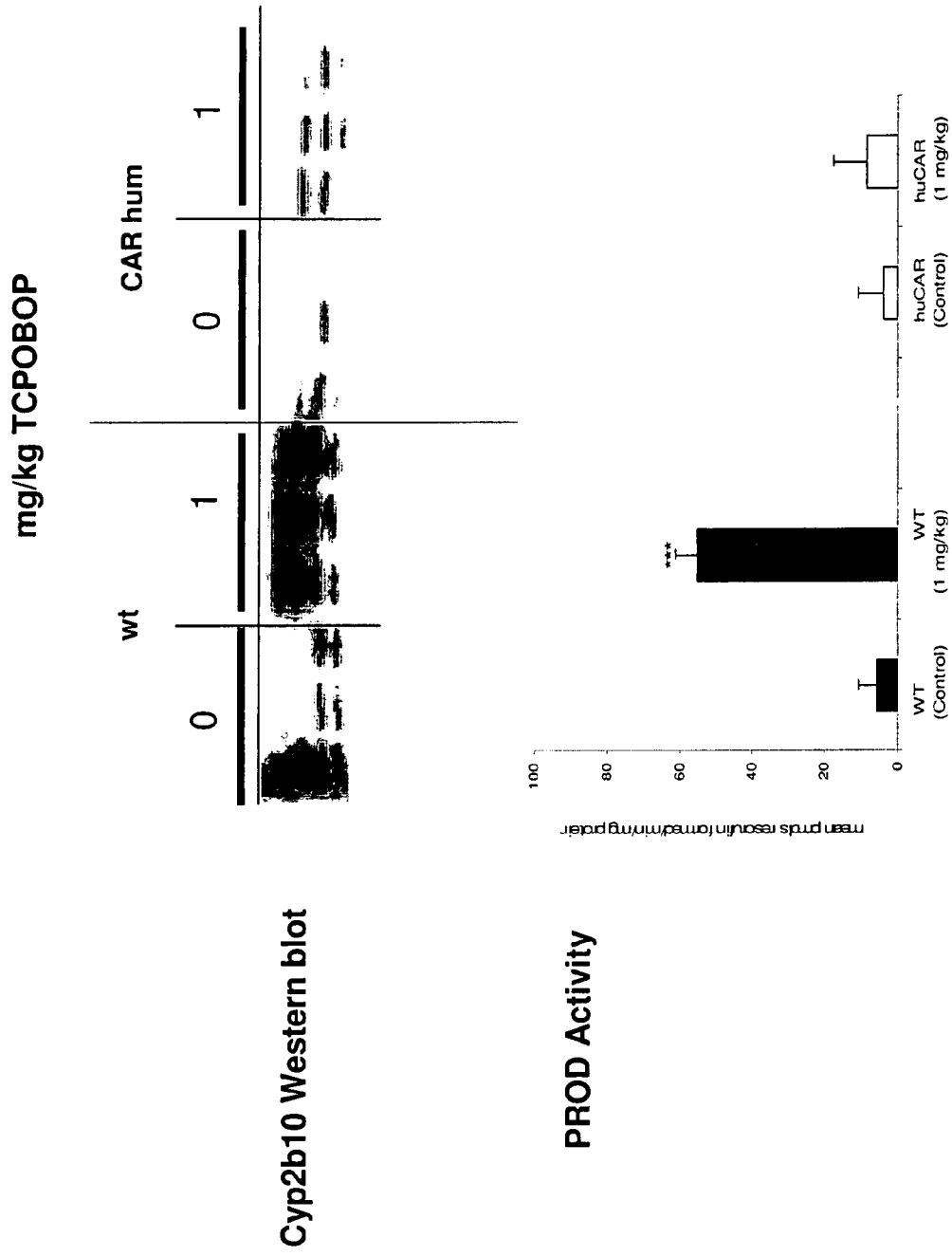
FIG. 49 shows effects of TCPOBOP on Cyp2b10 expression and activity in wild-type and huCAR mice.

Expression of Cyp2b10 was shown by Western blotting and the PROD activity assay to be induced by 1 mg/kg TCPOBOP in wild type mice, but not in huCAR mice (FIG. 49; experiments conducted in triplicate). This is consistent with the observation that TCPOBOP induces cytochrome P450 metabolism more strongly in mice than in humans.

The induction profile of Cyp2b10 in wild-type and huCAR mice was analysed further, both in response to treatment with human-specific CITCO and in response to mouse-specific TCPOBOP. The results of Western blotting and the PROD assay obtained from liver microsome samples with increasing amounts of either CITCO or TCPOBOP are compared in FIG. 50. While TCPOBOP induced Cyp2b10 more strongly in the wild-type than huCAR mice, the situation was reversed for the human-specific inducer CITCO, which led to a stronger response in huCAR than in the wild-type. These data confirmed that a humanized response to CAR induction was obtained in the huCAR mouse.

Figure 51:
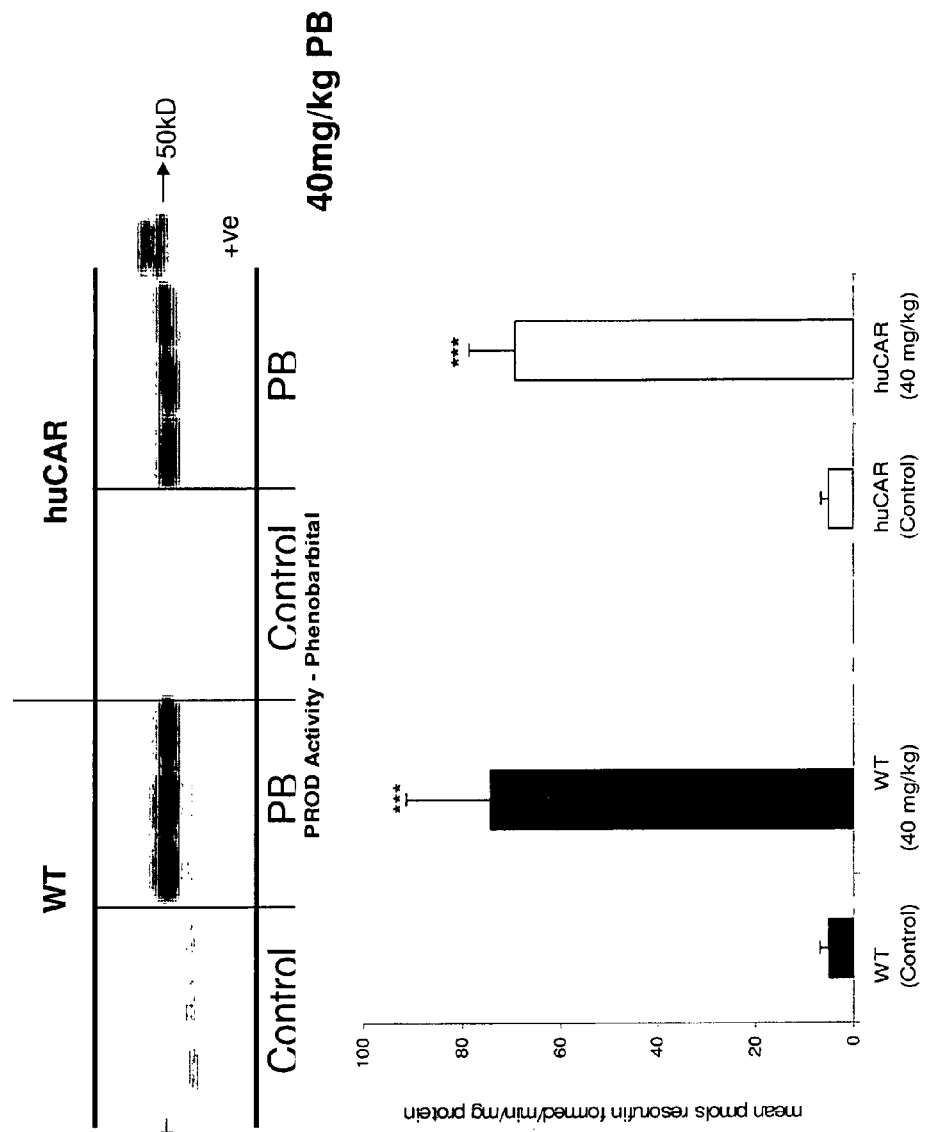
FIG. 51 shows effects of phenobarbital treatment on Cyp2b10 expression and activity in wild-type and huCAR mice.

In contrast, phenobarbital (at 40 mg/kg), which has been reported to induce cytochrome P450 metabolism to a comparable extent in mouse and in human, induced Cyp2b10 expression both in the wild-type and in huCAR mice. This is demonstrated by the results of both Western blotting analysis and the PROD activity assay in liver (FIG. 51).

Figure 52:
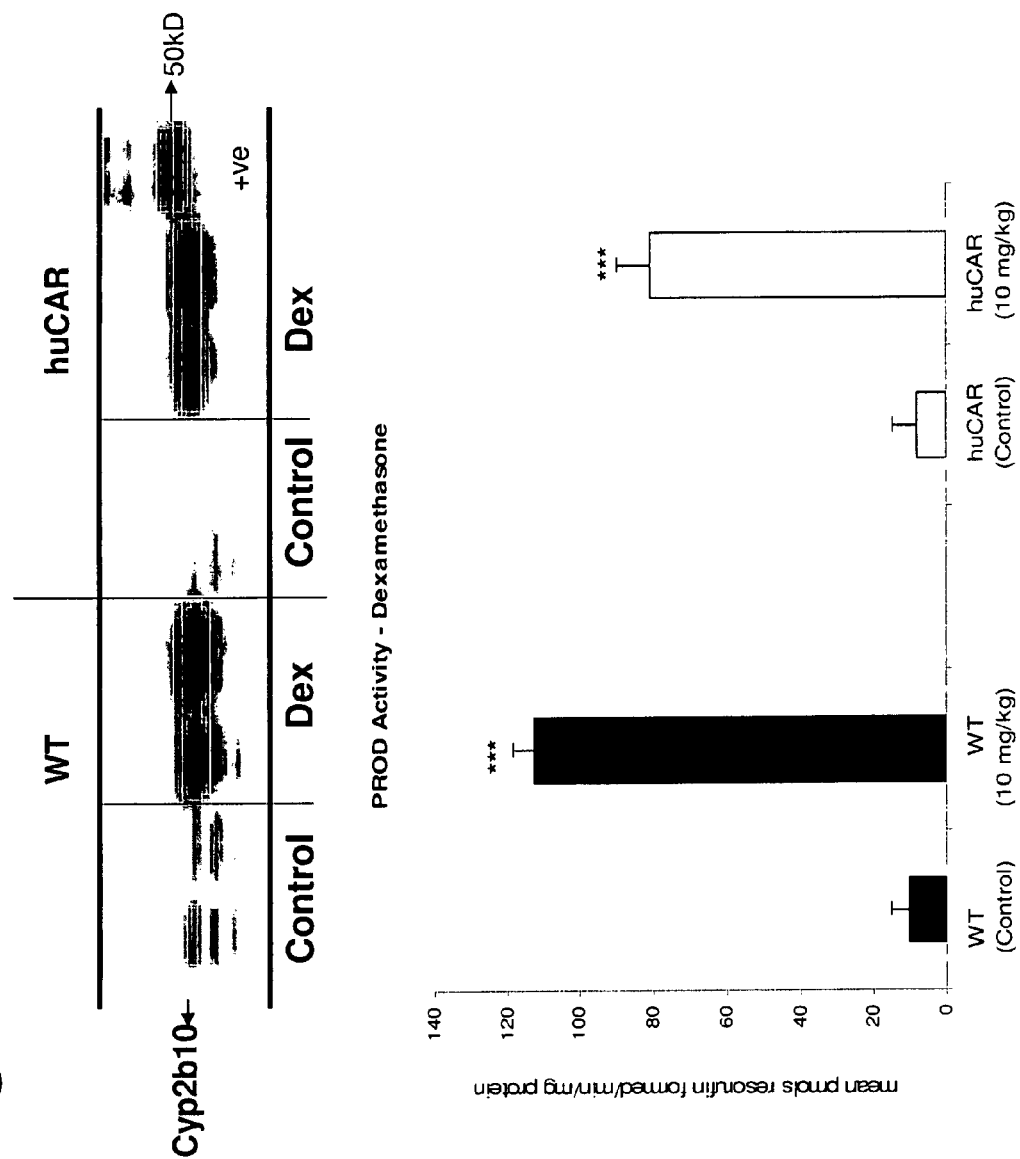
FIG. 52 shows effects of dexamethasone treatment on Cyp2b10 expression and activity in wild-type and huCAR mice.

Dexamethasone, which has been reported to induce cytochrome P450 metabolism more strongly in mice than in humans, induced Cyp2b10 expression in both wild-type and huCAR mice when administered at 10 mg/kg. However, Western blots indicate that induction is less pronounced in huCAR than in wild-type mice (FIG. 52), and the PROD activity assay confirmed that Cyp2b10 induction by dexamethasone was weaker in huCAR than in wild type mice. This result further confirms successful humanisation of the CAR-mediated response to cytochrome P450 inducers in huCAR mice.

Figure 53:
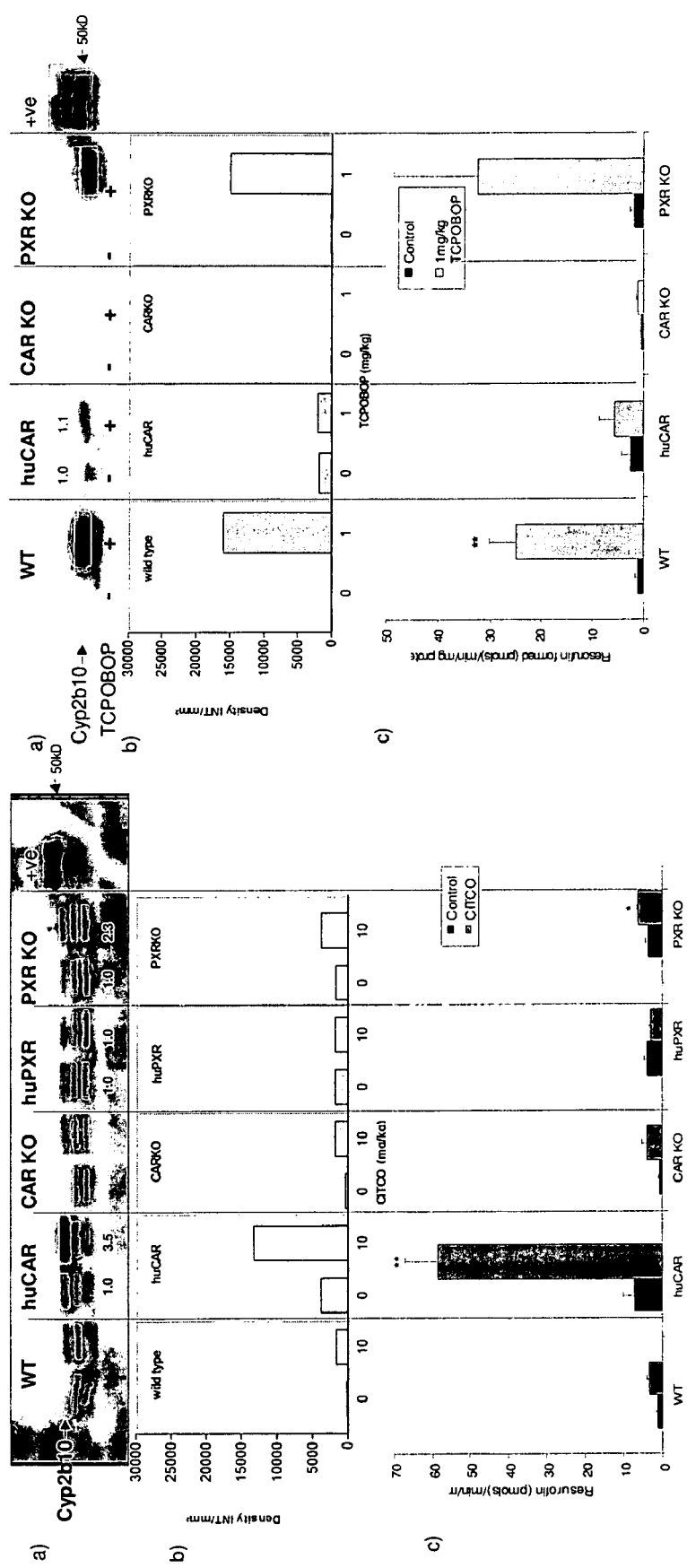
FIG. 53 shows effects of treatment with CITCO or TCPOBOP on Cyp2b10 expression and activity in wild-type, huCAR, koCAR, huPXR and koPXR mice.

Cyp2b10 induction by either CITCO or TCPOBOP in wild-type, huCAR, koCAR, huPXR (CITCO only) and koPXR mice is compared in FIG. 53. Both Western blots and the PROD activity test (resurofin formation) revealed strong induction of Cyp2b10 by human-specific CITCO (10 mg/kg) in the humanised huCAR mice, consistent with the conclusion that humanisation has been achieved in these mice (FIG. 53, left). In comparison, Cyp2b10 was not substantially induced by CITCOO in wild-type mice. Some induction was also observed in koPXR mice, which is consistent with the dependence of Cyp2b10 on CAR rather than PXR.

Figure 54:
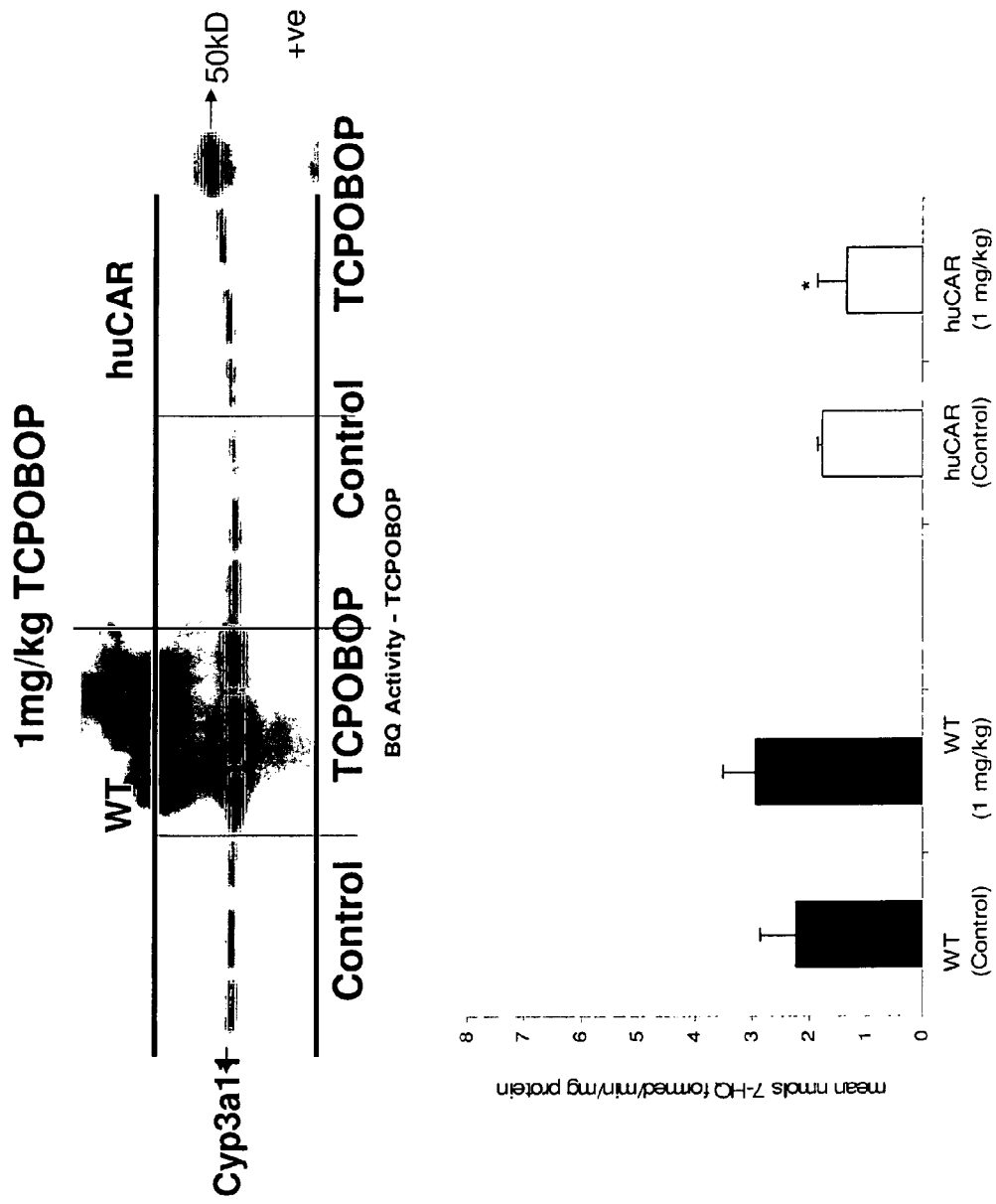
FIG. 54 shows effects of TCPOBOP treatment on Cyp3a11 expression and activity in wild-type and huCAR mice.

As expected, TCPOBOP (1 mg/kg) strongly induced Cyp2b10 protein expression and PROD activity in wild-type mice (FIG. 53, right). In koPXR mice, TCPOBOP induced Cyp2b10 protein expression and PROD activity to an extent that was comparable to wild type, confirming that Cyp2b10 induction depends on CAR rather than PXR. However, TCPOBOP did not significantly induce Cyp2b10 protein expression or PROD activity in humanized huCAR mice, consistent with the relative specificity of this agent for mouse rather than human. Expression of Cyp3a11 was shown by Western blotting and the BQ activity assay to be somewhat induced by 1 mg/kg TCPOBOP in wild type mice, but not in huCAR mice (FIG. 54; experiments conducted in triplicate). This is consistent with the observation that TCPOBOP induces cytochrome P450 metabolism more strongly in mouse than in human and further confirms successful humanization of the CAR-mediated response to cytochrome P450 inducers in huCAR mice.

An overview of the effects of selected drug-metabolism inducers on the expression of Cyp3a11 and Cyp2b10 in wild-type mouse and human is provided in FIG. 55.

An overview of various inducing agents on PXR and CAR target genes in wild-type, huPXR, koPXR, huCAR and koCAR mice is provided in FIG. 83.

Figure 56:
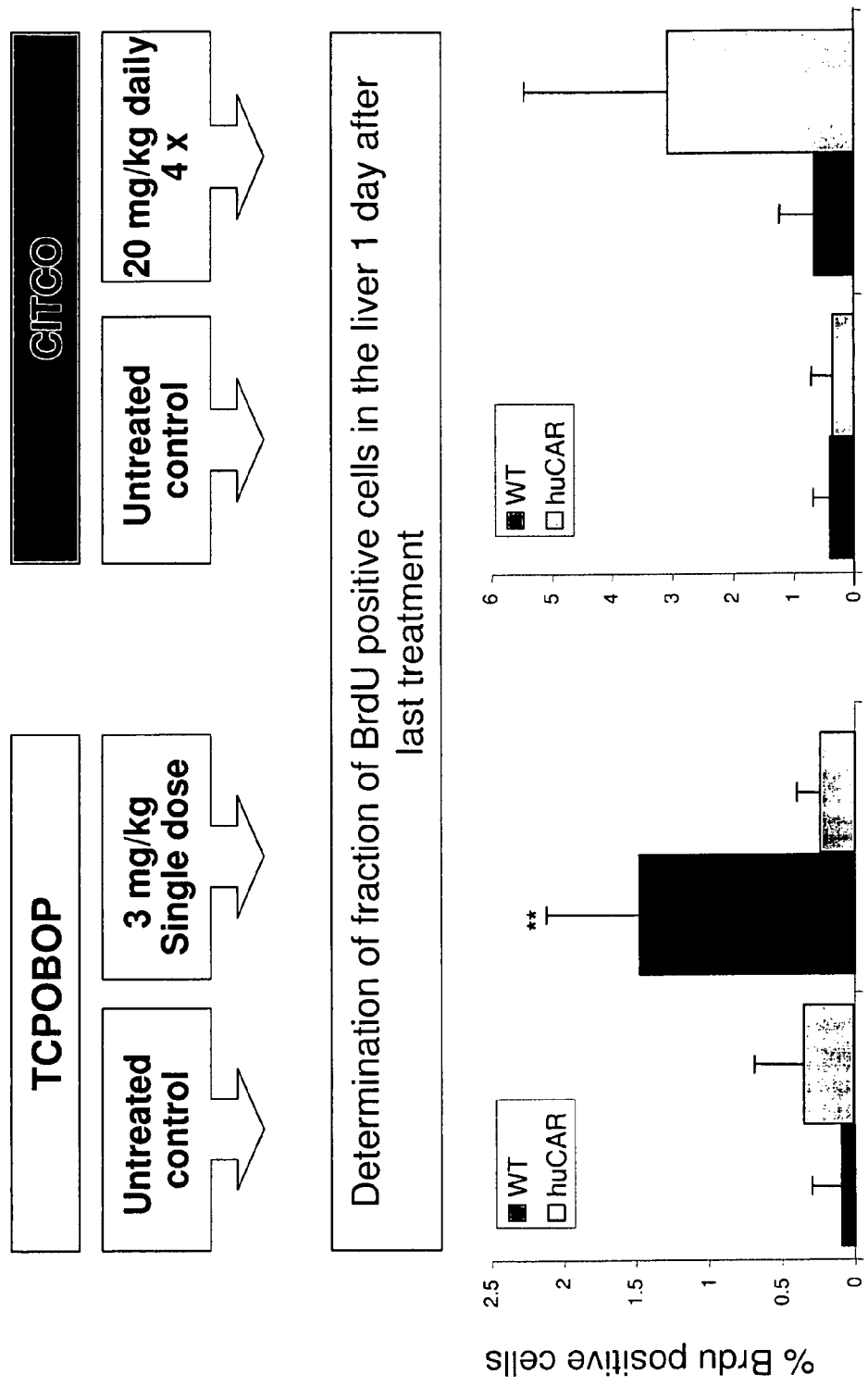
FIG. 56 illustrates species-specific differences in the hyperplastic response to CAR activators between wild-type and huCAR mice.

Non-genotoxic Carcinogenicity Study in huCAR Mice: Demonstration of CAR-dependent Species-specific Differences in Wild-type and huCAR Mice In order to assess the hyperplastic response in the huCAR mice, the fraction of BrdU positive cells in the liver was determined in wild-type and huCAR treated with CAR activators. Animals were treated either with TCPOBOP (a mouse-specific inducer) or CITCO (a human-specific inducer). Animals received a single dose of TCPOBOP (3 mg/kg) or 20 mg/kg CITCO 4 times daily. The fraction of BrdU positive cells in the liver of treated mice were determined one day after administration of the single or final dose, and compared to equivalent measurements obtained from untreated animals. As is shown in FIG. 56, the mouse-specific inducer TCPOBOP led to elevated counts of BrdU positive liver cells only in wild-type animals, whereas the human-specific inducer CITCO led to elevated counts of BrdU positive liver cells only in huCAR animals, not in the wild-type.

These results further confirm that the huCAR mouse line reproduces species-dependent differences in the response to CAR activators. In particular, these results show that huCAR mice are humanized with respect to their hyperplastic response to non-genotoxic carcinogens.

Figure 28:
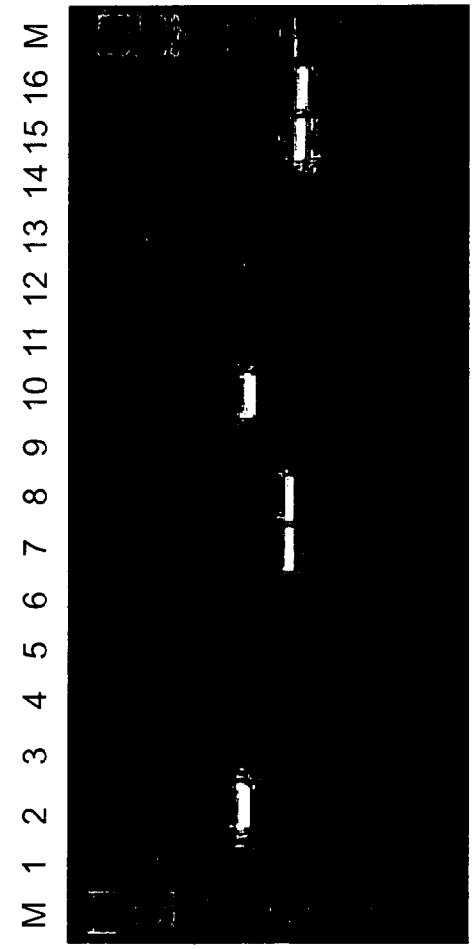
FIG. 28 shows PCR confirmation in two double homozygous PXR/CAR humanised mice that the murine PXR gene has been exchanged for the human counterpart.

PCR Confirmation in Two Double Homozygous PXR/CAR Humanised Mice that the Murine PXR Gene Has Been Exchanged for the Human Counterpart Humanised mice for PXR and CAR ("huPXR/huCAR") were generated using mice which contained humanised PXR and crossing these into mice which contained humanised CAR to produce mice containing both humanised PXR and humanised CAR. The mice are phenotypically normal following visual inspection. They have been typed using PCR (see FIG. 28) and are homozygously humanised for PXR and CAR. Examples include mice designated "42749" and "42752".

Figure 57:
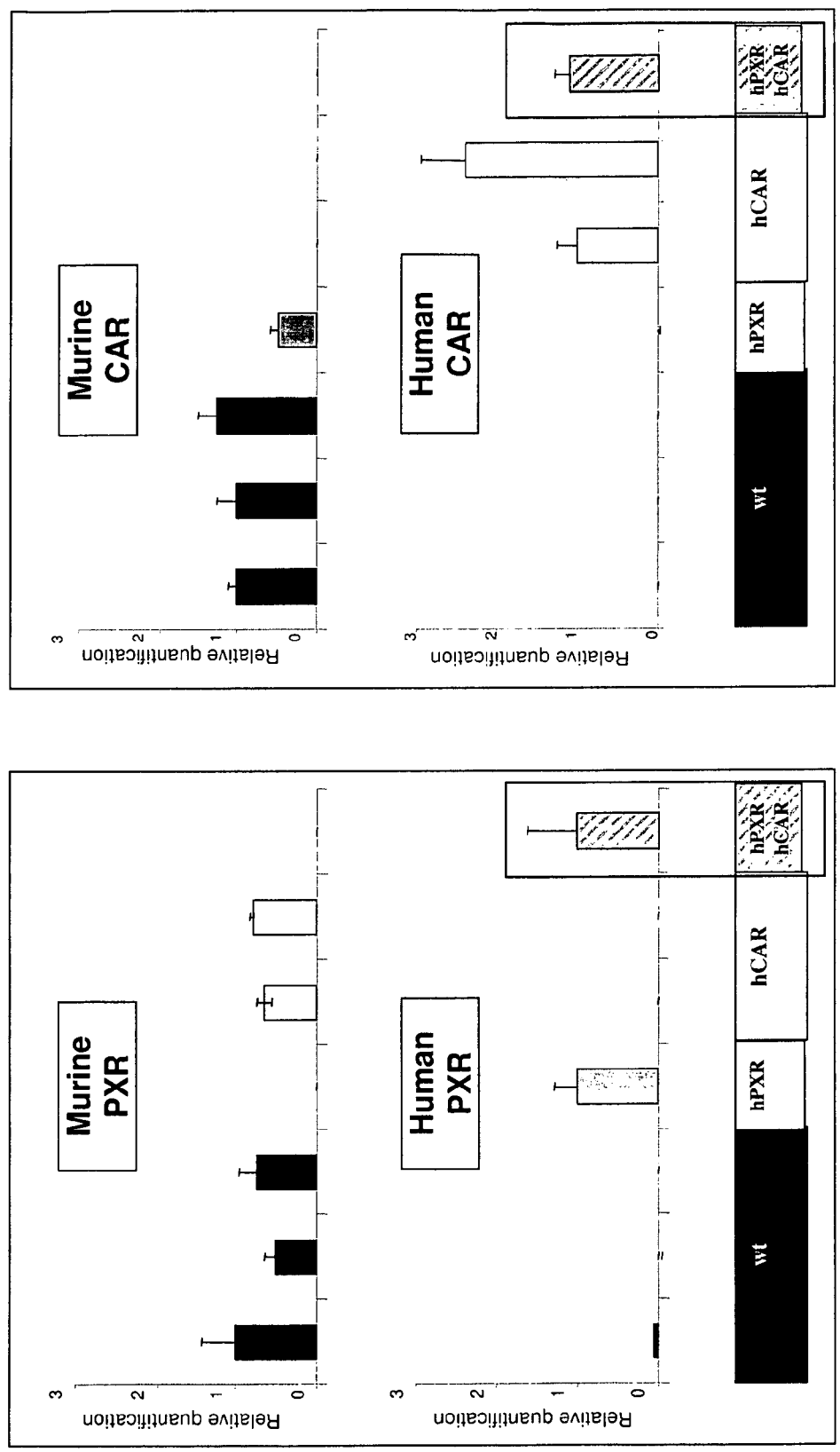
FIG. 57 shows PXR and CAR mRNA levels in huPXR/huCAR double-humanised mice and in wild-type, huPXR and huCAR mice. Human PXR and CAR mRNA expression is maintained in double humanised mice.

Transcription of PXR and CAR mRNA was quantified by RT-PCR in huPXR/huCAR mice and compared to the relative levels of corresponding mRNA expression in wild-type, huPXR and huCAR mice (FIG. 57). It was thereby confirmed that the huPXR/huCAR mice maintain the levels of human PXR and human CAR expression observed in mice humanised with respect to single genes.

Figure 58:
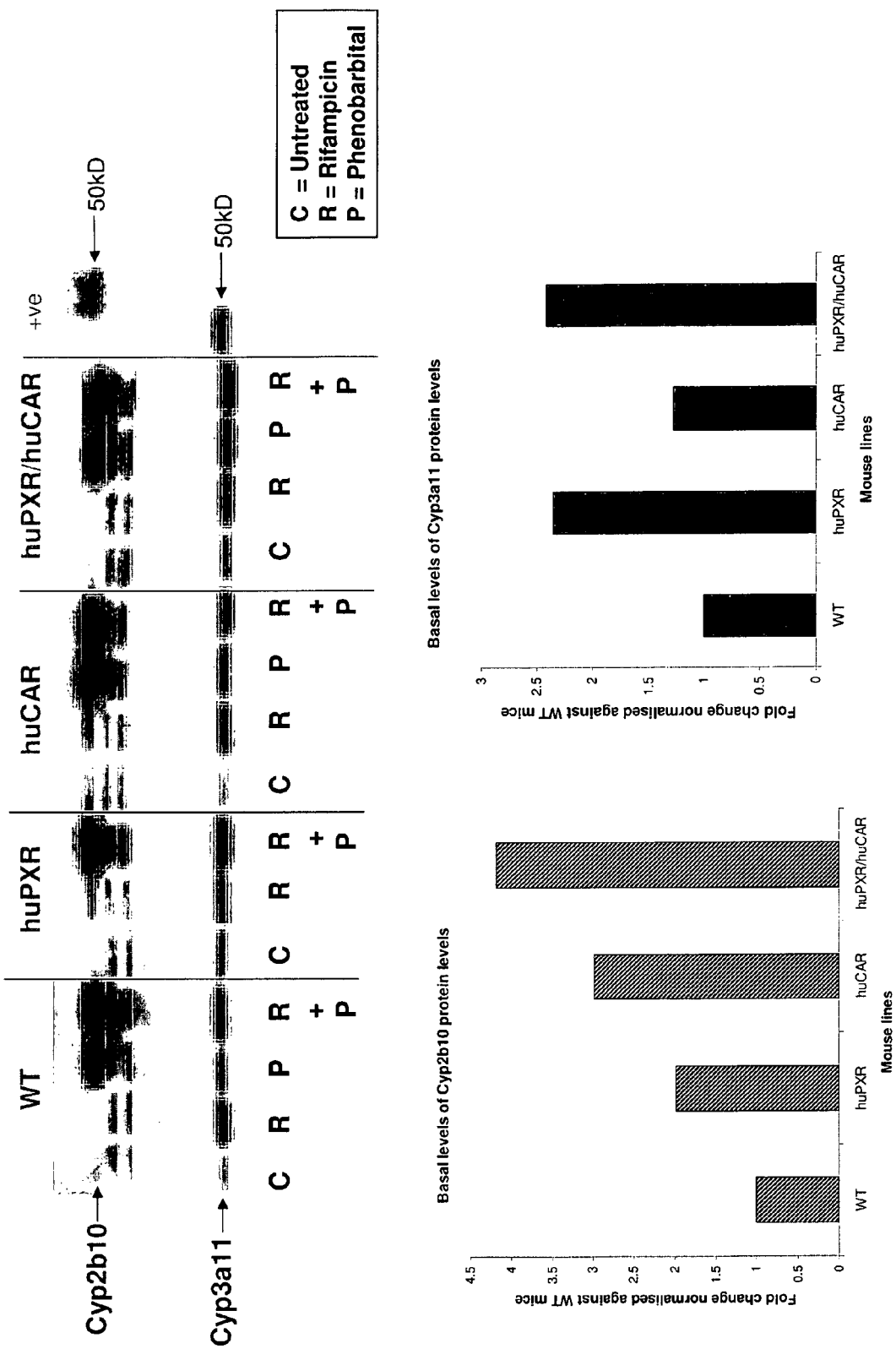
FIG. 58 shows effects of rifampicin and phenobarbital treatment in double-humanised huPXR/huCAR, wild-type, huPXR and huCAR mice, and basal levels of Cyp2b10 and Cyp3a11 protein in huPXR/huCAR, wild-type, huPXR and huCAR mice.

Double-humanised huPXR/huCAR mice, as well as wild-type, huPXR and huCAR mice were treated with the inducers rifampicin and/or phenobarbital. Expression of Cyp2b10 and Cyp3a11 in these inducer-treated mice, as well as in corresponding untreated mice, was visualised and compared by SDS-PAGE followed by Western blotting (FIG. 58). The basal levels of Cyp2b10 and Cyp3a11 in huPXR, huCAR and huPXR/huCAR mice are compared to the basal levels observed in wild-type mice in FIG. 58. This relative quantification shows that basal Cyp2b10 levels increase in the order huPXR→huCAR→huPXR/huCAR. However, basal Cyp3a11 were less markedly increased in huCAR mice. Cyp3a11 levels were increased to an approximately equal extent (more than 2 fold) in both huPXR and double-humanised huPXR/huCAR mice.

Treatment with the human-specific inducer rifampicin led to an increase in the levels of Cyp3a11 in all mice. Whereas the administration of rifampicin and phenobarbital in combination appeared to have no additional effect in the wild type, induction of Cyp3a11 was somewhat stronger in huPXR.

Pentobarbitone Sleeping Test

In this experiment, the activity of these transcription factors in combination was determined by measuring the barbiturate induced sleeping time. Sleeping time has been known for many years to be directly proportional to the hepatic cytochrome P450 activity and this activity can be at least in part ascribed to the P450 levels in the liver determined by CAR and PXR function.

Mice were given a single intraperitoneal dose of Narcoren (sodium pentobarbitone; purchased via a Veterinary Consultant; distributed by Merial GmbH, Germany) at 25 mg/kg of body weight. The time taken for the mice to lose, and subsequently to regain, their righting reflex was measured. Results are given in Table 4.1 below:

TABLE 4.1

Results of pentobarbitone sleeping test

| Genotype | Sex | Age (weeks) | ID | Weight (g) | Sleeping time (min) |
|---|---|---|---|---|---|
| wt | male | 10 | 42912 | 21.2 | 21 |
| PXR/CAR hum | male | 10 | 42749 | 24.8 | 34 |

Whereas wild type mice given a narcotic dose of pentobarbitone slept for 21 minutes, the double humanised mice for CAR and PXR slept for 34 minutes. These mice therefore demonstrate a significant difference to their wild type controls indicating that the double humanised mouse has a marked difference in its response to drugs relative to the wild type animals.

Summary of Work on Types 3 and 4 Above

A model has been developed where human PXR is expressed in both the liver and GI tract of mice in the predicted fashion at levels equivalent to those of the endogenous gene. The PXR protein has been shown to be functional as the mice are responsive to compounds known to induce gene expression via this pathway. Equivalent humanisation has also been achieved with respect to the CAR gene (huCAR mice). Strain differences between wild type and the humanised mice have been demonstrated and the humanised mice have been shown to be more responsive to compounds known to be more active in humans than in mice, i.e., to human PXR or human CAR rather than murine PXR or murine CAR. The construction of knock-out lines has also been confirmed for both the PXR and the CAR genes (koPXR and koCAR). Moreover, mice which contained humanised PXR have also been crossed into mice which contained humanised CAR to produce mice containing both humanised PXR and humanised CAR.

Type 5: Expression of a Hybrid of Human cDNA and Genomic Sequences from the Corresponding Human Promoter by Insertion into the ROSA26 Locus Projects: CYP3A4 and CYP2C9 Humanisation Methods: The targeting vectors are constructed with standard molecular cloning procedures. The basic ROSA26 targeting vector is designed in a way, that the neomycin gene will be expressed from the endogenous ROSA26 promoter in correctly targeted ES clones. The Neo transcript is terminated by a polyA motif.

In case of CYP3A4 the humanization cassette, 3' to the selection marker, contains the 13 kb human CYP3A4 promoter, exon1 and intron1 as in the normal genomic constitution and a human cDNA consisting of exons2-13. The transcript is terminated by a polyA motif (see FIG. 9).

In case of CYP2C9 the humanization cassette, 3' to the selection marker, contains the 12 kb human CYP2C9 promoter, a human cDNA of exons1-4, intron4 and a cDNA of exons5-9. The transcript is terminated by a polyA motif (see FIG. 10).

The targeting vector is transfected by standard electroporation into C57BL/6N mouse ES cells. Clones are selected with G418 and positive clones are identified by Southern blot analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background.

Type 6: Replacement of Large Genomic Regions (Cluster Exchanges)

Projects: CYP3A-cluster Exchange, CYP2C-cluster Exchange and UGT-humanization

Methods: The targeting vectors are constructed with standard molecular cloning procedures. The general principle is that two kinds of targeting vectors are constructed and used for two consecutive rounds of transfection by standard electroporation into C57BL/6N mouse ES cells. The first vector contains a functional TK cassette and a 5' deleted Neo gene interrupted from its tranlational Start-ATG and promoter by a wt-loxP site. The second vector carries functional TK and Hygromycin cassettes, a wt-loxP and a lox511 site. The final targeting vectors for each of the cluster exchanges are designed in such a way, that in correctly targeted ES clones the genomic sequences intermediate to the wt-loxP sites can be removed by Cre-mediated deletion. This results in a knock out of the loxP-flanked gene cluster. Modified Bacterial Artificial Chromosomes (BACs) will be used to introduce human sequences by Cre-mediated insertion into re-derived ES cells. The selection cassettes flanking the humanized clusters can be removed by FLP mediated deletion (see FIG. 11).

Example 4

Reporter Projects

Projects: CYP3A4-, CYP2C9-, CYP2C19-, CYP2B6-, CYP2D6- and MDR1-reporter

Methods: The targeting vectors are constructed with standard molecular cloning procedures. For all reporters human BACs are modified in such a way, that a reporter gene is fused to the translational start site of the corresponding human gene. Modified BACs carry an FRT-flanked Keo cassette, permitting the selection of bacterial colonies with kanamycin and mouse ES cell clones with G418. In case of CYP3A4, CYP2C9 and CYP2C19 the transcript of the reporter gene is not terminated by a polyA motif, but the constructs are designed such, that the endogenous polyA motif is potentially used. These constructs are therefore dependent on a correct splicing of the exons 3' to the reporter (see FIG. 12).

In case of CYP2D6 and CYP2B6 the transcript of the reporter gene is terminated by a polyA motif linked to the reporter gene with a synthetic intron (see FIG. 13).

In case of MDR1 the transcript of the reporter gene is terminated by a polyA motif without an additional intron (see FIG. 14).

The modified BAC are linearized with NotI and transfected into C57BL/6N mouse ES cells either by standard electroporation or lipofection with lipofectamin2000. For the construction of complex genotypes, the linearized modified BAC are transfected into an appropriate genetic background. For example, for construction of lines combining PXR or CAR humanisation with the desired reporter gene expression, the BAC is transfected into PXR or CAR humanized C57BL/6N mouse ES cells. Clones are selected with G418 and positive clones with randomly integrated DNA are identified by PCR analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

Validation of Reporter Strains

Figure 59:
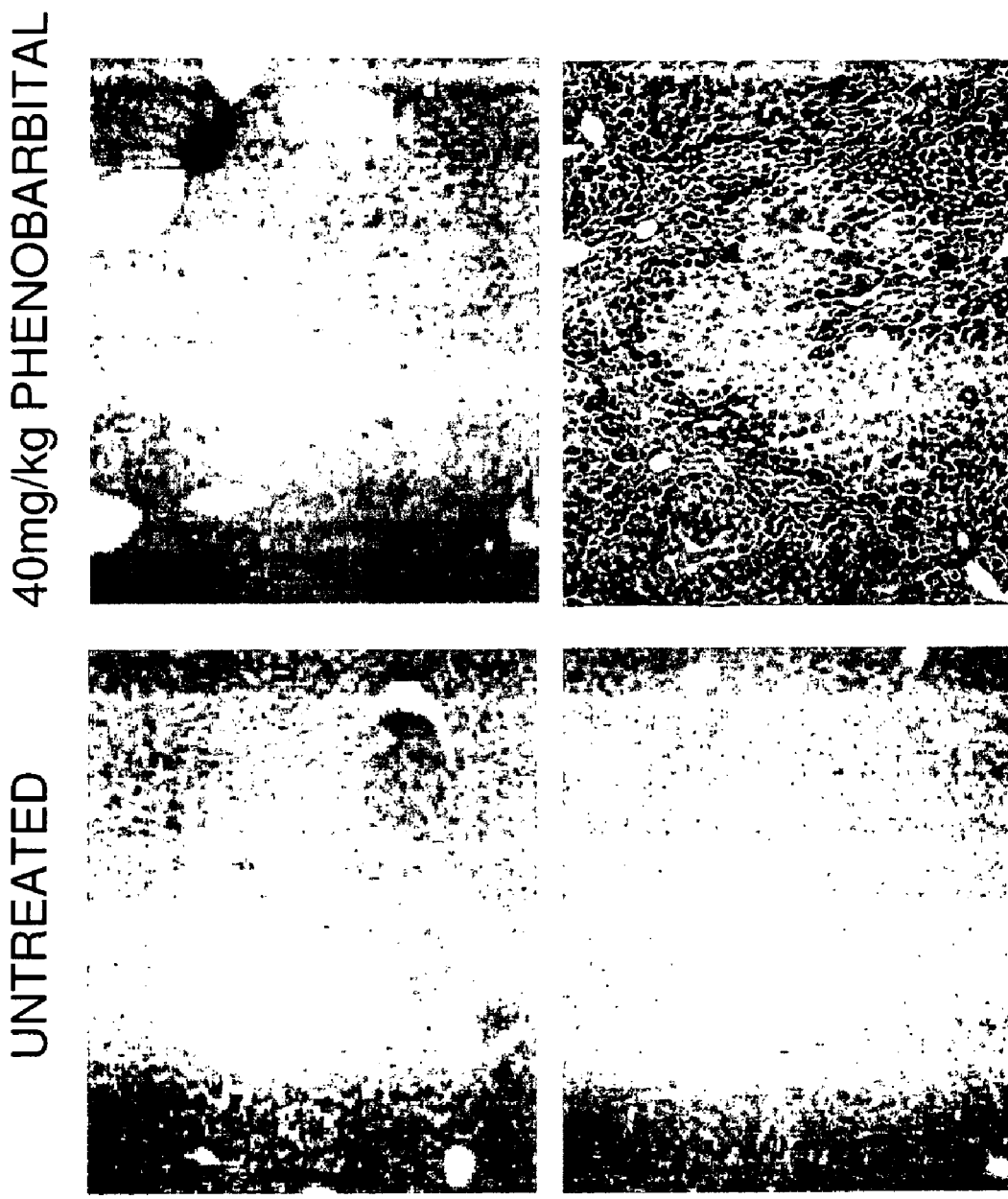
FIG. 59 shows tissue samples from wild-type and rCyp2B6/huCAR reporter mice, illustrating the spatial expression pattern for Cyp2B6 in liver microsomes.

The complex-genotype strain rCyp2B6/huCAR was generated according to the methods described herein and the targeting strategy provided herein (see Example 5 below for further details of preferred rCyp2b6 strains) and using standard methods that are well known to persons skilled in the art. Expression of the lacZ reporter gene was placed under the control of the Cyp2b6 promoter in a huCAR background. FIG. 59 shows tissue samples from wild-type and rCyp2b6/huCAR reporter mice (liver microsomes). After administration of 40 mg phenobarbital per kg body weight, the lacZ reporter gene allows straightforward localisation of Cyp2b6 promoter activity.

The complex-genotype strain rCyp2d6/huPXR was generated according to the methods described above and the targeting strategy provided herein (see Example 5, below for further details of preferred rCyp2d6 strains) and using standard methods that are well known to persons skilled in the art. Expression of the ZsYellow reporter gene was thus placed under the control of the Cyp2d6 promoter in a huPXR background.

FIG. 60 shows tissue samples from wild-type and rCyp2d6/huPXR reporter mice (liver microsomes). The ZsYellow reporter gene allowed the clear localisation of Cyp2d6 promoter activity.

Example 5

Additional Information Regarding Targeting Strategies

A. Transcription Factors huPXR and koPXR

Further strategies for PXR humanisation and knock-out have been identified by the inventors. As in the PXR humanisation strategy described above, the vectors are designed such that a hybrid of human PXR cDNA and genomic sequences is fused to the translational start site of the mouse PXR gene, whereby the mouse start site (ATG) in exon2 is retained.

Figure 61:
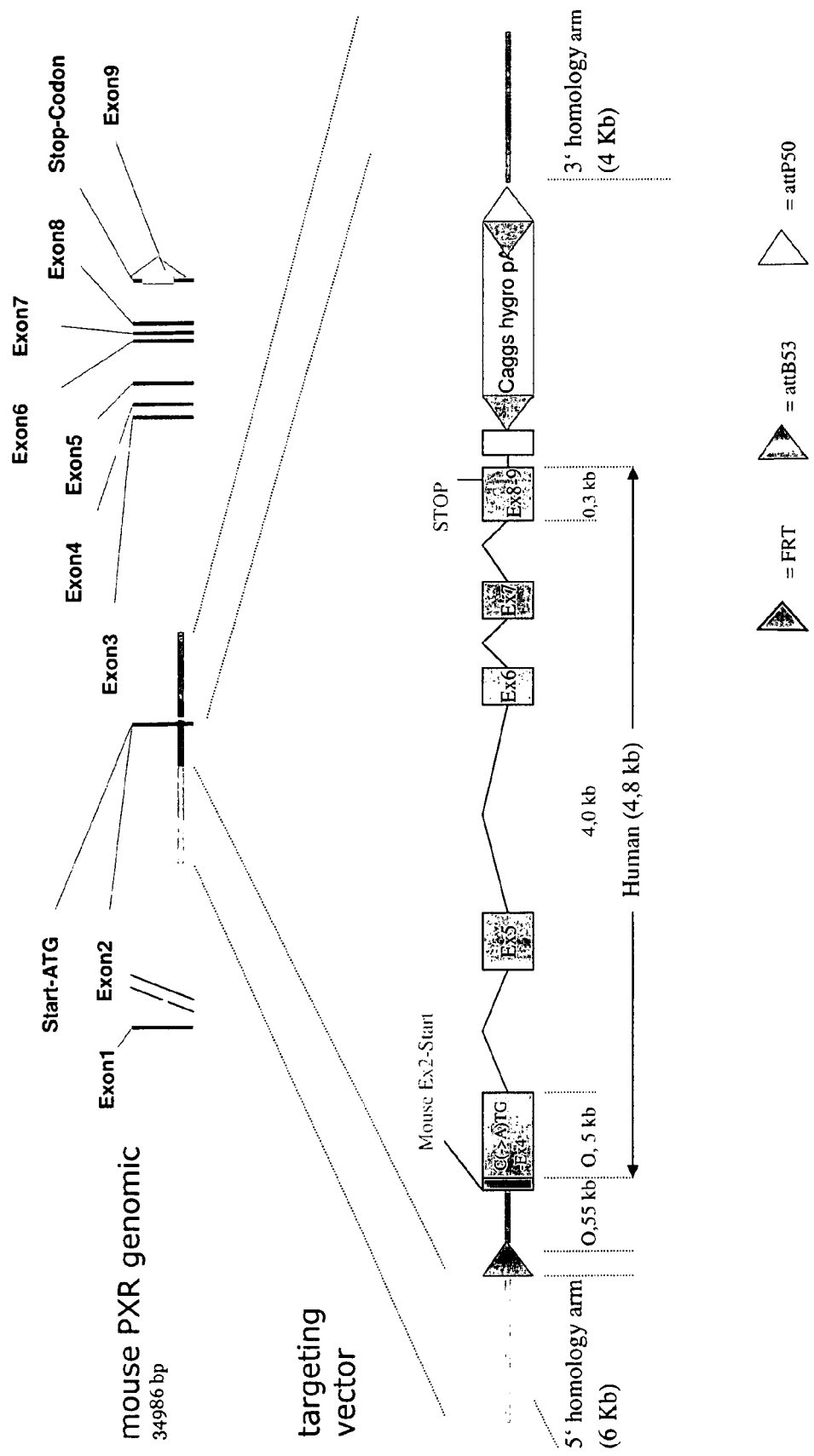
FIG. 61 shows a further possible targeting strategy for PXR humanisation (to produce mice of genotype huPXR).
Figure 62:
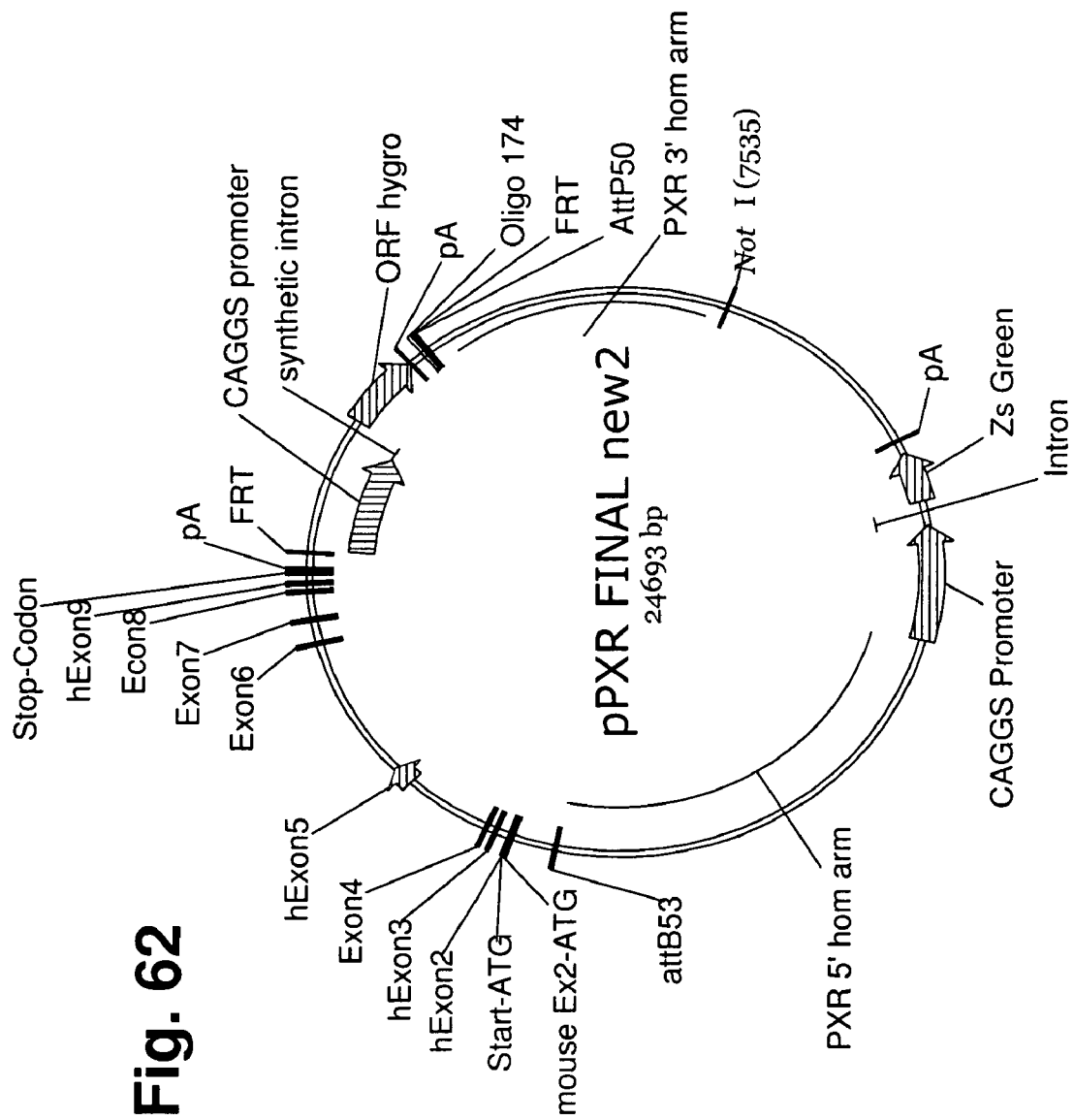
FIG. 62 shows a schematic map of a targeting vector useful for PXR humanisation.

In one strategy, the human PXR sequence contains a cDNA of exon2-4, genomic sequences of intron4, exon5, intron5, exon6, intron6, exon7 and intron7 and a cDNA of exon8-9 (see FIG. 61). This human PXR sequence is provided herein as SEQ ID NO:3 (in this sequence, the human "CTG" has been deleted and the initial "ATG" of SEQ ID NO:3 corresponds to the start site for translation in the mouse). The transcript is terminated by a polyA motif. The targeting vector carries an FRT-flanked hygromycin resistance cassette. Furthermore, att sites are inserted into mouse intron1 and at the 5' end of the 3' homology arm, which allows the generation of a PXR knock-out by removal of the intermediate sequences with the site-specific Phi-C31 recombinase (see below). A representation of the complete targeting vector comprising the above features is provided in FIG. 62.

This strategy enables expression of human PXR under the control of the mouse promoter, in absence of the mouse PXR expression. Assuming that splicing in mice mimics the human situation, the known human splice variants between Exon4 and Exon8 will be expressed.

The targeting vector is transfected by standard electroporation into C57BL/6N mouse ES cells. Clones are selected with hygromycin and positive clones are identified by Southern blot analysis. Selected clones are expanded, injected into BALBc-blastocysts and transferred into foster mothers according to standard operation procedures. Litters from these fosters are visually inspected and chimerism is determined by hair colour. Highly chimeric animals are used for further breeding in a C57BL/6N genetic background. Selection markers are removed in vivo by crossing to an FLP-deleter strain.

Figure 63:
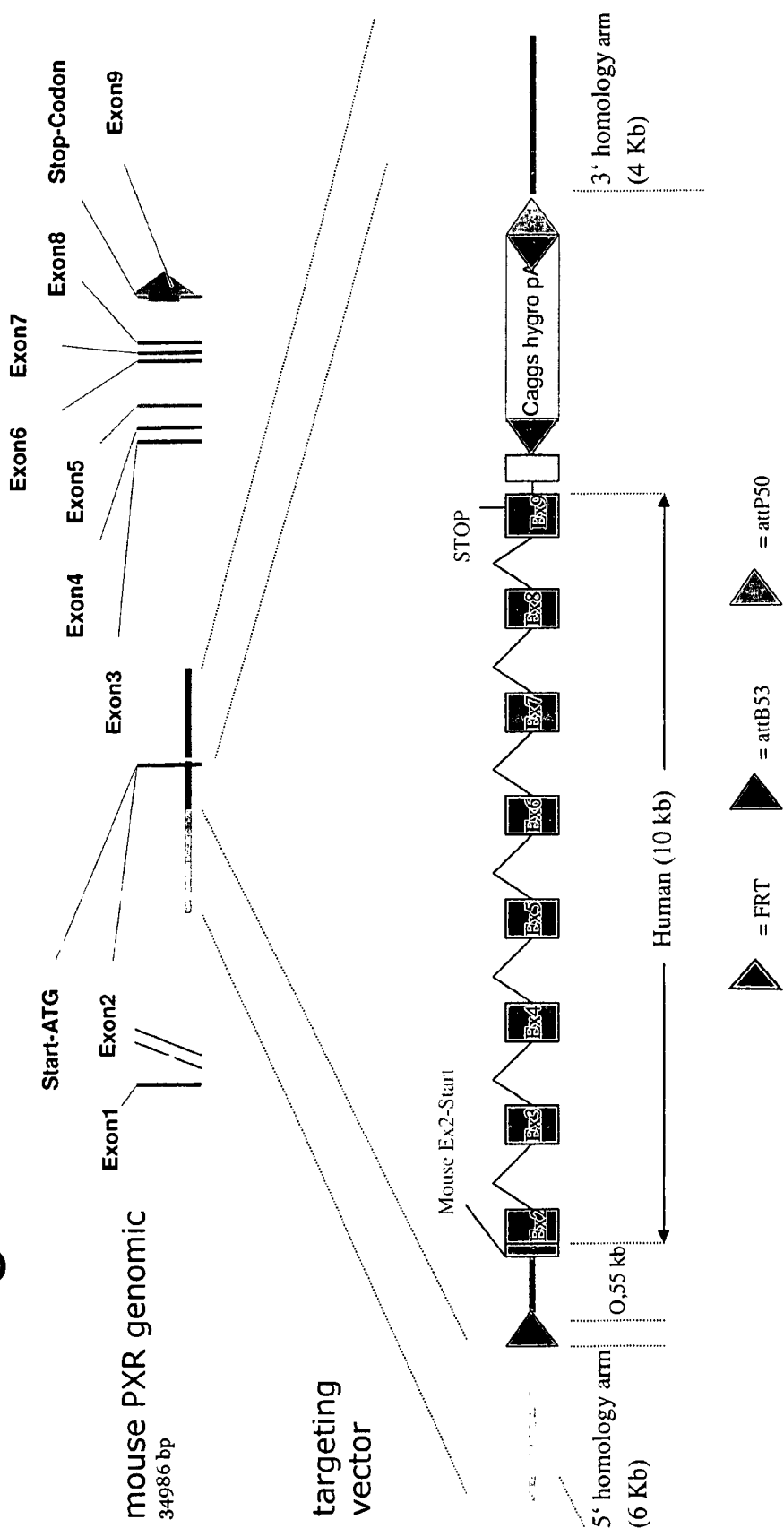
FIG. 63 shows a further possible targeting strategy for PXR humanisation (to produce mice of genotype huPXR).

Such PXR humanisation strategies, wherein the targeting construct contains PXR intron6 and intron7 provide mouse lines that are humanised with respect to PXR, but might not fully reflect the normal splicing pattern in humans (e.g. if a cryptic splice site is created by fusing exon7 and 8). Additional human PXR intron and exon sequences can be included in the targeting vector to improve the splicing pattern, if desired. For example, the targeting vector may retain all of the human PXR genomic sequences downstream of exon 2 (i.e., intron 2, exon 3, intron 3, exon 4, intron 4, exon 5, intron 5, exon 6, intron 6, exon 7, intron 7, exon 8 and intron 8 (see FIG. 63). A human PXR sequence including these additional genomic sequences is provided herein as SEQ ID NO:4 (in this sequence, the human "CTG" has been deleted and the initial "ATG" of SEQ ID NO:4 corresponds to the start site for translation in the mouse).

The type of targeting construct shown in FIG. 2 is preferred for generating PXR knock-out mice, because that targeting construct contains an additional splice acceptor polyA motif to prevent expression of undeleted mouse PXR exons.

Figure 64:
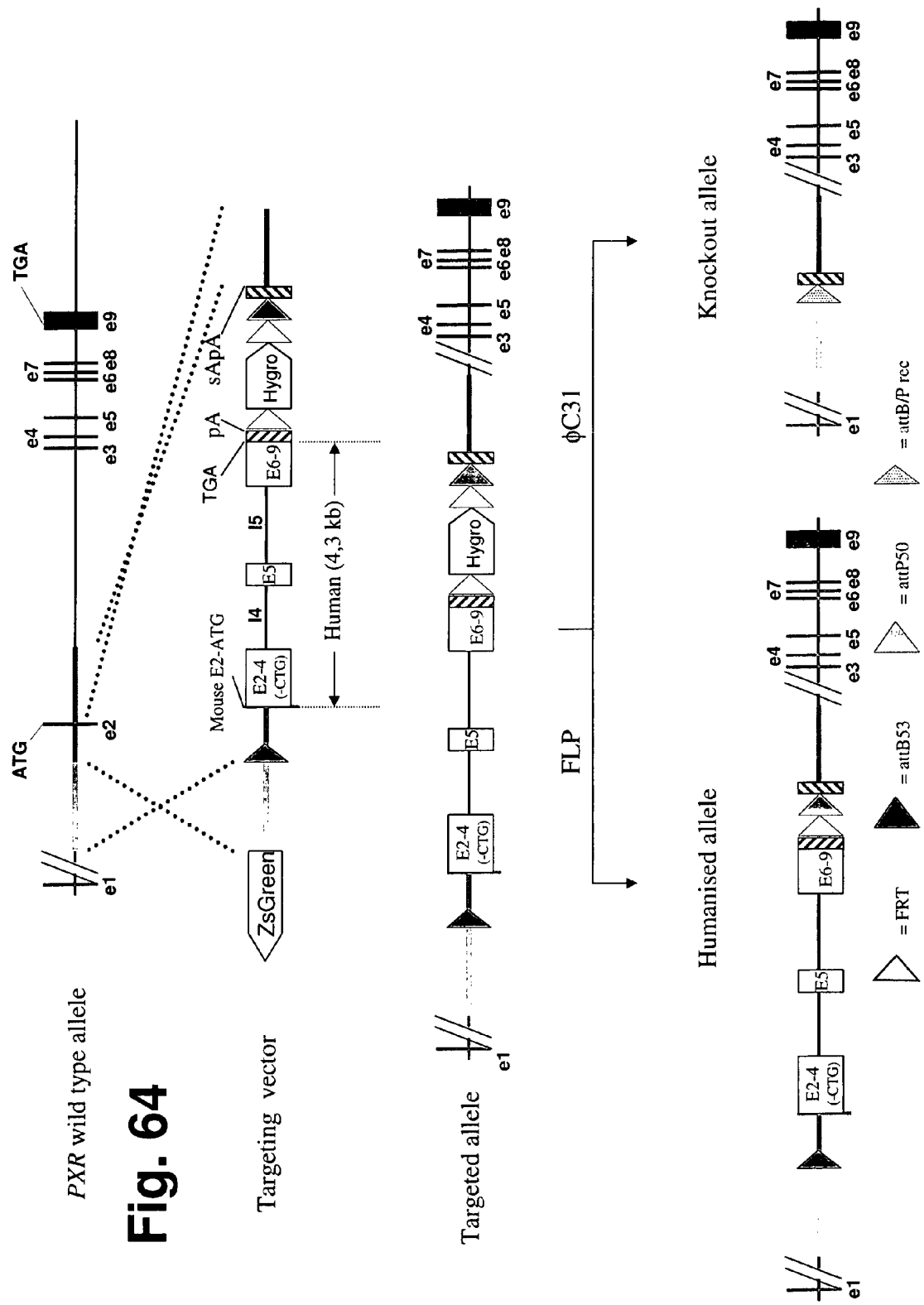
FIG. 64 shows a possible targeting strategy for PXR humanisation and knock-out (to produce mice of genotype huPXR and koPXR).

The insertion of att sites into mouse intron1 (attB53) and 3' to the splice acceptor polyA motif (attP50), allows the generation of a PXR knock-out mouse, referred to herein interchangeably as koPXR or PXR KO, etc. To generate this knock-out, sequences between the att sites were removed using the site-specific Phi-C31 recombinase (see FIG. 64).

huCAR and koCAR

Figure 65:
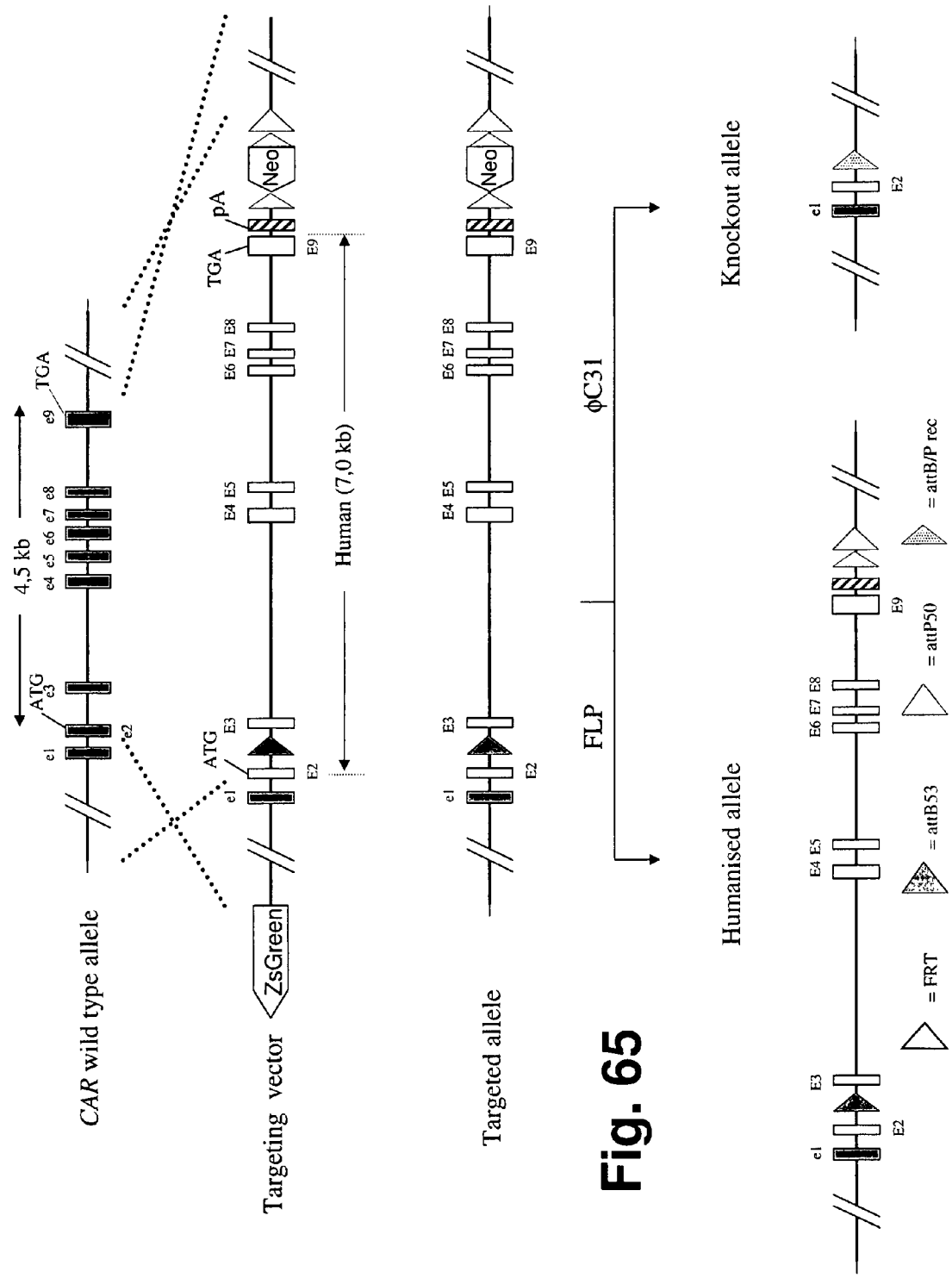
FIG. 65 shows a possible targeting strategy for CAR humanisation and knock-out (to produce mice of genotype huCAR and koCAR).
Figure 66:
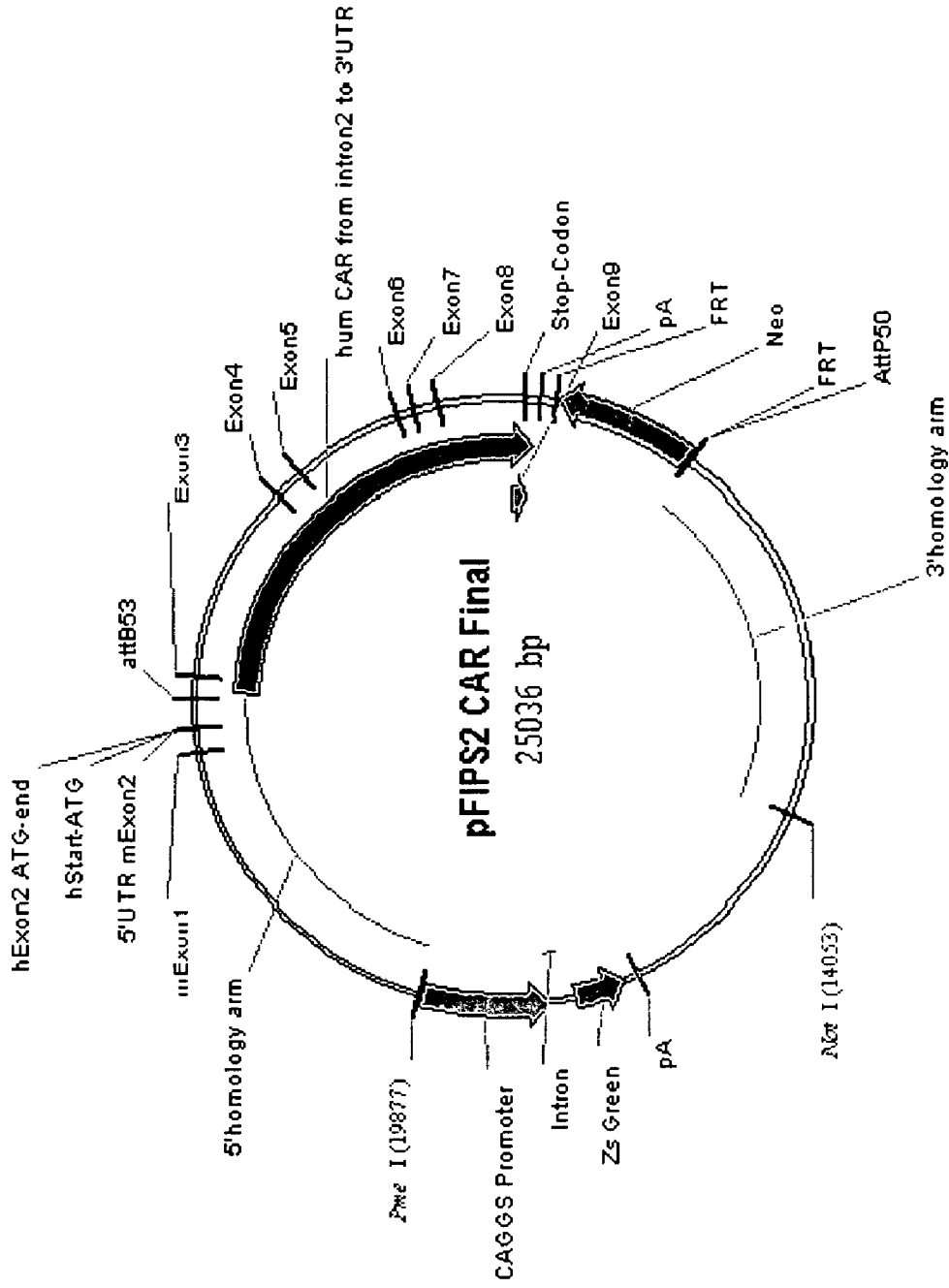
FIG. 66 shows a schematic map of a targeting vector useful for CAR humanisation and knock-out.

As noted elsewhere above, a preferred human CAR sequence is provided herein as SEQ ID NO:2. This sequence contains a 53 bp Phi-C31 recognition site (attB53) within intron2. A preferred targeting strategy is shown in FIG. 65. A preferred targeting vector is shown in FIG. 66.

huPPARα and koPPARα

Figure 67:
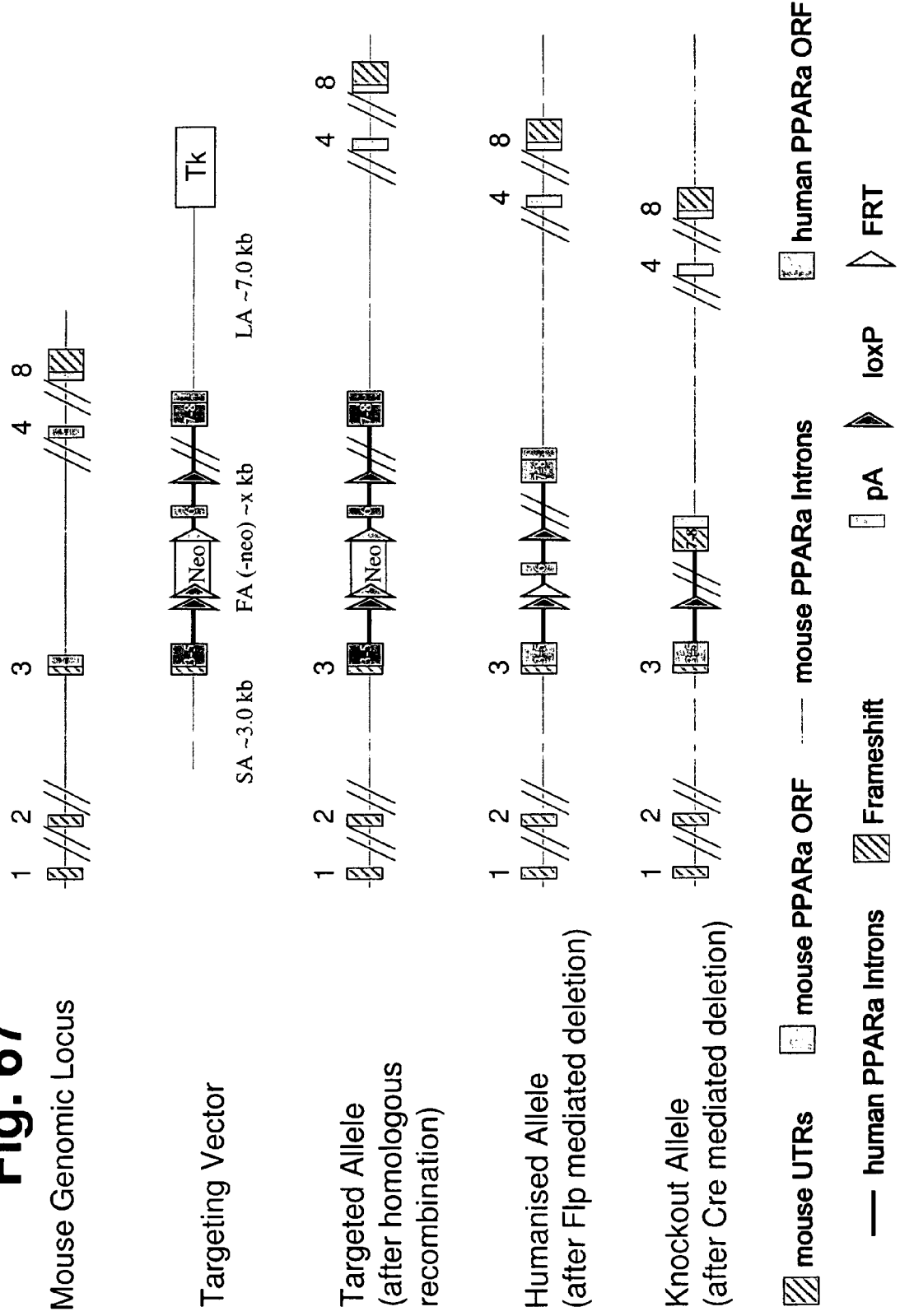
FIG. 67 shows a possible targeting strategy for the PPARα humanisation and knock-out in mice (to produce mice of genotype huPPARα and koPPARα).

A DNA sequence encoding human PPARα is inserted into the mouse PPARα locus, as shown in FIG. 67, enabling expression of human PPARα under the control of the mouse PPARα promoter. The DNA sequence encoding human PPARα comprises at least part of intron 5 and intron 6 of the human PPARα gene (FIG. 67). The targeting vector(s) include sequence elements that enable Cre-mediated PPARα knock-out to produce koPPARα (FIG. 67).

huAhRα and koAhR

Figure 68:
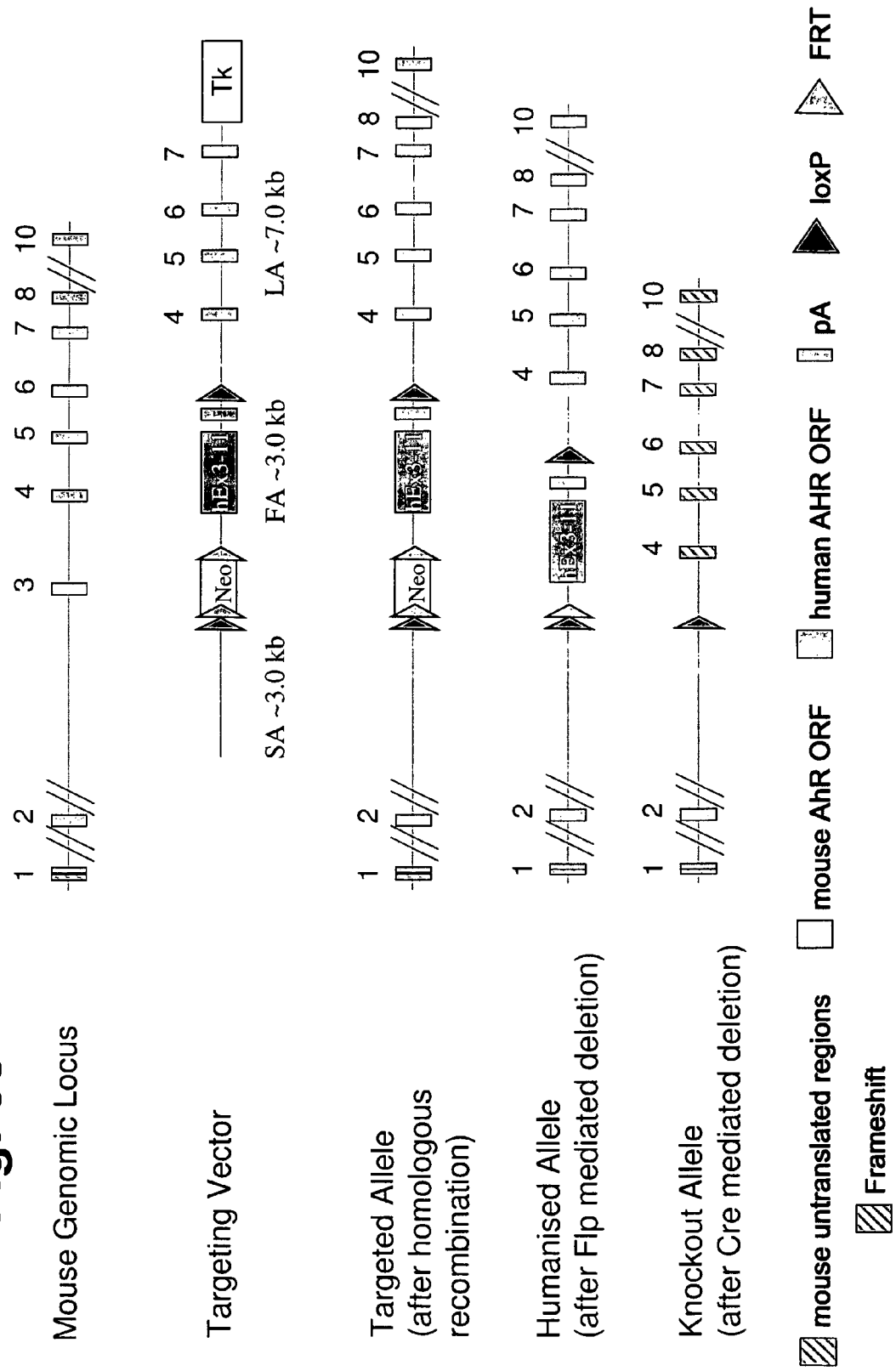
FIG. 68 shows a possible targeting strategy for AhR humanisation and knock-out in mice (to produce mice of genotype huAhR and koAhR).

A DNA sequence encoding human AhR is inserted into the mouse AhR locus (knock-in) as shown in FIG. 68, enabling expression of human AhR under the control of the mouse AhR promoter. The DNA sequence encoding human AhR comprises exons 3-11 of the human AhR gene (FIG. 68). The targeting vector(s) include sequence elements that enable Cre-mediated AhR knock-out to produce koAhR (FIG. 68).

B. Drug-Metabolizing Enzymes huCYP3A4

Figure 69:
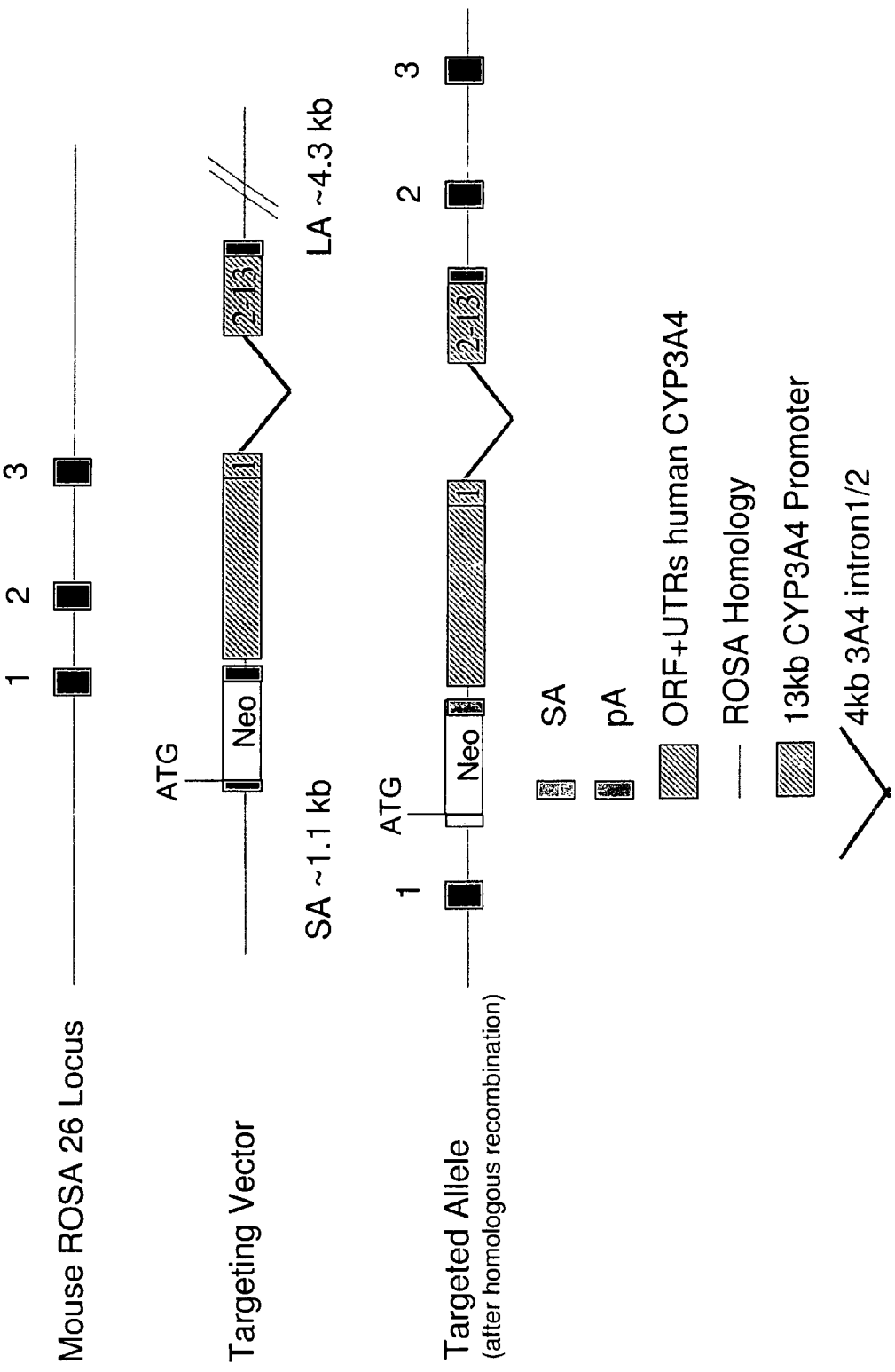
FIG. 69 shows a possible targeting strategy for CYP3A4 humanisation in mice (to produce mice of genotype huCYP3A4).

A DNA sequence encoding human CYP3A4 is inserted into the mouse Rosa26 locus (knock-in), as shown in FIG. 69, enabling expression of human CYP3A4 under the control of a human CYP3A4 promoter. The DNA sequence encoding human CYP3A4 preferably comprises intron 1 of the human CYP3A4 gene.

koCyp3a11

Figure 70:
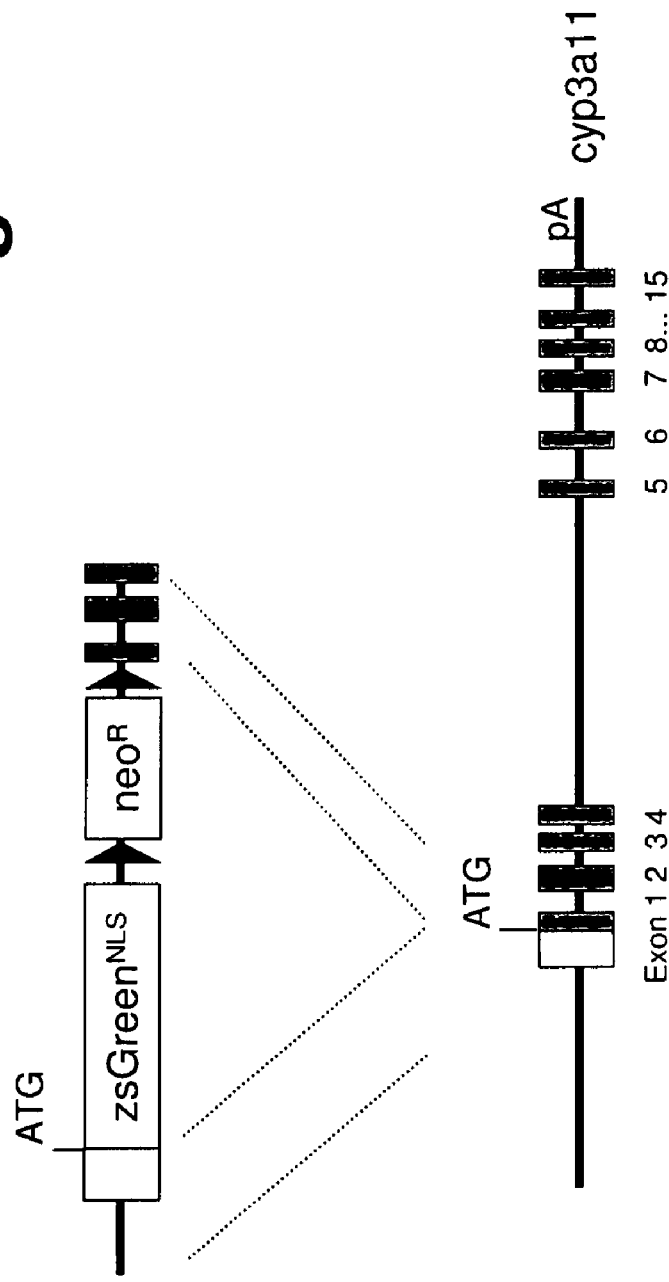
FIG. 70 shows a possible targeting strategy for Cyp3a11 knock-out in mice (to produce mice of genotype koCyp3a11), which at the same time produces a reporter construct (of the genotype rCyp3a11).

The ZsGreen reporter gene is inserted into the mouse Cyp3a11 locus by homologous recombination, as shown in FIG. 70, eliminating expression of mouse Cyp3a11, and enabling ZsGreen under the control of the mouse Cyp3a11 promoter.

huCYP3A Cluster and koCYP3A Cluster

Figure 71:
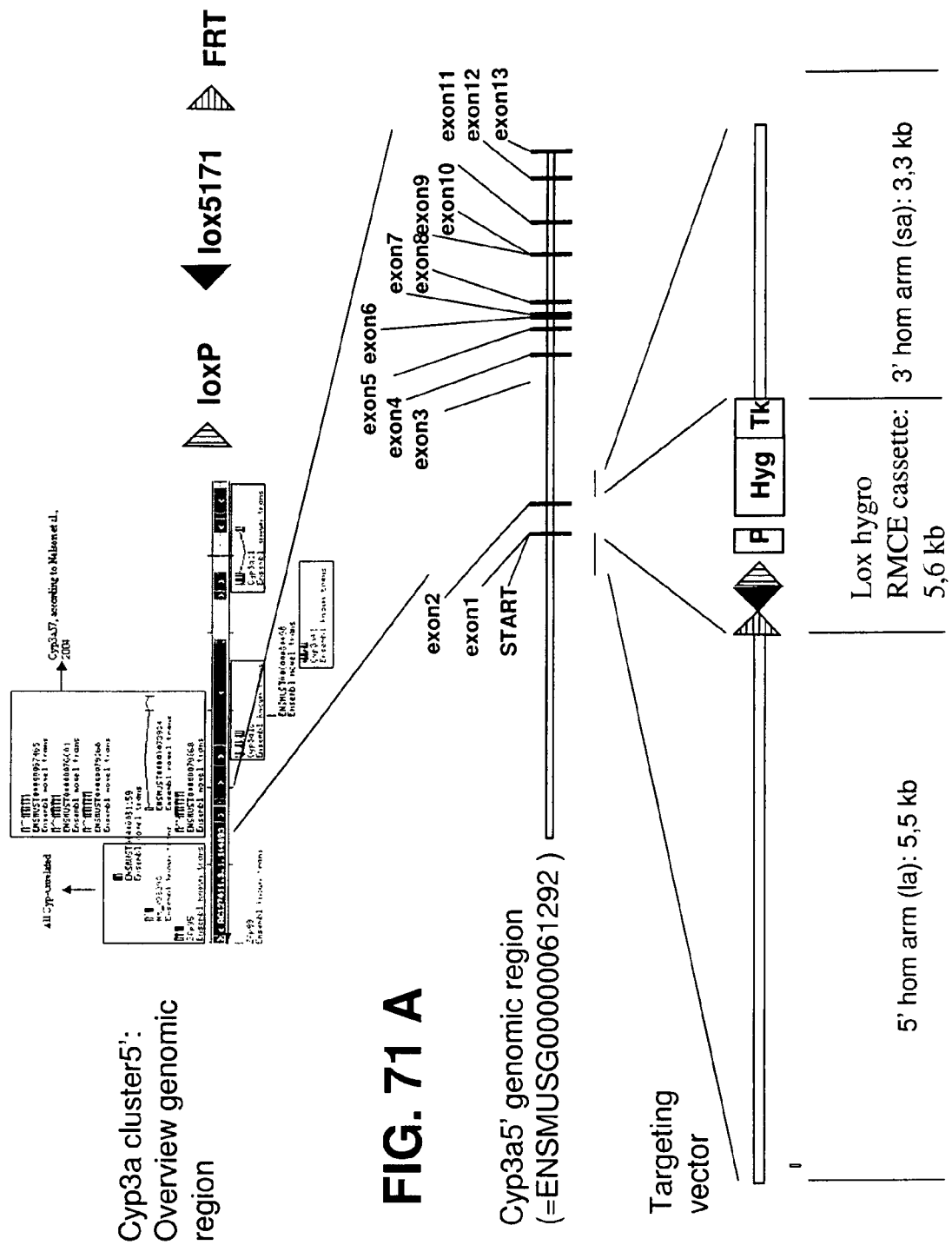
FIG. 71 panels A-C show a possible targeting strategy for the generation of mice humanised with respect to the CYP3A cluster or wherein the CYP3A cluster is knocked out (to produce mice of genotype huCYP3A cluster and koCYP3A cluster).
Figure 71:
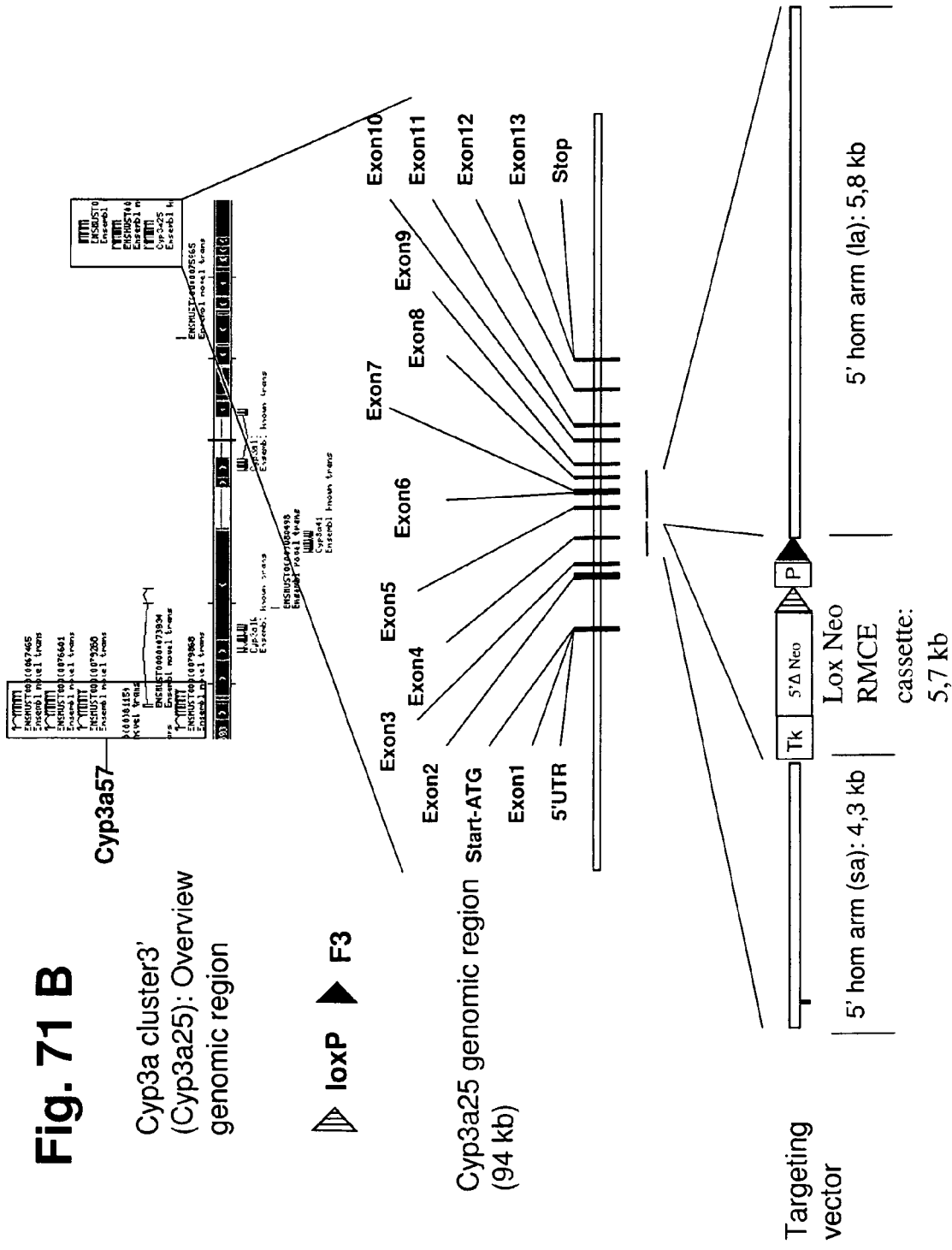
Figure 71C:
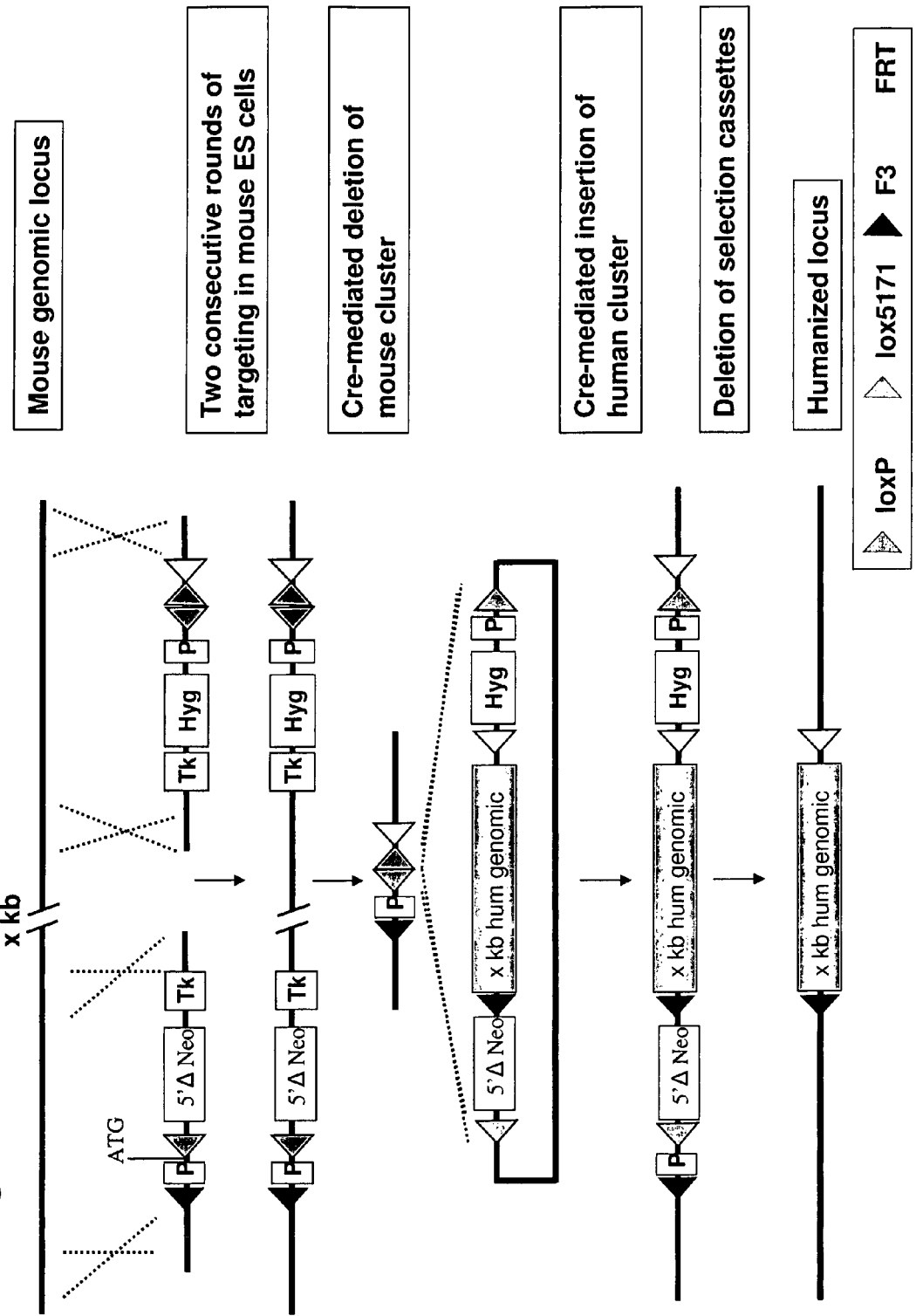
FIG. 71C shows an overview of a cluster exchange strategy.

A DNA sequence encoding the human CYP3A cluster is inserted into the loxP-flanked mouse CYP3A cluster, as shown in FIG. 71, enabling expression of the human CYP3A cluster under the control of human CYP3A promoters. The targeting vector includes loxP sequence elements that enable Cre-mediated deletion of the mouse CYP3A cluster, to produce koCYP3A (see FIG. 71C). Cre-mediated deletion of the mouse CYP3A cluster is followed by Cre-mediated insertion of the human CYP3A cluster, to produce huCYP3A (FIG. 71C). After the insertion of the human CYP3A cluster into the mouse CYP3A cluster, selection cassettes are deleted, using FRT sites that are also present in the targeting vector (FIG. 71C).

huCYP3A4 and koCyp3a Cluster

A DNA sequence encoding human CYP3A4 is inserted into the mouse Cyp3a cluster at the Cyp3a25 locus, enabling expression of human CYP3A4 under the control of the 13 kb human CYP3A4 promoter. Mice in which the mouse Cyp3a cluster is deleted may also be generated.

huCYP2C9

Figure 72:
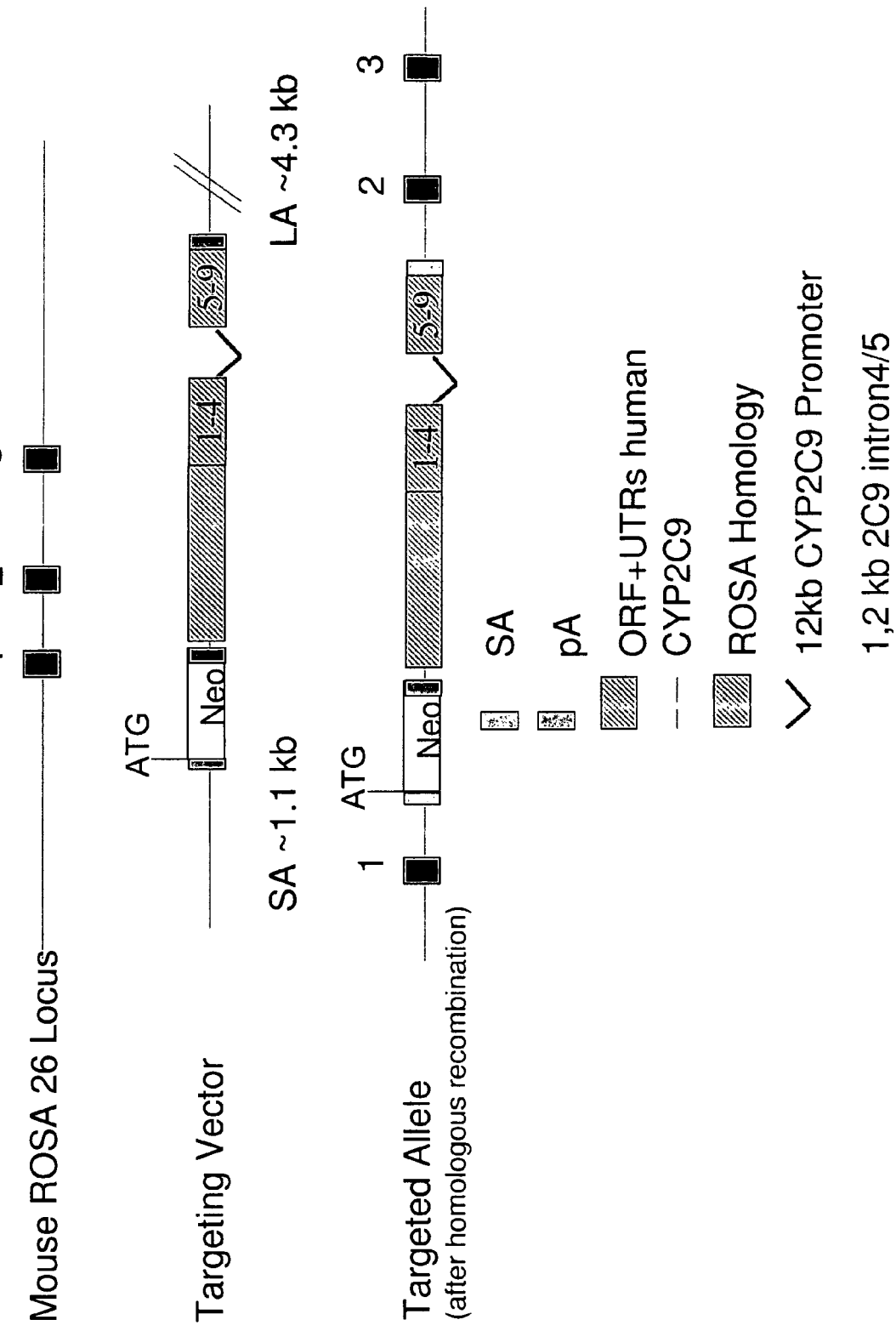
FIG. 72 shows a possible targeting strategy for CYP2C9 humanisation in mice (to produce mice of genotype huCYP2C9).

A DNA sequence encoding human CYP2C9 is inserted into the mouse Rosa26 locus, as shown in FIG. 72, enabling expression of human CYP2C9 under the control of the 12 kb human CYP2C9 promoter. The DNA sequence encoding human CYP2C9 comprises a 1,2 kb sequence of human CYP2C9 intron 4 (FIG. 72).

huCYP2C Cluster and koCYP2C Cluster

Figure 73:
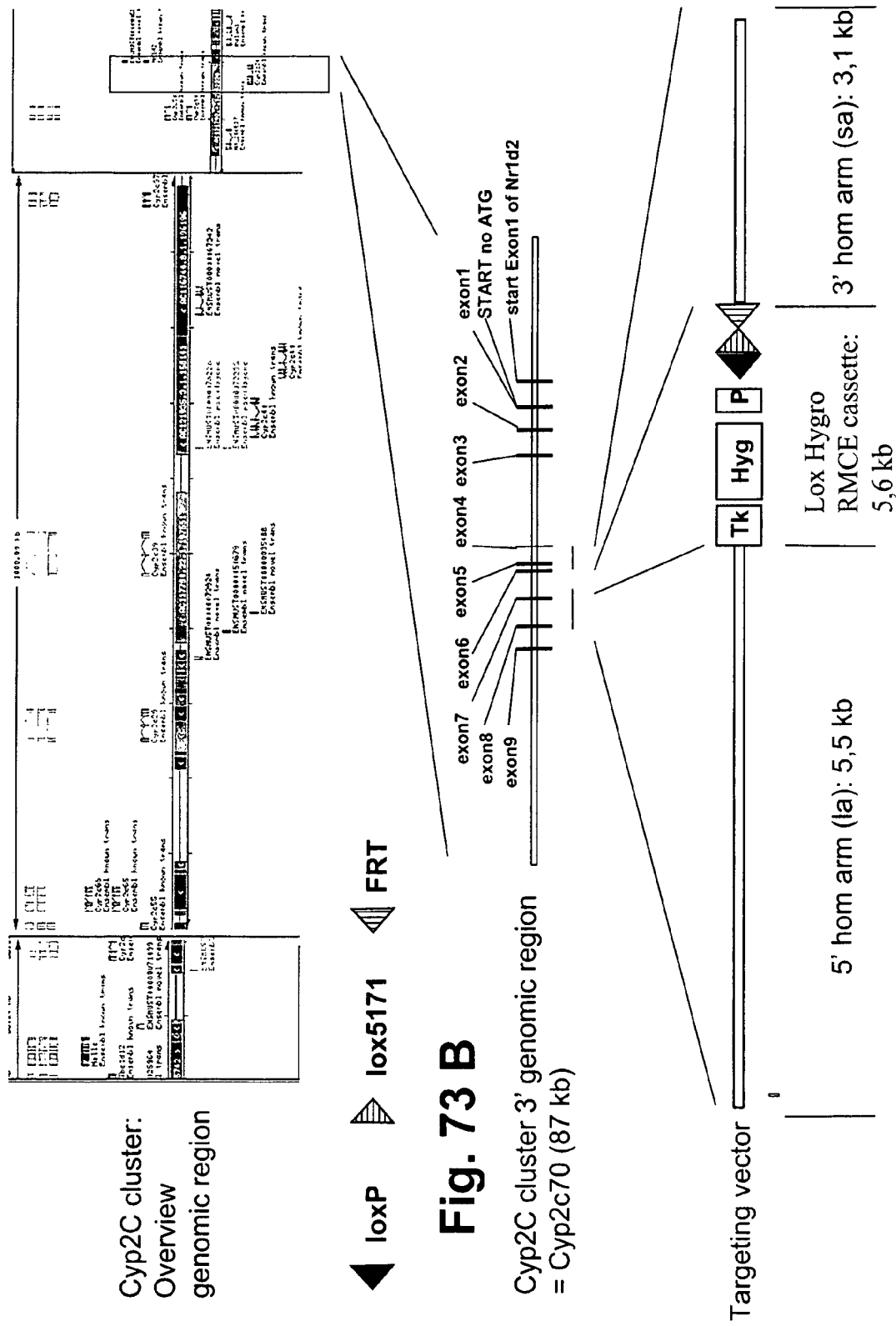
FIG. 73 panels A-C show a possible targeting strategy for the generation of mice humanised with respect to the CYP2C cluster or wherein the CYP2C cluster is knocked out (to produce mice of genotypes huCYP2C cluster and koCYP2C cluster).
Figure 73:
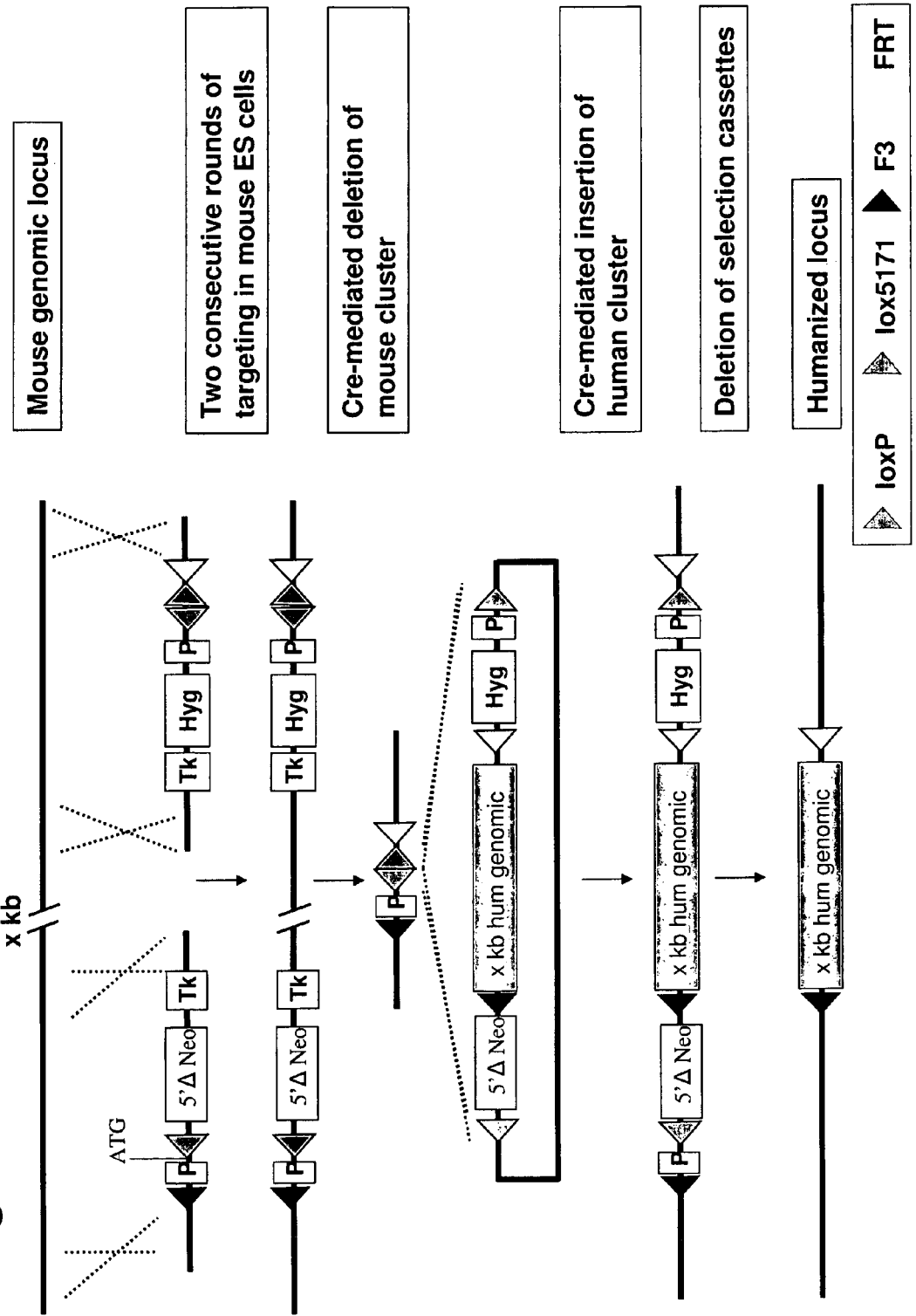

A DNA sequence encoding the human CYP2C cluster is inserted into the mouse CYP2C cluster, as shown in FIG. 73, enabling expression of the human CYP2C cluster under the control of human CYP2C promoters. The targeting vector includes loxP sequence elements that enable Cre-mediated deletion of the mouse CYP2C cluster, to produce koCYP2C (FIG. 73C). Cre-mediated deletion of the mouse CYP2C cluster is followed by Cre-mediated insertion of the human CYP2C cluster, to produce huCYP2C (FIG. 73C). After the insertion of the human CYP2C cluster into the mouse CYP2C cluster, selection cassettes are deleted, using FRT sites that are also present in the targeting vector (FIG. 73C).

huCYP2C9 and koCyp2c Cluster

A DNA sequence encoding human CYP2C9 is inserted into the mouse Cyp2c cluster, enabling expression of human CYP2C9 under the control of the 12 kb human CYP2C9 promoter. Mice in which the mouse Cyp2c cluster is deleted may also be generated.

huCYP2D6 and koCYP2D Cluster

A DNA sequence encoding human CYP2D6 is inserted into the mouse Cyp2d cluster, enabling expression of human CYP2D6 under the control of the 9 kb human CYP2D6 promoter. Mice in which the mouse Cyp2d cluster is deleted may also be generated.

huCYP3A4 and koCyp3a11

A DNA sequence encoding human CYP3A4 is inserted into the mouse Cyp3a cluster at the Cyp3a11 locus, enabling expression of human CYP3A4 under the control of the mouse Cyp3a11 promoter. Mice in which the mouse Cyp3a cluster is deleted may also be generated.

huCYP1A1/CYP1A2 and koCYP1A1/CYP1A2

DNA sequences encoding human CYP1A1 and human CYP1A2 are inserted into the mouse Cyp1a cluster, enabling expression of human CYP1A1 and human CYP1A2 under the control of the human CYP1A1 and CYP1A2 promoters. Mice in which the mouse Cyp1a cluster is deleted may also be generated.

huUGT Cluster and koUGT Cluster

Figure 74:
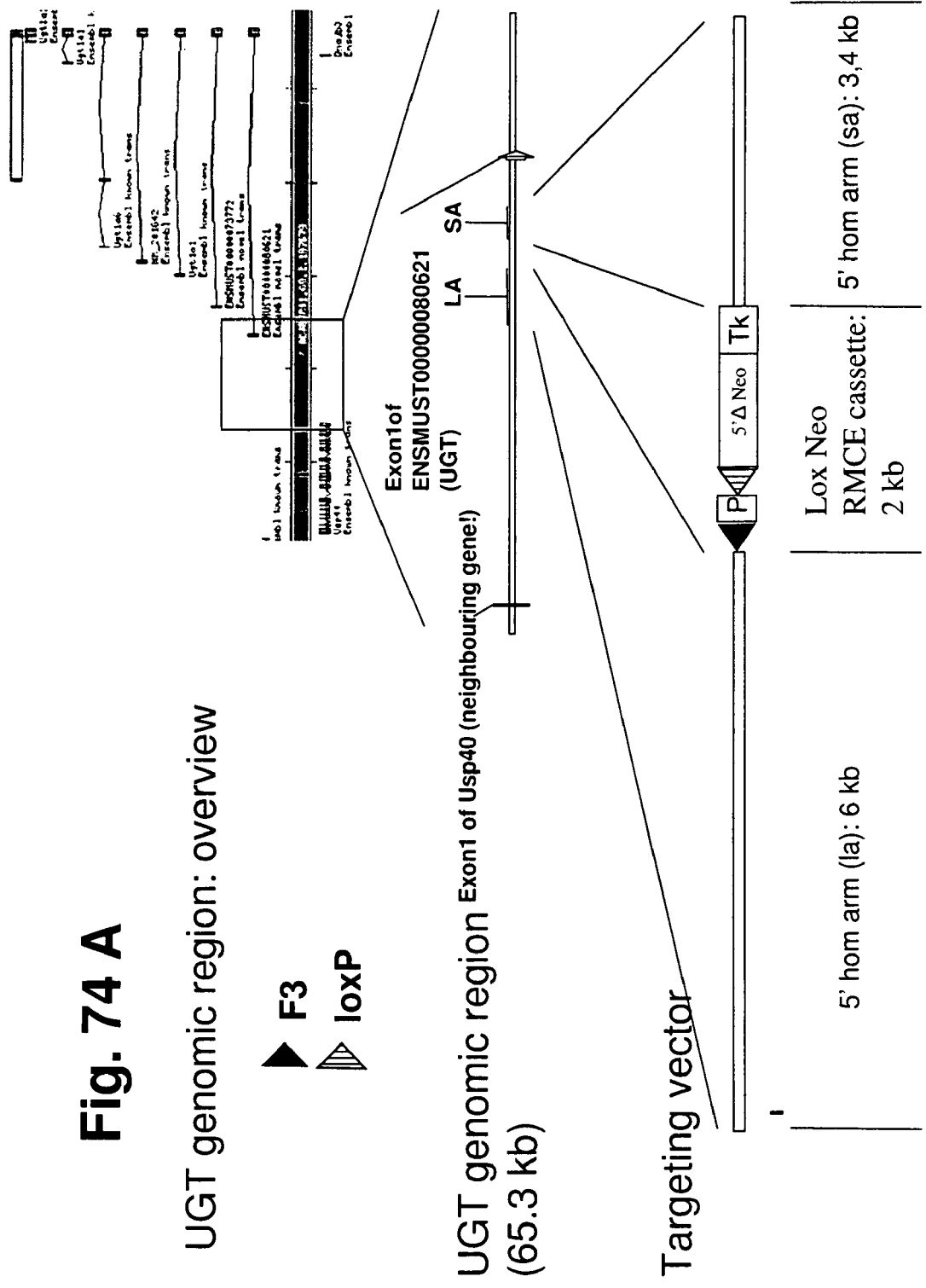
FIG. 74 panels A-C show a possible targeting strategy for the generation of mice humanised with respect to the Ugt1 cluster or wherein the Ugt1 cluster is knocked out (to produce mice of genotypes huUGT cluster and koUGT cluster).
Figure 74:
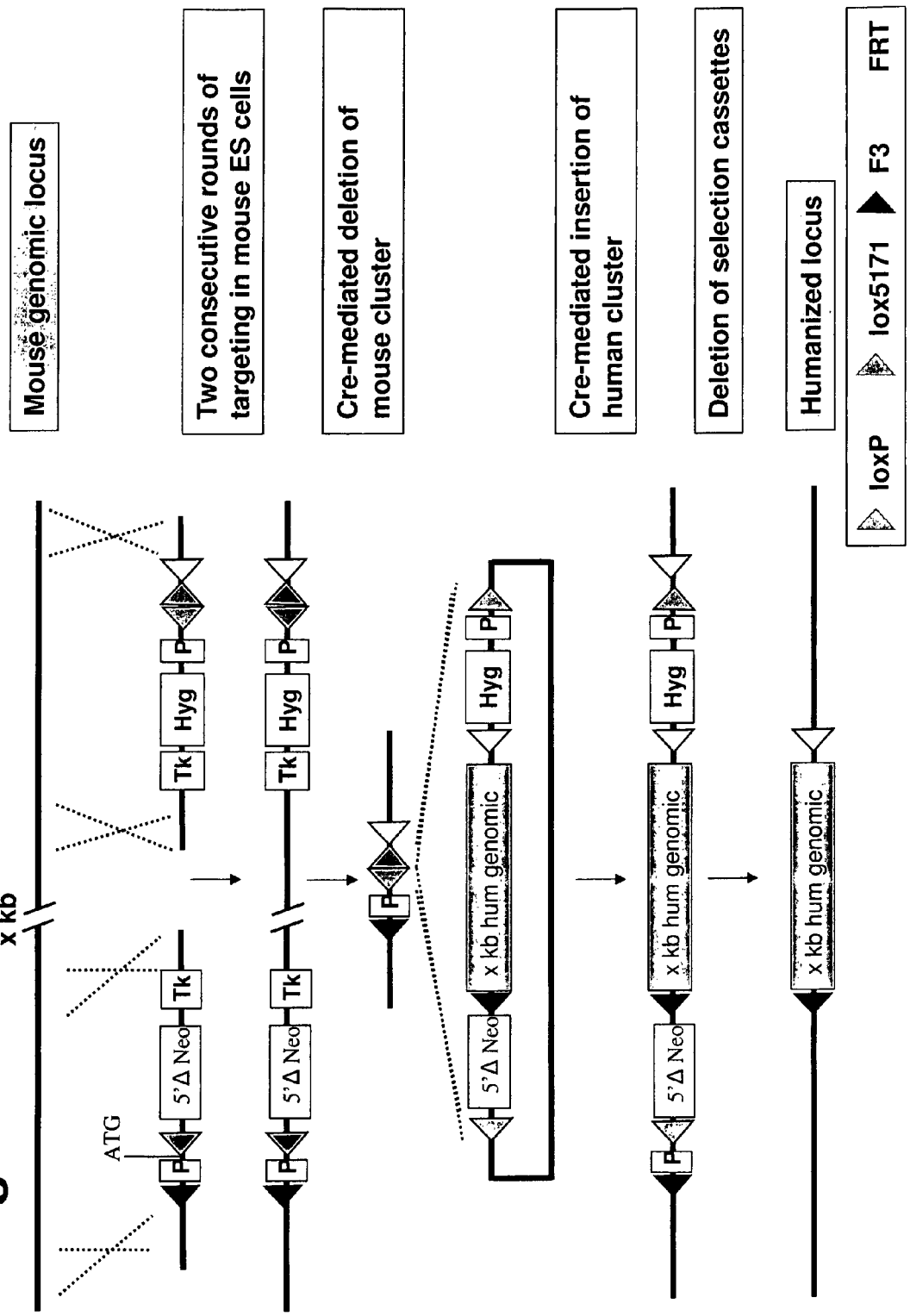

A DNA sequence encoding the human Ugt1 cluster is inserted into the mouse Ugt1 cluster, as shown in FIG. 74, enabling expression of the human Ugt1 cluster under the control of human Ugt1 promoters. The targeting vector includes loxP sequence elements that enable Cre-mediated deletion of the mouse Ugt1 cluster, to produce koUGT (FIG. 74C). Cre-mediated deletion of the mouse Ugt1 cluster is followed by Cre-mediated insertion of the human Ugt1 cluster, to produce huUGT (FIG. 74C). After the insertion of the human Ugt1 cluster into the mouse Ugt1 cluster, selection cassettes are deleted, using FRT sites that are also present in the targeting vector (FIG. 74C).

C. Drug Transporter Proteins huMDR1/mdr1a$^{-/-}$

Figure 75:
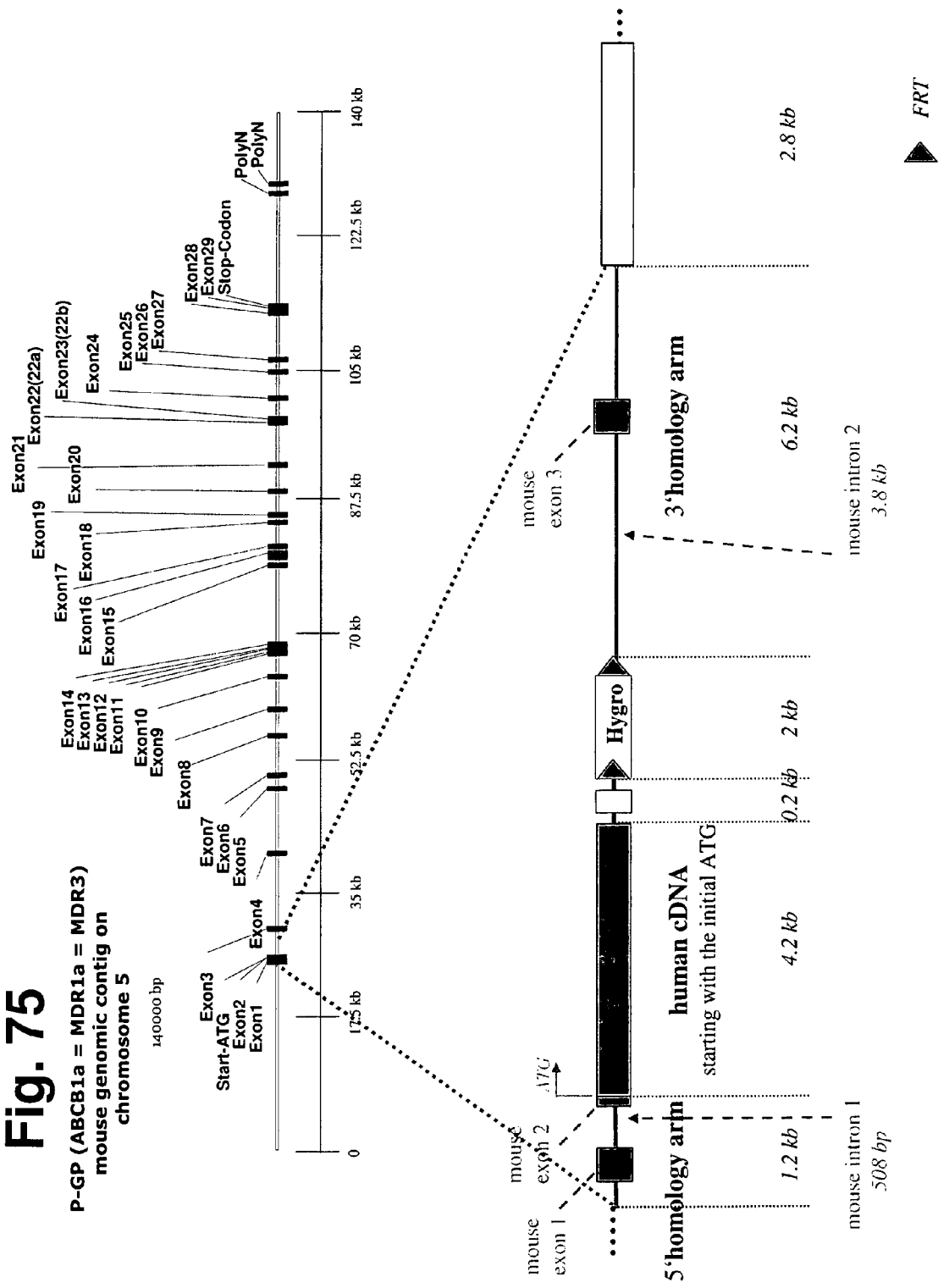
FIG. 75 shows a possible targeting strategy for MDR1 humanisation at the mouse Mdr1a locus (to produce mice of genotype huMDR1/mdr1a−/−).

A DNA sequence encoding human MDR1 is inserted into the mouse Mdr1a locus, as shown in FIG. 75, enabling expression of human MDR1 under the control of the mouse Mdr1a promoter. The DNA sequence encoding human MDR1 is the human MDR1 cDNA sequence, starting with the initial ATG.

huMDR1/mdr1b$^{-/-}$

Figure 76:
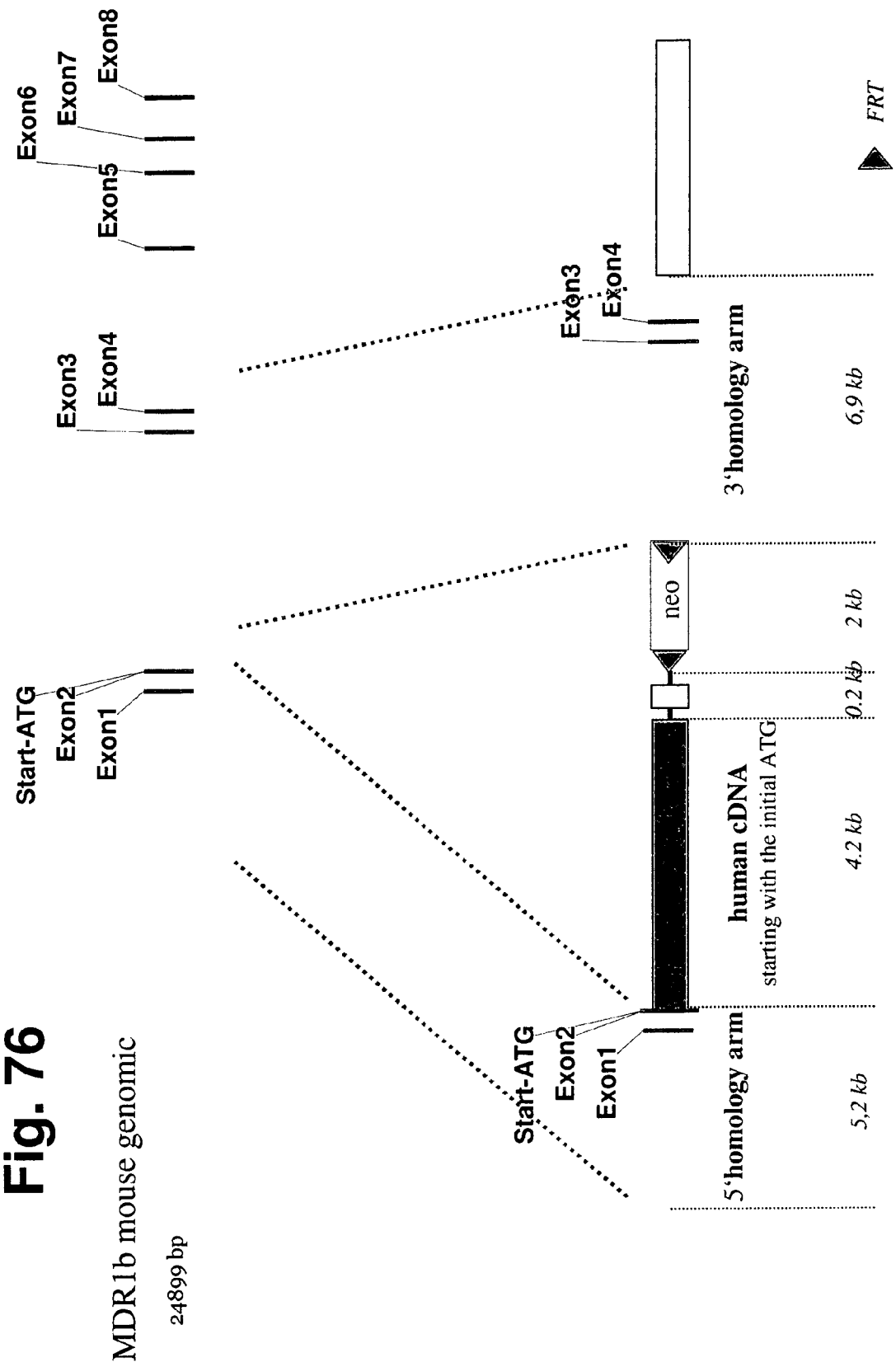
FIG. 76 shows a possible targeting strategy for MDR1 humanisation at the mouse Mdr1b locus (to produce mice of genotype huMDR1/mdr1b−/−).

A DNA sequence encoding human MDR1 is inserted into the mouse Mdr1b locus, as shown in FIG. 76, enabling expression of human MDR1 under the control of the mouse Mdr1b promoter. The DNA sequence encoding human MDR1 is the human MDR1 cDNA sequence, starting with the initial ATG.

huMDR1/mdr1a$^{-/-}$/mdr1b$^{-/-}$

The cDNA sequence for human MDR1, starting with the initial ATG, is inserted into both the mouse Mdr1a and Mdr1b loci, enabling expression of human MDR1 under the control of the mouse Mdr1a and Mdr1b promoters. The targeting is achieved in the same way as for the Mdr1a and Mdr1b single humanisation, wherein Mdr1b is targeted as shown in FIG. 76 in ES cells that have previously been manipulated at the Mdr1a locus according to the strategy provided in FIG. 75.

huMRP2

Figure 77:
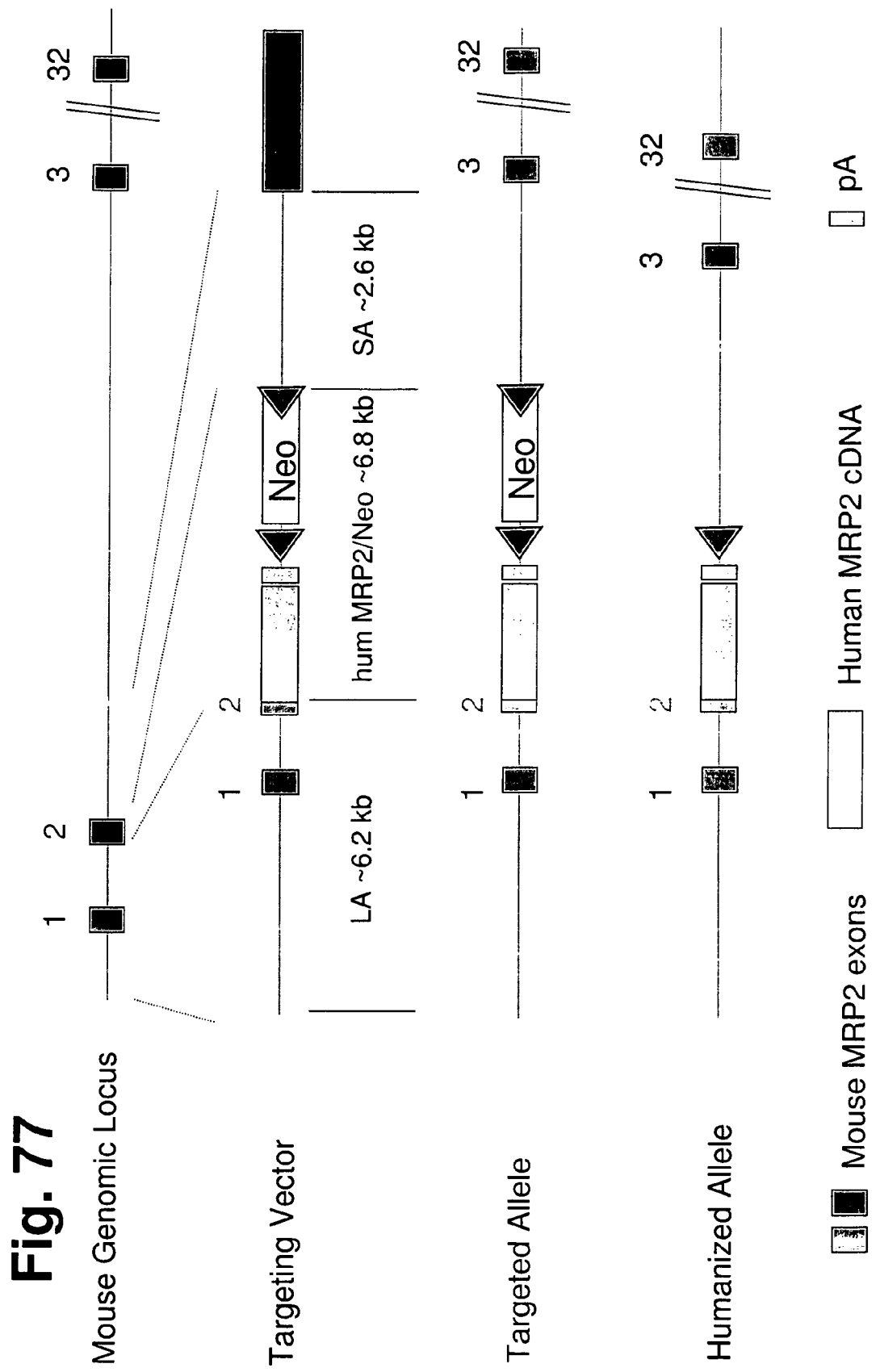
FIG. 77 shows a possible targeting strategy for MRP2 humanisation (to produce mice of genotype huMRP2).

The cDNA sequence encoding human MPR2 is inserted into the mouse Mrp2 locus, as shown in FIG. 77, enabling expression of human MRP2 under the control of the mouse Mrp2 promoter. In this strategy, (i) the mouse leader encoded by exon 1 is retained, (ii) the human cDNA will be introduced on exon2, and splice site retained, (iii) the human transcript is terminated by a polyA motif, and (iv) the complete intron 2 sequence is retained.

D. Reporter Strategies rCYP2B6

Figure 78:
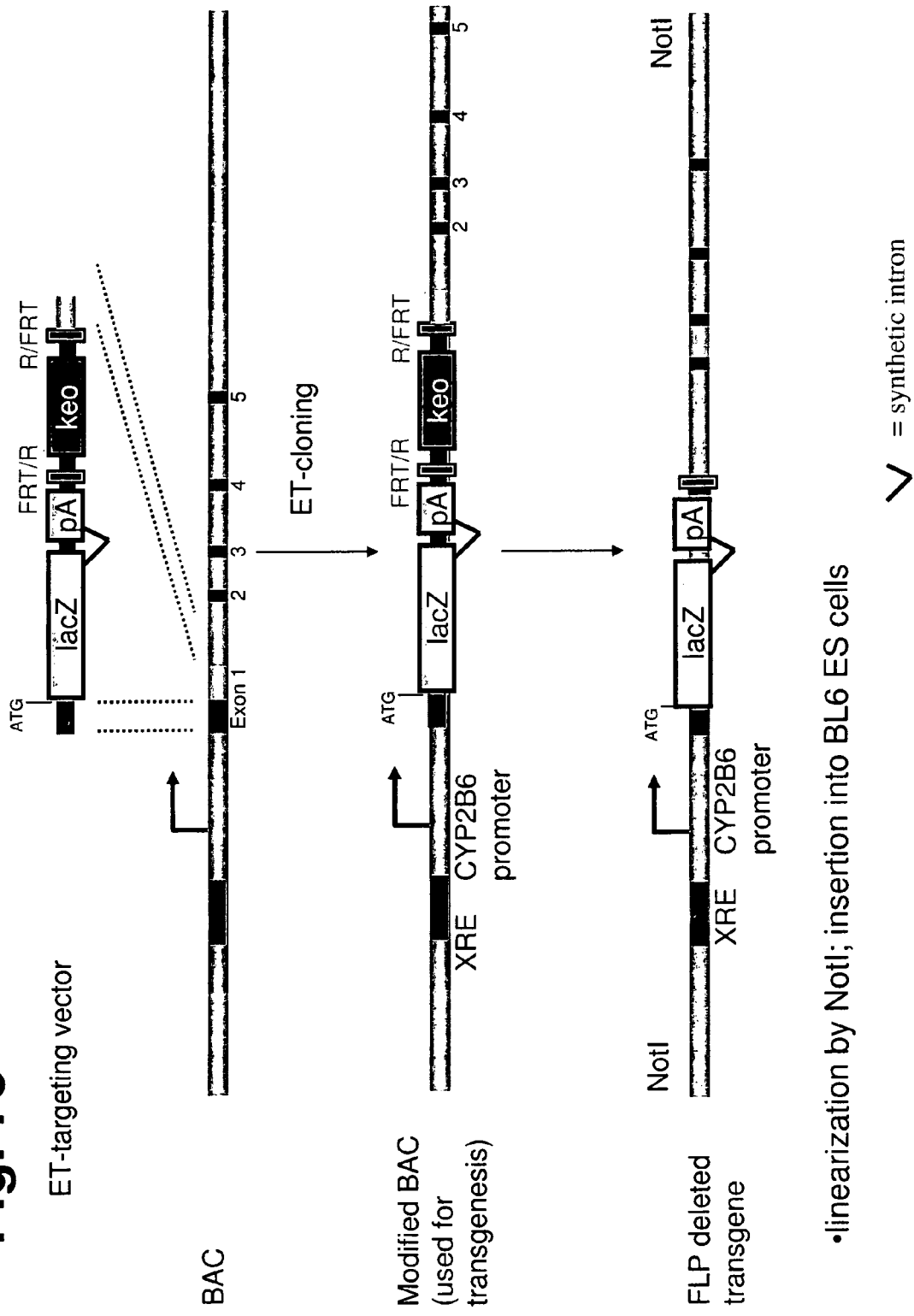
FIG. 78 shows a possible targeting strategy for the generation of a CYP2B6 reporter system in mice (to produce mice of genotype rCYP2B6).
Figure 79:
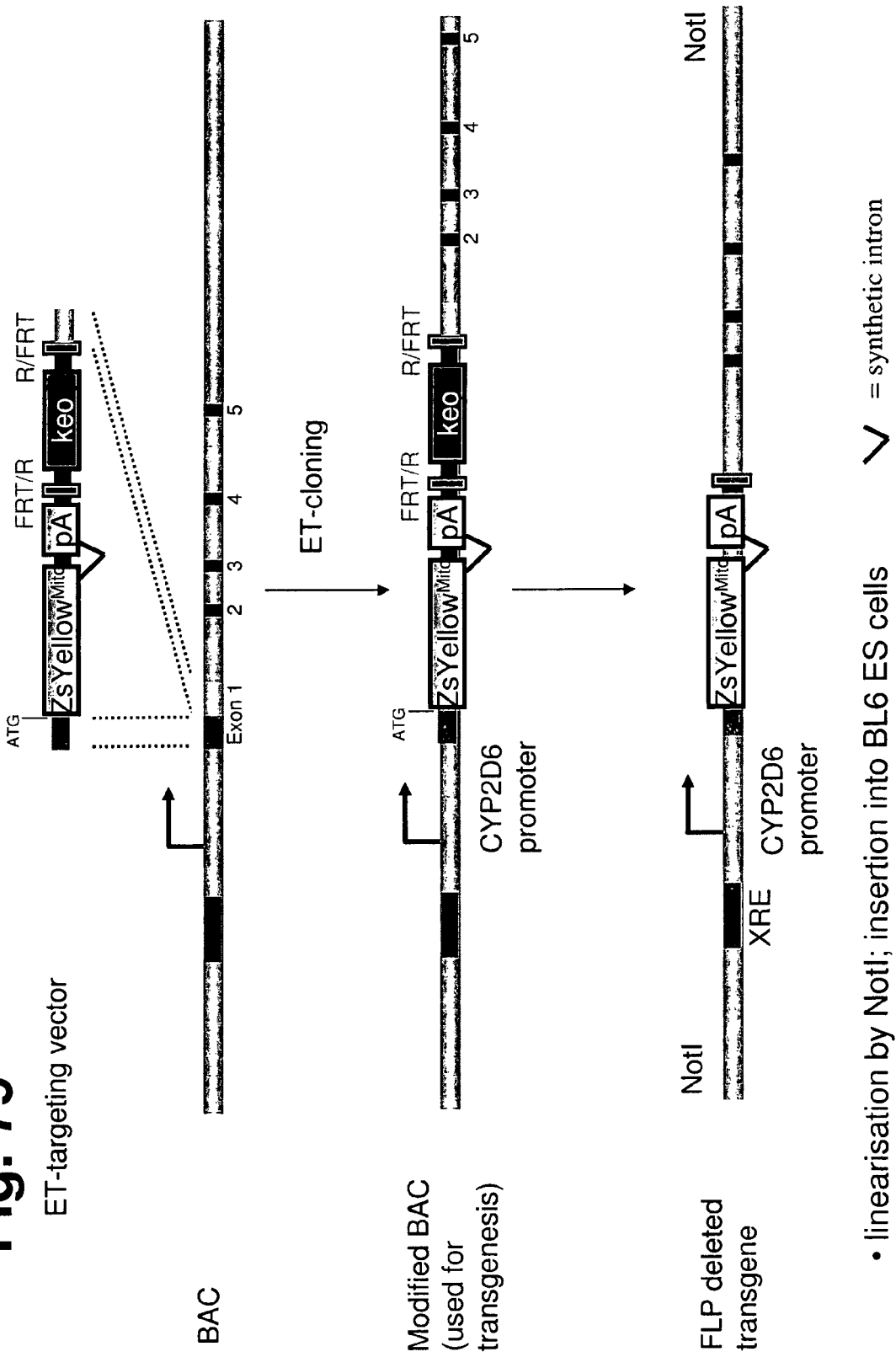
FIG. 79 shows a possible targeting strategy for the generation of a CYP2D6 reporter system in mice (to produce mice of genotype rCYP2D6).

The LacZ reporter gene and the transcriptionally linked human CYP2B6 promoter (up to 70 kb, depending on the extent of BAC insertion) are inserted into exon 1 of the mouse Cyp2b6 locus in BL6 ES cells, as shown in FIG. 78. The selection marker keo is deleted using the FRP sites and FLP recombinase, as indicated in FIG. 79. This strategy allows expression of the LacZ reporter gene in mice under the control of the human CYP2B6 promoter.

rCYP2D6

The ZsYellow reporter gene and the transcriptionally linked human CYP2D6 promoter (up to 50 kb, depending on the extent of BAC insertion) are inserted into exon 1 of the mouse Cyp2d6 locus in BL6 ES cells, as shown in FIG. 79. The selection marker keo is deleted using the FRP sites and FLP recombinase, as indicated in FIG. 79. This strategy allows expression of the ZsYellow reporter gene in mice under the control of the human CYP2D6 promoter.

rCYP3A4

Figure 80:
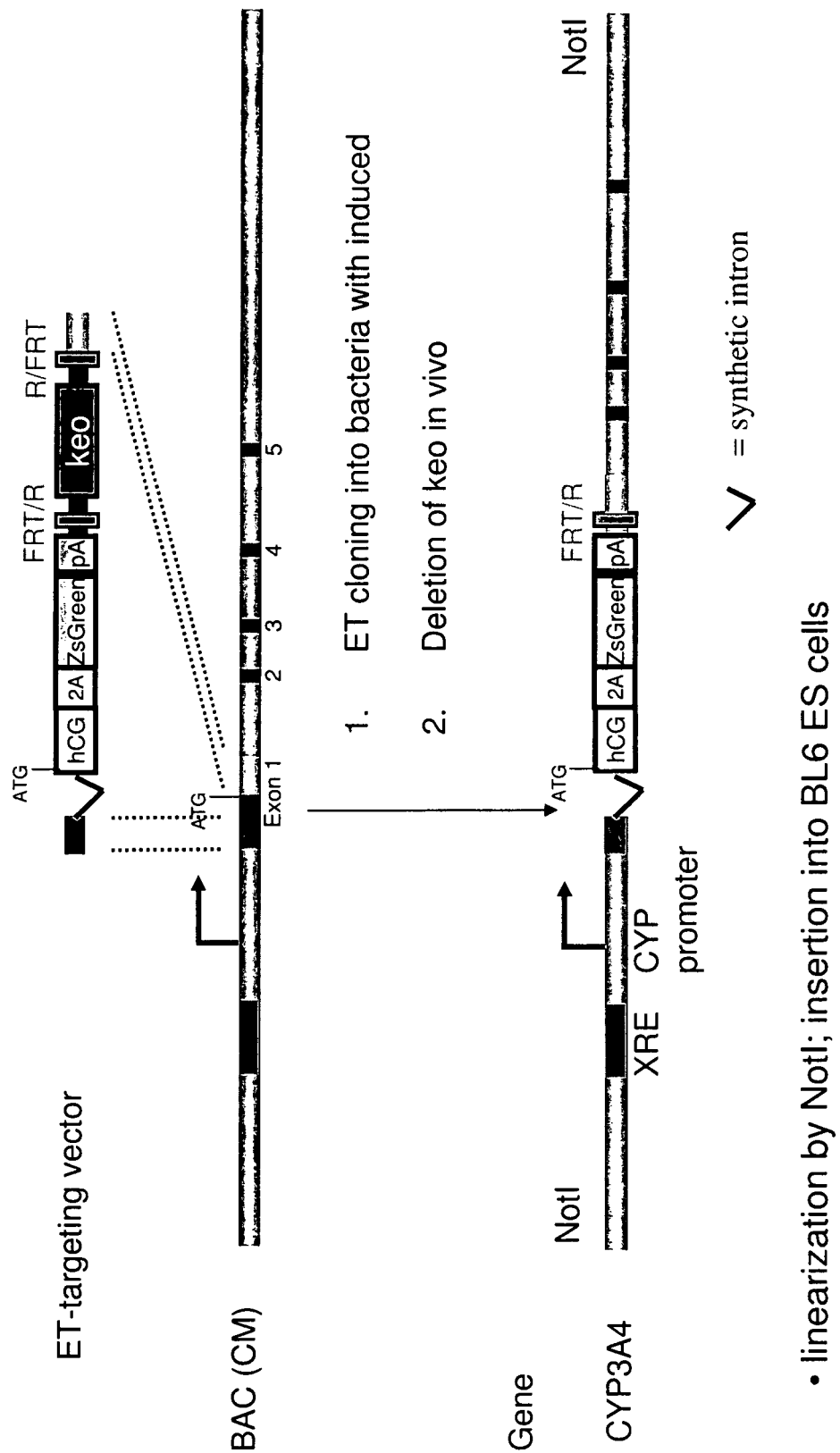
FIG. 80 shows a possible targeting strategy for the generation of a CYP3A4 reporter system in mice (to produce mice of genotype rCYP3A4 mice).

The hCG-ZsGreen reporter gene and the transcriptionally linked human CYP3A4 promoter (up to 40 kb, depending on the extent of BAC insertion) are inserted into exon 1 of the mouse Cyp3a4 locus in BL6 ES cells, as shown in FIG. 80. The selection marker keo is deleted using the FRP sites and FLP recombinase, as indicated in FIG. 80. This strategy allows expression of the hCG-ZsGreen reporter gene in mice under the control of the human CYP3A4 promoter.

rCyp3a11

Figure 81:
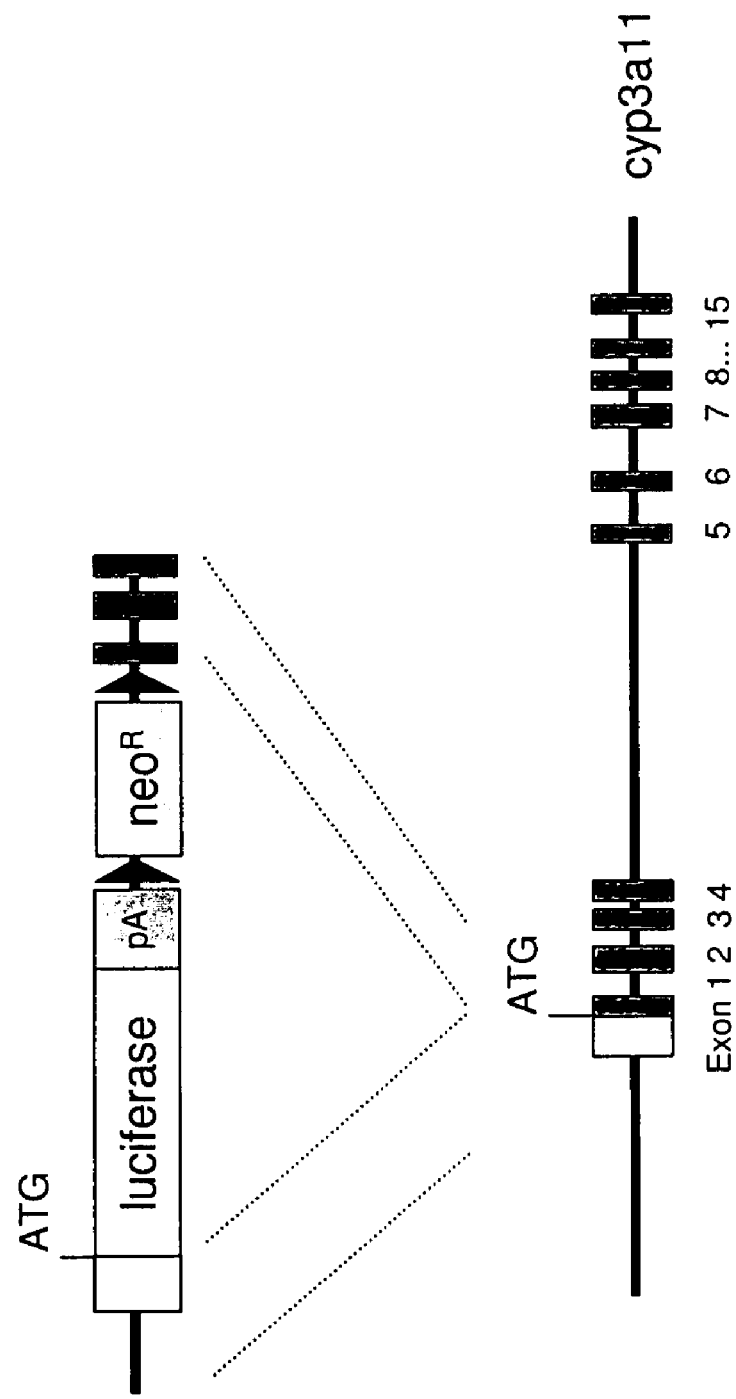
FIG. 81 shows a possible targeting strategy for the generation of a Cyp3a11 reporter system in mice (to produce mice of genotype rCyp3a11).

The Firefly luciferase reporter gene is inserted into exon 1 of the mouse Cyp3a11 locus, as shown in FIG. 81. This strategy allows expression of the hCG-ZsGreen reporter gene in mice under the control of the mouse Cyp3a11 promoter. The procedure is alternatively carried out using the ZsGreen reporter gene (FIG. 70).

rMDR1

Figure 82:
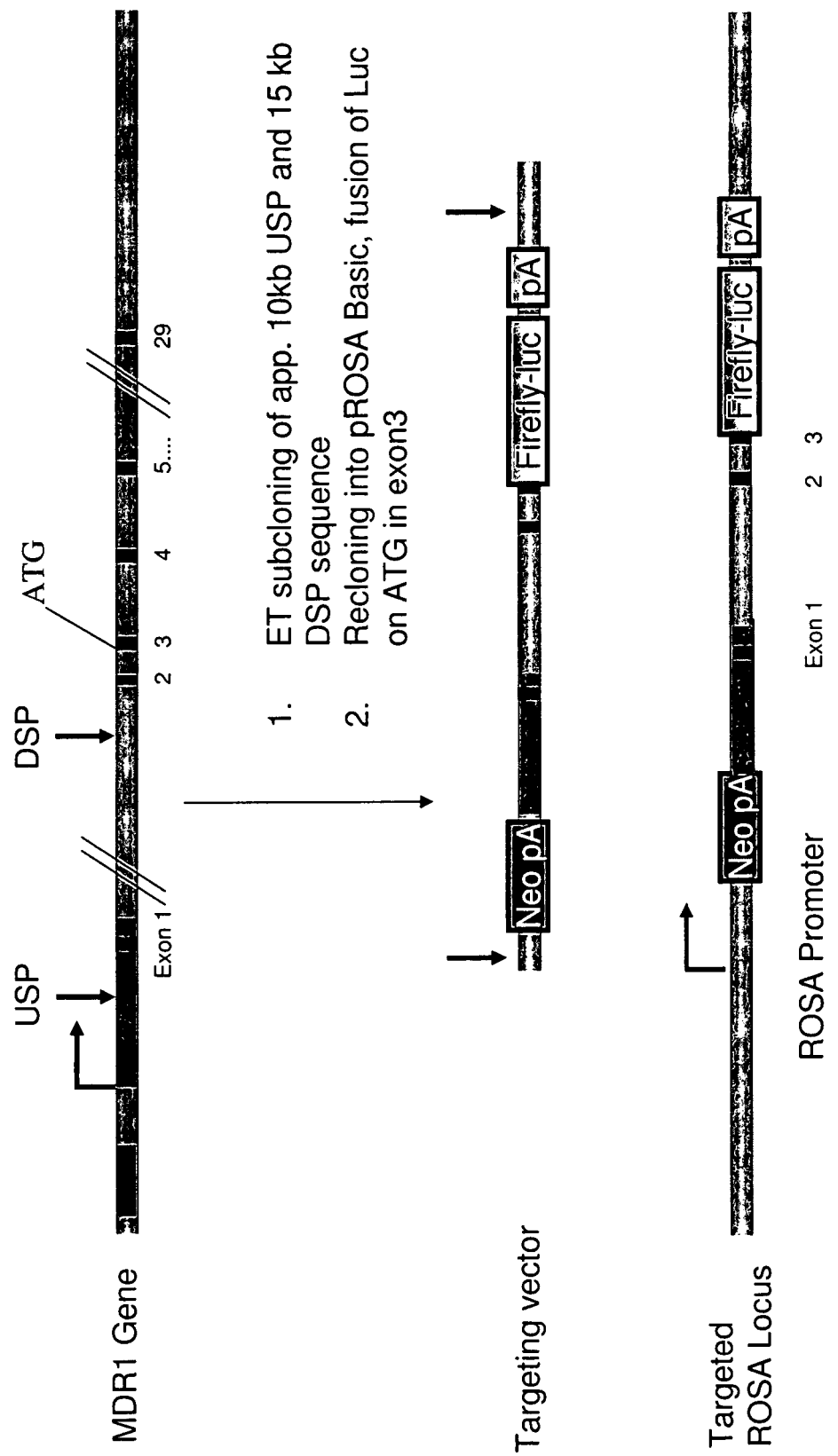
FIG. 82 shows a possible targeting strategy for the generation of a MDR1 reporter system in mice (to produce mice of genotype rMDR1).

10 kb of the human MDR1 upstream promoter (USP) including exon1 and 15 kb of the downstream promoter (DSP) including exons 2 and 3 are fused to the start ATG of the firefly luciferase, as shown in FIG. 82. USP and DSP have been described in several publications as essential elements for MDR1 expression (Ueda K, Pastan I and Gottesman M M, 1987. Isolation and sequence of the promoter region of the human multidrug-resistance (P-glycoprotein) gene. J Biol. Chem., December 25; 262(36):17432-6; Chen C J, Clark D, Ueda K, Pastan I, Gottesman M M and Roninson I B, 1990. Genomic organization of the human multidrug resistance (MDR1) gene and origin of P-glycoproteins. J Biol. Chem., January 5; 265(1):506-14; Raguz S, Tamburo De Bella M, Tripuraneni G, Slade M J, Higgins C F, Coombes R C and Yague E, 2004. Activation of the MDR1 upstream promoter in breast carcinoma as a surrogate for metastatic invasion. Clin Cancer Res. April 15; 10(8):2776-83.). The targeting vector is used for targeted transgenesis into the ROSA26 locus by homologous recombination as shown in FIG. 82.

These specific targeting strategies are preferred strategies for generating transgenic mice, tissues or cells derived therefrom having the genotypes (including the complex genotypes) described herein.

What is claimed:

1. A transgenic mouse, or tissue or cells derived therefrom, whose genome comprises:
   (i) an annulled PXR gene;
   (ii) a DNA sequence encoding a human PXR gene knocked-into the mouse PXR locus, wherein expression of the human PXR gene is under the control of a mouse PXR promoter;
   (iii) an annulled mouse gene equivalent to a human CYP3A4 gene; and
   (iv) a DNA sequence encoding human CYP3A4 operably linked to a human CYP3A4 promoter.

* * * * *

SEQUENCE LISTING

```
<160> NUMBER OF SEQ ID NOS: 4

<210> SEQ ID NO 1
<211> LENGTH: 4282
<212> TYPE: DNA
<213> ORGANISM: Homo Sapiens

<400> SEQUENCE: 1
atggaggtga gacccaaaga aagctggaac catgctgact ttgtacactg tgaggacaca      60
gagtctgttc ctggaaagcc cagtgtcaac gcagatgagg aagtcggagg tccccaaatc     120
tgccgtgtat gtgggacaa ggccactggc tatcacttca atgtcatgac atgtgaagga     180
tgcaagggct ttttcaggag ggccatgaaa cgcaacgccc ggctgaggtg ccccttccgg     240
aagggcgcct gcgagatcac ccggaagacc cggcgacagt gccaggcctg ccgcctgcgc     300
aagtgcctgg agagcggcat gaagaaggag atgatcatgt ccgacgaggc cgtggaggag     360
aggcgggcct tgatcaagcg gaagaaaagt gaacggacag ggactcagcc actgggagtg     420
caggggctga cagaggagca gcggatgatg atcagggagc tgatggacgc tcagatgaaa     480
acctttgaca ctaccttctc ccatttcaag aatttccggg taggaggaac tgcacagtga     540
cccgaggtgt cactgccatc ttcattctca catagaaact gaggttcccc aaggataaga     600
```

-continued

```
aacttataca aggtcacagc taatcagtgg tggagggtag atttggagag ctggtcctgc    660
atctgtgcta gctcctcaaa gccttagtct cattcccaaa ggttctgaaa gtgtggtccc    720
tgggtcagca gcatcagcat gcagattttc aggtcacctc agatctcctg aatctgaagc    780
tccagggagg ggcaggaccc cccggtgatt ctgttgcagg ttcaggtttg aaaaatcact    840
gctctctcct ttaaggcagg taggaactgg gtctaagcaa taagtggagg gaaagctagg    900
cagttcccca gtgttgctgg cattcggggc tttatgagga caggatcagg acctgttggg    960
ggtgtgactt ttgtgaactg gtgtttcttg atcccagcac attaactatg tctgtgctct   1020
aagtgccctc cttcccfttt gcactgatag atatctcaag tgggcccttca cagcccaaat   1080 aactggatta gcccagtgac ctcagatctg ctcttcccat ccatagcacc ctaaaccttc   1140
tgagtctcct gagcccaaca tctggaatgc ttgggatgac acaccatggt tgcagtcccc   1200
cttaccctcc attttaacca agcagggatg tgtgtgacca ttaattcata gatccccaaa   1260
gcaccttcat ctgatagaga acaccagaga aagaaacaa atgctgtgtg tgtatatgtg   1320
tgaggacaca cgcatgcatg tgggtgtgaa tgcctgcatt tgtgcatcct ctcgagctgc   1380
aactgtggct gtgcatgttt ggctggggcc tgagttggga cctgtctatg aaagcacatg   1440
ctgtctctcc tctgtccacc tcctggcatg tgtcctagct gccaggggtg cttagcagtg   1500
gctgcgagtt gccagagtct ctgcaggccc catcgaggga agaagctgcc aagtggagcc   1560
aggtccggaa agatctgtgc tctttgaagg tctctctgca gctgcggggg gaggatggca   1620
gtgtctggaa ctacaaaccc ccagccgaca gtggcgggaa agagatcttc tccctgctgc   1680
cccacatggc tgacatgtca acctacatgt tcaaaggcat catcagcttt gccaaagtca   1740
tctcctactt caggtaggac atggagactg ggtggttggg tgtggaaaag aactggaagt   1800
ggccaggagg ttcaaagggc ctggggtaga tcctgaattt gggggatatt ggtgtcagaa   1860
gaccctcctt ttcctgtgcc ctttccccgg gcagccagtg ctgctgggga gtagagccct   1920
tgctgtatgg ctggttagtt ttgtggctgt gggcctgcca gtgtctctgc ctcttcacct   1980
gctcaatgga agctaaaaat gcctcccctg cagggctgtt ctgtgaaata gaacacatc    2040 cgaagaacac ccagcacaga gtgggcattc agatagtctt ttgtactctc ccttaaaggg   2100
gcaggaatca catgttgaca gttccagagc aaggaatgag aggaatagaa aagataaggc   2160
tgtgaaggcc atggggaggg cgggtggtcc tcagagccca agggtcaggt ctccccagag   2220
ctagatgtgg aggcaacaac catcgggcaa ctgggggttag tgggagacat gggaacttcc   2280
tggggtggca ggaaccacag ccccagaata tgtgtgcagt cgtaggatta gggatggtgc   2340
caggtgtatc tgtccttggg taggccacct tgccttgcca agcctggtca gtggggctg    2400 aaacacacct gccacaagct cctggtttct tcagcaggtt gagggtaggt tatactctag   2460
gagcccagag gttcttctct ggccctgtag gagtcatgcg tgacttattt aatgggtga    2520 tgctgacagc aggtttggaa tggggttcag atggtagcaa ataagcttaa aggggcaggg   2580
agagaagaat acttataaat gtggacattg ggagatcttt ggtgaaatcc agtgactgac   2640
aatttaacac cagggcttcc cacttgctat ttctcaaggc caccaatgtc gagcacagtg   2700
acctgaggtg tcactgccat cttcattctc agatagaaac tgaagttccc caaggataag   2760
aaacttgtac aaggtcacag ctaatcagtg gtggaggcta gatttggaag taccaaagcc   2820
agctcgatgc caggtcctaa gctgggcaat ggggaggcac agaagaataa gatcaattac   2880
atggcatttg tagctcagtg ttagggatct aaaagaagga tgggcgccag tagcacaggg   2940
tctgaattcc caaggccaag aggtagtgtt tcctcaaaac ccagagtaag cagcctccct   3000
```

```
ctcaggctgt gaagcttcct ccttgtaagg aatgcctcct tactgggagg gtgggggccc       3060
ctcccaggtt gggagggagt gatccctgca ggaccggaag ggtatccatg taaccataat       3120
ctcagaggct tgttaagccg cctccatggt taggcctgtg cttcagcgct aggagtgggg       3180
cttcaggcat ctgggctgca gggaaacagt agaaatacat gtgtgcacat taaacccaac       3240
accgacagca ggaagcaaac atccccacta ctggaactca ggccaaaagg gcggcacttt       3300
cactctggaa aggggagact gcactctgga aagacttctg agaggggcaa agacatagca       3360
tggcctgagg ggctagcagg atatactaaa ggggaagtca ttccaagggg gaaactgagg       3420
cagaaaggag gaggccaggg accagaagcc aaagcactag ctgtaggtca ggatttgtat       3480
aggagctgaa ggagatgggg ccagcctgta agggacctgg atgccaagct cagtgggtgg       3540
agttcccgga ggttggaggg gaggagagga tgctgcgggg cagagctgtc tgctgggttg       3600
tgaggggaga gatgagaggc agccagacag cagccacagt catcctcagg gaaaggagcc       3660
atcctccctc ttcctctcgc ccccaacttc tggattatgg gatggctgct ggtgccggtc       3720
tgtgggctgc ctcccaggga gctgtcctcc cctccccatc cttgctgcca gggacttgcc       3780
catcgaggac cagatctccc tgctgaaggg ggccgctttc gagctgtgtc aactgagatt       3840
caacacagtg ttcaatgcgg agactggaac ctgggagtgt ggccggctgt cctactgctt       3900
ggaagacact gcaggtggct ccagcaact tctactggag cccatgctga aattccacta       3960
catgctgaag aagctgcagc tgcatgagga ggagtatgtg ctgatgcagg ccatctccct       4020
cttctcccca gaccgcccag gtgtgctgca gcaccgcgtg gtggaccagc tgcaggagca       4080
attcgccatt actctgaagt cctacattga atgcaatcgg ccccagcctg ctcataggtt       4140
cttgttcctg aagatcatgg ctatgctcac cgagctccgc agcatcaatg ctcagcacac       4200
ccagcggctg ctgcgcatcc aggacataca ccccttgct acgcccctca tgcaggagtt       4260
gttcggcatc acaggtagct ga                                               4282
```

<210> SEQ ID NO 2
<211> LENGTH: 4769
<212> TYPE: DNA
<213> ORGANISM: Homo Sapiens

<400> SEQUENCE: 2

```
atggaggtga gacccaaaga aagctggaac catgctgact ttgtacactg tgaggacaca         60
gagtctgttc ctggaaagcc cagtgtcaac gcagatgagg aagtcggagg tccccaaatc        120
tgccgtgtat gtggggacaa ggccactggc tatcacttca atgtcatgac atgtgaagga        180
tgcaagggct ttttcaggag ggccatgaaa cgcaacgccc ggctgaggtg ccccttccgg        240
aagggcgcct gcgagatcac ccggaagacc cggcgacagt gccaggcctg ccgcctgcgc        300
aagtgcctgg agagcggcat gaagaaggag atgatcatgt ccgacgaggc cgtgaggag         360
aggcgggcct tgatcaagcg gaagaaaagt gaacggacag ggactcagcc actgggagtg        420
caggggctga cagaggagca gcggatgatg atcagggagc tgatggacgc tcagatgaaa        480
acctttgaca ctaccttctc ccatttcaag aatttccggg taggaggaac tgcacagtga        540
cccgaggtgt cactgccatc ttcattctca catagaaact gaggttcccc aaggataaga        600
aacttataca aggtcacagc taatcagtgg tggagggtag atttggagag ctggtcctgc        660
atctgtgcta gctcctcaaa gccttagtct cattcccaaa ggttctgaaa gtgtggtccc        720
tgggtcagca gcatcagcat gcagattttc aggtcacctc agatctcctg aatctgaagc        780
```

```
tccagggagg ggcaggaccc cccggtgatt ctgttgcagg ttcaggtttg aaaaatcact    840
gctctctcct ttaaggcagg taggaactgg gtctaagcaa taagtggagg gaaagctagg    900
cagttcccca gtgttgctgg cattcggggc tttatgagga caggatcagg acctgttggg    960
ggtgtgactt ttgtgaactg gtgtttcttg atcccagcac attaactatg tctgtgctct   1020
aagtgccctc cttcccctttt gcactgatag atatctcaag tggcccttca cagcccaaat   1080
aactggatta gcccagtgac ctcagatctg ctcttcccat ccatagcacc ctaaaccttc   1140
tgagtctcct gagcccaaca tctggaatgc ttgggatgac acaccatggt tgcagtcccc   1200
cttaccctcc attttaacca agcagggatg tgtgtgacca ttaattcata gatccccaaa   1260
gcaccttcat ctgatagaga acaccagaga gaagaaacaa atgctgtgtg tgtatatgtg   1320
tgaggacaca cgcatgcatg tgggtgtgaa tgcctgcatt tgtgcatcct ctcgagctgc   1380
aactgtggct gtgcatgttt ggctggggcc tgagttggga cctgtctatg aaagcacatg   1440
ctgtctctcc tctgtccacc tcctggcatg tgtcctagct gccaggggtg cttagcagtg   1500
gctgcgagtt gccagagtct ctgcaggccc catcgaggga agaagctgcc aagtggagcc   1560
aggtccggaa agatctgtgc tctttgaagg tctctctgca gctgcggggg gaggatggca   1620
gtgtctggaa ctacaaaccc ccagccgaca gtggcgggaa agagatcttc tccctgctgc   1680
cccacatggc tgacatgtca acctacatgt tcaaaggcat catcagcttt gccaaagtca   1740
tctcctactt caggtaggac atggagactg ggtggttggg tgtggaaaag aactggaagt   1800
ggccaggagg ttcaaaggcc ctggggtaga tcctgaattt gggggatatt ggtgtcagaa   1860
gaccctcctt ttcctgtgcc cttttcccgg gcagccagtg ctgctgggga gtagagccct   1920
tgctgtatgg ctggttagtt ttgtggctgt gggcctgcca gtgtctctgc ctcttcacct   1980
gctcaatgga agctaaaaat gcctccctg cagggctgtt ctgtgaaata agaacacatc   2040
cgaagaacac ccagcacaga gtgggcattc agatagtctt ttgtactctc ccttaaaggg   2100
gcaggaatca catgttgaca gttccagagc aaggaatgag aggaatagaa aagataaggc   2160
tgtgaaggcc atggggaggg cgggtggtcc tcagagccca aggtcaggt ctccccagag    2220 ctagatgtgg aggcaacaac catcgggcaa ctggggttag tgggagacat gggaacttcc   2280
tggggtggca ggaaccacag ccccagaata tgtgtgcagt cgtaggatta gggatggtgc   2340
caggtgtatc tgtccttggg taggccacct tgccttgcca agcctggtca agtggggctg   2400
aaacacacct gccacaagct cctggttttct tcagcaggtt gagggtaggt tatactctag   2460
gagcccagag gttcttctct ggccctgtag gagtcatgcg tgacttattt aatggggtga   2520
tgctgacagc aggtttggaa tggggttcag atggtagcaa ataagcttaa aggggcaggg   2580
agagaagaat acttataaat gtggacattg ggagatcttt ggtgaaatcc agtgactgac   2640
aatttaacac cagggcttcc cacttgctat ttctcaaggc caccaatgtc gagcacagtg   2700
acctgaggtg tcactgccat cttcattctc agatagaaac tgaagttccc caaggataag   2760
aaacttgtac aaggtcacag ctaatcagtg gtggaggcta gatttggaag taccaaagcc   2820
agctcgatgc caggtcctaa gctgggcaat ggggaggcac agaagaataa gatcaattac   2880
atggcatttg tagctcagtg ttagggatct aaaagaagga tgggcgccag tagcacaggg   2940
tctgaattcc caaggccaag aggtagtgtt tcctcaaaac ccagagtaag cagcctccct   3000
ctcaggctgt gaagcttcct ccttgtaagg aatgcctcct tactggggag gtggggcccc   3060
ctcccaggtt gggagggagt gatccctgca ggaccggaag ggtatccatg taaccataat   3120
ctcagaggct tgttaagccg cctccatggt taggcctgtg cttcagcgct aggagtgggg   3180
```

```
cttcaggcat ctgggctgca gggaaacagt agaaatacat gtgtgcacat taaacccaac    3240
accgacagca ggaagcaaac atccccacta ctggaactca ggccaaaagg gcggcacttt    3300
cactctggaa aggggagact gcactctgga aagacttctg agaggggcaa agacatagca    3360
tggcctgagg ggctagcagg atatactaaa ggggaagtca ttccaagggg gaaactgagg    3420
cagaaaggag gaggccaggg accagaagcc aaagcactag ctgtaggtca ggatttgtat    3480
aggagctgaa ggagatgggg ccagcctgta agggacctgg atgccaagct cagtgggtgg    3540
agttcccgga ggttggaggg gaggagagga tgctgcgggg cagagctgtc tgctgggttg    3600
tgaggggaga gatgagaggc agccagacag cagccacagt catcctcagg gaaaggagcc    3660
atcctccctc ttcctctcgc ccccaacttc tggattatgg gatggctgct ggtgccggtc    3720
tgtgggctgc ctcccaggga gctgtcctcc cctccccatc cttgctgcca gggacttgcc    3780
catcgaggac cagatctccc tgctgaaggg gccgctttc gagctgtgtc aactgagatt    3840
caacacagtg ttcaacgcgg agactggaac ctggagtgt ggccggctgt cctactgctt    3900
ggaagacact gcaggtgccc gagagagcct gcctgccctg gcagagggag ggaaacactg    3960
cagttatggg aggaagggag ctacgccagg atatgcaggt tctgggatgg cagggcagga    4020
agatggaatg gtgaaaaaca agatattggt gagggatgat tagatcttgg tcagcttgct    4080
gagaagctgc ccctccatcc tgttaccatc cacaggtggc ttccagcaac ttctactgga    4140
gcccatgctg aaattccact acatgctgaa gaagctgcag ctgcatgagg aggagtatgt    4200
gctgatgcag gccatctccc tcttctcccc aggtgaggat ctcccctagg ctgcctgaca    4260 tccccccag ccttatctgc cctccccagg gaaggtccca gtctatggcc ttgctcctca    4320
ttcactgcgc agccaggatg ggggctctcg ctggtttctc ctggggtcag tgggtgatgc    4380
ccagccctgg tcttccttca cttccctgcc tgggtgactc cagctctgga gggtggttgg    4440
cgagcaatgc cctgactctg ggctggactg agcttgtctt tgccccatga tcttgcacca    4500 cacctcccctc ccctccagac cgcccaggtg tgctgcagca ccgcgtggtg gaccagctgc    4560
aggagcaatt cgccattact ctgaagtcct acattgaatg caatcggccc cagcctgctc    4620
ataggttctt gttcctgaag atcatggcta tgctcaccga gctccgcagc atcaatgctc    4680
agcacaccca gcggctgctg cgcatccagg acatacaccc ctttgctacg cccctcatgc    4740
aggagttgtt cggcatcaca ggtagctga                                      4769

<210> SEQ ID NO 3
<211> LENGTH: 9962
<212> TYPE: DNA
<213> ORGANISM: Homo Sapiens

<400> SEQUENCE: 3
atggaggtga acccaaaga aagctggaac catgctgact ttgtacactg tgaggacaca      60
gagtctgttc ctggaaagcc cagtgtcaac gcagatgagg aagtcggagg tccccaaatc    120
tgccgtgtat gtggggacaa ggccactggc tatcacttca atgtcatgac atgtgaagga    180
tgcaagggct ttttcaggta gagttaccca tcagccttca cccacgtgcc accactgacc    240
cactgggtaa cgtctcaggg cctcagcttg acctgtcccc caggttcaga gtgtgggctg    300
gtggcccacc caaaggcctt gtaattagtc tcaagggagc catttatatc ccagaggaat    360
ccttcatctt cagtcttcct gttctaccca ggaaaggtct ccttccatta agatatccct    420
tggtttctcc atgtgctctt gaataaaatg gaaaatgact cagtgaaaga taaggaattt    480
```

```
gaaaatccca aatccaagtg ttcacatccg ccttctgggg tggttgttac ataaagaatg    540
gcataaaata aatgcttaga ccatgggaag agaaacagac cgaagggagg ggaagggcgg    600
ggagggggaga aagccatgtg tgaggaagca ctccaggtgc accctccgga gggcacaggg   660
tatgcaagga gcagctccca tctcgggagc cacatgtggg accctcatgc attcccaaga   720
cagccagcct gacagccctt tgcagagttc ttcgtggtgg ctgggcattc aaatggaaaa    780
gggcaggttc caggagaaa tgaacattcg tgttgcatga gttataacag gggtgagaca    840
catcagcagt gtcagactgg gttcagctac aagtcacagg acacttgtcg ccaattggtt   900
tggcaataag gaaaatgtgt tacctctcct aacaggaagt ctgaaggcct ccaggttagt   960
gagttcagca gctcatttct ttccattttt ctcttcagcc atcccacctg agagctctga   1020
ttgcagtctg gctccccttg tgggggcaca gtgctgggc cccaggcagg aatcattatg    1080
ttcagcagaa gcgcacaaag gcccatcttt gagagtaagg aaatctttcc caggagtccc   1140
ctcacattgg ctagagccgg gcccagccta tgcctgaact agtcactagc aaagagcagc   1200
aggtatgtcc ctgagctggg cacacgccac ttgactgtgt ggaagagggt ggatgtctgc   1260
accagctcca gatgctgctg gcacagaaga ggctgcccaa gcagtgttcg tgcatcctgc   1320
ctcagcatgc aggaatcttc tgctctccct tcctcatttg ggtactattc ctgggactct   1380
cagaaaaagg caacatgttg tagtgggcaa aagctaaatc cagtatcagg cagacctgga   1440
ttcaaatttc agcttgtcat gtacctggag acagctggg gatccatcgt ctccaagcct    1500
cagtctccct catctgtgct aggcagatga gattatgagt ttcacagggt tttagaacta   1560
aatttacaaa actgcaaaat acctagccta gcatctgata catagcatac ctttaaataa   1620
tgtgagcccc ggtttcatct tttacccatt ctcagtggac tttgatgtag catcagagtt   1680
ttcttaccca ggccagttgg gaaggcaaaa ggcagggatg gcatctgtga agaacatgcc   1740
cctgggctgg tcactggtcc gagggcccgag gcctccaagc tcaaacctgc caggtcactg   1800
cgggcttggc tcagcttccc aggcctgccc tcggggacct ctgcagccct acctggctgt   1860
tccatgctcc tgggccagcc ttccctcagt ttccactctg accagaatc agaggccaga    1920
gccaagggag agattgtttc tttccatcca gctgtggaga tggggaaagt aaaggtagga   1980
ctgcactgac cgtgtctttt gtgggacagg caggacttcc gggctgggag gaggagatct   2040
tgtaccagag tctccaaaag gcatctgccc cattgcctct ctgcgcaccg cagagagggg   2100
tgtgcgggcc cgtgggtccc gcctgcacgc tctgctgttc caggcgctcg acctctttgc   2160
cccctaggtc aacgagggga atccactctg ccatgggaa gtcgctgccc cgtagggtat    2220
aagaacttcc ccatagttca ccccttcctc cctggccgcc cagtctggaa ggggagctgg   2280
agaaggcggc gggggtggg gggaaggcgg ggggaaggc ggggggtgg ggcgggcttc      2340
tctggtttct tacccctcctg gggtcaggtt tcctcagctc cctcccttaa ggagggaaa   2400
tcgaggaaga ggcccatctc catggaaact ttctggtaac aaggctgtga agagaaggg    2460
gacaggtgtt tcaggaagaa gggaaggcgc tgaggatggg cctggagagg aagtgtccct   2520
gaaagtggtt ttggggctgc ccgcgccagc gaaaagcacg tgtcccattt cctgccggaa   2580
tggccagaaa aggtctcctc cccggctctg cccctctag ctgagtcctg gacctctagg    2640
gactcccacc tacaccctc ccataaagcc tgacccagct gggacgcaaa ggctagtgtc    2700
cccctccccg agtcggtagg ggctggggag ggaggtggta tggcccggag cccaggccg    2760
agggcccggg cacccgtgca tccccccttc tgctccccat tctctcacag gagggccatg   2820
aaacgcaacg cccggctgag gtgccccttc cggaagggcg cctgcgagat cacccggaag   2880
```

```
acccggcgac agtgccaggc ctgccgcctg cgcaagtgcc tggagagcgg catgaagaag    2940
gagagtgagc agtgggcgcg cgggcgggcc ggcgccgggg tgcacggctc tgagtaagga    3000
cgtgccgtgg gtgtgggcat gcttgtgtgg agatgcgcgc cgagtgtgcg cgtgaacaca    3060
cgtgcacatg tgagctggtg tccgtgtgca acaggcagcc acctggggga gcgcttgcag    3120
tcggccctct gggagatgga gggagtcggt aatctctgcc ctgggatgtg tgctgggcag    3180
ccctggacag ggcgtgccct ctgtctcccc tcagttgctc ctgcatcatt cttttgtcc     3240
ccttcataat tgttgtaatg gtttgaaacc acatttgcgg gtaggagtgt gaatctgggg    3300
gagggaagca ggagccacat gggtgatagg acccggggcc ttctaggtgc tagccccatc    3360
agctgcccca gacctggatc tttatagggg aactgtttgc agacaggtga catgaggtgt    3420
tctcattcta cctatttaac tttgatatat ttgtgctcct aggtcactat gagattaagg    3480
ctcatgcgga aaaggctagg tgtttctagt gcatatttgt ctccatggaa cacaaaggga    3540
cccaaagctg cttctttcaa ggacaagttc tctaggctgc tggcaggcat tcttgatctc    3600
tccccaccaa ggacctcata gctttgttct acacacatga gtgggctcca gaaatccaca    3660
gaagaccccta aggctctggg ctatataaga agtctctgga gttgctattt cttgctaagc    3720
tgtagcccag ctctctaggg tcttggagac ccagacacct ctgaagagtc ttggtatata    3780
attcaccaga aaatgataat tgtagatgcc atttactgaa catctcttat gtaccaggaa    3840
ctatattagg caccctacat gcaaggtctc atttaacagc ggtgcgaggt aaacacggtt    3900
tctccggatc acaaaggaga aacctggagg caggagaggt taaggaggtt gcttggggtc    3960
acaggtagta agtggcaaag ctttcatgca aacccagcgc ctttggattc tgaagcccgt    4020
gctcttgcca gggccccaca gtgtcctcac aaactccact gcagagggca aaacaccagc    4080
ctcacctcat ctctgtcctc acccaagtgt ttctccagaa gagcccacag gcctcttgag    4140
tccagacagg ggagaattgc ttgtcaccat tactttctct tttgcctaac ggcttctgct    4200
gccttgagag ggttacacag tggctctcca ggggctgga ggctcaccag gggcacgtgt     4260
gcctgagcca gcctcactgt ccctgcagtg atcatgtccg acgaggccgt ggaggagagg    4320
cgggccttga tcaagcggaa gaaaagtgaa cggacaggga ctcagccact gggagtgcag    4380
gggctgacag aggagcagcg gatgatgatc agggagctga tggacgctca gatgaaaacc    4440
tttgacacta ccttctccca tttcaagaat ttccgggtag gaggaactgc acagtgaccc    4500
gaggtgtcac tgccatcttc attctcacat agaaactgag gttccccaag gataagaaac    4560
ttatacaagg tcacagctaa tcagtggtgg agggtagatt tggagagctg gtcctgcatc    4620
tgtgctagct cctcaaagcc ttagtctcat tcccaaaggt tctgaaagtg tggtccctgg    4680
gtcagcagca tcagcatgca gattttcagg tcacctcaga tctcctgaat ctgaagctcc    4740
agggaggggc aggacccccc ggtgattctg ttgcaggttc aggtttgaaa aatcactgct    4800
ctctccttta aggcaggtag gaactgggtc taagcaataa gtggagggaa agctaggcag    4860
ttccccagtt ttgctggcat tcggggcttt atgaggacag gatcaggacc tgttgggggt    4920
gtgactttg tgaactggtg tttcttgatc ccagcacatt aactatgtct gtgctctaag     4980
tgccctcctt cccctttgca ctgatagata tctcaagtgg cccttcacag cccaaataac    5040
tggattagcc cagtgacctc agatctgctc ttcccatcca tagcacccta aaccttctga    5100
gtctcctgag cccaacatct ggaatgcttg ggatgacaca ccatggttgc agtccccctt    5160
accctccatt ttaaccaagc agggatgtgt gtgaccatta attcatagat ccccaaagca    5220
```

```
ccttcatctg atagagaaca ccagagagaa gaaacaaatg ctgtgtgtgt atatgtgtga    5280
ggacacacgc atgcatgtgg gtgtgaatgc ctgcatttgt gcatcctctc gagctgcaac    5340
tgtggctgtg catgtttggc tggggcctga gttgggacct gtctatgaaa gcacatgctg    5400
tctctcctct gtccacctcc tggcatgtgt cctagctgcc aggggtgctt agcagtggct    5460
gcgagttgcc agagtctctg caggccccat cgagggaaga agctgccaag tggagccagg    5520
tccggaaaga tctgtgctct ttgaaggtct ctctgcagct gcgggggag  gatggcagtg    5580 tctggaacta caaaccccca gccgacagtg gcgggaaaga gatcttctcc ctgctgcccc    5640
acatggctga catgtcaacc tacatgttca aaggcatcat cagctttgcc aaagtcatct    5700
cctacttcag gtaggacatg gagactgggt ggttgggtgt ggaaaagaac tggaagtggc    5760
caggaggttc aaagggcctg ggtagatcc  tgaatttggg ggatattggt gtcagaagac    5820
cctccttttc ctgtgccctt tccccgggca gccagtgctg ctggggagta gagcccttgc    5880
tgtatggctg gttagttttg tggctgtggg cctgccagtg tctctgcctc ttcacctgct    5940
caatggaagc taaaaatgcc tccctgcag  ggctgttctg tgaaataaga acacatccga    6000
agaacaccca gcacagagtg ggcattcaga tagtcttttg tactctccct taaagggca    6060 ggaatcacat gttgacagtt ccagagcaag gaatgagagg aatagaaaag ataaggctgt    6120
gaaggccatg ggagggcgg  gtggtcctca gagcccaagg gtcaggtctc cccagagcta    6180
gatgtggagg caacaaccat cgggcaactg gggttagtgg gagacatggg aacttcctgg    6240
ggtggcagga accacagccc cagaatatgt gtgcagtcgt aggattaggg atggtgccag    6300
gtgtatctgt ccttgggtag gccaccttgc cttgccaagc ctggtcaagt ggggctgaaa    6360
cacacctgcc acaagctcct ggtttcttca gcaggttgag ggtaggttat actctaggag    6420
cccagaggtt cttctctggc cctgtaggag tcatgcgtga cttatttaat ggggtgatgc    6480
tgacagcagg tttggaatgg ggttcagatg gtagcaaata agcttaaagg gcagggaga    6540 gaagaatact tataaatgtg gacattggga gatctttggt gaaatccagt gactgacaat    6600
ttaacaccag ggcttcccac ttgctatttc tcaaggccac caatgtcgag cacagtgacc    6660
tgaggtgtca ctgccatctt cattctcaga tagaaactga agttccccaa ggataagaaa    6720
cttgtacaag gtcacagcta atcagtggtg gaggctagat ttggaagtac caaagccagc    6780
tcgatgccag gtcctaagct gggcaatggg gaggcacaga agaataagat caattacatg    6840
gcatttgtag ctcagtgtta gggatctaaa agaaggatgg gcgccagtag cacagggtct    6900
gaattcccaa ggccaagagg tagtgtttcc tcaaaaccca gagtaagcag cctcctctc     6960 aggctgtgaa gcttcctcct tgtaaggaat gcctccttac tggggaggtg ggggcccctc    7020
ccaggttggg agggagtgat ccctgcagga ccggaaggg  atccatgtaa ccataatctc    7080
agaggcttgt taagccgcct ccatggttag gcctgtgctt cagcgctagg agtgggctt     7140 caggcatctg ggctgcaggg aaacagtaga aatacatgtg tgcacattaa acccaacacc    7200
gacagcagga agcaaacatc cccactactg gaactcaggc caaaagggcg gcactttcac    7260
tctgaaaagg ggagactgca ctctggaaag acttctgaga ggggcaaaga catagcatgg    7320
cctgaggggc tagcaggata tactaaaggg gaagtcattc caaggggga  actgaggcag    7380 aaaggaggag gccagggacc agaagccaaa gcactagctg taggtcagga tttgtatagg    7440
agctgaagga gatggggcca gcctgtaagg gacctggatg ccaagctcag tgggtggagt    7500
tcccggaggt tggaggggag gagaggatgc tgcggggcag agctgtctgc tgggttgtga    7560
ggggagagat gagaggcagc cagacagcag ccacagtcat cctcagggaa aggagccatc    7620
```

```
ctccctcttc ctctcgcccc caacttctgg attatgggat ggctgctggt gccggtctgt   7680
gggctgcctc ccagggagct gtcctcccct ccccatcctt gctgccaggg acttgcccat   7740
cgaggaccag atctccctgc tgaagggggc cgctttcgag ctgtgtcaac tgagattcaa   7800
cacagtgttc aatgcggaga ctggaacctg ggagtgtggc cggctgtcct actgcttgga   7860
agacactgca ggtgcccgag agagcctgcc tgccctggca gagggaggga aacactgcag   7920
ttatgggagg aagggagcta cgccaggata tgcaggttct gggatggcag gcaggaaga    7980 tggaatggtg gaaaacaaga tattggtgag ggatgattag atcttggtca gcttgctgag   8040
aagctgcccc tccatcctgt taccatccac aggtggcttc cagcaacttc tactggagcc   8100
catgctgaaa ttccactaca tgctgaagaa gctgcagctg catgaggagg agtatgtgct   8160
gatgcaggcc atctccctct tctccccagg tgaggatctc ccctaggctg cctgacatcc   8220
cccccagcct tatctgccct ccccagggaa ggtcccagtc tatggccttg ctcctcattc   8280
actgcgcagc caggatgggg gctctcgctg gtttctcctg gggtcagtgg gtgatgccca   8340
gccctggtct tccttcactt ccctgcctgg gtgactccag ctctggaggg tggttggcga   8400
gcaatgccct gactctgggc tggactgagc ttgtctttgc cccatgatct tgcaccacac   8460
ctccctcccc tccagaccgc ccaggtgtgc tgcagcaccg cgtggtggac cagctgcagg   8520
agcaattcgc cattactctg aagtcctaca ttgaatgcaa tcggcccag cctgctcata    8580 ggtgagcaca gcaggggtg aggacccgtg agggtgatgt gagggagccg aggttcaggg    8640
aaattgccca agacttcatg gccagagggt ggcatctgga ggtagcccca gccagaccag   8700
gtccaaagct cacacttttg agcactacct aaccacttcc caggaaaaac acaagcaaac   8760 aggggggacgt ggcccagaaa ggggcttcta taccttcact ggtcctcagt agctcctgtg   8820
acctactgcc cagactgatg cccacagacc cagagacaaa cttggatttt acggagccca   8880
aggccatgaa gggttaaggc caacactgag tattatagtg tgaacctata aactgaaatc   8940
cttatttggc ctgcacagct ttcttttttgg cttggtgtcc tgggatgctg ggagtggcca   9000
tgtctttatt tgctcaaccc ttccttgtat ggaggcagga ggctggaagt gccaactttc   9060
ttttccatca tggggatact gaggcatatg gtacatctca gacactagat ccaaagctag   9120
ttccaggaag ggattccagc ctgcagcccc taacctccac aacgactctg ctcagtcctg   9180
gcccctggac attaacgaag gcagtgacag ccccacaccc ccaaactggt agctgcaata   9240
tctacatttt cccacggaag tctctgtgta caaagatgca actcccgcag ctgggtgtcg   9300
tggctcacac ctataatccc agcactttga gaggtcaaga caggaggatc ccttggggcc   9360
aggagttcaa aaccagccta ggcaacatag ccagaccca actctagaaa aattttaaaa    9420
aattagccag gtatggtggc atgtgctcta gtcctagcta cccaggaggc tgaggctgga   9480
ggtctcttga gtccaggagt ttgacactgc agtgagtcca tgatcgtgcc atcatgctct   9540
agcctgggtg acagaacgag atcctgtccc tttaaagaaa aaaaaaaaa aaagacacag   9600 ctcccatgaa tgggatggga gtggggagag tattgggcag gctgttctgc ctttctcatc   9660
tacagggtaa aagagaagct tacggaattc agccaagcct tgtctcttgg ctgacctgaa   9720
atgtccagag attatgcttg tgcagcctca gagcagccct gaggcttgtg gtcagggcg    9780 ggctgcaccc acaatctttt ctctggctgg catgcaggtt cttgttcctg aagatcatgg   9840
ctatgctcac cgagctccgc agcatcaatg ctcagcacac ccagcggctg ctgcgcatcc   9900
aggacataca ccccttttgct acgcccctca tgcaggagtt gttcggcatc acaggtagct   9960
```

-continued

| | |
|---|---|
| ga | 9962 |

<210> SEQ ID NO 4
<211> LENGTH: 6971
<212> TYPE: DNA
<213> ORGANISM: Homo Sapiens

<400> SEQUENCE: 4

| | |
|---|---|
| atggccagta gggaagatga gctgaggaac tgtgtggtat gtggggacca agccacaggc | 60 |
| taccacttta atgcgctgac ttgtgagggc tgcaagggtt tcttcaggtg agagtctcct | 120 |
| ccccaatgga aatagccctc caaaccaaac tccctattag tcagccttta caccctcgct | 180 |
| ggtgcccaag cctgtccagc tacattactc ctttatctta gagtctaact accctgtggc | 240 |
| tggcatccta catcttgcca aacacatcac tgtataaact ggtggcataa cagagggaaa | 300 |
| gctgaatgtt tgtctgatgg acacagccca ttagtcaaga gcatttatta tgtacccact | 360 |
| taagcttgtg gagtacgcgc ccggggagcc caagggcacg ccctggcacc cgcaccgcgg | 420 |
| gtcgaggccg gcctgtgaag cacctagcta gtactacatc aactaggctt ctggagtga | 480 |
| tcctgtgttg ccatggaaat gcttgagatg tgttggatac tatccacccc tggggacctt | 540 |
| tgggcacagc tcagattagt ccatttcacc agattcccag gtcttttaga ccatgtcatc | 600 |
| tcagcccctc acctatccat tgcatcccag actctaacaa catctctgtg tctcacagga | 660 |
| gaacagtcag caaaagcatt ggtcccacct gccccttttgc tggaagctgt gaagtcagca | 720 |
| agactcagag gcgccactgc ccagcctgca ggttgcagaa gtgcttagat gctggcatga | 780 |
| ggaaagacag tgagttggcc ccctacatct caagaatcca ttgactgcgt ctgtctttgt | 840 |
| ccttgttccc aacagtgcat tctctacata gcaggcacag tactcttttt gaaactagtt | 900 |
| ggattatgtc actattcact caagacatcc aatggctccc catctcaaag tacgtgatct | 960 |
| catgatctag ctctcccaca acacctttca gactttattt catactcttc cccctttact | 1020 |
| caaccaattc tagccacact gacttcactg tcattcttag aaacaccagg ccgggcgcgg | 1080 |
| tggctcacgc ctgtaatccc agcactttgg gaggccgagg caggcggatc acgaggtcag | 1140 |
| gagatcgaga ccattctggc taacacagtg aaaccccgtc tctactaaaa aaatacaaaa | 1200 |
| aaaattagcc ggccgtagtg gcgggcgcct gtagtcccag ctactcggga ggctgaggca | 1260 |
| ggagaatggc gtgaacccgg gaggcggagc ttgcagtgag ccgagatcgc gccactgcac | 1320 |
| tccagcctgg gtgacagagc cagattccga ctcaaaaaaa aaaaaaaaaa aaaaaaaaac | 1380 |
| accaagcgca ctcttcccca aggcttttcc acttgccatt tcctctacct gaaatgcttt | 1440 |
| tctcctagat agccacatgg ctagtcttgt cttttctttt cttttctattt ttttttgatag | 1500 |
| agtctcatac tctgttgccc aggctggagt gcagtggcgc catctcggct cactgcaacc | 1560 |
| tccgcctcct gcgttcaagt gattctcctg cctcagcctc ctgcatagct gggattacag | 1620 |
| gcatgtgcca ccacacccag ctaatttttt gtattttagg tagagatgag ctttcaccat | 1680 |
| gttgaccacg ctggtctcaa actcctggcc tcaggcgatc tgcccacctc cgcctcccaa | 1740 |
| agtgctcaga ttacaggtgt gttttttatt ttctatctgt tgagtatagt gcctgtcacc | 1800 |
| tagtaggtgc tcaataactt aattaatgct ttctctgtgc caggtaactg tgctatgctc | 1860 |
| ccaaaggagg atgtaactgg ggctcacgga agttaatttg cccaagttaa ttcaactaaa | 1920 |
| aacttgtgca ggccgagcac ggtggctcac acctctaatc ccagcacttt ggaaggctga | 1980 |
| gacaagagga ttgttgaggt caggaattca agaccagcct ggtcaacaga gtgagatgtc | 2040 |
| ctctctagga aagaagaag gaagaagaag ttgtacagtc agtattcaaa ctcaagttta | 2100 |

```
cctgactccc aaactcttgc ttttccata tcacacgatt ctcactatgg aagaatgaaa    2160
ggaaactgta gaagtcaaag gatcttggtc tgaattcaag atcttggttt gatcttggat    2220
cttttgcaga agtcaaaaga ttttggtttg aattcaatct atattactta ttttgtgacc    2280
ttggttctgt caccagaatc taagcctgtc cacatttcta aaaaatgtga ttgggctggg    2340
tgcagtggct cacgcctgta atcccagcac tttgggaggc cgaggtgagt ggatcacttg    2400
aggtcaggag ttcgagacca gcctggccaa catggtgaaa ccccgtctct actaaaaata    2460
caaaaaaaaa aaaaaattag cagggcgtga tggtgggtgc ctgtaatccc agctagtcag    2520
gaggctgagg cagggagaat tgcttgaacc caggggggcag aggttgcagt gagccgagat    2580
tgctccattg cactccagcc tgggcgacag agtgacagac tccatctcaa aacaaaacaa    2640
aacaaacaaa aaatatata tatacacata tatatacaca tatatacaca tatatacatg    2700
tatacacata tatatacata tatacacata tatatacaca cacatataca cacacacaca    2760
cacacacaca cacacacaca cacacacaca cacacacata tatatgat gaataccagc    2820 cctgcctatc ctggggttgt ttcattcagt gggatttaac ctcagaagtt ttgaaattt    2880 gctaaaacat cagataaagg tttatttgaa aggattattt gattattttt gaaggattat    2940
ttgaaaacat catataaagt gatgttctag gtatgaagac ccctccctct acactgtttc    3000
cccaaaagcc ctcgcacctt tcctcacatc tttcatactt tcctcgccac ccttcccttc    3060
tcccccacag tgcagttttc tgctgcagtt cttcacaggt tggtggaagt gtataggagc    3120
cccctgcctc ctggagcctc taggacttta gccaagccca agaaagtctc aggaattccc    3180
cccactgccc ccatccttcg ttgtgcaggg cagctgaggg gccccagatc agggaccagc    3240
agagagaaat gctctgctgg tctcaacagc tttgtcatga tctcttgcct ggcacagtga    3300
tactgtcggc agaagccctg gcattgcggc gagcaaagca ggcccagcgg cgggcacagc    3360
aaacacctgt gcaactgagt aaggagcaag aagagctgat ccggacactc ctgggggccc    3420
acacccgcca catgggcacc atgtttgaac agtttgtgca gtttagggtg agcaccgaca    3480
ggatttgggt tggaatacaa ctaaaagggc acccaaaaat gctggtctga aggagagggg    3540
tgtatgccat gcactgatac tgagaacaga tctccagaac cccagcctga gcaggcttct    3600
cagcaaggaa ctcttccaag ataaggctgg cgaggcctaa aggagggccc tagggccaga    3660
gcctctagct aatgttctga tcattgcagc ctccagctca tctgttcatc catcaccagc    3720
ccttgcccac cctggcccct gtgctgcctc tggtcacaca cttcgcagac atcaacactt    3780
tcatggtact gcaagtcatc aagtttacta aggacctgcc cgtcttccgg tgagtgacct    3840
cccctcatct ttcaggaggc aaacacttca gtaaattgta tatccacccc gaaaagtcac    3900
tgactacaaa ttatcacatg cgtcagcctt tccaagcatt aggtcttgaa ttcccagctt    3960
tggttttaaa tgtgccaatc agaactggga gttcttctcc atctctgaag tacaggcttg    4020
catctaaagt gcccttgagg tgccgcgcag tggctcacac tagtaatccc agcactttgg    4080
gaggcggagg ctgcagatc gcttgagtcc agaagtttga gaccagcctc agcaacatga    4140
caaaacccca actctacaaa aaatacaaaa attagctggg catgatggtg ggtgcctgta    4200
gtcccaggta ctcaggaagc tgaagtggga ggatcacttg agcccaggag gttgaggctg    4260
cagtgagctc agatagcacc gctgcattcc agcctgggtg acagagtgag actctgtctc    4320
aaaaaatgaa agctaaaaat aataataata ggccaggcac ggtggctcat gcctgtaatc    4380
ccagcacttt gagaggccaa ggtgggtgga tcacttgagc tcaggaattt gagaccagcc    4440
```

```
tggccaacat ggtgaaatcc gtctctacta aaaatacaaa acttagctgg gtgtggtggt    4500
gggcgcctat aatcccagct tctcaggagg ctgaggcaga agaatcactt gaacccagga    4560
ggcggaggtt tgctgtagcc gagatcaggc cactacatcc agcctgggtg acagagcaac    4620
actctgtctc aaaaataaat taattaataa gaataataat aaggtgccct tgtcggctgg    4680
gcacagtggc tcacacctat aatcccagca ctttggaagg ccaaggcagg aggactgctt    4740
gagcctagga gttcgagacc accctgggca acatagtaag actccatctt tacaaaaaat    4800
aaaaacatat aaacaaacaa aaattaaaa agtgggccgg gtgcagtggc tcatgcctgt    4860
aatcccagca ctttgagagg tcaaggcagg tggatcacct gaggtcagta gttggagacc    4920
agcctggcca acatggtgaa acccgtctc tactaaaaat acaaaaaatc agccaggcat    4980
ggtggcacac gcctgtaatc caagctactt gggaggctga ggcaggagaa ttgcttgaac    5040
ccaggaggca gaggttacag tgagcagaga tcacgccact gcactccagc cagggtgaca    5100
gtgagactct gtctcagaaa aaaaaaaatt gaaaagtgtc cttgtttcct gctttccaca    5160
gttccctgcc cattgaagac cagatctccc ttctcaaggg agcagctgtg gaaatctgtc    5220
acatcgtact caataccact ttctgtctcc aaacacaaaa cttcctctgc gggcctcttc    5280
gctacacaat tgaagatgga gcccgtggtg agatggtgct agagcaatag ggggcatgtg    5340
tcctcatggt acaggatgtg tcaggtgac ctagaggctc ctaatcctag tatctcccac    5400
agtggggttc caggtagagt ttttggagtt gctctttcac ttccatggaa cactacgaaa    5460
actgcagctc caagagcctg agtatgtgct cttggctgcc atggccctct tctctcctgg    5520
tgagcacctc ccaaagccca gagccttttg ctgcaccacc tctgcccaaa tactcagctc    5580
cttgagtcca tccacccagg ccttctagcc tagctatcaa acctgcagac taggtctatc    5640
ccagcctcag tccccggggc accacgcagg cccaccctg ccacccaact tgtccttccc    5700
agctccctat cttacagacc gacctggagt tacccagaga gatgagattg atcagctgca    5760
agaggagatg gcactgactc tgcaaagcta catcaagggc cagcagcgaa ggccccggga    5820
tcggtacggt gggacactga gggcttggag gccacaccag ggcaggaagg ggttggtgaa    5880
acattgagct tgggaggaat gttttttac tgtcctttcc ttagggaatt caggtatcgt    5940
ggggtctagt ccttccccct ggccatccct gtctcacatc gtttcagcat ccaaattgct    6000
gtatttggat actgctgttt catctcactt tttccagatt ttttttttat tcagtacaga    6060
tgcaaagtag tagctcagag gctctgggta atagcattcc tgagattgat gacatccatt    6120
acctcactag tccaacttct ccagactaac gcagacttt ctcttccctt ggcctttcct    6180
ctcctcgcca ttgggccaat tccttcgatt tctcatttcc cttgaagtta gggccattca    6240
cagtttcatg gtcaaagcca gttccaggtt caatagtctg tgatttatcc aggctctgag    6300
gtatgcaccg cttctgtttt gctcgttcct ccaagagcta gtttggccag aaaggggatg    6360
ctttatacca tagaacacat ccaccttcta gaacctgctc tagaaggcca ggccctcaga    6420
ttccacatgg ttggagttct ggccaagtct ggagctttct tcacactcgg ctctcagagc    6480
tctgggttca gaaaaaactg agcatggtga gagaagacag tgtcagaccg aggcccctg    6540 gaggaccttt ggaacctctg atagtctgtc ataccagagc atgattttct ctaatgttca    6600
gacctggctt cactgaggaa tagttcaggg gatcagggcc tagagacaag actcccaact    6660
gccttatttc cctcctgttt tcctggcaac cccactactt cctccaaagg tttctgtatg    6720
cgaagttgct aggcctgctg gctgagctcc ggagcattaa tgaggcctac gggtaccaaa    6780
tccagcacat ccagggcctg tctgccatga tgccgctgct ccaggagatc tgcagctgag    6840
```

```
gccatgctca cttccttccc cagctcacct ggaacaccct ggatacactg gagtgggaaa    6900
atgctgggac caaagattgg gccgggttca aagggagccc agtggttgca atgaaagact    6960
aaagcaataa c                                                         6971
```